US011273214B2

(12) United States Patent
Collins et al.

(10) Patent No.: US 11,273,214 B2
(45) Date of Patent: Mar. 15, 2022

(54) RECOMBINANT CHIMERIC BOVINE/HUMAN PARAINFLUENZA VIRUS 3 EXPRESSING RSV G AND ITS USE

(71) Applicant: THE UNITED STATES OF AMERICA, AS REPRESENTED BY THE SECRETARY, DEPARTMENT OF HEALTH & HUMAN SERVICES, Bethesda, MD (US)

(72) Inventors: Peter L. Collins, Silver Spring, MD (US); Ursula J. Buchholz, Silver Spring, MD (US); Bo Liang, Bethesda, MD (US); Shirin Munir, Bethesda, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 48 days.

(21) Appl. No.: 16/616,873

(22) PCT Filed: May 29, 2018

(86) PCT No.: PCT/US2018/034848

§ 371 (c)(1),
(2) Date: Nov. 25, 2019

(87) PCT Pub. No.: WO2018/222573

PCT Pub. Date: Dec. 6, 2018

(65) Prior Publication Data

US 2021/0145958 A1 May 20, 2021

Related U.S. Application Data

(60) Provisional application No. 62/512,111, filed on May 29, 2017.

(51) Int. Cl.

| | |
|---|---|
| ***A61K 39/12*** | (2006.01) |
| ***C07K 14/005*** | (2006.01) |
| ***C12N 15/86*** | (2006.01) |
| ***A61K 39/00*** | (2006.01) |

(52) U.S. Cl.

CPC ............ *A61K 39/12* (2013.01); *C07K 14/005* (2013.01); *C12N 15/86* (2013.01); *A61K 2039/5254* (2013.01); *A61K 2039/5256* (2013.01); *A61K 2039/543* (2013.01); *A61K 2039/575* (2013.01); *C12N 2760/18534* (2013.01); *C12N 2760/18571* (2013.01); *C12N 2760/18643* (2013.01)

(58) Field of Classification Search

CPC ............ A61K 39/12; A61K 2039/5254; A61K 2039/5256; A61K 2039/543; A61K 2039/575; C07K 14/005; C12N 15/86; C12N 2760/18534; C12N 2760/18571; C12N 2760/18643; C12N 2760/18641

See application file for complete search history.

(56) References Cited

U.S. PATENT DOCUMENTS

| | | | | |
|---|---|---|---|---|
| 7,192,593 | B2 | 3/2007 | Murphy et al. | |
| 7,201,907 | B1 | 4/2007 | Schmidt et al. | |
| 7,208,161 | B1 | 4/2007 | Murphy et al. | |
| 7,250,171 | B1 | 7/2007 | Tao et al. | |
| 7,622,123 | B2 | 11/2009 | Skiadopoulos et al. | |
| 7,632,508 | B2 | 12/2009 | Schmidt et al. | |
| 2009/0017517 | A1 | 1/2009 | Schickli et al. | |
| 2009/0263883 | A1 | 10/2009 | Haller et al. | |
| 2010/0119547 | A1 | 5/2010 | Haller et al. | |
| 2011/0097355 | A1 * | 4/2011 | Morrison ................ | A61P 31/14 424/192.1 |
| 2012/0045471 | A1 | 2/2012 | Haller et al. | |

FOREIGN PATENT DOCUMENTS

| | | | | |
|---|---|---|---|---|
| WO | WO 2001/42445 A2 | 6/2001 | | |
| WO | WO 2001/70032 A1 | 9/2001 | | |
| WO | WO 2016/118642 A1 | 7/2016 | | |
| WO | WO-2016118642 A1 * | 7/2016 | ............. | A61P 31/14 |
| WO | WO-2017100759 A1 * | 6/2017 | ............... | C12N 7/00 |

OTHER PUBLICATIONS

Bernstein et al., "Phase 1 Study of the Safety and Immunogenicity of a Live, Attenuated Respiratory Syncytial Virus and Parainfluenza Virus Type 3 Vaccine in Seronegative Children," *Ped Infect Dis J. 31.2*: 109-114, Feb. 2012.

Boyoglu-Barnum et al., "Mutating the CX3C Motif in the G Protein Should Make a Live Respiratory Syncytial Virus Vaccine Safer and More Effective," *J Virol. 91.10*: e02059-16, May 2017.

(Continued)

*Primary Examiner* — Rachel B Gill

(74) *Attorney, Agent, or Firm* — Klarquist Sparkman, LLP

(57) ABSTRACT

Recombinant chimeric bovine/human parainfluenza virus 3 (rB/HPIV3) vectors expressing Respiratory Syncytial Virus (RSV) G protein or a recombinant RSV G protein, as well as methods of their use and manufacture, are provided. The rB/HPIV3 vector comprises a genome comprising a heterologous gene encoding the RSV G protein or the recombinant RSV G protein. Nucleic acid molecules comprising the sequence of the genome or antigenome of the disclosed rB/HPIV3 vectors are also provided. The disclosed rB/HPIV3 vectors can be used, for example, to induce an immune response to RSV and HPIV3 in a subject.

26 Claims, 23 Drawing Sheets

Specification includes a Sequence Listing.

(56) References Cited

OTHER PUBLICATIONS

Bukreyev et al., "The Secreted G Protein of Human Respiratory Syncytial Virus Antagonizes Antibody-Mediated Restriction of Replication Involving Macrophages and Complement," *J Virol. 86.19*: 10880-10884, Oct. 2012.
Chirkova et al., "Respiratory Syncytial Virus G Protein CX3C Motif Impairs Human Airway Epithelial and Immune Cell Responses," *J Virol. 87.24*: 13466-13479, Dec. 2013.
Collins et al., "Nucleotide Sequences for the Gene Junctions of Human Respiratory Syncytial Virus Reveal Distinctive Features of Intergenic Structure and Gene Order," *Proc Natl Acad Sci USA 83.13*: 4594-4598, Jul. 1986.
Collins et al., "Gene Overlap and Site-Specific Attenuation of Transcription of the Viral Polymerase L Gene of Human Respiratory Syncytial Virus," *Proc Natl Acad Sci USA 84.15*: 5134-5138, Aug. 1987.
Collins et al., "Production of Infectious Human Respiratory Syncytial Virus from Cloned cDNA Confirms an Essential Role for the Transcription Elongation Factor from the 5' Proximal Open Reading Frame of the M2 mRNA in Gene Expression and Provides a Capability for Vaccine Development," *Proc Natl Acad Sci USA 92.25*: 11563-11567, Dec. 1995.
Corry et al., "Preventing Cleavage of the Respiratory Syncytial Virus Attachment Protein in Vero Cells Rescues the Infectivity of Progeny Virus for Primary Human Airway Cultures," *J Virol. 90.3*: 1311-1320, Feb. 2016.
Eshagi, et al., "Genetic Variability of Human Respiratory Syncytial Virus A Strains Circulating in Ontario: A Novel Genotype with a 72 Nucleotide G Gene Duplication," *PLoS ONE 7.3*: 1-10, Mar. 2012.
Harcourt et al., "Respiratory Syncytial Virus G Protein and G Protein CX3C Motif Adversely Affect CX3CR1+ T Cell Responses," *J Immunol. 176.3*: 1600-1608, Feb. 2006.
Ilyushina et al., "Comparative Study of Influenza Virus Replication in MDCK Cells and in Primary Cells Derived from Adenoids and Airway Epithelium," *J Virol. 86.21*: 11725-11734, Nov. 2012.
International Search Report and Written Opinion, dated Sep. 4, 2018, by the European Patent Office, for PCT Application No. PCT/US2018/034848, 14 pp.
Johnson et al., "Priming with Secreted Glycoprotein G of Respiratory Syncytial Virus (RSV) Augments Interleukin-5 Production and Tissue Eosinophilia After RSV Challenge," *J Virol. 72.4*: 2871-2880, Apr. 1998.
Johnson et al., "Respiratory Syncytial Virus Glycoprotein G Interacts with DC-SIGN and L-SIGN to Activate ERK1 and ERK2," *J Virol. 86.3*: 1339-1347, Feb. 2012.
Johnson et al., "Respiratory Syncytial Virus Uses CX3CR1 as a Receptor on Primary Human Airway Epithelial Cultures," *PLoS Pathogens 11.12*: e1005318, Dec. 2015.
Joyce, et al., "Iterative Structure-Based Improvement of a Respiratory Syncytial Virus Fusion Glycoprotein Vaccine," *Nat Struct Mol Biol. 23.9*: 811-820, Sep. 2016.
Karron et al., "Respiratory Syncytial Virus (RSV) SH and G Proteins are not Essential for Viral Replication In Vitro: Clinical Evaluation and Molecular Characterization of a Cold-Passaged, Attenuated RSV Subgroup B Mutant," *Proc Natl Acad Sci USA 94.25*: 13961-13966, Dec. 1997.
Karron et al., "Identification of a Recombinant Live Attenuated Respiratory Syncytial Virus Vaccine Candidate that is Highly Attenuated in Infants," *J Infect Diseases 191.7*: 1093-1104, Apr. 2005.
Karron et al., "Evaluation of Two Chimeric Bovine-Human Parainfluenza Virus Type 3 Vaccines in Infants and Young Children," *Vaccine 30.26*: 3975-3981, Jun. 2012.
Kolakofsky, "Paramyxovirus RNA Synthesis, mRNA Editing, and Genome Hexamer Phase: A Review," *Virology 498*: 94-98, Aug. 2016.
Liang, et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection Against RSV Infection," *J Virol. 88.8*: 4237-4250, Apr. 2014.
Liang, et al., "Enhanced Neutralizing Antibody Response Induced by Respiratory Syncytial Virus Prefusion F Protein Expressed by a Vaccine Candidate," *J Virol. 89.18*: 9549-9510, Sep. 2015.
Liang et al., "Packaging and Prefusion Stabilization Separately and Additively Increase the Quantity and Quality of Respiratory Syncytial Virus (RSV)-Neutralizing Antibodies Induced by an RSV Fusion Protein Expressed by a Parainfluenza Virus Vector," *J Virol. 90.21*: 10022-10038, Nov. 2016.
Liang et al., "Improved Prefusion Stability, Optimized Codon Usage, and Augmented Virion Packaging Enhance the Immunogenicity of Respiratory Syncytial Virus Fusion Protein in a Vectored-Vaccine Candidate," *J Virol. 91.15*: e00189-17, Aug. 2017.
Liang et al., "Effects of Alterations to the CX3C Motif and Secreted Form of Human Respiratory Syncytial Virus (RSV) G Protein on Immune Responses to a Parainfluenza Virus Vector Expressing the RSV G Protein," *J Virol. 93.7*: e02043-18, Apr. 2019.
Mackow et al., "Attenuated Human Parainfluenza Virus Type 1 (HPIV1) Expressing the Fusion Glycoprotein of Human Respiratory Syncytial Virus (RSV) as a Bivalent HPIV1/RSV Vaccine," *J Virol. 89.20*: 10319-10332, Oct. 2015.
Maher et al., "Recombinant Respiratory Syncytial Virus Lacking Secreted Glycoprotein G is Attenuated, Non-Pathogenic but Induces Protective Immunity," *Microbes Infect. 6.12*: 1049-1055, Oct. 2004.
Munir et al., "Nonstructural Proteins 1 and 2 of Respiratory Syncytial Virus Suppress Maturation of Human Dendritic Cells," *J Virol. 82.17*: 8780-8796, Sep. 2008.
Polack et al., "The Cysteine-Rich Region of Respiratory Syncytial Virus Attachment Protein Inhibits Innate Immunity Elicited by the Virus and Endotoxin," *PNAS 102.25*: 8996-9001, Jun. 2005.
Roberts et al., "The Membrane-Associated and Secreted Forms of the Respiratory Syncytial Virus Attachment Glycoprotein G are Synthesized from Alternative Initiation Codons," *J Virol. 68.7*: 4538-4546, Jul. 1994.
Schaap-Nutt et al., "Growth Restriction of an Experimental Live Attenuated Human Parainfluenza Virus Type 2 Vaccine in Human Ciliated Airway Epithelium In Vitro Parallels Attenuation in African Green Monkeys," *Vaccine 28.15*: 2788-2798, Mar. 2010.
Schmidt et al., "Bovine Parainfluenza Virus Type 3 (BPIV3) Fusion and Hemagglutinin-Neuraminidase Glycoproteins Make an Important Contribution to the Restricted Replication of BPIV3 in Primates," *J Virol. 74.19*: 8922-8929, Oct. 2000.
Schmidt et al., "Recombinant Bovine/Human Parainfluenza Virus Type 3 (B/HPIV3) Expressing the Respiratory Syncytial Virus (RSV) G and F Proteins Can Be Used to Achieve Simultaneous Mucosal Immunization Against RSV and HPIV3," *J Virol. 75.10*: 4594-4603, May 2001.
Schneider-Ohrum et al., "Immunization with Low Doses of Recombinant Postfusion or Prefusion Respiratory Syncytial Virus F Primes for Vaccine-Enhanced Disease in the Cotton Rat Model Independently of the Presence of a Th1-Biasing (GLA-SE) or Th2-Biasing (Alum) Adjuvant," *J Virol. 91.8*: e02180-16, Apr. 2017.
Shingai et al., "Soluble G Protein of Respiratory Syncytial Virus Inhibits Toll-Like Receptor 3/4-Mediated IFN-beta Induction," *Internal Immunol. 20.9*: 1169-1180, Jul. 2008.
Tang et al., "Effects of Human Metapneumovirus and Respiratory Syncytial Virus Antigen Insertion in Two 3' Proximal Genome Positions of Bovine/Human Parainfluenza Virus Type 3 on Virus Replication and Immunogenicity," *J Virol. 77.20*: 10819-10828, Oct. 2003.
Tao et al., "A Live Attenuated Recombinant Chimeric Parainfluenza Virus (PIV) Candidate Vaccine Containing the Hemagglutinin-Neuraminidase and Fusion Glycoproteins of PIV1 and the Remaining Proteins from PIV3 Induces Resistance to PIV1 Even in Animals Immune to PIV3," *Vaccine 18.14*: 1359-1366, Jan. 2000.
Teng et al., "Contribution of the Respiratory Syncytial Virus G Glycoprotein and Its Secreted and Membrane-Bound Forms to Virus Replication In Vitro and In Vivo," *Virology 289.2*: 283-296, Oct. 2001.

(56) References Cited

OTHER PUBLICATIONS

Trento, et al., "Major Changes in the G Protein of Human Respiratory Syncytial Virus Isolates Introduced by a Duplication of 60 Nucleotides," *J Gen Virol. 84.11*: 3115-3120, Nov. 2003.
Tripp et al., "CX3C Chemokine Mimicry by Respiratory Syncytial Virus G Glycoprotein," *Nature Immunol. 2.8*: 732-738, Aug. 2001.
Yang et al., "Implication of Respiratory Syncytial Virus (RSV) F Transgene Sequence Heterogeneity Observed in Phase 1 Evaluation of MEDI-534, a Live Attenuated Parainfluenza Type 3 Vectored RSV Vaccine," *Vaccine 31.26*: 2822-2827, Jun. 2013.
Zhang et al., "Respiratory Syncytial Virus Infection of Human Airway Epithelial Cells is Polarized, Specific to Ciliated Cells, and Without Obvious Cytopathology," *J Virol. 76.11*: 5654-5666, Jun. 2002.
Zhang et al., "Infection of Ciliated Cells by Human Parainfluenza Virus Type 3 in an In Vitro Model of Human Airway Epithelium," *J Virol. 79.2*: 1113-1124, Jan. 2005.
Zhivaki et al., "Respiratory Syncytial Virus Infects Regulatory B Cells in Human Neonates via Chemokine Receptor CX3CR1 and Promotes Lung Disease Severity," *Immunity 46.2*: 301-314, Feb. 2017.

* cited by examiner

FIG. 1C

| | 182 | 183 | 184 | 185 | 186 | |
|---|---|---|---|---|---|---|
| | **C** | W | A | I | **C** | |
| Unmodified CX3C | TGC | TGG | GCT | ATC | TGC | |
| | **C** | W | A | I | R | |
| dCX3C | TGC | TGG | GCT | ATC | <u>C</u>GC | |
| | **C** | W | A | I | A | **C** |
| wCX4C | TGC | TGG | GCT | ATC | <u>GCA</u> | TGC |

Goat anti-RSV (ab20531) + MS456

131-2G + MS456 wt RSV wt RSV rB/HPIV3-wt G rB/HPIV3-sG rB/HPIV3-G_B3CT rB/HPIV3-G_B3TMCT rB/HPIV3-Empty vector RSV A2 neutralizing, without complement 1. rB/HPIV3
2. wtG
3. sG
4. mG
5. G_B3CT
6. G_B3TMCT
7. G_dCX3C
8. G_wCX4C
9. G_dCX3C_B3CT
10. G_dCX3C_B3TMCT
11. wt RSV
RSVF $Log_2 (PRNT_{60})$ wt RSV replication in NT wt RSV replication in Lungs Protection against wt RSV A2 challenge

SEQUENCE LISTING

```
<160> NUMBER OF SEQ ID NOS: 95

<210> SEQ ID NO 1
<211> LENGTH: 515
<212> TYPE: PRT
<213> ORGANISM: bovine parainfluenza virus 3

<400> SEQUENCE: 1

Met Leu Ser Leu Phe Asp Thr Phe Ser Ala Arg Arg Gln Glu Asn Ile
1               5                   10                  15

Thr Lys Ser Ala Gly Gly Ala Val Ile Pro Gly Gln Lys Asn Thr Val
            20                  25                  30

Ser Ile Phe Ala Leu Gly Pro Ser Ile Thr Asp Asp Asn Asp Lys Met
        35                  40                  45

Thr Leu Ala Leu Leu Phe Leu Ser His Ser Leu Asp Asn Glu Lys Gln
    50                  55                  60

His Ala Gln Arg Ala Gly Phe Leu Val Ser Leu Leu Ser Met Ala Tyr
65                  70                  75                  80

Ala Asn Pro Glu Leu Tyr Leu Thr Ser Asn Gly Ser Asn Ala Asp Val
                85                  90                  95

Lys Tyr Val Ile Tyr Met Ile Glu Lys Asp Pro Gly Arg Gln Lys Tyr
            100                 105                 110

Gly Gly Phe Val Val Lys Thr Arg Glu Met Val Tyr Glu Lys Thr Thr
        115                 120                 125

Asp Trp Met Phe Gly Ser Asp Leu Glu Tyr Asp Gln Asp Asn Met Leu
    130                 135                 140

Gln Asn Gly Arg Ser Thr Ser Thr Ile Glu Asp Leu Val His Thr Phe
145                 150                 155                 160

Gly Tyr Pro Ser Cys Leu Gly Ala Leu Ile Ile Gln Val Trp Ile Ile
                165                 170                 175

Leu Val Lys Ala Ile Thr Ser Ile Ser Gly Leu Arg Lys Gly Phe Phe
            180                 185                 190

Thr Arg Leu Glu Ala Phe Arg Gln Asp Gly Thr Val Lys Ser Ser Leu
        195                 200                 205

Val Leu Ser Gly Asp Ala Val Glu Gln Ile Gly Ser Ile Met Arg Ser
    210                 215                 220

Gln Gln Ser Leu Val Thr Leu Met Val Glu Thr Leu Ile Thr Met Asn
225                 230                 235                 240

Thr Gly Arg Asn Asp Leu Thr Thr Ile Glu Lys Asn Ile Gln Ile Val
                245                 250                 255

Gly Asn Tyr Ile Arg Asp Ala Gly Leu Ala Ser Phe Phe Asn Thr Ile
            260                 265                 270

Arg Tyr Gly Ile Glu Thr Arg Met Ala Ala Leu Thr Leu Ser Thr Leu
        275                 280                 285

Arg Pro Asp Ile Asn Arg Leu Lys Ala Leu Ile Glu Leu Tyr Leu Ser
    290                 295                 300

Lys Gly Pro Arg Ala Pro Phe Ile Cys Ile Leu Arg Asp Pro Val His
305                 310                 315                 320

Gly Glu Phe Ala Pro Gly Asn Tyr Pro Ala Leu Trp Ser Tyr Ala Met
                325                 330                 335
```

Gly Val Ala Val Val Gln Asn Lys Ala Met Gln Gln Tyr Val Thr Gly
340 345 350

Arg Ser Tyr Leu Asp Ile Glu Met Phe Gln Leu Gly Gln Ala Val Ala
355 360 365

Arg Asp Ala Glu Ser Gln Met Ser Ser Ile Leu Glu Asp Glu Leu Gly
370 375 380

Val Thr Gln Glu Ala Lys Gln Ser Leu Lys Lys His Met Lys Asn Ile
385 390 395 400

Ser Ser Ser Asp Thr Thr Phe His Lys Pro Thr Gly Gly Ser Ala Ile
405 410 415

Glu Met Ala Ile Asp Glu Glu Ala Gly Gln Pro Glu Ser Arg Gly Asp
420 425 430

Gln Asp Gln Gly Asp Glu Pro Arg Ser Ser Ile Val Pro Tyr Ala Trp
435 440 445

Ala Asp Glu Thr Gly Asn Asp Asn Gln Thr Glu Ser Thr Thr Glu Ile
450 455 460

Asp Ser Ile Lys Thr Glu Gln Arg Asn Ile Arg Asp Arg Leu Asn Lys
465 470 475 480

Arg Leu Asn Glu Lys Arg Lys Gln Ser Asp Pro Arg Ser Thr Asp Ile
485 490 495

Thr Asn Asn Thr Asn Gln Thr Glu Ile Asp Asp Leu Phe Ser Ala Phe
500 505 510

Gly Ser Asn
515

<210> SEQ ID NO 2
<211> LENGTH: 596
<212> TYPE: PRT
<213> ORGANISM: bovine parainfluenza virus 3

<400> SEQUENCE: 2

Met Glu Asp Asn Val Gln Asn Asn Gln Ile Met Asp Ser Trp Glu Glu
1 5 10 15

Gly Ser Gly Asp Lys Ser Ser Asp Ile Ser Ser Ala Leu Asp Ile Ile
20 25 30

Glu Phe Ile Leu Ser Thr Asp Ser Gln Glu Asn Thr Ala Asp Ser Asn
35 40 45

Glu Ile Asn Thr Gly Thr Thr Arg Leu Ser Thr Thr Ile Tyr Gln Pro
50 55 60

Glu Ser Lys Thr Thr Glu Thr Ser Lys Glu Asn Ser Gly Pro Ala Asn
65 70 75 80

Lys Asn Arg Gln Phe Gly Ala Ser His Glu Arg Ala Thr Glu Thr Lys
85 90 95

Asp Arg Asn Val Asn Gln Glu Thr Val Gln Gly Gly Tyr Arg Arg Gly
100 105 110

Ser Ser Pro Asp Ser Arg Thr Glu Thr Met Val Thr Arg Arg Ile Ser
115 120 125

Arg Ser Ser Pro Asp Pro Asn Asn Gly Thr Gln Ile Gln Glu Asp Ile
130 135 140

Asp Tyr Asn Glu Val Gly Glu Met Asp Lys Asp Ser Thr Lys Arg Glu
145 150 155 160

Met Arg Gln Phe Lys Asp Val Pro Val Lys Val Ser Gly Ser Asp Ala
165 170 175

Ile Pro Pro Thr Lys Gln Asp Gly Asp Gly Asp Asp Gly Arg Gly Leu

```
            180                 185                 190

Glu Ser Ile Ser Thr Phe Asp Ser Gly Tyr Thr Ser Ile Val Thr Ala
        195                 200                 205

Ala Thr Leu Asp Asp Glu Glu Glu Leu Leu Met Lys Asn Asn Arg Pro
    210                 215                 220

Arg Lys Tyr Gln Ser Thr Pro Gln Asn Ser Asp Lys Gly Ile Lys Lys
225                 230                 235                 240

Gly Val Gly Arg Pro Lys Asp Thr Asp Lys Gln Ser Ser Ile Leu Asp
                245                 250                 255

Tyr Glu Leu Asn Phe Lys Gly Ser Lys Lys Ser Gln Lys Ile Leu Lys
            260                 265                 270

Ala Ser Thr Asn Thr Gly Glu Pro Thr Arg Pro Gln Asn Gly Ser Gln
        275                 280                 285

Gly Lys Arg Ile Thr Ser Trp Asn Ile Leu Asn Ser Glu Ser Gly Asn
    290                 295                 300

Arg Thr Glu Ser Thr Asn Gln Thr His Gln Thr Ser Thr Ser Gly Gln
305                 310                 315                 320

Asn His Thr Met Gly Pro Ser Arg Thr Thr Ser Glu Pro Arg Ile Lys
                325                 330                 335

Thr Gln Lys Thr Asp Gly Lys Glu Arg Glu Asp Thr Glu Glu Ser Thr
            340                 345                 350

Arg Phe Thr Glu Arg Ala Ile Thr Leu Leu Gln Asn Leu Gly Val Ile
        355                 360                 365

Gln Ser Ala Ala Lys Leu Asp Leu Tyr Gln Asp Lys Arg Val Val Cys
    370                 375                 380

Val Ala Asn Val Leu Asn Asn Ala Asp Thr Ala Ser Lys Ile Asp Phe
385                 390                 395                 400

Leu Ala Gly Leu Met Ile Gly Val Ser Met Asp His Asp Thr Lys Leu
                405                 410                 415

Asn Gln Ile Gln Asn Glu Ile Leu Ser Leu Lys Thr Asp Leu Lys Lys
            420                 425                 430

Met Asp Glu Ser His Arg Arg Leu Ile Glu Asn Gln Lys Glu Gln Leu
        435                 440                 445

Ser Leu Ile Thr Ser Leu Ile Ser Asn Leu Lys Ile Met Thr Glu Arg
    450                 455                 460

Gly Gly Lys Lys Asp Gln Pro Glu Pro Ser Gly Arg Thr Ser Met Ile
465                 470                 475                 480

Lys Thr Lys Ala Lys Glu Glu Lys Ile Lys Lys Val Arg Phe Asp Pro
                485                 490                 495

Leu Met Glu Thr Gln Gly Ile Glu Lys Asn Ile Pro Asp Leu Tyr Arg
            500                 505                 510

Ser Ile Glu Lys Thr Pro Glu Asn Asp Thr Gln Ile Lys Ser Glu Ile
        515                 520                 525

Asn Arg Leu Asn Asp Glu Ser Asn Ala Thr Arg Leu Val Pro Arg Arg
    530                 535                 540

Ile Ser Ser Thr Met Arg Ser Leu Ile Ile Ile Ile Asn Asn Ser Asn
545                 550                 555                 560

Leu Ser Ser Lys Ala Lys Gln Ser Tyr Ile Asn Glu Leu Lys Leu Cys
                565                 570                 575

Lys Ser Asp Glu Glu Val Ser Glu Leu Met Asp Met Phe Asn Glu Asp
            580                 585                 590

Val Ser Ser Gln
        595
```

<210> SEQ ID NO 3
<211> LENGTH: 201
<212> TYPE: PRT
<213> ORGANISM: bovine parainfluenza virus 3

<400> SEQUENCE: 3

```
Met Phe Lys Thr Ile Lys Ser Trp Ile Leu Gly Lys Arg Asp Gln Glu
1               5                   10                  15

Ile Asn His Leu Thr Ser His Arg Pro Ser Thr Ser Leu Asn Ser Tyr
            20                  25                  30

Ser Ala Pro Thr Pro Lys Arg Thr Arg Gln Thr Ala Met Lys Ser Thr
        35                  40                  45

Gln Glu Pro Gln Asp Leu Ala Arg Gln Ser Thr Asn Leu Asn Pro Lys
    50                  55                  60

Gln Gln Lys Gln Ala Arg Lys Ile Val Asp Gln Leu Thr Lys Ile Asp
65                  70                  75                  80

Ser Leu Gly His His Thr Asn Val Pro Gln Arg Gln Lys Ile Glu Met
                85                  90                  95

Leu Ile Arg Arg Leu Tyr Arg Glu Asp Ile Gly Glu Glu Ala Ala Gln
            100                 105                 110

Ile Val Glu Leu Arg Leu Trp Ser Leu Glu Glu Ser Pro Glu Ala Ala
        115                 120                 125

Gln Ile Leu Thr Met Glu Pro Lys Ser Arg Lys Ile Leu Ile Thr Met
    130                 135                 140

Lys Leu Glu Arg Trp Ile Arg Thr Leu Leu Arg Gly Lys Cys Asp Asn
145                 150                 155                 160

Leu Lys Met Phe Gln Ser Arg Tyr Gln Glu Val Met Pro Phe Leu Gln
                165                 170                 175

Gln Asn Lys Met Glu Thr Val Met Met Glu Glu Ala Trp Asn Leu Ser
            180                 185                 190

Val His Leu Ile Gln Asp Ile Pro Val
        195                 200
```

<210> SEQ ID NO 4
<211> LENGTH: 412
<212> TYPE: PRT
<213> ORGANISM: bovine parainfluenza virus 3

<400> SEQUENCE: 4

```
Met Glu Asp Asn Val Gln Asn Asn Gln Ile Met Asp Ser Trp Glu Glu
1               5                   10                  15

Gly Ser Gly Asp Lys Ser Ser Asp Ile Ser Ser Ala Leu Asp Ile Ile
            20                  25                  30

Glu Phe Ile Leu Ser Thr Asp Ser Gln Glu Asn Thr Ala Asp Ser Asn
        35                  40                  45

Glu Ile Asn Thr Gly Thr Thr Arg Leu Ser Thr Thr Ile Tyr Gln Pro
    50                  55                  60

Glu Ser Lys Thr Thr Glu Thr Ser Lys Glu Asn Ser Gly Pro Ala Asn
65                  70                  75                  80

Lys Asn Arg Gln Phe Gly Ala Ser His Glu Arg Ala Thr Glu Thr Lys
                85                  90                  95

Asp Arg Asn Val Asn Gln Glu Thr Val Gln Gly Gly Tyr Arg Arg Gly
            100                 105                 110

Ser Ser Pro Asp Ser Arg Thr Glu Thr Met Val Thr Arg Arg Ile Ser
        115                 120                 125
```

Arg Ser Ser Pro Asp Pro Asn Asn Gly Thr Gln Ile Gln Glu Asp Ile
130 135 140

Asp Tyr Asn Glu Val Gly Glu Met Asp Lys Asp Ser Thr Lys Arg Glu
145 150 155 160

Met Arg Gln Phe Lys Asp Val Pro Val Lys Val Ser Gly Ser Asp Ala
165 170 175

Ile Pro Pro Thr Lys Gln Asp Gly Asp Gly Asp Asp Gly Arg Gly Leu
180 185 190

Glu Ser Ile Ser Thr Phe Asp Ser Gly Tyr Thr Ser Ile Val Thr Ala
195 200 205

Ala Thr Leu Asp Asp Glu Glu Glu Leu Leu Met Lys Asn Asn Arg Pro
210 215 220

Arg Lys Tyr Gln Ser Thr Pro Gln Asn Ser Asp Lys Gly Ile Lys Lys
225 230 235 240

Gly Gly Trp Lys Ala Lys Arg His Arg Gln Thr Ile Ile Asn Ile Gly
245 250 255

Leu Arg Thr Gln Leu Gln Arg Ile Glu Glu Glu Pro Glu Asn Pro Gln
260 265 270

Ser Gln His Glu Tyr Arg Arg Thr Asn Lys Thr Thr Glu Trp Ile Pro
275 280 285

Gly Glu Glu Asn His Ile Leu Glu His Pro Gln Gln Arg Glu Arg Gln
290 295 300

Ser Asn Arg Ile Asn Lys Pro Asn Pro Ser Asp Ile Asn Leu Gly Thr
305 310 315 320

Glu Pro His Asn Gly Thr Lys Gln Asn Asn Leu Arg Thr Lys Asp Gln
325 330 335

Asp Thr Lys Asp Gly Trp Lys Gly Lys Arg Gly His Arg Arg Glu His
340 345 350

Ser Ile Tyr Arg Lys Gly Asp Tyr Ile Ile Thr Glu Ser Trp Cys Asn
355 360 365

Pro Ile Cys Ser Lys Ile Arg Pro Ile Pro Arg Gln Glu Ser Cys Val
370 375 380

Cys Gly Glu Cys Pro Lys Gln Cys Arg Tyr Cys Ile Lys Asp Arg Leu
385 390 395 400

Pro Ser Arg Phe Asp Asp Arg Ser Val Asn Gly Ser
405 410

<210> SEQ ID NO 5
<211> LENGTH: 351
<212> TYPE: PRT
<213> ORGANISM: bovine parainfluenza virus 3

<400> SEQUENCE: 5

Met Ser Ile Thr Asn Ser Thr Ile Tyr Thr Phe Pro Glu Ser Ser Phe
1 5 10 15

Ser Glu Asn Gly Asn Ile Glu Pro Leu Pro Leu Lys Val Asn Glu Gln
20 25 30

Arg Lys Ala Ile Pro His Ile Arg Val Val Lys Ile Gly Asp Pro Pro
35 40 45

Lys His Gly Ser Arg Tyr Leu Asp Val Phe Leu Leu Gly Phe Phe Glu
50 55 60

Met Glu Arg Ser Lys Asp Arg Tyr Gly Ser Ile Ser Asp Leu Asp Asp
65 70 75 80

Asp Pro Ser Tyr Lys Val Cys Gly Ser Gly Ser Leu Pro Leu Gly Leu 85 90 95

Ala Arg Tyr Thr Gly Asn Asp Gln Glu Leu Leu Gln Ala Ala Thr Lys
100 105 110

Leu Asp Ile Glu Val Arg Arg Thr Val Lys Ala Thr Glu Met Ile Val
115 120 125

Tyr Thr Val Gln Asn Ile Lys Pro Glu Leu Tyr Pro Trp Ser Ser Arg
130 135 140

Leu Arg Lys Gly Met Leu Phe Asp Ala Asn Lys Val Ala Leu Ala Pro
145 150 155 160

Gln Cys Leu Pro Leu Asp Arg Gly Ile Lys Phe Arg Val Ile Phe Val
165 170 175

Asn Cys Thr Ala Ile Gly Ser Ile Thr Leu Phe Lys Ile Pro Lys Ser
180 185 190

Met Ala Leu Leu Ser Leu Pro Asn Thr Ile Ser Ile Asn Leu Gln Val
195 200 205

His Ile Lys Thr Gly Val Gln Thr Asp Ser Lys Gly Val Val Gln Ile
210 215 220

Leu Asp Glu Lys Gly Glu Lys Ser Leu Asn Phe Met Val His Leu Gly
225 230 235 240

Leu Ile Lys Arg Lys Met Gly Arg Met Tyr Ser Val Glu Tyr Cys Lys
245 250 255

Gln Lys Ile Glu Lys Met Arg Leu Leu Phe Ser Leu Gly Leu Val Gly
260 265 270

Gly Ile Ser Phe His Val Asn Ala Thr Gly Ser Ile Ser Lys Thr Leu
275 280 285

Ala Ser Gln Leu Ala Phe Lys Arg Glu Ile Cys Tyr Pro Leu Met Asp
290 295 300

Leu Asn Pro His Leu Asn Ser Val Ile Trp Ala Ser Ser Val Glu Ile
305 310 315 320

Thr Arg Val Asp Ala Val Leu Gln Pro Ser Leu Pro Gly Glu Phe Arg
325 330 335

Tyr Tyr Pro Asn Ile Ile Ala Lys Gly Val Gly Lys Ile Arg Gln
340 345 350

<210> SEQ ID NO 6
<211> LENGTH: 539
<212> TYPE: PRT
<213> ORGANISM: human parainfluenza virus 3

<400> SEQUENCE: 6

Met Pro Thr Ser Ile Leu Leu Ile Ile Thr Thr Met Ile Met Ala Ser
1 5 10 15

Phe Cys Gln Ile Asp Ile Thr Lys Leu Gln His Val Gly Val Leu Val
20 25 30

Asn Ser Pro Lys Gly Met Lys Ile Ser Gln Asn Phe Glu Thr Arg Tyr
35 40 45

Leu Ile Leu Ser Leu Ile Pro Lys Ile Glu Asp Ser Asn Ser Cys Gly
50 55 60

Asp Gln Gln Ile Lys Gln Tyr Lys Lys Leu Leu Asp Arg Leu Ile Ile
65 70 75 80

Pro Leu Tyr Asp Gly Leu Arg Leu Gln Lys Asp Val Ile Val Thr Asn
85 90 95

Gln Glu Ser Asn Glu Asn Thr Asp Pro Arg Thr Lys Arg Phe Phe Gly
100 105 110

-continued

```
Gly Val Ile Gly Thr Ile Ala Leu Gly Val Ala Thr Ser Ala Gln Ile
        115                 120                 125

Thr Ala Ala Val Ala Leu Val Glu Ala Lys Gln Ala Arg Ser Asp Ile
    130                 135                 140

Glu Lys Leu Lys Glu Ala Ile Arg Asp Thr Asn Lys Ala Val Gln Ser
145                 150                 155                 160

Val Gln Ser Ser Ile Gly Asn Leu Ile Val Ala Ile Lys Ser Val Gln
                165                 170                 175

Asp Tyr Val Asn Lys Glu Ile Val Pro Ser Ile Ala Arg Leu Gly Cys
            180                 185                 190

Glu Ala Ala Gly Leu Gln Leu Gly Ile Ala Leu Thr Gln His Tyr Ser
        195                 200                 205

Glu Leu Thr Asn Ile Phe Gly Asp Asn Ile Gly Ser Leu Gln Glu Lys
    210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
            260                 265                 270

Asp Tyr Ser Ile Thr Leu Gln Val Arg Leu Pro Leu Leu Thr Arg Leu
        275                 280                 285

Leu Asn Thr Gln Ile Tyr Lys Val Asp Ser Ile Ser Tyr Asn Ile Gln
    290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Ile
            340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
    370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Ser Thr Ile Gly Ile Asn Gly Met Leu Phe Asn Thr Asn Lys Glu
            420                 425                 430

Gly Thr Leu Ala Phe Tyr Thr Pro Asn Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Asn Trp His Gln Ser Ser Thr Thr Ile Ile Ile
                485                 490                 495

Ile Leu Ile Met Ile Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
```

-continued 530 535

<210> SEQ ID NO 7
<211> LENGTH: 572
<212> TYPE: PRT
<213> ORGANISM: human parainfluenza virus 3

<400> SEQUENCE: 7

Met Glu Tyr Trp Lys His Thr Asn His Gly Lys Asp Ala Gly Asn Glu
1 5 10 15

Leu Glu Thr Ser Met Ala Thr His Gly Asn Lys Leu Thr Asn Lys Ile
20 25 30

Ile Tyr Ile Leu Trp Thr Ile Ile Leu Val Leu Leu Ser Ile Val Phe
35 40 45

Ile Ile Val Leu Ile Asn Ser Ile Lys Ser Glu Lys Ala His Glu Ser
50 55 60

Leu Leu Gln Asp Ile Asn Asn Glu Phe Met Glu Ile Thr Glu Lys Ile
65 70 75 80

Gln Met Ala Ser Asp Asn Thr Asn Asp Leu Ile Gln Ser Gly Val Asn
85 90 95

Thr Arg Leu Leu Thr Ile Gln Ser His Val Gln Asn Tyr Ile Pro Ile
100 105 110

Ser Leu Thr Gln Gln Met Ser Asp Leu Arg Lys Phe Ile Ser Glu Ile
115 120 125

Thr Ile Arg Asn Asp Asn Gln Glu Val Leu Pro Gln Arg Ile Thr His
130 135 140

Asp Val Gly Ile Lys Pro Leu Asn Pro Asp Asp Phe Trp Arg Cys Thr
145 150 155 160

Ser Gly Leu Pro Ser Leu Met Lys Thr Pro Lys Ile Arg Leu Met Pro
165 170 175

Gly Pro Gly Leu Leu Ala Met Pro Thr Thr Val Asp Gly Cys Val Arg
180 185 190

Thr Pro Ser Leu Val Ile Asn Asp Leu Ile Tyr Ala Tyr Thr Ser Asn
195 200 205

Leu Ile Thr Arg Gly Cys Gln Asp Ile Gly Lys Ser Tyr Gln Val Leu
210 215 220

Gln Ile Gly Ile Ile Thr Val Asn Ser Asp Leu Val Pro Asp Leu Asn
225 230 235 240

Pro Arg Ile Ser His Thr Phe Asn Ile Asn Asp Asn Arg Lys Ser Cys
245 250 255

Ser Leu Ala Leu Leu Asn Thr Asp Val Tyr Gln Leu Cys Ser Thr Pro
260 265 270

Lys Val Asp Glu Arg Ser Asp Tyr Ala Ser Ser Gly Ile Glu Asp Ile
275 280 285

Val Leu Asp Ile Val Asn Tyr Asp Gly Ser Ile Ser Thr Thr Arg Phe
290 295 300

Lys Asn Asn Asn Ile Ser Phe Asp Gln Pro Tyr Ala Ala Leu Tyr Pro
305 310 315 320

Ser Val Gly Pro Gly Ile Tyr Tyr Lys Gly Lys Ile Ile Phe Leu Gly
325 330 335

Tyr Gly Gly Leu Glu His Pro Ile Asn Glu Asn Val Ile Cys Asn Thr
340 345 350

Thr Gly Cys Pro Gly Lys Thr Gln Arg Asp Cys Asn Gln Ala Ser His
355 360 365

```
Ser Pro Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Leu Asn Arg Thr Leu Ser Ala
        515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570


<210> SEQ ID NO 8
<211> LENGTH: 572
<212> TYPE: PRT
<213> ORGANISM: human parainfluenza virus 3

<400> SEQUENCE: 8

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175
```

```
Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Ile Asp Val Tyr Gln Leu Cys Ser Thr Pro
            260                 265                 270

Lys Val Asp Glu Arg Ser Asp Tyr Ala Ser Ser Gly Ile Glu Asp Ile
        275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
        355                 360                 365

Ser Thr Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Leu Asn Arg Thr Leu Ser Ala
        515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570
```

<210> SEQ ID NO 9
<211> LENGTH: 1719

<212> TYPE: DNA
<213> ORGANISM: human parainfluenza virus 3

<400> SEQUENCE: 9
atggaatact ggaagcatac caatcacgga aaggatgctg gtaatgagct ggagacgtct 60
atggctactc atggcaacaa gctcactaat aagataatat acatattatg gacaataatc 120
ctggtgttat tatcaatagt cttcatcata gtgctaatta attccatcaa aagtgaaaag 180
gcccacgaat cattgctgca agacataaat aatgagttta tggaaattac agaaaagatc 240
caaatggcat cggataatac caatgatcta atacagtcag gagtgaatac aaggcttctt 300
acaattcaga gtcatgtcca gaattacata ccaatatcat tgacacaaca gatgtcagat 360
cttaggaaat tcattagtga aattacaatt agaaatgata atcaagaagt gctgccacaa 420
agaataacac atgatgtagg tataaaacct ttaaatccag atgatttttg gagatgcacg 480
tctggtcttc catctttaat gaaaactcca aaaataaggt taatgccagg gccgggatta 540
ttagctatgc caacgactgt tgatggctgt gttagaactc cgtctttagt tataaatgat 600
ctgatttatg cttatacctc aaatctaatt actcgaggtt gtcaggatat aggaaaatca 660
tatcaagtct tacagatagg gataataact gtaaactcag acttggtacc tgacttaaat 720
cctaggatct ctcatacctt taacataaat gacaatagga agtcatgttc tctagcactc 780
ctaaatatag atgtatatca actgtgttca actcccaaag ttgatgaaag atcagattat 840
gcatcatcag gcatagaaga tattgtactt gatattgtca attatgatgg ttcaatctca 900
acaacaagat ttaagaataa taacataagc tttgatcaac catatgctgc actataccca 960
tctgttggac cagggatata ctacaaaggc aaaataatat ttctcgggta tggaggtctt 1020
gaacatccaa taaatgagaa tgtaatctgc aacacaactg ggtgccccgg gaaaacacag 1080
agagactgta atcaagcatc tcatagtact tggttttcag ataggaggat ggtcaactcc 1140
atcattgttg ttgacaaagg cttaaactca attccaaaat tgaaagtatg gacgatatct 1200
atgcgacaaa attactgggg gtcagaagga aggttacttc tactaggtaa caagatctat 1260
atatatacaa gatctacaag ttggcatagc aagttacaat taggaataat tgatattact 1320
gattacagtg atataaggat aaaatggaca tggcataatg tgctatcaag accaggaaac 1380
aatgaatgtc catggggaca ttcatgtcca gatggatgta taacaggagt atatactgat 1440
gcatatccac tcaatcccac agggagcatt gtgtcatctg tcatattaga ctcacaaaaa 1500
tcgagagtga acccagtcat aacttactca acagcaaccg aaagagtaaa cgagctggcc 1560
atcctaaaca gaacactctc agctggatat acaacaacaa gctgcattac acactataac 1620
aaaggatatt gttttcatat agtagaaata aatcataaaa gcttaaacac atttcaaccc 1680
atgttgttca aaacagagat tccaaaaagc tgcagttaa 1719

<210> SEQ ID NO 10
<211> LENGTH: 2233
<212> TYPE: PRT
<213> ORGANISM: bovine parainfluenza virus 3

<400> SEQUENCE: 10

Met Asp Thr Glu Ser His Ser Gly Thr Thr Ser Asp Ile Leu Tyr Pro
1 5 10 15

Glu Cys His Leu Asn Ser Pro Ile Val Lys Gly Lys Ile Ala Gln Leu
20 25 30

His Thr Ile Met Ser Leu Pro Gln Pro Tyr Asp Met Asp Asp Asp Ser
35 40 45

-continued

```
Ile Leu Ile Ile Thr Arg Gln Lys Ile Lys Leu Asn Lys Leu Asp Lys
    50                  55                  60

Arg Gln Arg Ser Ile Arg Lys Leu Arg Ser Val Leu Met Glu Arg Val
65                  70                  75                  80

Ser Asp Leu Gly Lys Tyr Thr Phe Ile Arg Tyr Pro Glu Met Ser Ser
                85                  90                  95

Glu Met Phe Gln Leu Cys Ile Pro Gly Ile Asn Asn Lys Ile Asn Glu
            100                 105                 110

Leu Leu Ser Lys Ala Ser Lys Thr Tyr Asn Gln Met Thr Asp Gly Leu
        115                 120                 125

Arg Asp Leu Trp Val Thr Ile Leu Ser Lys Leu Ala Ser Lys Asn Asp
    130                 135                 140

Gly Ser Asn Tyr Asp Ile Asn Glu Asp Ile Ser Asn Ile Ser Asn Val
145                 150                 155                 160

His Met Thr Tyr Gln Ser Asp Lys Trp Tyr Asn Pro Phe Lys Thr Trp
                165                 170                 175

Phe Thr Ile Lys Tyr Asp Met Arg Arg Leu Gln Lys Ala Lys Asn Glu
            180                 185                 190

Ile Thr Phe Asn Arg His Lys Asp Tyr Asn Leu Leu Glu Asp Gln Lys
        195                 200                 205

Asn Ile Leu Leu Ile His Pro Glu Leu Val Leu Ile Leu Asp Lys Gln
    210                 215                 220

Asn Tyr Asn Gly Tyr Ile Met Thr Pro Glu Leu Val Leu Met Tyr Cys
225                 230                 235                 240

Asp Val Val Glu Gly Arg Trp Asn Ile Ser Ser Cys Ala Lys Leu Asp
                245                 250                 255

Pro Lys Leu Gln Ser Met Tyr Tyr Lys Gly Asn Asn Leu Trp Glu Ile
            260                 265                 270

Ile Asp Gly Leu Phe Ser Thr Leu Gly Glu Arg Thr Phe Asp Ile Ile
        275                 280                 285

Ser Leu Leu Glu Pro Leu Ala Leu Ser Leu Ile Gln Thr Tyr Asp Pro
    290                 295                 300

Val Lys Gln Leu Arg Gly Ala Phe Leu Asn His Val Leu Ser Glu Met
305                 310                 315                 320

Glu Leu Ile Phe Ala Ala Glu Cys Thr Thr Glu Glu Ile Pro Asn Val
                325                 330                 335

Asp Tyr Ile Asp Lys Ile Leu Asp Val Phe Lys Glu Ser Thr Ile Asp
            340                 345                 350

Glu Ile Ala Glu Ile Phe Ser Phe Phe Arg Thr Phe Gly His Pro Pro
        355                 360                 365

Leu Glu Ala Ser Ile Ala Ala Glu Lys Val Arg Lys Tyr Met Tyr Thr
    370                 375                 380

Glu Lys Cys Leu Lys Phe Asp Thr Ile Asn Lys Cys His Ala Ile Phe
385                 390                 395                 400

Cys Thr Ile Ile Ile Asn Gly Tyr Arg Glu Arg His Gly Gly Gln Trp
                405                 410                 415

Pro Pro Val Thr Leu Pro Val His Ala His Glu Phe Ile Ile Asn Ala
            420                 425                 430

Tyr Gly Ser Asn Ser Ala Ile Ser Tyr Glu Asn Ala Val Asp Tyr Tyr
        435                 440                 445

Lys Ser Phe Ile Gly Ile Lys Phe Asp Lys Phe Ile Glu Pro Gln Leu
    450                 455                 460
```

-continued

```
Asp Glu Asp Leu Thr Ile Tyr Met Lys Asp Lys Ala Leu Ser Pro Lys
465                 470                 475                 480

Lys Ser Asn Trp Asp Thr Val Tyr Pro Ala Ser Asn Leu Leu Tyr Arg
                485                 490                 495

Thr Asn Val Ser His Asp Ser Arg Arg Leu Val Glu Val Phe Ile Ala
            500                 505                 510

Asp Ser Lys Phe Asp Pro His Gln Val Leu Asp Tyr Val Glu Ser Gly
        515                 520                 525

Tyr Trp Leu Asp Asp Pro Glu Phe Asn Ile Ser Tyr Ser Leu Lys Glu
    530                 535                 540

Lys Glu Ile Lys Gln Glu Gly Arg Leu Phe Ala Lys Met Thr Tyr Lys
545                 550                 555                 560

Met Arg Ala Thr Gln Val Leu Ser Glu Thr Leu Leu Ala Asn Asn Ile
                565                 570                 575

Gly Lys Phe Phe Gln Glu Asn Gly Met Val Lys Gly Glu Ile Glu Leu
            580                 585                 590

Leu Lys Arg Leu Thr Thr Ile Ser Met Ser Gly Val Pro Arg Tyr Asn
        595                 600                 605

Glu Val Tyr Asn Asn Ser Lys Ser His Thr Glu Glu Leu Gln Ala Tyr
    610                 615                 620

Asn Ala Ile Ser Ser Ser Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
            660                 665                 670

Tyr Glu Ser Thr Ala Leu Phe Gly Asp Thr Cys Asn Gln Ile Phe Gly
        675                 680                 685

Leu Lys Glu Leu Phe Asn Trp Leu His Pro Arg Leu Glu Lys Ser Thr
    690                 695                 700

Ile Tyr Val Gly Asp Pro Tyr Cys Pro Pro Ser Asp Ile Glu His Leu
705                 710                 715                 720

Pro Leu Asp Asp His Pro Asp Ser Gly Phe Tyr Val His Asn Pro Lys
                725                 730                 735

Gly Gly Ile Glu Gly Phe Cys Gln Lys Leu Trp Thr Leu Ile Ser Ile
            740                 745                 750

Ser Ala Ile His Leu Ala Ala Val Lys Ile Gly Val Arg Val Thr Ala
        755                 760                 765

Met Val Gln Gly Asp Asn Gln Ala Ile Ala Val Thr Thr Arg Val Pro
    770                 775                 780

Asn Asn Tyr Asp Tyr Lys Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
            820                 825                 830

Ser Lys Arg Ile Tyr Tyr Asp Gly Arg Ile Leu Pro Gln Ala Leu Lys
        835                 840                 845

Ala Leu Ser Arg Cys Val Phe Trp Ser Glu Thr Ile Ile Asp Glu Thr
    850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Val Cys Ser Ile Phe Lys Asn
```

```
                885                 890                 895

Ile Gln Gln Leu Tyr Ile Ala Leu Gly Met Asn Ile Asn Pro Thr Ile
            900                 905                 910

Thr Gln Asn Ile Lys Asp Gln Tyr Phe Arg Asn Ile His Trp Met Gln
        915                 920                 925

Tyr Ala Ser Leu Ile Pro Ala Ser Val Gly Gly Phe Asn Tyr Met Ala
    930                 935                 940

Met Ser Arg Cys Phe Val Arg Asn Ile Gly Asp Pro Thr Val Ala Ala
945                 950                 955                 960

Leu Ala Asp Ile Lys Arg Phe Ile Lys Ala Asn Leu Leu Asp Arg Gly
                965                 970                 975

Val Leu Tyr Arg Ile Met Asn Gln Glu Pro Gly Glu Ser Ser Phe Leu
            980                 985                 990

Asp Trp Ala Ser Asp Pro Tyr Ser  Cys Asn Leu Pro Gln  Ser Gln Asn
        995                 1000                 1005

Ile Thr  Thr Met Ile Lys Asn  Ile Thr Ala Arg Asn  Val Leu Gln
    1010                 1015                 1020

Asp Ser  Pro Asn Pro Leu Leu  Ser Gly Leu Phe Thr  Ser Thr Met
    1025                 1030                 1035

Ile Glu  Glu Asp Glu Glu Leu  Ala Glu Phe Leu Met  Asp Arg Arg
    1040                 1045                 1050

Ile Ile  Leu Pro Arg Val Ala  His Asp Ile Leu Asp  Asn Ser Leu
    1055                 1060                 1065

Thr Gly  Ile Arg Asn Ala Ile  Ala Gly Met Leu Asp  Thr Thr Lys
    1070                 1075                 1080

Ser Leu  Ile Arg Val Gly Ile  Ser Arg Gly Gly Leu  Thr Tyr Asn
    1085                 1090                 1095

Leu Leu  Arg Lys Ile Ser Asn  Tyr Asp Leu Val Gln  Tyr Glu Thr
    1100                 1105                 1110

Leu Ser  Lys Thr Leu Arg Leu  Ile Val Ser Asp Lys  Ile Lys Tyr
    1115                 1120                 1125

Glu Asp  Met Cys Ser Val Asp  Leu Ala Ile Ser Leu  Arg Gln Lys
    1130                 1135                 1140

Met Trp  Met His Leu Ser Gly  Gly Arg Met Ile Asn  Gly Leu Glu
    1145                 1150                 1155

Thr Pro  Asp Pro Leu Glu Leu  Leu Ser Gly Val Ile  Ile Thr Gly
    1160                 1165                 1170

Ser Glu  His Cys Arg Ile Cys  Tyr Ser Thr Glu Gly  Glu Ser Pro
    1175                 1180                 1185

Tyr Thr  Trp Met Tyr Leu Pro  Gly Asn Leu Asn Ile  Gly Ser Ala
    1190                 1195                 1200

Glu Thr  Gly Ile Ala Ser Leu  Arg Val Pro Tyr Phe  Gly Ser Val
    1205                 1210                 1215

Thr Asp  Glu Arg Ser Glu Ala  Gln Leu Gly Tyr Ile  Lys Asn Leu
    1220                 1225                 1230

Ser Lys  Pro Ala Lys Ala Ala  Ile Arg Ile Ala Met  Ile Tyr Thr
    1235                 1240                 1245

Trp Ala  Phe Gly Asn Asp Glu  Ile Ser Trp Met Glu  Ala Ser Gln
    1250                 1255                 1260

Ile Ala  Gln Thr Arg Ala Asn  Phe Thr Leu Asp Ser  Leu Lys Ile
    1265                 1270                 1275

Leu Thr  Pro Val Thr Thr Ser  Thr Asn Leu Ser His  Arg Leu Lys
    1280                 1285                 1290
```

-continued

```
Asp Thr  Ala Thr Gln Met Lys  Phe Ser Ser Thr Ser  Leu Ile Arg
    1295                 1300                 1305

Val Ser  Arg Phe Ile Thr Ile  Ser Asn Asp Asn Met  Ser Ile Lys
    1310                 1315                 1320

Glu Ala  Asn Glu Thr Lys Asp  Thr Asn Leu Ile Tyr  Gln Gln Val
    1325                 1330                 1335

Met Leu  Thr Gly Leu Ser Val  Phe Glu Tyr Leu Phe  Arg Leu Glu
    1340                 1345                 1350

Glu Ser  Thr Gly His Asn Pro  Met Val Met His Leu  His Ile Glu
    1355                 1360                 1365

Asp Gly  Cys Cys Ile Lys Glu  Ser Tyr Asn Asp Glu  His Ile Asn
    1370                 1375                 1380

Pro Glu  Ser Thr Leu Glu Leu  Ile Lys Tyr Pro Glu  Ser Asn Glu
    1385                 1390                 1395

Phe Ile  Tyr Asp Lys Asp Pro  Leu Lys Asp Ile Asp  Leu Ser Lys
    1400                 1405                 1410

Leu Met  Val Ile Arg Asp His  Ser Tyr Thr Ile Asp  Met Asn Tyr
    1415                 1420                 1425

Trp Asp  Asp Thr Asp Ile Val  His Ala Ile Ser Ile  Cys Thr Ala
    1430                 1435                 1440

Val Thr  Ile Ala Asp Thr Met  Ser Gln Leu Asp Arg  Asp Asn Leu
    1445                 1450                 1455

Lys Glu  Leu Val Val Ile Ala  Asn Asp Asp Asp Ile  Asn Ser Leu
    1460                 1465                 1470

Ile Thr  Glu Phe Leu Thr Leu  Asp Ile Leu Val Phe  Leu Lys Thr
    1475                 1480                 1485

Phe Gly  Gly Leu Leu Val Asn  Gln Phe Ala Tyr Thr  Leu Tyr Gly
    1490                 1495                 1500

Leu Lys  Ile Glu Gly Arg Asp  Pro Ile Trp Asp Tyr  Ile Met Arg
    1505                 1510                 1515

Thr Leu  Lys Asp Thr Ser His  Ser Val Leu Lys Val  Leu Ser Asn
    1520                 1525                 1530

Ala Leu  Ser His Pro Lys Val  Phe Lys Arg Phe Trp  Asp Cys Gly
    1535                 1540                 1545

Val Leu  Asn Pro Ile Tyr Gly  Pro Asn Thr Ala Ser  Gln Asp Gln
    1550                 1555                 1560

Val Lys  Leu Ala Leu Ser Ile  Cys Glu Tyr Ser Leu  Asp Leu Phe
    1565                 1570                 1575

Met Arg  Glu Trp Leu Asn Gly  Ala Ser Leu Glu Ile  Tyr Ile Cys
    1580                 1585                 1590

Asp Ser  Asp Met Glu Ile Ala  Asn Asp Arg Arg Gln  Ala Phe Leu
    1595                 1600                 1605

Ser Arg  His Leu Ala Phe Val  Cys Cys Leu Ala Glu  Ile Ala Ser
    1610                 1615                 1620

Phe Gly  Pro Asn Leu Leu Asn  Leu Thr Tyr Leu Glu  Arg Leu Asp
    1625                 1630                 1635

Glu Leu  Lys Gln Tyr Leu Asp  Leu Asn Ile Lys Glu  Asp Pro Thr
    1640                 1645                 1650

Leu Lys  Tyr Val Gln Val Ser  Gly Leu Leu Ile Lys  Ser Phe Pro
    1655                 1660                 1665

Ser Thr  Val Thr Tyr Val Arg  Lys Thr Ala Ile Lys  Tyr Leu Arg
    1670                 1675                 1680
```

-continued

```
Ile Arg  Gly Ile Asn Pro Pro  Glu Thr Ile Glu Asp  Trp Asp Pro
    1685                 1690                 1695

Ile Glu  Asp Glu Asn Ile Leu  Asp Asn Ile Val Lys  Thr Val Asn
    1700                 1705                 1710

Asp Asn  Cys Ser Asp Asn Gln  Lys Arg Asn Lys Ser  Ser Tyr Phe
    1715                 1720                 1725

Trp Gly  Leu Ala Leu Lys Asn  Tyr Gln Val Val Lys  Ile Arg Ser
    1730                 1735                 1740

Ile Thr  Ser Asp Ser Glu Val  Asn Glu Ala Ser Asn  Val Thr Thr
    1745                 1750                 1755

His Gly  Met Thr Leu Pro Gln  Gly Gly Ser Tyr Leu  Ser His Gln
    1760                 1765                 1770

Leu Arg  Leu Phe Gly Val Asn  Ser Thr Ser Cys Leu  Lys Ala Leu
    1775                 1780                 1785

Glu Leu  Ser Gln Ile Leu Met  Arg Glu Val Lys Lys  Asp Lys Asp
    1790                 1795                 1800

Arg Leu  Phe Leu Gly Glu Gly  Ala Gly Ala Met Leu  Ala Cys Tyr
    1805                 1810                 1815

Asp Ala  Thr Leu Gly Pro Ala  Ile Asn Tyr Tyr Asn  Ser Gly Leu
    1820                 1825                 1830

Asn Ile  Thr Asp Val Ile Gly  Gln Arg Glu Leu Lys  Ile Phe Pro
    1835                 1840                 1845

Ser Glu  Val Ser Leu Val Gly  Lys Lys Leu Gly Asn  Val Thr Gln
    1850                 1855                 1860

Ile Leu  Asn Arg Val Arg Val  Leu Phe Asn Gly Asn  Pro Asn Ser
    1865                 1870                 1875

Thr Trp  Ile Gly Asn Met Glu  Cys Glu Ser Leu Ile  Trp Ser Glu
    1880                 1885                 1890

Leu Asn  Asp Lys Ser Ile Gly  Leu Val His Cys Asp  Met Glu Gly
    1895                 1900                 1905

Ala Ile  Gly Lys Ser Glu Glu  Thr Val Leu His Glu  His Tyr Ser
    1910                 1915                 1920

Ile Ile  Arg Ile Thr Tyr Leu  Ile Gly Asp Asp Asp  Val Val Leu
    1925                 1930                 1935

Val Ser  Lys Ile Ile Pro Thr  Ile Thr Pro Asn Trp  Ser Lys Ile
    1940                 1945                 1950

Leu Tyr  Leu Tyr Lys Leu Tyr  Trp Lys Asp Val Ser  Val Val Ser
    1955                 1960                 1965

Leu Lys  Thr Ser Asn Pro Ala  Ser Thr Glu Leu Tyr  Leu Ile Ser
    1970                 1975                 1980

Lys Asp  Ala Tyr Cys Thr Val  Met Glu Pro Ser Asn  Leu Val Leu
    1985                 1990                 1995

Ser Lys  Leu Lys Arg Ile Ser  Ser Ile Glu Glu Asn  Asn Leu Leu
    2000                 2005                 2010

Lys Trp  Ile Ile Leu Ser Lys  Arg Lys Asn Asn Glu  Trp Leu Gln
    2015                 2020                 2025

His Glu  Ile Lys Glu Gly Glu  Arg Asp Tyr Gly Ile  Met Arg Pro
    2030                 2035                 2040

Tyr His  Thr Ala Leu Gln Ile  Phe Gly Phe Gln Ile  Asn Leu Asn
    2045                 2050                 2055

His Leu  Ala Arg Glu Phe Leu  Ser Thr Pro Asp Leu  Thr Asn Ile
    2060                 2065                 2070

Asn Asn  Ile Ile Gln Ser Phe  Thr Arg Thr Ile Lys  Asp Val Met
```

```
    2075                2080                2085

Phe Glu  Trp Val Asn Ile Thr  His Asp Asn Lys Arg  His Lys Leu
    2090                2095                2100

Gly Gly  Arg Tyr Asn Leu Phe  Pro Leu Lys Asn Lys  Gly Lys Leu
    2105                2110                2115

Arg Leu  Leu Ser Arg Arg Leu  Val Leu Ser Trp Ile  Ser Leu Ser
    2120                2125                2130

Leu Ser  Thr Arg Leu Leu Thr  Gly Arg Phe Pro Asp  Glu Lys Phe
    2135                2140                2145

Glu Asn  Arg Ala Gln Thr Gly  Tyr Val Ser Leu Ala  Asp Ile Asp
    2150                2155                2160

Leu Glu  Ser Leu Lys Leu Leu  Ser Arg Asn Ile Val  Lys Asn Tyr
    2165                2170                2175

Lys Glu  His Ile Gly Leu Ile  Ser Tyr Trp Phe Leu  Thr Lys Glu
    2180                2185                2190

Val Lys  Ile Leu Met Lys Leu  Ile Gly Gly Val Lys  Leu Leu Gly
    2195                2200                2205

Ile Pro  Lys Gln Tyr Lys Glu  Leu Glu Asp Arg Ser  Ser Gln Gly
    2210                2215                2220

Tyr Glu  Tyr Asp Asn Glu Phe  Asp Ile Asp
    2225                2230
```

<210> SEQ ID NO 11
<211> LENGTH: 12
<212> TYPE: DNA
<213> ORGANISM: bovine parainfluenza virus 3

<400> SEQUENCE: 11
aggattaaag ac 12

<210> SEQ ID NO 12
<211> LENGTH: 10
<212> TYPE: DNA
<213> ORGANISM: bovine parainfluenza virus 3

<400> SEQUENCE: 12
aggattaaag 10

<210> SEQ ID NO 13
<211> LENGTH: 10
<212> TYPE: DNA
<213> ORGANISM: bovine parainfluenza virus 3

<400> SEQUENCE: 13
aggacaaaag 10

<210> SEQ ID NO 14
<211> LENGTH: 10
<212> TYPE: DNA
<213> ORGANISM: bovine parainfluenza virus 3

<400> SEQUENCE: 14
aggagtaaag 10

<210> SEQ ID NO 15
<211> LENGTH: 10
<212> TYPE: DNA
<213> ORGANISM: bovine parainfluenza virus 3

<400> SEQUENCE: 15
aggagcaaag 10

<210> SEQ ID NO 16
<211> LENGTH: 12
<212> TYPE: DNA
<213> ORGANISM: bovine parainfluenza virus 3

<400> SEQUENCE: 16
aaataagaaa aa 12

<210> SEQ ID NO 17
<211> LENGTH: 12
<212> TYPE: DNA
<213> ORGANISM: bovine parainfluenza virus 3

<400> SEQUENCE: 17
aaataagaaa aa 12

<210> SEQ ID NO 18
<211> LENGTH: 20
<212> TYPE: DNA
<213> ORGANISM: bovine parainfluenza virus 3

<400> SEQUENCE: 18
aaataaagga taatcaaaaa 20

<210> SEQ ID NO 19
<211> LENGTH: 12
<212> TYPE: DNA
<213> ORGANISM: bovine parainfluenza virus 3

<400> SEQUENCE: 19
aattataaaa aa 12

<210> SEQ ID NO 20
<211> LENGTH: 12
<212> TYPE: DNA
<213> ORGANISM: bovine parainfluenza virus 3

<400> SEQUENCE: 20
aaatataaaa aa 12

<210> SEQ ID NO 21
<211> LENGTH: 13
<212> TYPE: DNA
<213> ORGANISM: bovine parainfluenza virus 3

<400> SEQUENCE: 21
aaagtaagaa aaa 13

<210> SEQ ID NO 22
<211> LENGTH: 298
<212> TYPE: PRT
<213> ORGANISM: respiratory syncytial virus

<400> SEQUENCE: 22

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

```
Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295
```

<210> SEQ ID NO 23
<211> LENGTH: 233
<212> TYPE: PRT
<213> ORGANISM: respiratory syncytial virus

<400> SEQUENCE: 23

```
Asn His Lys Val Thr Pro Thr Thr Ala Ile Ile Gln Asp Ala Thr Ser
1               5                   10                  15

Gln Ile Lys Asn Thr Thr Pro Thr Tyr Leu Thr Gln Asn Pro Gln Leu
            20                  25                  30

Gly Ile Ser Pro Ser Asn Pro Ser Glu Ile Thr Ser Gln Ile Thr Thr
        35                  40                  45

Ile Leu Ala Ser Thr Thr Pro Gly Val Lys Ser Thr Leu Gln Ser Thr
    50                  55                  60

Thr Val Lys Thr Lys Asn Thr Thr Thr Thr Gln Thr Gln Pro Ser Lys
65                  70                  75                  80

Pro Thr Thr Lys Gln Arg Gln Asn Lys Pro Pro Ser Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
```

```
        115                 120                 125

Pro Gly Lys Lys Thr Thr Thr Lys Pro Thr Lys Lys Pro Thr Leu Lys
    130                 135                 140

Thr Thr Lys Lys Asp Pro Lys Pro Gln Thr Thr Lys Ser Lys Glu Val
145                 150                 155                 160

Pro Thr Thr Lys Pro Thr Glu Glu Pro Thr Ile Asn Thr Thr Lys Thr
                165                 170                 175

Asn Ile Ile Thr Thr Leu Leu Thr Ser Asn Thr Thr Gly Asn Pro Glu
            180                 185                 190

Leu Thr Ser Gln Met Glu Thr Phe His Ser Thr Ser Ser Glu Gly Asn
        195                 200                 205

Pro Ser Pro Ser Gln Val Ser Thr Thr Ser Glu Tyr Pro Ser Gln Pro
    210                 215                 220

Ser Ser Pro Pro Asn Thr Pro Arg Gln
225                 230


<210> SEQ ID NO 24
<211> LENGTH: 37
<212> TYPE: PRT
<213> ORGANISM: respiratory syncytial virus

<400> SEQUENCE: 24

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser
        35


<210> SEQ ID NO 25
<211> LENGTH: 28
<212> TYPE: PRT
<213> ORGANISM: respiratory syncytial virus

<400> SEQUENCE: 25

Val Ala Gln Ile Thr Leu Ser Ile Leu Ala Met Ile Ile Ser Thr Ser
1               5                   10                  15

Leu Ile Ile Ala Ala Ile Ile Phe Ile Ala Ser Ala
            20                  25


<210> SEQ ID NO 26
<211> LENGTH: 65
<212> TYPE: PRT
<213> ORGANISM: respiratory syncytial virus

<400> SEQUENCE: 26

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala
65


<210> SEQ ID NO 27
```

<211> LENGTH: 30
<212> TYPE: PRT
<213> ORGANISM: bovine parainfluenza virus 3

<400> SEQUENCE: 27

Met Glu Tyr Trp Lys His Thr Asn Ser Ile Asn Asn Thr Asn Asn Glu
1 5 10 15

Thr Glu Thr Ala Arg Gly Lys His Ser Ser Lys Val Thr Asn
20 25 30

<210> SEQ ID NO 28
<211> LENGTH: 26
<212> TYPE: PRT
<213> ORGANISM: bovine parainfluenza virus 3

<400> SEQUENCE: 28

Ile Ile Met Tyr Thr Phe Trp Thr Ile Thr Leu Thr Ile Leu Ser Val
1 5 10 15

Ile Phe Ile Met Ile Leu Thr Asn Leu Ile
20 25

<210> SEQ ID NO 29
<211> LENGTH: 56
<212> TYPE: PRT
<213> ORGANISM: bovine parainfluenza virus 3

<400> SEQUENCE: 29

Met Glu Tyr Trp Lys His Thr Asn Ser Ile Asn Asn Thr Asn Asn Glu
1 5 10 15

Thr Glu Thr Ala Arg Gly Lys His Ser Ser Lys Val Thr Asn Ile Ile
20 25 30

Met Tyr Thr Phe Trp Thr Ile Thr Leu Thr Ile Leu Ser Val Ile Phe
35 40 45

Ile Met Ile Leu Thr Asn Leu Ile
50 55

<210> SEQ ID NO 30
<211> LENGTH: 291
<212> TYPE: PRT
<213> ORGANISM: Artificial Sequence
<220> FEATURE:
<223> OTHER INFORMATION: Recombinant RSV G protein

<400> SEQUENCE: 30

Met Glu Tyr Trp Lys His Thr Asn Ser Ile Asn Asn Thr Asn Asn Glu
1 5 10 15

Thr Glu Thr Ala Arg Gly Lys His Ser Ser Lys Val Thr Asn Val Ala
20 25 30

Gln Ile Thr Leu Ser Ile Leu Ala Met Ile Ile Ser Thr Ser Leu Ile
35 40 45

Ile Ala Ala Ile Ile Phe Ile Ala Ser Ala Asn His Lys Val Thr Pro
50 55 60

Thr Thr Ala Ile Ile Gln Asp Ala Thr Ser Gln Ile Lys Asn Thr Thr
65 70 75 80

Pro Thr Tyr Leu Thr Gln Asn Pro Gln Leu Gly Ile Ser Pro Ser Asn
85 90 95

Pro Ser Glu Ile Thr Ser Gln Ile Thr Thr Ile Leu Ala Ser Thr Thr
100 105 110

Pro Gly Val Lys Ser Thr Leu Gln Ser Thr Thr Val Lys Thr Lys Asn
115 120 125

```
Thr Thr Thr Thr Gln Thr Gln Pro Ser Lys Pro Thr Thr Lys Gln Arg
    130                 135                 140

Gln Asn Lys Pro Pro Ser Lys Pro Asn Asn Asp Phe His Phe Glu Val
145                 150                 155                 160

Phe Asn Phe Val Pro Cys Ser Ile Cys Ser Asn Asn Pro Thr Cys Trp
                165                 170                 175

Ala Ile Cys Lys Arg Ile Pro Asn Lys Lys Pro Gly Lys Lys Thr Thr
            180                 185                 190

Thr Lys Pro Thr Lys Lys Pro Thr Leu Lys Thr Thr Lys Lys Asp Pro
        195                 200                 205

Lys Pro Gln Thr Thr Lys Ser Lys Glu Val Pro Thr Thr Lys Pro Thr
    210                 215                 220

Glu Glu Pro Thr Ile Asn Thr Thr Lys Thr Asn Ile Ile Thr Thr Leu
225                 230                 235                 240

Leu Thr Ser Asn Thr Thr Gly Asn Pro Glu Leu Thr Ser Gln Met Glu
                245                 250                 255

Thr Phe His Ser Thr Ser Ser Glu Gly Asn Pro Ser Pro Ser Gln Val
            260                 265                 270

Ser Thr Thr Ser Glu Tyr Pro Ser Gln Pro Ser Ser Pro Pro Asn Thr
        275                 280                 285

Pro Arg Gln
    290
```

<210> SEQ ID NO 31
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 31

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Pro Thr Thr
    50                  55                  60

Ala Ile Ile Gln Asp Ala Thr Ser Gln Ile Lys Asn Thr Thr Pro Thr
65                  70                  75                  80

Tyr Leu Thr Gln Asn Pro Gln Leu Gly Ile Ser Pro Ser Asn Pro Ser
                85                  90                  95

Glu Ile Thr Ser Gln Ile Thr Thr Ile Leu Ala Ser Thr Thr Pro Gly
            100                 105                 110

Val Lys Ser Thr Leu Gln Ser Thr Thr Val Lys Thr Lys Asn Thr Thr
        115                 120                 125

Thr Thr Gln Thr Gln Pro Ser Lys Pro Thr Thr Lys Gln Arg Gln Asn
    130                 135                 140

Lys Pro Pro Ser Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Lys Lys Thr Thr Thr Lys
            180                 185                 190
```

Pro Thr Lys Lys Pro Thr Leu Lys Thr Thr Lys Lys Asp Pro Lys Pro
195 200 205

Gln Thr Thr Lys Ser Lys Glu Val Pro Thr Thr Lys Pro Thr Glu Glu
210 215 220

Pro Thr Ile Asn Thr Thr Lys Thr Asn Ile Ile Thr Thr Leu Leu Thr
225 230 235 240

Ser Asn Thr Thr Gly Asn Pro Glu Leu Thr Ser Gln Met Glu Thr Phe
245 250 255

His Ser Thr Ser Ser Glu Gly Asn Pro Ser Pro Ser Gln Val Ser Thr
260 265 270

Thr Ser Glu Tyr Pro Ser Gln Pro Ser Ser Pro Pro Asn Thr Pro Arg
275 280 285

Gln

<210> SEQ ID NO 32
<211> LENGTH: 46
<212> TYPE: DNA
<213> ORGANISM: Artificial Sequence
<220> FEATURE:
<223> OTHER INFORMATION: Recombinant vector sequence

<400> SEQUENCE: 32
ggcgcgccaa gtaagaaaaa cttaggatta atggacctgc aggatg 46

<210> SEQ ID NO 33
<211> LENGTH: 55
<212> TYPE: DNA
<213> ORGANISM: Artificial Sequence
<220> FEATURE:
<223> OTHER INFORMATION: Recombinant vector sequence

<400> SEQUENCE: 33
tagtgatagc tagcggcgcg ccagcaacaa gtaagaaaaa cttaggatta atgga 55

<210> SEQ ID NO 34
<211> LENGTH: 77
<212> TYPE: PRT
<213> ORGANISM: respiratory syncytial virus

<400> SEQUENCE: 34

Met Ser Lys Asn Lys Asp Gln Arg Thr Ala Lys Thr Leu Glu Arg Thr
1 5 10 15

Trp Asp Thr Leu Asn His Leu Leu Phe Ile Ser Ser Cys Leu Tyr Lys
20 25 30

Leu Asn Leu Lys Ser Val Ala Gln Ile Thr Leu Ser Ile Leu Ala Met
35 40 45

Ile Ile Ser Thr Ser Leu Ile Ile Ala Ala Ile Ile Phe Ile Ala Ser
50 55 60

Ala Asn His Lys Val Thr Pro Thr Thr Ala Ile Ile Gln
65 70 75

<210> SEQ ID NO 35
<211> LENGTH: 77
<212> TYPE: PRT
<213> ORGANISM: respiratory syncytial virus

<400> SEQUENCE: 35

Met Ser Lys Asn Lys Asp Gln Arg Thr Ala Lys Thr Leu Glu Arg Thr
1 5 10 15

```
Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Val Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln
65                  70                  75


<210> SEQ ID NO 36
<211> LENGTH: 30
<212> TYPE: PRT
<213> ORGANISM: respiratory syncytial virus

<400> SEQUENCE: 36

Met Ile Ile Ser Thr Ser Leu Ile Ile Ala Ala Ile Ile Phe Ile Ala
1               5                   10                  15

Ser Ala Asn His Lys Val Thr Pro Thr Thr Ala Ile Ile Gln
            20                  25                  30


<210> SEQ ID NO 37
<211> LENGTH: 70
<212> TYPE: PRT
<213> ORGANISM: Artificial sequence
<220> FEATURE:
<223> OTHER INFORMATION: Recombinant RSV G protein

<400> SEQUENCE: 37

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Val Ala
            20                  25                  30

Gln Ile Thr Leu Ser Ile Leu Ala Met Ile Ile Ser Thr Ser Leu Ile
        35                  40                  45

Ile Ala Ala Ile Ile Phe Ile Ala Ser Ala Asn His Lys Val Thr Pro
    50                  55                  60

Thr Thr Ala Ile Ile Gln
65                  70


<210> SEQ ID NO 38
<211> LENGTH: 68
<212> TYPE: PRT
<213> ORGANISM: Artificial sequence
<220> FEATURE:
<223> OTHER INFORMATION: Recombinant RSV G protein

<400> SEQUENCE: 38

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Pro Thr Thr
    50                  55                  60

Ala Ile Ile Gln
65


<210> SEQ ID NO 39
<211> LENGTH: 71
```

<212> TYPE: PRT
<213> ORGANISM: bovine parainfluenza virus 3

<400> SEQUENCE: 39

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Gln Glu Asn Asn His Asn Lys Leu
    50                  55                  60

Met Leu Gln Glu Ile Arg Lys
65                  70

<210> SEQ ID NO 40
<211> LENGTH: 70
<212> TYPE: PRT
<213> ORGANISM: human parainfluenza virus 3

<400> SEQUENCE: 40

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn
65                  70

<210> SEQ ID NO 41
<211> LENGTH: 5
<212> TYPE: PRT
<213> ORGANISM: respiratory syncytial virus

<400> SEQUENCE: 41

Cys Trp Ala Ile Cys
1               5

<210> SEQ ID NO 42
<211> LENGTH: 15
<212> TYPE: DNA
<213> ORGANISM: respiratory syncytial virus

<400> SEQUENCE: 42
tgctgggcta tctgc                                                    15

<210> SEQ ID NO 43
<211> LENGTH: 5
<212> TYPE: PRT
<213> ORGANISM: Artificial sequence
<220> FEATURE:
<223> OTHER INFORMATION: Recombinant RSV G protein

<400> SEQUENCE: 43

Cys Trp Ala Ile Arg
1               5

<210> SEQ ID NO 44

-continued

<211> LENGTH: 15
<212> TYPE: DNA
<213> ORGANISM: Artificial sequence
<220> FEATURE:
<223> OTHER INFORMATION: Recombinant RSV G protein

<400> SEQUENCE: 44
tgctgggcta tccgc 15

<210> SEQ ID NO 45
<211> LENGTH: 6
<212> TYPE: PRT
<213> ORGANISM: Artificial sequence
<220> FEATURE:
<223> OTHER INFORMATION: Recombinant RSV G protein

<400> SEQUENCE: 45

Cys Trp Ala Ile Ala Cys
1 5

<210> SEQ ID NO 46
<211> LENGTH: 18
<212> TYPE: DNA
<213> ORGANISM: Artificial sequence
<220> FEATURE:
<223> OTHER INFORMATION: Recombinant RSV G protein

<400> SEQUENCE: 46
tgctgggcta tcgcatgc 18

<210> SEQ ID NO 47
<211> LENGTH: 298
<212> TYPE: PRT
<213> ORGANISM: respiratory syncytial virus

<400> SEQUENCE: 47

Met Ser Lys Thr Lys Asp Gln Arg Thr Ala Lys Thr Leu Glu Arg Thr
1 5 10 15

Trp Asp Thr Leu Asn His Leu Leu Phe Ile Ser Ser Cys Leu Tyr Lys
20 25 30

Leu Asn Leu Lys Ser Ile Ala Gln Ile Thr Leu Ser Ile Leu Ala Met
35 40 45

Ile Ile Ser Thr Ser Leu Ile Ile Ala Ala Ile Ile Phe Ile Ala Ser
50 55 60

Ala Asn His Lys Val Thr Leu Thr Thr Ala Ile Ile Gln Asp Ala Thr
65 70 75 80

Asn Gln Ile Lys Asn Thr Thr Pro Thr Tyr Leu Thr Gln Asn Pro Gln
85 90 95

Leu Gly Ile Ser Leu Ser Asn Leu Ser Glu Thr Thr Ser Lys Pro Thr
100 105 110

Thr Ile Leu Ala Leu Thr Thr Pro Asn Ala Glu Ser Thr Pro Gln Ser
115 120 125

Thr Thr Val Lys Thr Lys Asn Thr Thr Thr Thr Gln Ile Gln Pro Ser
130 135 140

Lys Pro Thr Thr Lys Gln Arg Gln Asn Lys Pro Gln Asn Lys Pro Asn
145 150 155 160

Asn Asp Phe His Phe Glu Val Phe Asn Phe Val Pro Cys Ser Ile Cys
165 170 175

Ser Asn Asn Pro Thr Cys Trp Ala Ile Cys Lys Arg Ile Pro Asn Lys
180 185 190

```
Lys Pro Gly Arg Lys Thr Thr Thr Lys Pro Thr Lys Gln Pro Ala Ile
        195                 200                 205

Lys Thr Thr Lys Lys Asp Pro Lys Pro Gln Thr Thr Lys Pro Lys Glu
    210                 215                 220

Val Leu Thr Thr Lys Pro Thr Glu Lys Pro Thr Ile Asn Thr Thr Lys
225                 230                 235                 240

Thr Asn Ile Arg Thr Thr Leu Leu Thr Ser Asn Ile Thr Glu Asn Gln
                245                 250                 255

Glu His Thr Ser Gln Lys Glu Thr Leu His Ser Thr Thr Ser Glu Gly
            260                 265                 270

Asn Pro Ser Pro Ser Gln Val Tyr Thr Thr Ser Glu Tyr Leu Ser Gln
        275                 280                 285

Ser Leu Ser Pro Ser Asn Thr Thr Arg Trp
    290                 295


<210> SEQ ID NO 48
<211> LENGTH: 233
<212> TYPE: PRT
<213> ORGANISM: respiratory syncytial virus

<400> SEQUENCE: 48

Asn His Lys Val Thr Leu Thr Thr Ala Ile Ile Gln Asp Ala Thr Asn
1               5                   10                  15

Gln Ile Lys Asn Thr Thr Pro Thr Tyr Leu Thr Gln Asn Pro Gln Leu
            20                  25                  30

Gly Ile Ser Leu Ser Asn Leu Ser Glu Thr Thr Ser Lys Pro Thr Thr
        35                  40                  45

Ile Leu Ala Leu Thr Thr Pro Asn Ala Glu Ser Thr Pro Gln Ser Thr
    50                  55                  60

Thr Val Lys Thr Lys Asn Thr Thr Thr Thr Gln Ile Gln Pro Ser Lys
65                  70                  75                  80

Pro Thr Thr Lys Gln Arg Gln Asn Lys Pro Gln Asn Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
        115                 120                 125

Pro Gly Arg Lys Thr Thr Thr Lys Pro Thr Lys Gln Pro Ala Ile Lys
    130                 135                 140

Thr Thr Lys Lys Asp Pro Lys Pro Gln Thr Thr Lys Pro Lys Glu Val
145                 150                 155                 160

Leu Thr Thr Lys Pro Thr Glu Lys Pro Thr Ile Asn Thr Thr Lys Thr
                165                 170                 175

Asn Ile Arg Thr Thr Leu Leu Thr Ser Asn Ile Thr Glu Asn Gln Glu
            180                 185                 190

His Thr Ser Gln Lys Glu Thr Leu His Ser Thr Thr Ser Glu Gly Asn
        195                 200                 205

Pro Ser Pro Ser Gln Val Tyr Thr Thr Ser Glu Tyr Leu Ser Gln Ser
    210                 215                 220

Leu Ser Pro Ser Asn Thr Thr Arg Trp
225                 230


<210> SEQ ID NO 49
<211> LENGTH: 299
<212> TYPE: PRT
<213> ORGANISM: respiratory syncytial virus
```

<400> SEQUENCE: 49

Met Ser Lys His Lys Asn Gln Arg Thr Ala Arg Thr Leu Glu Lys Thr
1 5 10 15

Trp Asp Thr Leu Asn His Leu Ile Val Ile Ser Ser Cys Leu Tyr Arg
20 25 30

Leu Asn Leu Lys Ser Ile Ala Gln Ile Ala Leu Ser Val Leu Ala Met
35 40 45

Ile Ile Ser Thr Ser Leu Ile Ile Ala Ala Ile Ile Phe Ile Ile Ser
50 55 60

Ala Asn His Lys Val Thr Leu Thr Thr Val Thr Val Gln Thr Ile Lys
65 70 75 80

Asn His Thr Glu Lys Asn Ile Thr Thr Tyr Leu Thr Gln Val Pro Pro
85 90 95

Glu Arg Val Ser Ser Ser Lys Gln Pro Thr Thr Thr Ser Pro Ile His
100 105 110

Thr Asn Ser Ala Thr Thr Ser Pro Asn Thr Lys Ser Glu Thr His His
115 120 125

Thr Thr Ala Gln Thr Lys Gly Arg Thr Thr Thr Ser Thr Gln Thr Asn
130 135 140

Lys Pro Ser Thr Lys Pro Arg Leu Lys Asn Pro Pro Lys Lys Pro Lys
145 150 155 160

Asp Asp Tyr His Phe Glu Val Phe Asn Phe Val Pro Cys Ser Ile Cys
165 170 175

Gly Asn Asn Gln Leu Cys Lys Ser Ile Cys Lys Thr Ile Pro Ser Asn
180 185 190

Lys Pro Lys Lys Lys Pro Thr Ile Lys Pro Thr Asn Lys Pro Thr Thr
195 200 205

Lys Thr Thr Asn Lys Arg Asp Pro Lys Thr Pro Ala Lys Thr Thr Lys
210 215 220

Lys Glu Thr Thr Thr Asn Pro Thr Lys Lys Pro Thr Leu Thr Thr Thr
225 230 235 240

Glu Arg Asp Thr Ser Thr Ser Gln Ser Thr Val Leu Asp Thr Thr Thr
245 250 255

Leu Glu His Thr Ile Gln Gln Gln Ser Leu His Ser Thr Thr Pro Glu
260 265 270

Asn Thr Pro Asn Ser Thr Gln Thr Pro Thr Ala Ser Glu Pro Ser Thr
275 280 285

Ser Asn Ser Thr Gln Asn Thr Gln Ser His Ala
290 295

<210> SEQ ID NO 50
<211> LENGTH: 234
<212> TYPE: PRT
<213> ORGANISM: respiratory syncytial virus

<400> SEQUENCE: 50

Asn His Lys Val Thr Leu Thr Thr Val Thr Val Gln Thr Ile Lys Asn
1 5 10 15

His Thr Glu Lys Asn Ile Thr Thr Tyr Leu Thr Gln Val Pro Pro Glu
20 25 30

Arg Val Ser Ser Ser Lys Gln Pro Thr Thr Thr Ser Pro Ile His Thr
35 40 45

Asn Ser Ala Thr Thr Ser Pro Asn Thr Lys Ser Glu Thr His His Thr
50 55 60

-continued

```
Thr Ala Gln Thr Lys Gly Arg Thr Thr Thr Ser Thr Gln Thr Asn Lys
65                  70                  75                  80

Pro Ser Thr Lys Pro Arg Leu Lys Asn Pro Pro Lys Lys Pro Lys Asp
                85                  90                  95

Asp Tyr His Phe Glu Val Phe Asn Phe Val Pro Cys Ser Ile Cys Gly
            100                 105                 110

Asn Asn Gln Leu Cys Lys Ser Ile Cys Lys Thr Ile Pro Ser Asn Lys
        115                 120                 125

Pro Lys Lys Lys Pro Thr Ile Lys Pro Thr Asn Lys Pro Thr Thr Lys
    130                 135                 140

Thr Thr Asn Lys Arg Asp Pro Lys Thr Pro Ala Lys Thr Thr Lys Lys
145                 150                 155                 160

Glu Thr Thr Thr Asn Pro Thr Lys Lys Pro Thr Leu Thr Thr Thr Glu
                165                 170                 175

Arg Asp Thr Ser Thr Ser Gln Ser Thr Val Leu Asp Thr Thr Thr Leu
            180                 185                 190

Glu His Thr Ile Gln Gln Gln Ser Leu His Ser Thr Thr Pro Glu Asn
        195                 200                 205

Thr Pro Asn Ser Thr Gln Thr Pro Thr Ala Ser Glu Pro Ser Thr Ser
    210                 215                 220

Asn Ser Thr Gln Asn Thr Gln Ser His Ala
225                 230


<210> SEQ ID NO 51
<211> LENGTH: 321
<212> TYPE: PRT
<213> ORGANISM: respiratory syncytial virus

<400> SEQUENCE: 51

Met Ser Lys Thr Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Leu Thr Thr Ala Ile Ile Gln Asp Ala Thr
65                  70                  75                  80

Asn Gln Ile Lys Asn Thr Thr Pro Thr Tyr Leu Thr Gln Asn Pro Gln
                85                  90                  95

Leu Gly Ile Ser Phe Ser Asn Leu Ser Gly Thr Thr Ser Gln Ser Thr
            100                 105                 110

Thr Ile Leu Ala Ser Thr Thr Pro Ser Ala Glu Ser Thr Pro Gln Ser
        115                 120                 125

Thr Thr Val Lys Ile Lys Asn Thr Thr Thr Thr Gln Ile Leu Pro Ser
    130                 135                 140

Lys Pro Thr Thr Lys Gln Arg Gln Asn Lys Pro Gln Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
```

```
        195                 200                 205

Lys Thr Thr Lys Lys Asp Pro Lys Pro Gln Thr Thr Lys Pro Lys Glu
    210                 215                 220

Val Leu Thr Thr Lys Pro Thr Gly Lys Pro Thr Ile Asn Thr Thr Lys
225                 230                 235                 240

Thr Asn Ile Arg Thr Thr Leu Leu Thr Ser Asn Thr Lys Gly Asn Pro
                245                 250                 255

Glu His Thr Ser Gln Glu Glu Thr Leu His Ser Thr Thr Ser Glu Gly
            260                 265                 270

Tyr Leu Ser Pro Ser Gln Val Tyr Thr Thr Ser Gly Gln Glu Glu Thr
        275                 280                 285

Leu His Ser Thr Thr Ser Glu Gly Tyr Leu Ser Pro Ser Gln Val Tyr
    290                 295                 300

Thr Thr Ser Glu Tyr Leu Ser Gln Ser Leu Ser Ser Ser Asn Thr Thr
305                 310                 315                 320

Lys


<210> SEQ ID NO 52
<211> LENGTH: 256
<212> TYPE: PRT
<213> ORGANISM: respiratory syncytial virus

<400> SEQUENCE: 52

Asn His Lys Val Thr Leu Thr Thr Ala Ile Ile Gln Asp Ala Thr Asn
1               5                   10                  15

Gln Ile Lys Asn Thr Thr Pro Thr Tyr Leu Thr Gln Asn Pro Gln Leu
            20                  25                  30

Gly Ile Ser Phe Ser Asn Leu Ser Gly Thr Thr Ser Gln Ser Thr Thr
        35                  40                  45

Ile Leu Ala Ser Thr Thr Pro Ser Ala Glu Ser Thr Pro Gln Ser Thr
    50                  55                  60

Thr Val Lys Ile Lys Asn Thr Thr Thr Thr Gln Ile Leu Pro Ser Lys
65                  70                  75                  80

Pro Thr Thr Lys Gln Arg Gln Asn Lys Pro Gln Asn Lys Pro Asn Asn
                85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
        115                 120                 125

Pro Gly Lys Lys Thr Thr Thr Lys Pro Thr Lys Lys Pro Thr Leu Lys
    130                 135                 140

Thr Thr Lys Lys Asp Pro Lys Pro Gln Thr Thr Lys Pro Lys Glu Val
145                 150                 155                 160

Leu Thr Thr Lys Pro Thr Gly Lys Pro Thr Ile Asn Thr Thr Lys Thr
                165                 170                 175

Asn Ile Arg Thr Thr Leu Leu Thr Ser Asn Thr Lys Gly Asn Pro Glu
            180                 185                 190

His Thr Ser Gln Glu Glu Thr Leu His Ser Thr Thr Ser Glu Gly Tyr
        195                 200                 205

Leu Ser Pro Ser Gln Val Tyr Thr Thr Ser Gly Gln Glu Glu Thr Leu
    210                 215                 220

His Ser Thr Thr Ser Glu Gly Tyr Leu Ser Pro Ser Gln Val Tyr Thr
225                 230                 235                 240

Thr Ser Glu Tyr Leu Ser Gln Ser Leu Ser Ser Ser Asn Thr Thr Lys
```

-continued

```
            245                 250                 255


<210> SEQ ID NO 53
<211> LENGTH: 315
<212> TYPE: PRT
<213> ORGANISM: respiratory syncytial virus

<400> SEQUENCE: 53

Met Ser Lys Asn Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Lys
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Ser Pro
                85                  90                  95

Glu Arg Val Ser Pro Ser Lys Gln Leu Thr Thr Thr Pro Pro Ile Tyr
            100                 105                 110

Thr Asn Ser Ala Thr Ile Ser Pro Asn Thr Lys Ser Glu Thr His His
        115                 120                 125

Thr Thr Ala Gln Thr Lys Gly Arg Thr Thr Thr Pro Thr Gln Asn Asn
    130                 135                 140

Lys Pro Ser Thr Lys Pro Arg Pro Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Pro Thr
        195                 200                 205

Lys Thr Thr Asn Lys Arg Asp Pro Lys Lys Leu Ala Lys Thr Leu Lys
    210                 215                 220

Lys Glu Thr Thr Ile Asn Pro Thr Lys Lys Pro Thr Pro Lys Thr Thr
225                 230                 235                 240

Glu Arg Asp Thr Ser Thr Ser Gln Ser Thr Val Leu Asp Thr Thr Thr
                245                 250                 255

Ser Lys His Thr Glu Arg Asp Thr Ser Thr Ser Gln Ser Thr Val Leu
            260                 265                 270

Asp Thr Thr Thr Ser Lys His Thr Ile Gln Gln Gln Ser Leu His Ser
        275                 280                 285

Thr Thr Pro Glu Asn Thr Pro Asn Ser Thr Gln Thr Pro Thr Ala Ser
    290                 295                 300

Glu Pro Ser Thr Ser Asn Ser Thr Gln Lys Leu
305                 310                 315


<210> SEQ ID NO 54
<211> LENGTH: 250
<212> TYPE: PRT
<213> ORGANISM: respiratory syncytial virus

<400> SEQUENCE: 54

Asn His Lys Val Thr Leu Thr Thr Val Thr Val Gln Thr Ile Lys Asn
```

-continued

```
1               5                   10                  15

His Thr Glu Lys Asn Ile Thr Thr Tyr Leu Thr Gln Val Ser Pro Glu
            20                  25                  30

Arg Val Ser Pro Ser Lys Gln Leu Thr Thr Thr Pro Pro Ile Tyr Thr
        35                  40                  45

Asn Ser Ala Thr Ile Ser Pro Asn Thr Lys Ser Glu Thr His His Thr
    50                  55                  60

Thr Ala Gln Thr Lys Gly Arg Thr Thr Thr Pro Thr Gln Asn Asn Lys
65                  70                  75                  80

Pro Ser Thr Lys Pro Arg Pro Lys Asn Pro Pro Lys Lys Pro Lys Asp
                85                  90                  95

Asp Tyr His Phe Glu Val Phe Asn Phe Val Pro Cys Ser Ile Cys Gly
            100                 105                 110

Asn Asn Gln Leu Cys Lys Ser Ile Cys Lys Thr Ile Pro Ser Asn Lys
        115                 120                 125

Pro Lys Lys Lys Pro Thr Ile Lys Pro Thr Asn Lys Pro Pro Thr Lys
    130                 135                 140

Thr Thr Asn Lys Arg Asp Pro Lys Lys Leu Ala Lys Thr Leu Lys Lys
145                 150                 155                 160

Glu Thr Thr Ile Asn Pro Thr Lys Lys Pro Thr Pro Lys Thr Thr Glu
                165                 170                 175

Arg Asp Thr Ser Thr Ser Gln Ser Thr Val Leu Asp Thr Thr Thr Ser
            180                 185                 190

Lys His Thr Glu Arg Asp Thr Ser Thr Ser Gln Ser Thr Val Leu Asp
        195                 200                 205

Thr Thr Thr Ser Lys His Thr Ile Gln Gln Gln Ser Leu His Ser Thr
    210                 215                 220

Thr Pro Glu Asn Thr Pro Asn Ser Thr Gln Thr Pro Thr Ala Ser Glu
225                 230                 235                 240

Pro Ser Thr Ser Asn Ser Thr Gln Lys Leu
                245                 250


<210> SEQ ID NO 55
<211> LENGTH: 31
<212> TYPE: PRT
<213> ORGANISM: human parainfluenza virus 3

<400> SEQUENCE: 55

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys
            20                  25                  30


<210> SEQ ID NO 56
<211> LENGTH: 25
<212> TYPE: PRT
<213> ORGANISM: human parainfluenza virus 3

<400> SEQUENCE: 56

Ile Ile Tyr Ile Leu Trp Thr Ile Ile Leu Val Leu Leu Ser Ile Val
1               5                   10                  15

Phe Ile Ile Val Leu Ile Asn Ser Ile
            20                  25


<210> SEQ ID NO 57
<211> LENGTH: 56
<212> TYPE: PRT
```

<213> ORGANISM: human parainfluenza virus 3

<400> SEQUENCE: 57

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile
    50                  55
```

<210> SEQ ID NO 58
<211> LENGTH: 35
<212> TYPE: PRT
<213> ORGANISM: human parainfluenza virus 1

<400> SEQUENCE: 58

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp
        35
```

<210> SEQ ID NO 59
<211> LENGTH: 25
<212> TYPE: PRT
<213> ORGANISM: human parainfluenza virus 1

<400> SEQUENCE: 59

```
Ile Leu Leu Ile Ala Thr Thr Met His Thr Val Leu Ser Phe Ile Ile
1               5                   10                  15

Met Ile Leu Cys Ile Asp Leu Ile Ile
            20                  25
```

<210> SEQ ID NO 60
<211> LENGTH: 60
<212> TYPE: PRT
<213> ORGANISM: human parainfluenza virus 1

<400> SEQUENCE: 60

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile
    50                  55                  60
```

<210> SEQ ID NO 61
<211> LENGTH: 292
<212> TYPE: PRT
<213> ORGANISM: Artificial Sequence
<220> FEATURE:
<223> OTHER INFORMATION: Recombinant RSV G protein

<400> SEQUENCE: 61

```
Met Glu Tyr Trp Lys His Thr Asn Ser Ile Asn Asn Thr Asn Asn Glu
1               5                   10                  15
```

```
Thr Glu Thr Ala Arg Gly Lys His Ser Ser Lys Val Thr Asn Ile Ala
            20                  25                  30

Gln Ile Ala Leu Ser Val Leu Ala Met Ile Ile Ser Thr Ser Leu Ile
        35                  40                  45

Ile Ala Ala Ile Ile Phe Ile Ile Ser Ala Asn His Lys Val Thr Leu
    50                  55                  60

Thr Thr Val Thr Val Gln Thr Ile Lys Asn His Thr Glu Lys Asn Ile
65                  70                  75                  80

Thr Thr Tyr Leu Thr Gln Val Pro Pro Glu Arg Val Ser Ser Ser Lys
                85                  90                  95

Gln Pro Thr Thr Thr Ser Pro Ile His Thr Asn Ser Ala Thr Thr Ser
            100                 105                 110

Pro Asn Thr Lys Ser Glu Thr His His Thr Thr Ala Gln Thr Lys Gly
        115                 120                 125

Arg Thr Thr Thr Ser Thr Gln Thr Asn Lys Pro Ser Thr Lys Pro Arg
    130                 135                 140

Leu Lys Asn Pro Pro Lys Lys Pro Lys Asp Asp Tyr His Phe Glu Val
145                 150                 155                 160

Phe Asn Phe Val Pro Cys Ser Ile Cys Gly Asn Asn Gln Leu Cys Lys
                165                 170                 175

Ser Ile Cys Lys Thr Ile Pro Ser Asn Lys Pro Lys Lys Lys Pro Thr
            180                 185                 190

Ile Lys Pro Thr Asn Lys Pro Thr Thr Lys Thr Thr Asn Lys Arg Asp
        195                 200                 205

Pro Lys Thr Pro Ala Lys Thr Thr Lys Lys Glu Thr Thr Thr Asn Pro
    210                 215                 220

Thr Lys Lys Pro Thr Leu Thr Thr Thr Glu Arg Asp Thr Ser Thr Ser
225                 230                 235                 240

Gln Ser Thr Val Leu Asp Thr Thr Thr Leu Glu His Thr Ile Gln Gln
                245                 250                 255

Gln Ser Leu His Ser Thr Thr Pro Glu Asn Thr Pro Asn Ser Thr Gln
            260                 265                 270

Thr Pro Thr Ala Ser Glu Pro Ser Thr Ser Asn Ser Thr Gln Asn Thr
        275                 280                 285

Gln Ser His Ala
    290
```

<210> SEQ ID NO 62
<211> LENGTH: 290
<212> TYPE: PRT
<213> ORGANISM: Artificial Sequence
<220> FEATURE:
<223> OTHER INFORMATION: Recombinant RSV G protein

<400> SEQUENCE: 62

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Leu Thr Thr
    50                  55                  60

Val Thr Val Gln Thr Ile Lys Asn His Thr Glu Lys Asn Ile Thr Thr
65                  70                  75                  80
```

Tyr Leu Thr Gln Val Pro Pro Glu Arg Val Ser Ser Ser Lys Gln Pro
85 90 95

Thr Thr Thr Ser Pro Ile His Thr Asn Ser Ala Thr Thr Ser Pro Asn
100 105 110

Thr Lys Ser Glu Thr His His Thr Thr Ala Gln Thr Lys Gly Arg Thr
115 120 125

Thr Thr Ser Thr Gln Thr Asn Lys Pro Ser Thr Lys Pro Arg Leu Lys
130 135 140

Asn Pro Pro Lys Lys Pro Lys Asp Asp Tyr His Phe Glu Val Phe Asn
145 150 155 160

Phe Val Pro Cys Ser Ile Cys Gly Asn Asn Gln Leu Cys Lys Ser Ile
165 170 175

Cys Lys Thr Ile Pro Ser Asn Lys Pro Lys Lys Lys Pro Thr Ile Lys
180 185 190

Pro Thr Asn Lys Pro Thr Thr Lys Thr Thr Asn Lys Arg Asp Pro Lys
195 200 205

Thr Pro Ala Lys Thr Thr Lys Lys Glu Thr Thr Thr Asn Pro Thr Lys
210 215 220

Lys Pro Thr Leu Thr Thr Thr Glu Arg Asp Thr Ser Thr Ser Gln Ser
225 230 235 240

Thr Val Leu Asp Thr Thr Thr Leu Glu His Thr Ile Gln Gln Gln Ser
245 250 255

Leu His Ser Thr Thr Pro Glu Asn Thr Pro Asn Ser Thr Gln Thr Pro
260 265 270

Thr Ala Ser Glu Pro Ser Thr Ser Asn Ser Thr Gln Asn Thr Gln Ser
275 280 285

His Ala
290

<210> SEQ ID NO 63
<211> LENGTH: 291
<212> TYPE: PRT
<213> ORGANISM: Artificial Sequence
<220> FEATURE:
<223> OTHER INFORMATION: Recombinant RSV G protein

<400> SEQUENCE: 63

Met Glu Tyr Trp Lys His Thr Asn Ser Ile Asn Asn Thr Asn Asn Glu
1 5 10 15

Thr Glu Thr Ala Arg Gly Lys His Ser Ser Lys Val Thr Asn Ile Ala
20 25 30

Gln Ile Thr Leu Ser Ile Leu Ala Met Ile Ile Ser Thr Ser Leu Ile
35 40 45

Ile Ala Ala Ile Ile Phe Ile Ala Ser Ala Asn His Lys Val Thr Leu
50 55 60

Thr Thr Ala Ile Ile Gln Asp Ala Thr Asn Gln Ile Lys Asn Thr Thr
65 70 75 80

Pro Thr Tyr Leu Thr Gln Asn Pro Gln Leu Gly Ile Ser Leu Ser Asn
85 90 95

Leu Ser Glu Thr Thr Ser Lys Pro Thr Thr Ile Leu Ala Leu Thr Thr
100 105 110

Pro Asn Ala Glu Ser Thr Pro Gln Ser Thr Thr Val Lys Thr Lys Asn
115 120 125

Thr Thr Thr Thr Gln Ile Gln Pro Ser Lys Pro Thr Thr Lys Gln Arg
130 135 140

Gln Asn Lys Pro Gln Asn Lys Pro Asn Asn Asp Phe His Phe Glu Val
145 150 155 160

Phe Asn Phe Val Pro Cys Ser Ile Cys Ser Asn Asn Pro Thr Cys Trp
165 170 175

Ala Ile Cys Lys Arg Ile Pro Asn Lys Lys Pro Gly Arg Lys Thr Thr
180 185 190

Thr Lys Pro Thr Lys Gln Pro Ala Ile Lys Thr Thr Lys Lys Asp Pro
195 200 205

Lys Pro Gln Thr Thr Lys Pro Lys Glu Val Leu Thr Thr Lys Pro Thr
210 215 220

Glu Lys Pro Thr Ile Asn Thr Thr Lys Thr Asn Ile Arg Thr Thr Leu
225 230 235 240

Leu Thr Ser Asn Ile Thr Glu Asn Gln Glu His Thr Ser Gln Lys Glu
245 250 255

Thr Leu His Ser Thr Thr Ser Glu Gly Asn Pro Ser Pro Ser Gln Val
260 265 270

Tyr Thr Thr Ser Glu Tyr Leu Ser Gln Ser Leu Ser Pro Ser Asn Thr
275 280 285

Thr Arg Trp
290

<210> SEQ ID NO 64
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 64

Met Glu Tyr Trp Lys His Thr Asn Ser Ile Asn Asn Thr Asn Asn Glu
1 5 10 15

Thr Glu Thr Ala Arg Gly Lys His Ser Ser Lys Val Thr Asn Ile Ile
20 25 30

Met Tyr Thr Phe Trp Thr Ile Thr Leu Thr Ile Leu Ser Val Ile Phe
35 40 45

Ile Met Ile Leu Thr Asn Leu Ile Asn His Lys Val Thr Leu Thr Thr
50 55 60

Ala Ile Ile Gln Asp Ala Thr Asn Gln Ile Lys Asn Thr Thr Pro Thr
65 70 75 80

Tyr Leu Thr Gln Asn Pro Gln Leu Gly Ile Ser Leu Ser Asn Leu Ser
85 90 95

Glu Thr Thr Ser Lys Pro Thr Thr Ile Leu Ala Leu Thr Thr Pro Asn
100 105 110

Ala Glu Ser Thr Pro Gln Ser Thr Thr Val Lys Thr Lys Asn Thr Thr
115 120 125

Thr Thr Gln Ile Gln Pro Ser Lys Pro Thr Thr Lys Gln Arg Gln Asn
130 135 140

Lys Pro Gln Asn Lys Pro Asn Asn Asp Phe His Phe Glu Val Phe Asn
145 150 155 160

Phe Val Pro Cys Ser Ile Cys Ser Asn Asn Pro Thr Cys Trp Ala Ile
165 170 175

Cys Lys Arg Ile Pro Asn Lys Lys Pro Gly Arg Lys Thr Thr Thr Lys
180 185 190

Pro Thr Lys Gln Pro Ala Ile Lys Thr Thr Lys Lys Asp Pro Lys Pro
195 200 205

Gln Thr Thr Lys Pro Lys Glu Val Leu Thr Thr Lys Pro Thr Glu Lys
    210                 215                 220

Pro Thr Ile Asn Thr Thr Lys Thr Asn Ile Arg Thr Thr Leu Leu Thr
225                 230                 235                 240

Ser Asn Ile Thr Glu Asn Gln Glu His Thr Ser Gln Lys Glu Thr Leu
                245                 250                 255

His Ser Thr Thr Ser Glu Gly Asn Pro Ser Pro Ser Gln Val Tyr Thr
            260                 265                 270

Thr Ser Glu Tyr Leu Ser Gln Ser Leu Ser Pro Ser Asn Thr Thr Arg
        275                 280                 285

Trp

<210> SEQ ID NO 65
<211> LENGTH: 314
<212> TYPE: PRT
<213> ORGANISM: Artificial Sequence
<220> FEATURE:
<223> OTHER INFORMATION: Recombinant RSV G protein

<400> SEQUENCE: 65

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ala
            20                  25                  30

Gln Ile Thr Leu Ser Ile Leu Ala Met Ile Ile Ser Thr Ser Leu Ile
        35                  40                  45

Ile Ala Ala Ile Ile Phe Ile Ala Ser Ala Asn His Lys Val Thr Leu
    50                  55                  60

Thr Thr Ala Ile Ile Gln Asp Ala Thr Asn Gln Ile Lys Asn Thr Thr
65                  70                  75                  80

Pro Thr Tyr Leu Thr Gln Asn Pro Gln Leu Gly Ile Ser Phe Ser Asn
                85                  90                  95

Leu Ser Gly Thr Thr Ser Gln Ser Thr Thr Ile Leu Ala Ser Thr Thr
            100                 105                 110

Pro Ser Ala Glu Ser Thr Pro Gln Ser Thr Thr Val Lys Ile Lys Asn
        115                 120                 125

Thr Thr Thr Thr Gln Ile Leu Pro Ser Lys Pro Thr Thr Lys Gln Arg
    130                 135                 140

Gln Asn Lys Pro Gln Asn Lys Pro Asn Asn Asp Phe His Phe Glu Val
145                 150                 155                 160

Phe Asn Phe Val Pro Cys Ser Ile Cys Ser Asn Asn Pro Thr Cys Trp
                165                 170                 175

Ala Ile Cys Lys Arg Ile Pro Asn Lys Lys Pro Gly Lys Lys Thr Thr
            180                 185                 190

Thr Lys Pro Thr Lys Lys Pro Thr Leu Lys Thr Thr Lys Lys Asp Pro
        195                 200                 205

Lys Pro Gln Thr Thr Lys Pro Lys Glu Val Leu Thr Thr Lys Pro Thr
    210                 215                 220

Gly Lys Pro Thr Ile Asn Thr Thr Lys Thr Asn Ile Arg Thr Thr Leu
225                 230                 235                 240

Leu Thr Ser Asn Thr Lys Gly Asn Pro Glu His Thr Ser Gln Glu Glu
                245                 250                 255

Thr Leu His Ser Thr Thr Ser Glu Gly Tyr Leu Ser Pro Ser Gln Val
            260                 265                 270

```
Tyr Thr Thr Ser Gly Gln Glu Glu Thr Leu His Ser Thr Thr Ser Glu
        275                 280                 285

Gly Tyr Leu Ser Pro Ser Gln Val Tyr Thr Thr Ser Glu Tyr Leu Ser
    290                 295                 300

Gln Ser Leu Ser Ser Ser Asn Thr Thr Lys
305                 310


<210> SEQ ID NO 66
<211> LENGTH: 312
<212> TYPE: PRT
<213> ORGANISM: Artificial Sequence
<220> FEATURE:
<223> OTHER INFORMATION: Recombinant RSV G protein

<400> SEQUENCE: 66

Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Leu Thr Thr
    50                  55                  60

Ala Ile Ile Gln Asp Ala Thr Asn Gln Ile Lys Asn Thr Thr Pro Thr
65                  70                  75                  80

Tyr Leu Thr Gln Asn Pro Gln Leu Gly Ile Ser Phe Ser Asn Leu Ser
                85                  90                  95

Gly Thr Thr Ser Gln Ser Thr Thr Ile Leu Ala Ser Thr Thr Pro Ser
            100                 105                 110

Ala Glu Ser Thr Pro Gln Ser Thr Thr Val Lys Ile Lys Asn Thr Thr
        115                 120                 125

Thr Thr Gln Ile Leu Pro Ser Lys Pro Thr Thr Lys Gln Arg Gln Asn
    130                 135                 140

Lys Pro Gln Asn Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Lys Lys Thr Thr Thr Lys
            180                 185                 190

Pro Thr Lys Lys Pro Thr Leu Lys Thr Thr Lys Lys Asp Pro Lys Pro
        195                 200                 205

Gln Thr Thr Lys Pro Lys Glu Val Leu Thr Thr Lys Pro Thr Gly Lys
    210                 215                 220

Pro Thr Ile Asn Thr Thr Lys Thr Asn Ile Arg Thr Thr Leu Leu Thr
225                 230                 235                 240

Ser Asn Thr Lys Gly Asn Pro Glu His Thr Ser Gln Glu Glu Thr Leu
                245                 250                 255

His Ser Thr Thr Ser Glu Gly Tyr Leu Ser Pro Ser Gln Val Tyr Thr
            260                 265                 270

Thr Ser Gly Gln Glu Glu Thr Leu His Ser Thr Thr Ser Glu Gly Tyr
        275                 280                 285

Leu Ser Pro Ser Gln Val Tyr Thr Thr Ser Glu Tyr Leu Ser Gln Ser
    290                 295                 300

Leu Ser Ser Ser Asn Thr Thr Lys
305                 310
```

<210> SEQ ID NO 67
<211> LENGTH: 308
<212> TYPE: PRT
<213> ORGANISM: Artificial Sequence
<220> FEATURE:
<223> OTHER INFORMATION: Recombinant RSV G protein

<400> SEQUENCE: 67

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ala
            20                  25                  30

Gln Ile Ala Leu Ser Val Leu Ala Met Ile Ile Ser Thr Ser Leu Ile
        35                  40                  45

Ile Ala Ala Ile Ile Phe Ile Ile Ser Ala Asn His Lys Val Thr Leu
    50                  55                  60

Thr Thr Val Thr Val Gln Thr Ile Lys Asn His Thr Glu Lys Asn Ile
65                  70                  75                  80

Thr Thr Tyr Leu Thr Gln Val Ser Pro Glu Arg Val Ser Pro Ser Lys
                85                  90                  95

Gln Leu Thr Thr Thr Pro Pro Ile Tyr Thr Asn Ser Ala Thr Ile Ser
            100                 105                 110

Pro Asn Thr Lys Ser Glu Thr His His Thr Thr Ala Gln Thr Lys Gly
        115                 120                 125

Arg Thr Thr Thr Pro Thr Gln Asn Asn Lys Pro Ser Thr Lys Pro Arg
    130                 135                 140

Pro Lys Asn Pro Pro Lys Lys Pro Lys Asp Asp Tyr His Phe Glu Val
145                 150                 155                 160

Phe Asn Phe Val Pro Cys Ser Ile Cys Gly Asn Asn Gln Leu Cys Lys
                165                 170                 175

Ser Ile Cys Lys Thr Ile Pro Ser Asn Lys Pro Lys Lys Lys Pro Thr
            180                 185                 190

Ile Lys Pro Thr Asn Lys Pro Pro Thr Lys Thr Thr Asn Lys Arg Asp
        195                 200                 205

Pro Lys Lys Leu Ala Lys Thr Leu Lys Lys Glu Thr Thr Ile Asn Pro
    210                 215                 220

Thr Lys Lys Pro Thr Pro Lys Thr Thr Glu Arg Asp Thr Ser Thr Ser
225                 230                 235                 240

Gln Ser Thr Val Leu Asp Thr Thr Thr Ser Lys His Thr Glu Arg Asp
                245                 250                 255

Thr Ser Thr Ser Gln Ser Thr Val Leu Asp Thr Thr Thr Ser Lys His
            260                 265                 270

Thr Ile Gln Gln Gln Ser Leu His Ser Thr Thr Pro Glu Asn Thr Pro
        275                 280                 285

Asn Ser Thr Gln Thr Pro Thr Ala Ser Glu Pro Ser Thr Ser Asn Ser
    290                 295                 300

Thr Gln Lys Leu
305
```

<210> SEQ ID NO 68
<211> LENGTH: 306
<212> TYPE: PRT
<213> ORGANISM: Artificial Sequence
<220> FEATURE:
<223> OTHER INFORMATION: Recombinant RSV G protein

<400> SEQUENCE: 68

```
Met Glu Tyr Trp Lys His Thr Asn Ser Ile Asn Asn Thr Asn Asn Glu
1               5                   10                  15

Thr Glu Thr Ala Arg Gly Lys His Ser Ser Lys Val Thr Asn Ile Ile
            20                  25                  30

Met Tyr Thr Phe Trp Thr Ile Thr Leu Thr Ile Leu Ser Val Ile Phe
        35                  40                  45

Ile Met Ile Leu Thr Asn Leu Ile Asn His Lys Val Thr Leu Thr Thr
    50                  55                  60

Val Thr Val Gln Thr Ile Lys Asn His Thr Glu Lys Asn Ile Thr Thr
65                  70                  75                  80

Tyr Leu Thr Gln Val Ser Pro Glu Arg Val Ser Pro Ser Lys Gln Leu
                85                  90                  95

Thr Thr Thr Pro Pro Ile Tyr Thr Asn Ser Ala Thr Ile Ser Pro Asn
            100                 105                 110

Thr Lys Ser Glu Thr His His Thr Thr Ala Gln Thr Lys Gly Arg Thr
        115                 120                 125

Thr Thr Pro Thr Gln Asn Asn Lys Pro Ser Thr Lys Pro Arg Pro Lys
    130                 135                 140

Asn Pro Pro Lys Lys Pro Lys Asp Asp Tyr His Phe Glu Val Phe Asn
145                 150                 155                 160

Phe Val Pro Cys Ser Ile Cys Gly Asn Asn Gln Leu Cys Lys Ser Ile
                165                 170                 175

Cys Lys Thr Ile Pro Ser Asn Lys Pro Lys Lys Lys Pro Thr Ile Lys
            180                 185                 190

Pro Thr Asn Lys Pro Pro Thr Lys Thr Thr Asn Lys Arg Asp Pro Lys
        195                 200                 205

Lys Leu Ala Lys Thr Leu Lys Lys Glu Thr Thr Ile Asn Pro Thr Lys
    210                 215                 220

Lys Pro Thr Pro Lys Thr Thr Glu Arg Asp Thr Ser Thr Ser Gln Ser
225                 230                 235                 240

Thr Val Leu Asp Thr Thr Thr Ser Lys His Thr Glu Arg Asp Thr Ser
                245                 250                 255

Thr Ser Gln Ser Thr Val Leu Asp Thr Thr Thr Ser Lys His Thr Ile
            260                 265                 270

Gln Gln Gln Ser Leu His Ser Thr Thr Pro Glu Asn Thr Pro Asn Ser
        275                 280                 285

Thr Gln Thr Pro Thr Ala Ser Glu Pro Ser Thr Ser Asn Ser Thr Gln
    290                 295                 300

Lys Leu
305
```

<210> SEQ ID NO 69
<211> LENGTH: 292
<212> TYPE: PRT
<213> ORGANISM: Artificial Sequence
<220> FEATURE:
<223> OTHER INFORMATION: Recombinant RSV G protein

<400> SEQUENCE: 69

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Val
            20                  25                  30

Ala Gln Ile Thr Leu Ser Ile Leu Ala Met Ile Ile Ser Thr Ser Leu
        35                  40                  45
```

```
Ile Ile Ala Ala Ile Ile Phe Ile Ala Ser Ala Asn His Lys Val Thr
    50                  55                  60

Pro Thr Thr Ala Ile Ile Gln Asp Ala Thr Ser Gln Ile Lys Asn Thr
65                  70                  75                  80

Thr Pro Thr Tyr Leu Thr Gln Asn Pro Gln Leu Gly Ile Ser Pro Ser
                85                  90                  95

Asn Pro Ser Glu Ile Thr Ser Gln Ile Thr Thr Ile Leu Ala Ser Thr
            100                 105                 110

Thr Pro Gly Val Lys Ser Thr Leu Gln Ser Thr Thr Val Lys Thr Lys
        115                 120                 125

Asn Thr Thr Thr Thr Gln Thr Gln Pro Ser Lys Pro Thr Thr Lys Gln
    130                 135                 140

Arg Gln Asn Lys Pro Pro Ser Lys Pro Asn Asn Asp Phe His Phe Glu
145                 150                 155                 160

Val Phe Asn Phe Val Pro Cys Ser Ile Cys Ser Asn Asn Pro Thr Cys
                165                 170                 175

Trp Ala Ile Cys Lys Arg Ile Pro Asn Lys Lys Pro Gly Lys Lys Thr
            180                 185                 190

Thr Thr Lys Pro Thr Lys Lys Pro Thr Leu Lys Thr Thr Lys Lys Asp
        195                 200                 205

Pro Lys Pro Gln Thr Thr Lys Ser Lys Glu Val Pro Thr Thr Lys Pro
    210                 215                 220

Thr Glu Glu Pro Thr Ile Asn Thr Thr Lys Thr Asn Ile Ile Thr Thr
225                 230                 235                 240

Leu Leu Thr Ser Asn Thr Thr Gly Asn Pro Glu Leu Thr Ser Gln Met
                245                 250                 255

Glu Thr Phe His Ser Thr Ser Ser Glu Gly Asn Pro Ser Pro Ser Gln
            260                 265                 270

Val Ser Thr Thr Ser Glu Tyr Pro Ser Gln Pro Ser Ser Pro Pro Asn
        275                 280                 285

Thr Pro Arg Gln
    290


<210> SEQ ID NO 70
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 70

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Pro Thr Thr
    50                  55                  60

Ala Ile Ile Gln Asp Ala Thr Ser Gln Ile Lys Asn Thr Thr Pro Thr
65                  70                  75                  80

Tyr Leu Thr Gln Asn Pro Gln Leu Gly Ile Ser Pro Ser Asn Pro Ser
                85                  90                  95

Glu Ile Thr Ser Gln Ile Thr Thr Ile Leu Ala Ser Thr Thr Pro Gly
            100                 105                 110
```

```
Val Lys Ser Thr Leu Gln Ser Thr Thr Val Lys Thr Lys Asn Thr Thr
        115                 120                 125

Thr Thr Gln Thr Gln Pro Ser Lys Pro Thr Thr Lys Gln Arg Gln Asn
    130                 135                 140

Lys Pro Pro Ser Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Lys Lys Thr Thr Thr Lys
            180                 185                 190

Pro Thr Lys Lys Pro Thr Leu Lys Thr Thr Lys Lys Asp Pro Lys Pro
        195                 200                 205

Gln Thr Thr Lys Ser Lys Glu Val Pro Thr Thr Lys Pro Thr Glu Glu
    210                 215                 220

Pro Thr Ile Asn Thr Thr Lys Thr Asn Ile Ile Thr Thr Leu Leu Thr
225                 230                 235                 240

Ser Asn Thr Thr Gly Asn Pro Glu Leu Thr Ser Gln Met Glu Thr Phe
                245                 250                 255

His Ser Thr Ser Ser Glu Gly Asn Pro Ser Pro Ser Gln Val Ser Thr
            260                 265                 270

Thr Ser Glu Tyr Pro Ser Gln Pro Ser Ser Pro Pro Asn Thr Pro Arg
        275                 280                 285

Gln


<210> SEQ ID NO 71
<211> LENGTH: 293
<212> TYPE: PRT
<213> ORGANISM: Artificial Sequence
<220> FEATURE:
<223> OTHER INFORMATION: Recombinant RSV G protein

<400> SEQUENCE: 71

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ala Gln Ile Ala Leu Ser Val Leu Ala Met Ile Ile Ser Thr Ser Leu
        35                  40                  45

Ile Ile Ala Ala Ile Ile Phe Ile Ile Ser Ala Asn His Lys Val Thr
    50                  55                  60

Leu Thr Thr Val Thr Val Gln Thr Ile Lys Asn His Thr Glu Lys Asn
65                  70                  75                  80

Ile Thr Thr Tyr Leu Thr Gln Val Pro Pro Glu Arg Val Ser Ser Ser
                85                  90                  95

Lys Gln Pro Thr Thr Thr Ser Pro Ile His Thr Asn Ser Ala Thr Thr
            100                 105                 110

Ser Pro Asn Thr Lys Ser Glu Thr His His Thr Thr Ala Gln Thr Lys
        115                 120                 125

Gly Arg Thr Thr Thr Ser Thr Gln Thr Asn Lys Pro Ser Thr Lys Pro
    130                 135                 140

Arg Leu Lys Asn Pro Pro Lys Lys Pro Lys Asp Asp Tyr His Phe Glu
145                 150                 155                 160

Val Phe Asn Phe Val Pro Cys Ser Ile Cys Gly Asn Asn Gln Leu Cys
                165                 170                 175
```

```
Lys Ser Ile Cys Lys Thr Ile Pro Ser Asn Lys Pro Lys Lys Lys Pro
            180                 185                 190

Thr Ile Lys Pro Thr Asn Lys Pro Thr Thr Lys Thr Thr Asn Lys Arg
        195                 200                 205

Asp Pro Lys Thr Pro Ala Lys Thr Thr Lys Lys Glu Thr Thr Thr Asn
    210                 215                 220

Pro Thr Lys Lys Pro Thr Leu Thr Thr Thr Glu Arg Asp Thr Ser Thr
225                 230                 235                 240

Ser Gln Ser Thr Val Leu Asp Thr Thr Thr Leu Glu His Thr Ile Gln
                245                 250                 255

Gln Gln Ser Leu His Ser Thr Thr Pro Glu Asn Thr Pro Asn Ser Thr
            260                 265                 270

Gln Thr Pro Thr Ala Ser Glu Pro Ser Thr Ser Asn Ser Thr Gln Asn
        275                 280                 285

Thr Gln Ser His Ala
    290


<210> SEQ ID NO 72
<211> LENGTH: 290
<212> TYPE: PRT
<213> ORGANISM: Artificial Sequence
<220> FEATURE:
<223> OTHER INFORMATION: Recombinant RSV G protein

<400> SEQUENCE: 72

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Leu Thr Thr
    50                  55                  60

Val Thr Val Gln Thr Ile Lys Asn His Thr Glu Lys Asn Ile Thr Thr
65                  70                  75                  80

Tyr Leu Thr Gln Val Pro Pro Glu Arg Val Ser Ser Ser Lys Gln Pro
                85                  90                  95

Thr Thr Thr Ser Pro Ile His Thr Asn Ser Ala Thr Thr Ser Pro Asn
            100                 105                 110

Thr Lys Ser Glu Thr His His Thr Thr Ala Gln Thr Lys Gly Arg Thr
        115                 120                 125

Thr Thr Ser Thr Gln Thr Asn Lys Pro Ser Thr Lys Pro Arg Leu Lys
    130                 135                 140

Asn Pro Pro Lys Lys Pro Lys Asp Asp Tyr His Phe Glu Val Phe Asn
145                 150                 155                 160

Phe Val Pro Cys Ser Ile Cys Gly Asn Asn Gln Leu Cys Lys Ser Ile
                165                 170                 175

Cys Lys Thr Ile Pro Ser Asn Lys Pro Lys Lys Lys Pro Thr Ile Lys
            180                 185                 190

Pro Thr Asn Lys Pro Thr Thr Lys Thr Thr Asn Lys Arg Asp Pro Lys
        195                 200                 205

Thr Pro Ala Lys Thr Thr Lys Lys Glu Thr Thr Thr Asn Pro Thr Lys
    210                 215                 220

Lys Pro Thr Leu Thr Thr Thr Glu Arg Asp Thr Ser Thr Ser Gln Ser
225                 230                 235                 240
```

```
Thr Val Leu Asp Thr Thr Thr Leu Glu His Thr Ile Gln Gln Gln Ser
                245                 250                 255

Leu His Ser Thr Thr Pro Glu Asn Thr Pro Asn Ser Thr Gln Thr Pro
            260                 265                 270

Thr Ala Ser Glu Pro Ser Thr Ser Asn Ser Thr Gln Asn Thr Gln Ser
        275                 280                 285

His Ala
    290


<210> SEQ ID NO 73
<211> LENGTH: 292
<212> TYPE: PRT
<213> ORGANISM: Artificial Sequence
<220> FEATURE:
<223> OTHER INFORMATION: Recombinant RSV G protein

<400> SEQUENCE: 73

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ala Gln Ile Thr Leu Ser Ile Leu Ala Met Ile Ile Ser Thr Ser Leu
        35                  40                  45

Ile Ile Ala Ala Ile Ile Phe Ile Ala Ser Ala Asn His Lys Val Thr
    50                  55                  60

Leu Thr Thr Ala Ile Ile Gln Asp Ala Thr Asn Gln Ile Lys Asn Thr
65                  70                  75                  80

Thr Pro Thr Tyr Leu Thr Gln Asn Pro Gln Leu Gly Ile Ser Leu Ser
                85                  90                  95

Asn Leu Ser Glu Thr Thr Ser Lys Pro Thr Thr Ile Leu Ala Leu Thr
            100                 105                 110

Thr Pro Asn Ala Glu Ser Thr Pro Gln Ser Thr Thr Val Lys Thr Lys
        115                 120                 125

Asn Thr Thr Thr Thr Gln Ile Gln Pro Ser Lys Pro Thr Thr Lys Gln
    130                 135                 140

Arg Gln Asn Lys Pro Gln Asn Lys Pro Asn Asn Asp Phe His Phe Glu
145                 150                 155                 160

Val Phe Asn Phe Val Pro Cys Ser Ile Cys Ser Asn Asn Pro Thr Cys
                165                 170                 175

Trp Ala Ile Cys Lys Arg Ile Pro Asn Lys Lys Pro Gly Arg Lys Thr
            180                 185                 190

Thr Thr Lys Pro Thr Lys Gln Pro Ala Ile Lys Thr Thr Lys Lys Asp
        195                 200                 205

Pro Lys Pro Gln Thr Thr Lys Pro Lys Glu Val Leu Thr Thr Lys Pro
    210                 215                 220

Thr Glu Lys Pro Thr Ile Asn Thr Thr Lys Thr Asn Ile Arg Thr Thr
225                 230                 235                 240

Leu Leu Thr Ser Asn Ile Thr Glu Asn Gln Glu His Thr Ser Gln Lys
                245                 250                 255

Glu Thr Leu His Ser Thr Thr Ser Glu Gly Asn Pro Ser Pro Ser Gln
            260                 265                 270

Val Tyr Thr Thr Ser Glu Tyr Leu Ser Gln Ser Leu Ser Pro Ser Asn
        275                 280                 285

Thr Thr Arg Trp
    290
```

<210> SEQ ID NO 74
<211> LENGTH: 289
<212> TYPE: PRT
<213> ORGANISM: Artificial Sequence
<220> FEATURE:
<223> OTHER INFORMATION: Recombinant RSV G protein

<400> SEQUENCE: 74

```
Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Leu Thr Thr
    50                  55                  60

Ala Ile Ile Gln Asp Ala Thr Asn Gln Ile Lys Asn Thr Thr Pro Thr
65                  70                  75                  80

Tyr Leu Thr Gln Asn Pro Gln Leu Gly Ile Ser Leu Ser Asn Leu Ser
                85                  90                  95

Glu Thr Thr Ser Lys Pro Thr Thr Ile Leu Ala Leu Thr Thr Pro Asn
            100                 105                 110

Ala Glu Ser Thr Pro Gln Ser Thr Thr Val Lys Thr Lys Asn Thr Thr
        115                 120                 125

Thr Thr Gln Ile Gln Pro Ser Lys Pro Thr Thr Lys Gln Arg Gln Asn
    130                 135                 140

Lys Pro Gln Asn Lys Pro Asn Asn Asp Phe His Phe Glu Val Phe Asn
145                 150                 155                 160

Phe Val Pro Cys Ser Ile Cys Ser Asn Asn Pro Thr Cys Trp Ala Ile
                165                 170                 175

Cys Lys Arg Ile Pro Asn Lys Lys Pro Gly Arg Lys Thr Thr Thr Lys
            180                 185                 190

Pro Thr Lys Gln Pro Ala Ile Lys Thr Thr Lys Lys Asp Pro Lys Pro
        195                 200                 205

Gln Thr Thr Lys Pro Lys Glu Val Leu Thr Thr Lys Pro Thr Glu Lys
    210                 215                 220

Pro Thr Ile Asn Thr Thr Lys Thr Asn Ile Arg Thr Thr Leu Leu Thr
225                 230                 235                 240

Ser Asn Ile Thr Glu Asn Gln Glu His Thr Ser Gln Lys Glu Thr Leu
                245                 250                 255

His Ser Thr Thr Ser Glu Gly Asn Pro Ser Pro Ser Gln Val Tyr Thr
            260                 265                 270

Thr Ser Glu Tyr Leu Ser Gln Ser Leu Ser Pro Ser Asn Thr Thr Arg
        275                 280                 285

Trp
```

<210> SEQ ID NO 75
<211> LENGTH: 315
<212> TYPE: PRT
<213> ORGANISM: Artificial Sequence
<220> FEATURE:
<223> OTHER INFORMATION: Recombinant RSV G protein

<400> SEQUENCE: 75

```
Met Glu Tyr Trp Lys His Thr Asn His Gly Lys Asp Ala Gly Asn Glu
1               5                   10                  15
```

```
Leu Glu Thr Ser Met Ala Thr His Gly Asn Lys Leu Thr Asn Lys Ile
            20                  25                  30

Ala Gln Ile Thr Leu Ser Ile Leu Ala Met Ile Ile Ser Thr Ser Leu
        35                  40                  45

Ile Ile Ala Ala Ile Ile Phe Ile Ala Ser Ala Asn His Lys Val Thr
    50                  55                  60

Leu Thr Thr Ala Ile Ile Gln Asp Ala Thr Asn Gln Ile Lys Asn Thr
65                  70                  75                  80

Thr Pro Thr Tyr Leu Thr Gln Asn Pro Gln Leu Gly Ile Ser Phe Ser
                85                  90                  95

Asn Leu Ser Gly Thr Thr Ser Gln Ser Thr Thr Ile Leu Ala Ser Thr
            100                 105                 110

Thr Pro Ser Ala Glu Ser Thr Pro Gln Ser Thr Thr Val Lys Ile Lys
        115                 120                 125

Asn Thr Thr Thr Thr Gln Ile Leu Pro Ser Lys Pro Thr Thr Lys Gln
    130                 135                 140

Arg Gln Asn Lys Pro Gln Asn Lys Pro Asn Asn Asp Phe His Phe Glu
145                 150                 155                 160

Val Phe Asn Phe Val Pro Cys Ser Ile Cys Ser Asn Asn Pro Thr Cys
                165                 170                 175

Trp Ala Ile Cys Lys Arg Ile Pro Asn Lys Lys Pro Gly Lys Lys Thr
            180                 185                 190

Thr Thr Lys Pro Thr Lys Lys Pro Thr Leu Lys Thr Thr Lys Lys Asp
        195                 200                 205

Pro Lys Pro Gln Thr Thr Lys Pro Lys Glu Val Leu Thr Thr Lys Pro
    210                 215                 220

Thr Gly Lys Pro Thr Ile Asn Thr Thr Lys Thr Asn Ile Arg Thr Thr
225                 230                 235                 240

Leu Leu Thr Ser Asn Thr Lys Gly Asn Pro Glu His Thr Ser Gln Glu
                245                 250                 255

Glu Thr Leu His Ser Thr Thr Ser Glu Gly Tyr Leu Ser Pro Ser Gln
            260                 265                 270

Val Tyr Thr Thr Ser Gly Gln Glu Glu Thr Leu His Ser Thr Thr Ser
        275                 280                 285

Glu Gly Tyr Leu Ser Pro Ser Gln Val Tyr Thr Thr Ser Glu Tyr Leu
    290                 295                 300

Ser Gln Ser Leu Ser Ser Ser Asn Thr Thr Lys
305                 310                 315


<210> SEQ ID NO 76
<211> LENGTH: 312
<212> TYPE: PRT
<213> ORGANISM: Artificial Sequence
<220> FEATURE:
<223> OTHER INFORMATION: Recombinant RSV G protein

<400> SEQUENCE: 76

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Leu Thr Thr
    50                  55                  60
```

Ala Ile Ile Gln Asp Ala Thr Asn Gln Ile Lys Asn Thr Thr Pro Thr
65 70 75 80

Tyr Leu Thr Gln Asn Pro Gln Leu Gly Ile Ser Phe Ser Asn Leu Ser
85 90 95

Gly Thr Thr Ser Gln Ser Thr Thr Ile Leu Ala Ser Thr Thr Pro Ser
100 105 110

Ala Glu Ser Thr Pro Gln Ser Thr Thr Val Lys Ile Lys Asn Thr Thr
115 120 125

Thr Thr Gln Ile Leu Pro Ser Lys Pro Thr Thr Lys Gln Arg Gln Asn
130 135 140

Lys Pro Gln Asn Lys Pro Asn Asn Asp Phe His Phe Glu Val Phe Asn
145 150 155 160

Phe Val Pro Cys Ser Ile Cys Ser Asn Asn Pro Thr Cys Trp Ala Ile
165 170 175

Cys Lys Arg Ile Pro Asn Lys Lys Pro Gly Lys Lys Thr Thr Thr Lys
180 185 190

Pro Thr Lys Lys Pro Thr Leu Lys Thr Thr Lys Lys Asp Pro Lys Pro
195 200 205

Gln Thr Thr Lys Pro Lys Glu Val Leu Thr Thr Lys Pro Thr Gly Lys
210 215 220

Pro Thr Ile Asn Thr Thr Lys Thr Asn Ile Arg Thr Thr Leu Leu Thr
225 230 235 240

Ser Asn Thr Lys Gly Asn Pro Glu His Thr Ser Gln Glu Glu Thr Leu
245 250 255

His Ser Thr Thr Ser Glu Gly Tyr Leu Ser Pro Ser Gln Val Tyr Thr
260 265 270

Thr Ser Gly Gln Glu Glu Thr Leu His Ser Thr Thr Ser Glu Gly Tyr
275 280 285

Leu Ser Pro Ser Gln Val Tyr Thr Thr Ser Glu Tyr Leu Ser Gln Ser
290 295 300

Leu Ser Ser Ser Asn Thr Thr Lys
305 310

<210> SEQ ID NO 77
<211> LENGTH: 309
<212> TYPE: PRT
<213> ORGANISM: Artificial Sequence
<220> FEATURE:
<223> OTHER INFORMATION: Recombinant RSV G protein

<400> SEQUENCE: 77

Met Glu Tyr Trp Lys His Thr Asn His Gly Lys Asp Ala Gly Asn Glu
1 5 10 15

Leu Glu Thr Ser Met Ala Thr His Gly Asn Lys Leu Thr Asn Lys Ile
20 25 30

Ala Gln Ile Ala Leu Ser Val Leu Ala Met Ile Ile Ser Thr Ser Leu
35 40 45

Ile Ile Ala Ala Ile Ile Phe Ile Ile Ser Ala Asn His Lys Val Thr
50 55 60

Leu Thr Thr Val Thr Val Gln Thr Ile Lys Asn His Thr Glu Lys Asn
65 70 75 80

Ile Thr Thr Tyr Leu Thr Gln Val Ser Pro Glu Arg Val Ser Pro Ser
85 90 95

Lys Gln Leu Thr Thr Thr Pro Pro Ile Tyr Thr Asn Ser Ala Thr Ile
100 105 110

-continued

```
Ser Pro Asn Thr Lys Ser Glu Thr His His Thr Thr Ala Gln Thr Lys
        115                 120                 125

Gly Arg Thr Thr Thr Pro Thr Gln Asn Asn Lys Pro Ser Thr Lys Pro
    130                 135                 140

Arg Pro Lys Asn Pro Pro Lys Lys Pro Lys Asp Asp Tyr His Phe Glu
145                 150                 155                 160

Val Phe Asn Phe Val Pro Cys Ser Ile Cys Gly Asn Asn Gln Leu Cys
                165                 170                 175

Lys Ser Ile Cys Lys Thr Ile Pro Ser Asn Lys Pro Lys Lys Lys Pro
            180                 185                 190

Thr Ile Lys Pro Thr Asn Lys Pro Pro Thr Lys Thr Thr Asn Lys Arg
        195                 200                 205

Asp Pro Lys Lys Leu Ala Lys Thr Leu Lys Lys Glu Thr Thr Ile Asn
    210                 215                 220

Pro Thr Lys Lys Pro Thr Pro Lys Thr Thr Glu Arg Asp Thr Ser Thr
225                 230                 235                 240

Ser Gln Ser Thr Val Leu Asp Thr Thr Thr Ser Lys His Thr Glu Arg
                245                 250                 255

Asp Thr Ser Thr Ser Gln Ser Thr Val Leu Asp Thr Thr Thr Ser Lys
            260                 265                 270

His Thr Ile Gln Gln Gln Ser Leu His Ser Thr Thr Pro Glu Asn Thr
        275                 280                 285

Pro Asn Ser Thr Gln Thr Pro Thr Ala Ser Glu Pro Ser Thr Ser Asn
    290                 295                 300

Ser Thr Gln Lys Leu
305


<210> SEQ ID NO 78
<211> LENGTH: 306
<212> TYPE: PRT
<213> ORGANISM: Artificial Sequence
<220> FEATURE:
<223> OTHER INFORMATION: Recombinant RSV G protein

<400> SEQUENCE: 78

Met Glu Tyr Trp Lys His Thr Asn His Gly Lys Asp Ala Gly Asn Glu
1               5                   10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Asn His Lys Val Thr Leu Thr Thr
    50                  55                  60

Val Thr Val Gln Thr Ile Lys Asn His Thr Glu Lys Asn Ile Thr Thr
65                  70                  75                  80

Tyr Leu Thr Gln Val Ser Pro Glu Arg Val Ser Pro Ser Lys Gln Leu
                85                  90                  95

Thr Thr Thr Pro Pro Ile Tyr Thr Asn Ser Ala Thr Ile Ser Pro Asn
            100                 105                 110

Thr Lys Ser Glu Thr His His Thr Thr Ala Gln Thr Lys Gly Arg Thr
        115                 120                 125

Thr Thr Pro Thr Gln Asn Asn Lys Pro Ser Thr Lys Pro Arg Pro Lys
    130                 135                 140

Asn Pro Pro Lys Lys Pro Lys Asp Asp Tyr His Phe Glu Val Phe Asn
145                 150                 155                 160
```

-continued

```
Phe Val Pro Cys Ser Ile Cys Gly Asn Asn Gln Leu Cys Lys Ser Ile
                165                 170                 175

Cys Lys Thr Ile Pro Ser Asn Lys Pro Lys Lys Lys Pro Thr Ile Lys
            180                 185                 190

Pro Thr Asn Lys Pro Pro Thr Lys Thr Thr Asn Lys Arg Asp Pro Lys
        195                 200                 205

Lys Leu Ala Lys Thr Leu Lys Lys Glu Thr Thr Ile Asn Pro Thr Lys
    210                 215                 220

Lys Pro Thr Pro Lys Thr Thr Glu Arg Asp Thr Ser Thr Ser Gln Ser
225                 230                 235                 240

Thr Val Leu Asp Thr Thr Thr Ser Lys His Thr Glu Arg Asp Thr Ser
                245                 250                 255

Thr Ser Gln Ser Thr Val Leu Asp Thr Thr Thr Ser Lys His Thr Ile
            260                 265                 270

Gln Gln Gln Ser Leu His Ser Thr Thr Pro Glu Asn Thr Pro Asn Ser
        275                 280                 285

Thr Gln Thr Pro Thr Ala Ser Glu Pro Ser Thr Ser Asn Ser Thr Gln
    290                 295                 300

Lys Leu
305
```

<210> SEQ ID NO 79
<211> LENGTH: 296
<212> TYPE: PRT
<213> ORGANISM: Artificial Sequence
<220> FEATURE:
<223> OTHER INFORMATION: Recombinant RSV G protein

<400> SEQUENCE: 79

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Val Ala Gln Ile Thr Leu Ser Ile Leu Ala Met Ile Ile
        35                  40                  45

Ser Thr Ser Leu Ile Ile Ala Ala Ile Ile Phe Ile Ala Ser Ala Asn
    50                  55                  60

His Lys Val Thr Pro Thr Thr Ala Ile Ile Gln Asp Ala Thr Ser Gln
65                  70                  75                  80

Ile Lys Asn Thr Thr Pro Thr Tyr Leu Thr Gln Asn Pro Gln Leu Gly
                85                  90                  95

Ile Ser Pro Ser Asn Pro Ser Glu Ile Thr Ser Gln Ile Thr Thr Ile
            100                 105                 110

Leu Ala Ser Thr Thr Pro Gly Val Lys Ser Thr Leu Gln Ser Thr Thr
        115                 120                 125

Val Lys Thr Lys Asn Thr Thr Thr Thr Gln Thr Gln Pro Ser Lys Pro
    130                 135                 140

Thr Thr Lys Gln Arg Gln Asn Lys Pro Pro Ser Lys Pro Asn Asn Asp
145                 150                 155                 160

Phe His Phe Glu Val Phe Asn Phe Val Pro Cys Ser Ile Cys Ser Asn
                165                 170                 175

Asn Pro Thr Cys Trp Ala Ile Cys Lys Arg Ile Pro Asn Lys Lys Pro
            180                 185                 190

Gly Lys Lys Thr Thr Thr Lys Pro Thr Lys Lys Pro Thr Leu Lys Thr
        195                 200                 205
```

-continued

```
Thr Lys Lys Asp Pro Lys Pro Gln Thr Thr Lys Ser Lys Glu Val Pro
    210                 215                 220

Thr Thr Lys Pro Thr Glu Glu Pro Thr Ile Asn Thr Thr Lys Thr Asn
225                 230                 235                 240

Ile Ile Thr Thr Leu Leu Thr Ser Asn Thr Thr Gly Asn Pro Glu Leu
                245                 250                 255

Thr Ser Gln Met Glu Thr Phe His Ser Thr Ser Ser Glu Gly Asn Pro
            260                 265                 270

Ser Pro Ser Gln Val Ser Thr Thr Ser Glu Tyr Pro Ser Gln Pro Ser
        275                 280                 285

Ser Pro Pro Asn Thr Pro Arg Gln
    290                 295


<210> SEQ ID NO 80
<211> LENGTH: 293
<212> TYPE: PRT
<213> ORGANISM: Artificial Sequence
<220> FEATURE:
<223> OTHER INFORMATION: Recombinant RSV G protein

<400> SEQUENCE: 80

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Pro Thr Thr Ala Ile Ile Gln Asp Ala Thr Ser Gln Ile Lys Asn
65                  70                  75                  80

Thr Thr Pro Thr Tyr Leu Thr Gln Asn Pro Gln Leu Gly Ile Ser Pro
                85                  90                  95

Ser Asn Pro Ser Glu Ile Thr Ser Gln Ile Thr Thr Ile Leu Ala Ser
            100                 105                 110

Thr Thr Pro Gly Val Lys Ser Thr Leu Gln Ser Thr Thr Val Lys Thr
        115                 120                 125

Lys Asn Thr Thr Thr Thr Gln Thr Gln Pro Ser Lys Pro Thr Thr Lys
    130                 135                 140

Gln Arg Gln Asn Lys Pro Pro Ser Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Lys Lys
            180                 185                 190

Thr Thr Thr Lys Pro Thr Lys Lys Pro Thr Leu Lys Thr Thr Lys Lys
        195                 200                 205

Asp Pro Lys Pro Gln Thr Thr Lys Ser Lys Glu Val Pro Thr Thr Lys
    210                 215                 220

Pro Thr Glu Glu Pro Thr Ile Asn Thr Thr Lys Thr Asn Ile Ile Thr
225                 230                 235                 240

Thr Leu Leu Thr Ser Asn Thr Thr Gly Asn Pro Glu Leu Thr Ser Gln
                245                 250                 255

Met Glu Thr Phe His Ser Thr Ser Ser Glu Gly Asn Pro Ser Pro Ser
            260                 265                 270
```

```
Gln Val Ser Thr Thr Ser Glu Tyr Pro Ser Gln Pro Ser Ser Pro Pro
        275                 280                 285

Asn Thr Pro Arg Gln
    290


<210> SEQ ID NO 81
<211> LENGTH: 297
<212> TYPE: PRT
<213> ORGANISM: Artificial Sequence
<220> FEATURE:
<223> OTHER INFORMATION: Recombinant RSV G protein

<400> SEQUENCE: 81

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Ala Gln Ile Ala Leu Ser Val Leu Ala Met Ile Ile
        35                  40                  45

Ser Thr Ser Leu Ile Ile Ala Ala Ile Ile Phe Ile Ile Ser Ala Asn
    50                  55                  60

His Lys Val Thr Leu Thr Thr Val Thr Val Gln Thr Ile Lys Asn His
65                  70                  75                  80

Thr Glu Lys Asn Ile Thr Thr Tyr Leu Thr Gln Val Pro Pro Glu Arg
                85                  90                  95

Val Ser Ser Ser Lys Gln Pro Thr Thr Thr Ser Pro Ile His Thr Asn
            100                 105                 110

Ser Ala Thr Thr Ser Pro Asn Thr Lys Ser Glu Thr His His Thr Thr
        115                 120                 125

Ala Gln Thr Lys Gly Arg Thr Thr Thr Ser Thr Gln Thr Asn Lys Pro
    130                 135                 140

Ser Thr Lys Pro Arg Leu Lys Asn Pro Pro Lys Lys Pro Lys Asp Asp
145                 150                 155                 160

Tyr His Phe Glu Val Phe Asn Phe Val Pro Cys Ser Ile Cys Gly Asn
                165                 170                 175

Asn Gln Leu Cys Lys Ser Ile Cys Lys Thr Ile Pro Ser Asn Lys Pro
            180                 185                 190

Lys Lys Lys Pro Thr Ile Lys Pro Thr Asn Lys Pro Thr Thr Lys Thr
        195                 200                 205

Thr Asn Lys Arg Asp Pro Lys Thr Pro Ala Lys Thr Thr Lys Lys Glu
    210                 215                 220

Thr Thr Thr Asn Pro Thr Lys Lys Pro Thr Leu Thr Thr Thr Glu Arg
225                 230                 235                 240

Asp Thr Ser Thr Ser Gln Ser Thr Val Leu Asp Thr Thr Thr Leu Glu
                245                 250                 255

His Thr Ile Gln Gln Gln Ser Leu His Ser Thr Thr Pro Glu Asn Thr
            260                 265                 270

Pro Asn Ser Thr Gln Thr Pro Thr Ala Ser Glu Pro Ser Thr Ser Asn
        275                 280                 285

Ser Thr Gln Asn Thr Gln Ser His Ala
    290                 295


<210> SEQ ID NO 82
<211> LENGTH: 294
<212> TYPE: PRT
<213> ORGANISM: Artificial Sequence
<220> FEATURE:
```

<223> OTHER INFORMATION: Recombinant RSV G protein

<400> SEQUENCE: 82

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Leu Thr Thr Val Thr Val Gln Thr Ile Lys Asn His Thr Glu Lys
65                  70                  75                  80

Asn Ile Thr Thr Tyr Leu Thr Gln Val Pro Pro Glu Arg Val Ser Ser
                85                  90                  95

Ser Lys Gln Pro Thr Thr Thr Ser Pro Ile His Thr Asn Ser Ala Thr
            100                 105                 110

Thr Ser Pro Asn Thr Lys Ser Glu Thr His His Thr Thr Ala Gln Thr
        115                 120                 125

Lys Gly Arg Thr Thr Thr Ser Thr Gln Thr Asn Lys Pro Ser Thr Lys
    130                 135                 140

Pro Arg Leu Lys Asn Pro Pro Lys Lys Pro Lys Asp Asp Tyr His Phe
145                 150                 155                 160

Glu Val Phe Asn Phe Val Pro Cys Ser Ile Cys Gly Asn Asn Gln Leu
                165                 170                 175

Cys Lys Ser Ile Cys Lys Thr Ile Pro Ser Asn Lys Pro Lys Lys Lys
            180                 185                 190

Pro Thr Ile Lys Pro Thr Asn Lys Pro Thr Thr Lys Thr Thr Asn Lys
        195                 200                 205

Arg Asp Pro Lys Thr Pro Ala Lys Thr Thr Lys Lys Glu Thr Thr Thr
    210                 215                 220

Asn Pro Thr Lys Lys Pro Thr Leu Thr Thr Thr Glu Arg Asp Thr Ser
225                 230                 235                 240

Thr Ser Gln Ser Thr Val Leu Asp Thr Thr Thr Leu Glu His Thr Ile
                245                 250                 255

Gln Gln Gln Ser Leu His Ser Thr Thr Pro Glu Asn Thr Pro Asn Ser
            260                 265                 270

Thr Gln Thr Pro Thr Ala Ser Glu Pro Ser Thr Ser Asn Ser Thr Gln
        275                 280                 285

Asn Thr Gln Ser His Ala
    290
```

<210> SEQ ID NO 83
<211> LENGTH: 296
<212> TYPE: PRT
<213> ORGANISM: Artificial Sequence
<220> FEATURE:
<223> OTHER INFORMATION: Recombinant RSV G protein

<400> SEQUENCE: 83

```
Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Ala Gln Ile Thr Leu Ser Ile Leu Ala Met Ile Ile
        35                  40                  45
```

-continued

```
Ser Thr Ser Leu Ile Ile Ala Ala Ile Ile Phe Ile Ala Ser Ala Asn
    50                  55                  60

His Lys Val Thr Leu Thr Thr Ala Ile Ile Gln Asp Ala Thr Asn Gln
65                  70                  75                  80

Ile Lys Asn Thr Thr Pro Thr Tyr Leu Thr Gln Asn Pro Gln Leu Gly
                85                  90                  95

Ile Ser Leu Ser Asn Leu Ser Glu Thr Thr Ser Lys Pro Thr Thr Ile
            100                 105                 110

Leu Ala Leu Thr Thr Pro Asn Ala Glu Ser Thr Pro Gln Ser Thr Thr
        115                 120                 125

Val Lys Thr Lys Asn Thr Thr Thr Thr Gln Ile Gln Pro Ser Lys Pro
    130                 135                 140

Thr Thr Lys Gln Arg Gln Asn Lys Pro Gln Asn Lys Pro Asn Asn Asp
145                 150                 155                 160

Phe His Phe Glu Val Phe Asn Phe Val Pro Cys Ser Ile Cys Ser Asn
                165                 170                 175

Asn Pro Thr Cys Trp Ala Ile Cys Lys Arg Ile Pro Asn Lys Lys Pro
            180                 185                 190

Gly Arg Lys Thr Thr Thr Lys Pro Thr Lys Gln Pro Ala Ile Lys Thr
        195                 200                 205

Thr Lys Lys Asp Pro Lys Pro Gln Thr Thr Lys Pro Lys Glu Val Leu
    210                 215                 220

Thr Thr Lys Pro Thr Glu Lys Pro Thr Ile Asn Thr Thr Lys Thr Asn
225                 230                 235                 240

Ile Arg Thr Thr Leu Leu Thr Ser Asn Ile Thr Glu Asn Gln Glu His
                245                 250                 255

Thr Ser Gln Lys Glu Thr Leu His Ser Thr Thr Ser Glu Gly Asn Pro
            260                 265                 270

Ser Pro Ser Gln Val Tyr Thr Thr Ser Glu Tyr Leu Ser Gln Ser Leu
        275                 280                 285

Ser Pro Ser Asn Thr Thr Arg Trp
    290                 295


<210> SEQ ID NO 84
<211> LENGTH: 293
<212> TYPE: PRT
<213> ORGANISM: Artificial Sequence
<220> FEATURE:
<223> OTHER INFORMATION: Recombinant RSV G protein

<400> SEQUENCE: 84

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Leu Thr Thr Ala Ile Ile Gln Asp Ala Thr Asn Gln Ile Lys Asn
65                  70                  75                  80

Thr Thr Pro Thr Tyr Leu Thr Gln Asn Pro Gln Leu Gly Ile Ser Leu
                85                  90                  95

Ser Asn Leu Ser Glu Thr Thr Ser Lys Pro Thr Thr Ile Leu Ala Leu
            100                 105                 110
```

-continued

```
Thr Thr Pro Asn Ala Glu Ser Thr Pro Gln Ser Thr Thr Val Lys Thr
        115                 120                 125

Lys Asn Thr Thr Thr Thr Gln Ile Gln Pro Ser Lys Pro Thr Thr Lys
    130                 135                 140

Gln Arg Gln Asn Lys Pro Gln Asn Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Arg Lys
            180                 185                 190

Thr Thr Thr Lys Pro Thr Lys Gln Pro Ala Ile Lys Thr Thr Lys Lys
        195                 200                 205

Asp Pro Lys Pro Gln Thr Thr Lys Pro Lys Glu Val Leu Thr Thr Lys
    210                 215                 220

Pro Thr Glu Lys Pro Thr Ile Asn Thr Thr Lys Thr Asn Ile Arg Thr
225                 230                 235                 240

Thr Leu Leu Thr Ser Asn Ile Thr Glu Asn Gln Glu His Thr Ser Gln
                245                 250                 255

Lys Glu Thr Leu His Ser Thr Thr Ser Glu Gly Asn Pro Ser Pro Ser
            260                 265                 270

Gln Val Tyr Thr Thr Ser Glu Tyr Leu Ser Gln Ser Leu Ser Pro Ser
        275                 280                 285

Asn Thr Thr Arg Trp
    290


<210> SEQ ID NO 85
<211> LENGTH: 319
<212> TYPE: PRT
<213> ORGANISM: Artificial Sequence
<220> FEATURE:
<223> OTHER INFORMATION: Recombinant RSV G protein

<400> SEQUENCE: 85

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Ala Gln Ile Thr Leu Ser Ile Leu Ala Met Ile Ile
        35                  40                  45

Ser Thr Ser Leu Ile Ile Ala Ala Ile Ile Phe Ile Ala Ser Ala Asn
    50                  55                  60

His Lys Val Thr Leu Thr Thr Ala Ile Ile Gln Asp Ala Thr Asn Gln
65                  70                  75                  80

Ile Lys Asn Thr Thr Pro Thr Tyr Leu Thr Gln Asn Pro Gln Leu Gly
                85                  90                  95

Ile Ser Phe Ser Asn Leu Ser Gly Thr Thr Ser Gln Ser Thr Thr Ile
            100                 105                 110

Leu Ala Ser Thr Thr Pro Ser Ala Glu Ser Thr Pro Gln Ser Thr Thr
        115                 120                 125

Val Lys Ile Lys Asn Thr Thr Thr Thr Gln Ile Leu Pro Ser Lys Pro
    130                 135                 140

Thr Thr Lys Gln Arg Gln Asn Lys Pro Gln Asn Lys Pro Asn Asn Asp
145                 150                 155                 160

Phe His Phe Glu Val Phe Asn Phe Val Pro Cys Ser Ile Cys Ser Asn
                165                 170                 175
```

```
Asn Pro Thr Cys Trp Ala Ile Cys Lys Arg Ile Pro Asn Lys Lys Pro
            180                 185                 190

Gly Lys Lys Thr Thr Thr Lys Pro Thr Lys Lys Pro Thr Leu Lys Thr
        195                 200                 205

Thr Lys Lys Asp Pro Lys Pro Gln Thr Thr Lys Pro Lys Glu Val Leu
    210                 215                 220

Thr Thr Lys Pro Thr Gly Lys Pro Thr Ile Asn Thr Thr Lys Thr Asn
225                 230                 235                 240

Ile Arg Thr Thr Leu Leu Thr Ser Asn Thr Lys Gly Asn Pro Glu His
                245                 250                 255

Thr Ser Gln Glu Glu Thr Leu His Ser Thr Thr Ser Glu Gly Tyr Leu
            260                 265                 270

Ser Pro Ser Gln Val Tyr Thr Thr Ser Gly Gln Glu Glu Thr Leu His
        275                 280                 285

Ser Thr Thr Ser Glu Gly Tyr Leu Ser Pro Ser Gln Val Tyr Thr Thr
    290                 295                 300

Ser Glu Tyr Leu Ser Gln Ser Leu Ser Ser Ser Asn Thr Thr Lys
305                 310                 315


<210> SEQ ID NO 86
<211> LENGTH: 316
<212> TYPE: PRT
<213> ORGANISM: Artificial Sequence
<220> FEATURE:
<223> OTHER INFORMATION: Recombinant RSV G protein

<400> SEQUENCE: 86

Met Ala Glu Lys Gly Lys Thr Asn Ser Ser Tyr Trp Ser Thr Thr Arg
1               5                   10                  15

Asn Asp Asn Ser Thr Val Asn Thr His Ile Asn Thr Pro Ala Gly Arg
            20                  25                  30

Thr His Trp Ile Leu Leu Ile Ala Thr Thr Met His Thr Val Leu Ser
        35                  40                  45

Phe Ile Ile Met Ile Leu Cys Ile Asp Leu Ile Ile Asn His Lys Val
    50                  55                  60

Thr Leu Thr Thr Ala Ile Ile Gln Asp Ala Thr Asn Gln Ile Lys Asn
65                  70                  75                  80

Thr Thr Pro Thr Tyr Leu Thr Gln Asn Pro Gln Leu Gly Ile Ser Phe
                85                  90                  95

Ser Asn Leu Ser Gly Thr Thr Ser Gln Ser Thr Thr Ile Leu Ala Ser
            100                 105                 110

Thr Thr Pro Ser Ala Glu Ser Thr Pro Gln Ser Thr Thr Val Lys Ile
        115                 120                 125

Lys Asn Thr Thr Thr Thr Gln Ile Leu Pro Ser Lys Pro Thr Thr Lys
    130                 135                 140

Gln Arg Gln Asn Lys Pro Gln Asn Lys Pro Asn Asn Asp Phe His Phe
145                 150                 155                 160

Glu Val Phe Asn Phe Val Pro Cys Ser Ile Cys Ser Asn Asn Pro Thr
                165                 170                 175

Cys Trp Ala Ile Cys Lys Arg Ile Pro Asn Lys Lys Pro Gly Lys Lys
            180                 185                 190

Thr Thr Thr Lys Pro Thr Lys Lys Pro Thr Leu Lys Thr Thr Lys Lys
        195                 200                 205

Asp Pro Lys Pro Gln Thr Thr Lys Pro Lys Glu Val Leu Thr Thr Lys
    210                 215                 220
```

Pro Thr Gly Lys Pro Thr Ile Asn Thr Thr Lys Thr Asn Ile Arg Thr
225 230 235 240

Thr Leu Leu Thr Ser Asn Thr Lys Gly Asn Pro Glu His Thr Ser Gln
245 250 255

Glu Glu Thr Leu His Ser Thr Thr Ser Glu Gly Tyr Leu Ser Pro Ser
260 265 270

Gln Val Tyr Thr Thr Ser Gly Gln Glu Glu Thr Leu His Ser Thr Thr
275 280 285

Ser Glu Gly Tyr Leu Ser Pro Ser Gln Val Tyr Thr Thr Ser Glu Tyr
290 295 300

Leu Ser Gln Ser Leu Ser Ser Ser Asn Thr Thr Lys
305 310 315

<210> SEQ ID NO 87
<211> LENGTH: 313
<212> TYPE: PRT
<213> ORGANISM: Artificial Sequence
<220> FEATURE:
<223> OTHER INFORMATION: Recombinant RSV G protein

<400> SEQUENCE: 87

Met Ala Glu Lys Gly Lys Thr Asn Ser Ser Tyr Trp Ser Thr Thr Arg
1 5 10 15

Asn Asp Asn Ser Thr Val Asn Thr His Ile Asn Thr Pro Ala Gly Arg
20 25 30

Thr His Trp Ile Ala Gln Ile Ala Leu Ser Val Leu Ala Met Ile Ile
35 40 45

Ser Thr Ser Leu Ile Ile Ala Ala Ile Ile Phe Ile Ile Ser Ala Asn
50 55 60

His Lys Val Thr Leu Thr Thr Val Thr Val Gln Thr Ile Lys Asn His
65 70 75 80

Thr Glu Lys Asn Ile Thr Thr Tyr Leu Thr Gln Val Ser Pro Glu Arg
85 90 95

Val Ser Pro Ser Lys Gln Leu Thr Thr Thr Pro Pro Ile Tyr Thr Asn
100 105 110

Ser Ala Thr Ile Ser Pro Asn Thr Lys Ser Glu Thr His His Thr Thr
115 120 125

Ala Gln Thr Lys Gly Arg Thr Thr Thr Pro Thr Gln Asn Asn Lys Pro
130 135 140

Ser Thr Lys Pro Arg Pro Lys Asn Pro Pro Lys Lys Pro Lys Asp Asp
145 150 155 160

Tyr His Phe Glu Val Phe Asn Phe Val Pro Cys Ser Ile Cys Gly Asn
165 170 175

Asn Gln Leu Cys Lys Ser Ile Cys Lys Thr Ile Pro Ser Asn Lys Pro
180 185 190

Lys Lys Lys Pro Thr Ile Lys Pro Thr Asn Lys Pro Pro Thr Lys Thr
195 200 205

Thr Asn Lys Arg Asp Pro Lys Lys Leu Ala Lys Thr Leu Lys Lys Glu
210 215 220

Thr Thr Ile Asn Pro Thr Lys Lys Pro Thr Pro Lys Thr Thr Glu Arg
225 230 235 240

Asp Thr Ser Thr Ser Gln Ser Thr Val Leu Asp Thr Thr Thr Ser Lys
245 250 255

His Thr Glu Arg Asp Thr Ser Thr Ser Gln Ser Thr Val Leu Asp Thr
260 265 270

Thr Thr Ser Lys His Thr Ile Gln Gln Gln Ser Leu His Ser Thr Thr
275 280 285

Pro Glu Asn Thr Pro Asn Ser Thr Gln Thr Pro Thr Ala Ser Glu Pro
290 295 300

Ser Thr Ser Asn Ser Thr Gln Lys Leu
305 310

<210> SEQ ID NO 88
<211> LENGTH: 310
<212> TYPE: PRT
<213> ORGANISM: Artificial Sequence
<220> FEATURE:
<223> OTHER INFORMATION: Recombinant RSV G protein

<400> SEQUENCE: 88

Met Ala Glu Lys Gly Lys Thr Asn Ser Ser Tyr Trp Ser Thr Thr Arg
1 5 10 15

Asn Asp Asn Ser Thr Val Asn Thr His Ile Asn Thr Pro Ala Gly Arg
20 25 30

Thr His Trp Ile Leu Leu Ile Ala Thr Thr Met His Thr Val Leu Ser
35 40 45

Phe Ile Ile Met Ile Leu Cys Ile Asp Leu Ile Ile Asn His Lys Val
50 55 60

Thr Leu Thr Thr Val Thr Val Gln Thr Ile Lys Asn His Thr Glu Lys
65 70 75 80

Asn Ile Thr Thr Tyr Leu Thr Gln Val Ser Pro Glu Arg Val Ser Pro
85 90 95

Ser Lys Gln Leu Thr Thr Thr Pro Pro Ile Tyr Thr Asn Ser Ala Thr
100 105 110

Ile Ser Pro Asn Thr Lys Ser Glu Thr His His Thr Thr Ala Gln Thr
115 120 125

Lys Gly Arg Thr Thr Thr Pro Thr Gln Asn Asn Lys Pro Ser Thr Lys
130 135 140

Pro Arg Pro Lys Asn Pro Pro Lys Lys Pro Lys Asp Asp Tyr His Phe
145 150 155 160

Glu Val Phe Asn Phe Val Pro Cys Ser Ile Cys Gly Asn Asn Gln Leu
165 170 175

Cys Lys Ser Ile Cys Lys Thr Ile Pro Ser Asn Lys Pro Lys Lys Lys
180 185 190

Pro Thr Ile Lys Pro Thr Asn Lys Pro Pro Thr Lys Thr Thr Asn Lys
195 200 205

Arg Asp Pro Lys Lys Leu Ala Lys Thr Leu Lys Lys Glu Thr Thr Ile
210 215 220

Asn Pro Thr Lys Lys Pro Thr Pro Lys Thr Thr Glu Arg Asp Thr Ser
225 230 235 240

Thr Ser Gln Ser Thr Val Leu Asp Thr Thr Thr Ser Lys His Thr Glu
245 250 255

Arg Asp Thr Ser Thr Ser Gln Ser Thr Val Leu Asp Thr Thr Thr Ser
260 265 270

Lys His Thr Ile Gln Gln Gln Ser Leu His Ser Thr Thr Pro Glu Asn
275 280 285

Thr Pro Asn Ser Thr Gln Thr Pro Thr Ala Ser Glu Pro Ser Thr Ser
290 295 300

Asn Ser Thr Gln Lys Leu
305 310

<210> SEQ ID NO 89
<211> LENGTH: 897
<212> TYPE: DNA
<213> ORGANISM: Artificial Sequence
<220> FEATURE:
<223> OTHER INFORMATION: Recombinant RSV G protein

<400> SEQUENCE: 89
atgtcaaaga acaaggatca gagaactgcc aagaccctgg aaagaacctg ggacaccctg 60
aaccacctgc tgtttatctc aagctgcctg tacaagctga atctgaaaag tgtggcccag 120
atcaccctgt caattctggc tatgatcatt tcaacaagcc tgatcattgc cgctatcatt 180
ttcatcgcaa gcgccaacca caaggtcacc cccaccacag ctatcattca ggacgcaaca 240
tcccagatta agaacactac ccccacctat ctgacacaga atcctcagct gggaatctcc 300
ccatctaacc cctcagagat taccagccag atcacaacta ttctggcctc caccacacct 360
ggcgtgaagt ccactctgca gtctactacc gtcaagacca aaaatacaac taccacacag 420
acacagcctt ctaagccaac taccaaacag cggcagaata agccccctag taaaccaaac 480
aatgacttcc attttgaggt gttcaacttt gtcccatgca gcatctgttc caacaatccc 540
acctgctggg ccatctgtaa gagaattcca aacaagaaac ccggcaagaa gaccactacc 600
aaacctacta agaaaccaac cctgaagaca actaagaaag atcctaaacc acagaccaca 660
aagtctaaag aagtgcccac taccaagcct acagaggaac caactatcaa cacaactaag 720
actaacatca tcaccacact gctgacaagc aacactaccg gcaatcccga gctgaccagc 780
cagatggaaa cctttcactc cacaagctcc gaggggaatc ccagtccttc acaggtgtct 840
acaactagtg aataccccag ccagccttct agtccaccca acacccctag gcagtga 897

<210> SEQ ID NO 90
<211> LENGTH: 899
<212> TYPE: DNA
<213> ORGANISM: Artificial Sequence
<220> FEATURE:
<223> OTHER INFORMATION: Recombinant RSV G protein

<400> SEQUENCE: 90
agtctaaaca caagaatcag cggaccgccc ggaccttgga aaagacttgg gataccctta 60
accaccttat cgtgatttcc tcctgcctgt accgcctcaa cctcaagagc attgctcaga 120
tcgcgctctc agtgctggcc atgataatct ccacttcctt gataattgcc gccattatct 180
tcattatttc tgcaaaccac aaagtcaccc tgaccaccgt taccgtgcaa accattaaaa 240
accacacgga gaagaacatc actacatacc tgactcaggt tcccccggag cgagtgagca 300
gctccaagca gcccacaaca acaagcccta tccatacaaa ttcagcaaca acaagtccaa 360
acacaaagtc tgaaacgcat cacacaaccg ctcagacgaa aggcaggacc acaacatcca 420
cccagactaa taaacccagt actaagccta gactgaagaa ccctcccaag aaacctaagg 480
acgactatca tttcgaggtg tttaattttg taccttgcag catctgtggc aacaatcagc 540
tctgcaaaag catctgtaag accatcccgt ctaataagcc aaagaagaag cccacgataa 600
aaccaacaaa taaaccaact accaagacaa caaataagag ggacccaaag acccccgcta 660
aaactaccaa gaaggagact accaccaacc cgacaaagaa acccaccctg acgactactg 720
agagagatac ttcaacttca caaagcaccg tcctggatac aactaccctg gagcacacaa 780
tccagcaaca gagcctgcat agtactacgc ctgaaaacac tccaaactct acccagacgc 840
ccacagcctc agaaccttct acctccaata gtacccaaaa tacccagagt catgcatag 899

<210> SEQ ID NO 91
<211> LENGTH: 16386
<212> TYPE: DNA
<213> ORGANISM: Artificial Sequence
<220> FEATURE:
<223> OTHER INFORMATION: Recombinant rB/HPIV3 sequence

<400> SEQUENCE: 91
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180
ttattcccgg gcaaaaaaac actgtgtcta tatttgctct tggaccatca ataacagatg 240
acaatgataa aatgacattg gctcttctct tttgtctca ttctttagac aatgaaaagc 300
agcatgcgca aagagctgga tttttagttt ctctgttatc aatggcttat gccaacccag 360
aattatattt aacatcaaat ggtagtaatg cagatgttaa atatgttatc tacatgatag 420
agaaagaccc aggaagacag aaatatggtg ggtttgtcgt caagactaga gagatggttt 480
atgaaaagac aactgattgg atgttcggga gtgatcttga gtatgatcaa gacaatatgt 540
tgcaaaatgg tagaagcact tctacaatcg aggatcttgt tcatactttt ggatatccat 600
cgtgtcttgg agcccttata atccaagttt ggataatact tgttaaggct ataaccagta 660
tatcaggatt gaggaaagga ttctttactc ggttagaagc atttcgacaa gatggaacag 720
ttaaatccag tctagtgttg agcggtgatg cagtagaaca aattggatca attatgaggt 780
cccaacagag cttggtaaca ctcatggttg aaacactgat aacaatgaac acaggcagga 840
atgatctgac aacaatagaa aagaatatac agattgtagg aaactacatc agagatgcag 900
gtcttgcttc atttttcaac acaatcagat atggcattga gactagaatg gcagctctaa 960
ctctgtctac ccttagaccg gatatcaaca gactcaaggc actgatcgag ttatatctat 1020
caaaggggcc acgtgctcct tttatatgca ttttgagaga tcccgtgcat ggtgagtttg 1080
caccaggcaa ctatcctgcc ctctggagtt atgcgatggg tgtagcagtt gtacaaaaca 1140
aggccatgca acagtatgta acaggaaggt cttatctgga tattgaaatg ttccaacttg 1200
gtcaagcagt ggcacgtgat gccgagtcgc agatgagttc aatattagag gatgaactgg 1260
gggtcacaca agaagccaag caaagcttga agaaacacat gaagaacatc agcagttcag 1320
atacaacctt tcataagcct acaggggat cagccataga aatggcgata gatgaagaag 1380
cagggcagcc tgaatccaga ggagatcagg atcaaggaga tgagcctcgg tcatccatag 1440
ttccttatgc atgggcagac gaaaccggga atgacaatca aactgaatca actacagaaa 1500
ttgacagcat caaaactgaa caaagaaaca tcagagacag gctgaacaaa agactcaacg 1560
agaaaaggaa acagagtgac ccgagatcaa ctgacatcac aaacaacaca aatcaaactg 1620
aaatagatga tttgttcagt gcattcggaa gcaactagtc acaaagagat gaccaggcgc 1680
gccaagtaag aaaaacttag gattaatgga cctgcaggat gtccaaaaac aaggaccaac 1740
gcaccgctaa gacattagaa aggacctggg acactctcaa tcatttatta ttcatatcat 1800
cgtgcttata taagttaaat cttaaatctg tagcacaaat cacattatcc attctggcaa 1860
tgataatctc aacttcactt ataattgcag ccatcatatt catagcctcg gcaaaccaca 1920
aagtcacacc aacaactgca atcatacaag atgcaacaag ccagatcaag aacacaaccc 1980
caacatacct cacccagaat cctcagcttg gaatcagtcc ctctaatccg tctgaaatta 2040
catcacaaat caccaccata ctagcttcaa caacaccagg agtcaagtca accctgcaat 2100
ccacaacagt caagaccaaa aacacaacaa caactcaaac acaacccagc aagcccacca 2160
caaaacaacg ccaaaacaaa ccaccaagca aacccaataa tgattttcac tttgaagtgt 2220
tcaactttgt accctgcagc atatgcagca acaatccaac ctgctgggct atctgcaaaa 2280
gaataccaaa caaaaaacca ggaaagaaaa ccactaccaa gcccacaaaa aaaccaaccc 2340
tcaagacaac caaaaaagat cccaaacctc aaaccactaa atcaaaggaa gtacccacca 2400
ccaagcccac agaagagcca accatcaaca ccaccaaaac aaacatcata actacactac 2460
tcacctccaa caccacagga aatccagaac tcacaagtca aatggaaacc ttccactcaa 2520
cttcctccga aggcaatcca agcccttctc aagtctctac aacatccgag tacccatcac 2580
aaccttcatc tccacccaac acaccacgcc agtgatagct agcggcgcgc cagcaacaag 2640
taagaaaaac ttaggattaa tggaaattat ccaatccaga gacggaagga caaatccaga 2700
atccaaccac aactcaatca accaaagatt catggaagac aatgttcaaa acaatcaaat 2760
catggattct tgggaagagg gatcaggaga taaatcatct gacatctcat cggccctcga 2820
catcattgaa ttcatactca gcaccgactc ccaagagaac acggcagaca gcaatgaaat 2880
caacacagga accacaagac ttagcacgac aatctaccaa cctgaatcca aaacaacaga 2940
aacaagcaag gaaaatagtg gaccagctaa caaaaatcga cagtttgggg catcacacga 3000
acgtgccaca gagacaaaag atagaaatgt taatcaggag actgtacagg gaggatatag 3060
gagaggaagc agcccagata gtagaactga gactatggtc actcgaagaa tctccagaag 3120
cagcccagat cctaacaatg gaacccaaat ccaggaagat attgattaca atgaagttgg 3180
agagatggat aaggactcta ctaagaggga aatgcgacaa tttaaagatg ttccagtcaa 3240
ggtatcagga agtgatgcca ttcctccaac aaaacaagat ggagacggtg atgatggaag 3300
aggcctggaa tctatcagta catttgattc aggatatacc agtatagtga ctgccgcaac 3360
actagatgac gaagaagaac tccttatgaa gaacaacagg ccaagaaagt atcaatcaac 3420
accccagaac agtgacaagg gaattaaaaa aggggttgga aggccaaaag acacagacaa 3480
acaatcatca atattggact acgaactcaa cttcaaagga tcgaagaaga gccagaaaat 3540
cctcaaagcc agcacgaata caggagaacc aacaagacca cagaatggat cccaggggaa 3600
gagaatcaca tcctggaaca tcctcaacag cgagagcggc aatcgaacag aatcaacaaa 3660
ccaaacccat cagacatcaa cctcgggaca gaaccacaca atgggaccaa gcagaacaac 3720
ctccgaacca aggatcaaga cacaaaagac ggatggaaag gaaagagagg acacagaaga 3780
gagcactcga tttacagaaa gggcgattac attattacag aatcttggtg taatccaatc 3840
tgcagcaaaa ttagacctat accaagacaa gagagttgtg tgtgtggcga atgtcctaaa 3900
caatgcagat actgcatcaa agatagactt cctagcaggt ttgatgatag gagtgtcaat 3960
ggatcatgat accaaattaa atcagattca gaacgagata ttaagtttga aaactgatct 4020
taaaaagatg gatgaatcac atagaagact aattgagaat caaaaagaac aattatcact 4080
gatcacatca ttaatctcaa atcttaaaat tatgacagag agaggaggga agaaggacca 4140
accagaacct agcgggagga catccatgat caagacaaaa gcaaaagaag agaaaataaa 4200
gaaagtcagg tttgaccctc ttatggaaac acagggcatc gagaaaaaca tccctgacct 4260
ctatagatca atagagaaaa caccagaaaa cgacacacag atcaaatcag aaataaacag 4320
attgaatgat gaatccaatg ccactagatt agtacctaga agaataagca gtacaatgag 4380

-continued

```
atcattaata ataatcatta acaacagcaa tttatcatca aaagcaaagc aatcatacat   4440
caacgaactc aagctctgca agagtgacga ggaagtgtct gagttgatgg acatgttcaa   4500
tgaggatgtc agctcccagt aaaccgccaa ccaagggtca acaccaagaa aaccaatagc   4560
acaaaacagc caatcagaga ccaccccaat acaccaaacc aatcaacaca taacaaagat   4620
cgcggccgca tagatgatta agaaaaactt aggatgaaag gactaatcaa tcctccgaaa   4680
caatgagcat caccaactcc acaatctaca cattcccaga atcctctttc tccgagaatg   4740
gcaacataga gccgttacca ctcaaggtca atgaacagag aaaggccata cctcatatta   4800
gggttgtcaa gataggagat ccgcccaaac atggatccag atatctggat gtctttttac   4860
tgggcttctt tgagatggaa aggtcaaaag acaggtatgg gagcataagt gatctagatg   4920
atgatccaag ttacaaggtt tgtggctctg gatcattgcc acttgggttg gctagataca   4980
ccggaaatga tcaggaactc ctacaggctg caaccaagct cgatatagaa gtaagaagaa   5040
ctgtaaaggc tacggagatg atagtttaca ctgtacaaaa catcaaacct gaactatatc   5100
catggtccag tagattaaga aaagggatgt tatttgacgc taataaggtt gcacttgctc   5160
ctcaatgtct tccactagat agagggataa aattcagggt gatatttgtg aactgcacag   5220
caattggatc aataactcta ttcaaaatcc ctaagtccat ggcattgtta tcattgccta   5280
atacaatatc aataaatcta caagtacata tcaaaacagg agttcagaca gattccaaag   5340
gagtagttca gattctagat gaaaaaggtg aaaaatcact aaatttcatg gttcatctcg   5400
ggttgatcaa aaggaagatg ggcagaatgt actcagttga atattgtaag cagaagatcg   5460
agaagatgag attattattc tcattgggat tagttggagg gatcagcttc cacgtcaacg   5520
caactggctc tatatcaaag acattagcaa gtcaattagc attcaaaaga gaaatctgct   5580
atcccctaat ggatctgaat ccacacttaa attcagttat atgggcatca tcagttgaaa   5640
ttacaagggt agatgcagtt ctccagcctt cattacctgg cgaattcaga tactacccaa   5700
acatcatagc aaaaggggtc gggaaaatca gacagtaaaa tcaacaaccc tgatatccac   5760
cggtgtatta agccgaagca aataaaggat aatcaaaaac ttaggacaaa agaggtcaat   5820
accaacaact attagcagtc acactcgcaa gaataagaga gaagggacca aaaaagtcaa   5880
ataggagaaa tcaaaacaaa aggtacagaa caccagaaca acaaaatcaa aacatccaac   5940
tcactcaaaa caaaaattcc aaaagagacc ggcaacacaa caagcactga acacaatgcc   6000
aacttcaata ctgctaatta ttacaaccat gatcatggca tctttctgcc aaatagatat   6060
cacaaaacta cagcacgtag gtgtattggt caacagtccc aaagggatga agatatcaca   6120
aaactttgaa acaagatatc taattttgag cctcatacca aaaatagaag actctaactc   6180
ttgtggtgac caacagatca agcaatacaa gaagttattg gatagactga tcatcccttt   6240
atatgatgga ttaagattac agaaagatgt gatagtaacc aatcaagaat ccaatgaaaa   6300
cactgatccc agaacaaaac gattctttgg aggggtaatt ggaaccattg ctctgggagt   6360
agcaacctca gcacaaatta cagcggcagt tgctctggtt gaagccaagc aggcaagatc   6420
agacatcgaa aaactcaaag aagcaattag ggacacaaac aaagcagtgc agtcagttca   6480
gagctccata ggaaatttaa tagtagcaat taaatcagtc caggattatg ttaacaaaga   6540
aatcgtgcca tcgattgcga ggctaggttg tgaagcagca ggacttcaat taggaattgc   6600
attaacacag cattactcag aattaacaaa catatttggt gataacatag gatcgttaca   6660
agaaaaagga ataaaattac aaggtatagc atcattatac cgcacaaata tcacagaaat   6720
attcacaaca tcaacagttg ataaatatga tatctatgat ctgttattta cagaatcaat   6780
```

aaaggtgaga gttatagatg ttgacttgaa tgattactca atcaccctcc aagtcagact 6840
ccctttatta actaggctgc tgaacactca gatctacaaa gtagattcca tatcatataa 6900
catccaaaac agagaatggt atatccctct tcccagccat atcatgacga aaggggcatt 6960
tctaggtgga gcagacgtca aagaatgtat agaagcattc agcagctata tatgcccttc 7020
tgatccagga tttgtattaa accatgaaat agagagctgc ttatcaggaa acatatccca 7080
atgtccaaga acaacggtca catcagacat tgttccaaga tatgcatttg tcaatggagg 7140
agtggttgca aactgtataa caaccacctg tacatgcaac ggaattggta atagaatcaa 7200
tcaaccacct gatcaaggag taaaaattat aacacataaa gaatgtagta caataggtat 7260
caacggaatg ctgttcaata caaataaaga aggaactctt gcattctata caccaaatga 7320
tataacacta aacaattctg ttgcacttga tccaattgac atatcaatcg agctcaacaa 7380
ggccaaatca gatctagaag aatcaaaaga atggataaga aggtcaaatc aaaaactaga 7440
ttctattgga aattggcatc aatctagcac tacaatcata attattttga taatgatcat 7500
tatattgttt ataattaata taacgataat tacaattgca attaagtatt acagaattca 7560
aaagagaaat cgagtggatc aaaatgacaa gccatatgta ctaacaaaca aataacatat 7620
ctacagatca ttagatatta aaattataaa aaacttagga gtaaagttac gcaatccaac 7680
tctactcata taattgagga aggacccaat agacaaatcc aaattcgaga tggaatactg 7740
gaagcatacc aatcacggaa aggatgctgg taatgagctg gagacgtcta tggctactca 7800
tggcaacaag ctcactaata agataatata catattatgg acaataatcc tggtgttatt 7860
atcaatagtc ttcatcatag tgctaattaa ttccatcaaa agtgaaaagg cccacgaatc 7920
attgctgcaa gacataaata atgagtttat ggaaattaca gaaaagatcc aaatggcatc 7980
ggataatacc aatgatctaa tacagtcagg agtgaataca aggcttctta caattcagag 8040
tcatgtccag aattacatac caatatcatt gacacaacag atgtcagatc ttaggaaatt 8100
cattagtgaa attacaatta gaaatgataa tcaagaagtg ctgccacaaa gaataacaca 8160
tgatgtaggt ataaaacctt taaatccaga tgatttttgg agatgcacgt ctggtcttcc 8220
atctttaatg aaaactccaa aaataaggtt aatgccaggg ccgggattat tagctatgcc 8280
aacgactgtt gatggctgtg ttagaactcc gtctttagtt ataaatgatc tgatttatgc 8340
ttatacctca aatctaatta ctcgaggttg tcaggatata ggaaaatcat atcaagtctt 8400
acagataggg ataataactg taaactcaga cttggtacct gacttaaatc ctaggatctc 8460
tcataccttt aacataaatg acaataggaa gtcatgttct ctagcactcc taaatacaga 8520
tgtatatcaa ctgtgttcaa ctcccaaagt tgatgaaaga tcagattatg catcatcagg 8580
catagaagat attgtacttg atattgtcaa ttatgatggt tcaatctcaa caacaagatt 8640
taagaataat aacataagct ttgatcaacc atatgctgca ctatacccat ctgttggacc 8700
agggatatac tacaaaggca aaataatatt tctcgggtat ggaggtcttg aacatccaat 8760
aaatgagaat gtaatctgca acacaactgg gtgccccggg aaaacacaga gagactgtaa 8820
tcaagcatct catagtccat ggttttcaga taggaggatg gtcaactcca tcattgttgt 8880
tgacaaaggc ttaaactcaa ttccaaaatt gaaagtatgg acgatatcta tgcgacaaaa 8940
ttactggggg tcagaaggaa ggttacttct actaggtaac aagatctata tatatacaag 9000
atctacaagt tggcatagca agttacaatt aggaataatt gatattactg attacagtga 9060
tataaggata aaatggacat ggcataatgt gctatcaaga ccaggaaaca atgaatgtcc 9120

-continued

```
atggggacat tcatgtccag atggatgtat aacaggagta tatactgatg catatccact   9180
caatcccaca gggagcattg tgtcatctgt catattagac tcacaaaaat cgagagtgaa   9240
cccagtcata acttactcaa cagcaaccga aagagtaaac gagctggcca tcctaaacag   9300
aacactctca gctggatata caacaacaag ctgcattaca cactataaca aaggatattg   9360
ttttcatata gtagaaataa atcataaaag cttaaacaca tttcaaccca tgttgttcaa   9420
aacagagatt ccaaaaagct gcagttaatc ataattaacc ataatatgca tcaatctatc   9480
tataatacaa gtatatgata agtaatcagc aatcagacaa tagacgtacg gaaataataa   9540
aaaacttagg agaaaagtgt gcaagaaaaa tggacaccga gtcccacagc ggcacaacat   9600
ctgacattct gtaccctgaa tgtcacctca attctcctat agttaaagga aagatagcac   9660
aactgcatac aataatgagt ttgcctcagc cctacgatat ggatgatgat tcaatactga   9720
ttattactag acaaaaaatt aaactcaata aattagataa aagacaacgg tcaattagga   9780
aattaagatc agtcttaatg gaaagagtaa gtgatctagg taaatatacc tttatcagat   9840
atccagagat gtctagtgaa atgttccaat tatgtatacc cggaattaat aataaaataa   9900
atgaattgct aagtaaagca agtaaaacat ataatcaaat gactgatgga ttaagagatc   9960
tatgggttac tatactatcg aagttagcat cgaaaaatga tggaagtaat tatgatatca  10020
atgaagatat tagcaatata tcaaatgttc acatgactta tcaatcagac aaatggtata  10080
atccattcaa gacatggttt actattaagt atgacatgag aagattacaa aaagccaaaa  10140
atgagattac attcaatagg cataaagatt ataatctatt agaagaccaa aagaatatat  10200
tgctgataca tccagaactc gtcttaatat tagataaaca aaattacaat gggtatataa  10260
tgactcctga attggtacta atgtattgtg atgtagttga agggaggtgg aatataagtt  10320
catgtgcaaa attggatcct aagttacaat caatgtatta taagggtaac aatttatggg  10380
aaataataga tggactattc tcgaccttag gagaaagaac atttgacata atatcactat  10440
tagaaccact tgcattatcg ctcattcaaa cttatgaccc ggttaaacag ctcagggggg  10500
ctttttttaaa tcacgtgtta tcagaaatgg aattaatatt tgcagctgag tgtacaacag  10560
aggaaatacc taatgtggat tatatagata aaattttaga tgtgttcaaa gaatcaacaa  10620
tagatgaaat agcagaaatt ttctctttct tccgaacttt tggacaccct ccattagagg  10680
cgagtatagc agcagagaaa gttagaaagt atatgtatac tgagaaatgc ttgaaatttg  10740
atactatcaa taaatgtcat gctatttttt gtacaataat tataaatgga tatagagaaa  10800
gacatggtgg tcaatggcct ccagttacat tacctgtcca tgcacatgaa tttatcataa  10860
atgcatacgg atcaaattct gccatatcat atgagaatgc tgtagattat tataagagct  10920
tcataggaat aaaatttgac aagtttatag agcctcaatt ggatgaagac ttaactattt  10980
atatgaaaga taaagcatta tccccaaaga aatcaaactg ggacacagtc tatccagctt  11040
caaacctgtt ataccgcact aatgtgtctc atgattcacg aagattggtt gaagtattta  11100
tagcagatag taaatttgat ccccaccaag tattagatta cgtagaatca ggatattggc  11160
tggatgatcc tgaatttaat atctcatata gtttaaaaga gaaagaaata aaacaagaag  11220
gtagactttt tgcaaaaatg acatacaaga tgagggctac acaagtatta tcagaaacat  11280
tattggcgaa taatataggg aaattcttcc aagagaatgg gatggttaaa ggagaaattg  11340
aattactcaa gagactaaca acaatatcta tgtctggagt tccgcggtat aatgaggtat  11400
acaataattc aaaaagtcac acagaagaac ttcaagctta taatgcaatt agcagttcca  11460
atttatcttc taatcagaag tcaaagaagt ttgaatttaa atctacagat atatacaatg  11520
```

atggatacga aaccgtaagc tgcttcttaa cgacagatct taaaaaatat tgtttaaatt 11580
ggaggtatga atcaacagct ttattcggtg atacttgtaa tcagatattt gggttaaagg 11640
aattatttaa ttggctgcac cctcgccttg aaaagagtac aatatatgtt ggagatcctt 11700
attgcccgcc atcagatatt gaacatttac cacttgatga ccatcctgat tcaggatttt 11760
atgttcataa tcctaaagga ggaatagaag ggttttgcca aaagttatgg acactcatat 11820
ctatcagtgc aatacattta gcagctgtca aaatcggtgt aagagttact gcaatggttc 11880
aaggggataa tcaagccata gctgttacca caagagtacc taataattat gattataaag 11940
ttaagaaaga gattgtttat aaagatgtgg taagattttt tgattccttg agagaggtga 12000
tggatgatct gggtcatgag ctcaaactaa atgaaactat aataagtagt aaaatgttta 12060
tatatagcaa aaggatatac tatgacggaa gaatccttcc tcaggcatta aaagcattgt 12120
ctagatgtgt tttttggtct gaaacaatca tagatgagac aagatcagca tcctcaaatc 12180
tggctacatc gtttgcaaag gccattgaga atggctactc acctgtattg ggatatgtat 12240
gctcaatctt caaaaatatc caacagttgt atatagcgct tggaatgaat ataaacccaa 12300
ctataaccca aaatattaaa gatcaatatt tcaggaatat tcattggatg caatatgcct 12360
ccttaatccc tgctagtgtc ggaggattta attatatggc catgtcaagg tgttttgtca 12420
gaaacattgg agatcctaca gtcgctgcgt tagccgatat taaaagattt ataaaagcaa 12480
atttgttaga tcgaggtgtc ctttacagaa ttatgaatca agaaccaggc gagtcttctt 12540
ttttagactg ggcctcagat ccctattcat gtaacttacc acaatctcaa aatataacca 12600
ccatgataaa gaatataact gcaagaaatg tactacagga ctcaccaaac ccattactat 12660
ctggattatt tacaagtaca atgatagaag aggatgagga attagctgag ttcctaatgg 12720
acaggagaat aatcctccca agagttgcac atgacatttt agataattct cttactggaa 12780
ttaggaatgc tatagctggt atgttggata caacaaaatc actaattcga gtagggataa 12840
gcagaggagg attaacctat aacttattaa gaaagataag caactatgat cttgtacaat 12900
atgagacact tagtaaaact ttaagactaa tagtcagtga caagattaag tatgaagata 12960
tgtgctcagt agacctagcc atatcattaa gacaaaaaat gtggatgcat ttatcaggag 13020
gaagaatgat aaatggactt gaaactccag atcctttaga gttactgtct ggagtaataa 13080
taacaggatc tgaacattgt aggatatgtt attcaactga aggtgaaagc ccatatacat 13140
ggatgtattt accaggcaat cttaatatag gatcagctga gacaggaata gcatcattaa 13200
gggtccctta ctttggatca gttacagatg agagatctga agcacaatta gggtatatca 13260
aaaatctaag caaaccagct aaggctgcta taagaatagc aatgatatat acttgggcat 13320
ttgggaatga cgaaatatct tggatggaag catcacagat tgcacaaaca cgtgcaaact 13380
ttacattgga tagcttaaag attttgacac cagtgacaac atcaacaaat ctatcacaca 13440
ggttaaaaga tactgctact cagatgaaat tttctagtac atcacttatt agagtaagca 13500
ggttcatcac aatatctaat gataatatgt ctattaaaga agcaaatgaa actaaagata 13560
caaatcttat ttatcaacag gtaatgttaa caggattaag tgtatttgaa tatctattta 13620
ggttagagga gagtacagga cataacccta tggtcatgca tctacatata gaggatggat 13680
gttgtataaa agagagttac aatgatgagc atatcaatcc ggagtctaca ttagagttaa 13740
tcaaataccc tgagagtaat gaatttatat atgataagga ccctttaaag gatatagatc 13800
tatcaaaatt aatggttata agagatcatt cttatacaat tgacatgaat tactgggatg 13860

-continued acacagatat tgtacatgca atatcaatat gtactgcagt tacaatagca gatacaatgt 13920
cgcagctaga tcgggataat cttaaggagc tggttgtgat tgcaaatgat gatgatatta 13980
acagtctgat aactgaattt ctgaccctag atatactagt gtttctcaaa acatttggag 14040
ggttactcgt gaatcaattt gcatataccc tttatggatt gaaaatagaa ggaagggatc 14100
ccatttggga ttatataatg agaacattaa aagacacctc acattcagta cttaaagtat 14160
tatctaatgc actatctcat ccaaaagtgt ttaagagatt ttgggattgt ggagttttga 14220
atcctattta tggtcctaat actgctagtc aagatcaagt taagcttgct ctctcgattt 14280
gcgagtactc cttggatcta tttatgagag aatggttgaa tggagcatca cttgagatct 14340
atatctgtga tagtgacatg gaaatagcaa atgacagaag acaagcattt ctctcaagac 14400
atcttgcctt tgtgtgttgt ttagcagaga tagcatcttt tggaccaaat ttattaaatc 14460
taacatatct agagagactt gatgaattaa aacaatactt agatctgaac atcaaagaag 14520
atcctactct taaatatgtg caagtatcag gactgttaat taaatcattc ccctcaactg 14580
ttacgtatgt aaggaaaact gcgattaagt atctgaggat tcgtggtatt aatccgcctg 14640
aaacgattga agattgggat cccatagaag atgagaatat cttagacaat attgttaaaa 14700
ctgtaaatga caattgcagt gataatcaaa agagaaataa aagtagttat ttctggggat 14760
tagctctaaa gaattatcaa gtcgtgaaaa taagatccat aacgagtgat tctgaagtta 14820
atgaagcttc gaatgttact acacatggaa tgacacttcc tcagggagga agttatctat 14880
cacatcagct gaggttattt ggagtaaaca gtacaagttg tcttaaagct cttgaattat 14940
cacaaatctt aatgagggaa gttaaaaaag ataaagatag actcttttta ggagaaggag 15000
caggagctat gttagcatgt tatgatgcta cactcggtcc tgcaataaat tattataatt 15060
ctggtttaaa tattacagat gtaattggtc aacgggaatt aaaaatcttc ccatcagaag 15120
tatcattagt aggtaaaaaa ctaggaaatg taacacagat tcttaatcgg gtgagggtgt 15180
tatttaatgg gaatcccaat tcaacatgga taggaaatat ggaatgtgag agtttaatat 15240
ggagtgaatt aaatgataag tcaattggtt tagtacattg tgacatggag ggagcgatag 15300
gcaaatcaga agaaactgtt ctacatgaac attatagtat tattaggatt acatatttaa 15360
tcggggatga tgatgttgtc ctagtatcaa aaattatacc aactattact ccgaattggt 15420
ctaaaatact ctatctatac aagttgtatt ggaaggatgt aagtgtagtg tcccttaaaa 15480
catccaatcc tgcctcaaca gagctttatt taatttcaaa agatgcttac tgtactgtaa 15540
tggaacccag taatcttgtt ttatcaaaac ttaaaaggat atcatcaata gaagaaaata 15600
atctattaaa gtggataatc ttatcaaaaa ggaagaataa cgagtggtta cagcatgaaa 15660
tcaaagaagg agaaagggat tatgggataa tgaggccata tcatacagca ctgcaaattt 15720
ttggattcca aattaactta aatcacttag ctagagaatt tttatcaact cctgatttaa 15780
ccaacattaa taatataatt caaagtttta caagaacaat taaagatgtt atgttcgaat 15840
gggtcaatat cactcatgac aataaaagac ataaattagg aggaagatat aatctattcc 15900
cgcttaaaaa taaggggaaa ttaagattat tatcacgaag attagtacta agctggatat 15960
cattatcctt atcaaccaga ttactgacgg gccgttttcc agatgaaaaa tttgaaaata 16020
gggcacagac cggatatgta tcattggctg atattgattt agaatcctta aagttattat 16080
caagaaatat tgtcaaaaat tacaaagaac acataggatt aatatcatac tggtttttga 16140
ccaaagaggt caaaatacta atgaagctta taggaggagt caaactacta ggaattccta 16200
aacagtacaa agagttagag gatcgatcat ctcagggtta tgaatatgat aatgaatttg 16260
atattgatta atacataaaa acataaaata aaacacctat tcctcaccca ttcacttcca 16320
acaaaatgaa aagtaagaaa aacatgtaat atatatatac caaacagagt tttctcttg 16380 tttggt 16386

<210> SEQ ID NO 92
<211> LENGTH: 16386
<212> TYPE: DNA
<213> ORGANISM: Artificial Sequence
<220> FEATURE:
<223> OTHER INFORMATION: Recombinant rB/HPIV3 sequence

<400> SEQUENCE: 92
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180
ttattcccgg gcaaaaaaac actgtgtcta tatttgctct tggaccatca ataacagatg 240
acaatgataa aatgacattg gctcttctct tttgtctca ttctttagac aatgaaaagc 300
agcatgcgca aagagctgga tttttagttt ctctgttatc aatggcttat gccaacccag 360
aattatattt aacatcaaat ggtagtaatg cagatgttaa atatgttatc tacatgatag 420
agaaagaccc aggaagacag aaatatggtg ggtttgtcgt caagactaga gagatggttt 480
atgaaaagac aactgattgg atgttcggga gtgatcttga gtatgatcaa gacaatatgt 540
tgcaaaatgg tagaagcact tctacaatcg aggatcttgt tcatactttt ggatatccat 600
cgtgtcttgg agcccttata atccaagttt ggataatact tgttaaggct ataaccagta 660
tatcaggatt gaggaaagga ttctttactc ggttagaagc atttcgacaa gatggaacag 720
ttaaatccag tctagtgttg agcggtgatg cagtagaaca aattggatca attatgaggt 780
cccaacagag cttggtaaca ctcatggttg aaacactgat aacaatgaac acaggcagga 840
atgatctgac aacaatagaa aagaatatac agattgtagg aaactacatc agagatgcag 900
gtcttgcttc atttttcaac acaatcagat atggcattga gactagaatg gcagctctaa 960
ctctgtctac ccttagaccg gatatcaaca gactcaaggc actgatcgag ttatatctat 1020
caaaggggcc acgtgctcct tttatatgca ttttgagaga tcccgtgcat ggtgagtttg 1080
caccaggcaa ctatcctgcc ctctggagtt atgcgatggg tgtagcagtt gtacaaaaca 1140
aggccatgca acagtatgta acaggaaggt cttatctgga tattgaaatg ttccaacttg 1200
gtcaagcagt ggcacgtgat gccgagtcgc agatgagttc aatattagag gatgaactgg 1260
gggtcacaca agaagccaag caaagcttga agaaacacat gaagaacatc agcagttcag 1320
atacaacctt tcataagcct acagggggat cagccataga aatggcgata gatgaagaag 1380
cagggcagcc tgaatccaga ggagatcagg atcaaggaga tgagcctcgg tcatccatag 1440
ttccttatgc atgggcagac gaaaccggga atgacaatca aactgaatca actacagaaa 1500
ttgacagcat caaaactgaa caaagaaaca tcagagacag gctgaacaaa agactcaacg 1560
agaaaaggaa acagagtgac ccgagatcaa ctgacatcac aaacaacaca aatcaaactg 1620
aaatagatga tttgttcagt gcattcggaa gcaactagtc acaaagagat gaccaggcgc 1680
gccaagtaag aaaaacttag gattaatgga cctgcaggat gtcaaagaac aaggatcaga 1740
gaactgccaa gaccctggaa agaacctggg acaccctgaa ccacctgctg tttatctcaa 1800
gctgcctgta caagctgaat ctgaaaagtg tggcccagat caccctgtca attctggcta 1860

-continued tgatcatttc aacaagcctg atcattgccg ctatcatttt catcgcaagc gccaaccaca 1920
aggtcacccc caccacagct atcattcagg acgcaacatc ccagattaag aacactaccc 1980
ccacctatct gacacagaat cctcagctgg gaatctcccc atctaacccc tcagagatta 2040
ccagccagat cacaactatt ctggcctcca ccacacctgg cgtgaagtcc actctgcagt 2100
ctactaccgt caagaccaaa aatacaacta ccacacagac acagccttct aagccaacta 2160
ccaaacagcg gcagaataag cccccctagta aaccaaacaa tgacttccat tttgaggtgt 2220
tcaactttgt cccatgcagc atctgttcca acaatcccac ctgctgggcc atctgtaaga 2280
gaattccaaa caagaaaccc ggcaagaaga ccactaccaa acctactaag aaaccaaccc 2340
tgaagacaac taagaaagat cctaaaccac agaccacaaa gtctaaagaa gtgcccacta 2400
ccaagcctac agaggaacca actatcaaca caactaagac taacatcatc accacactgc 2460
tgacaagcaa cactaccggc aatcccgagc tgaccagcca gatggaaacc tttcactcca 2520
caagctccga ggggaatccc agtccttcac aggtgtctac aactagtgaa taccccagcc 2580
agccttctag tccacccaac acccctaggc agtgatagct agcggcgcgc cagcaacaag 2640
taagaaaaac ttaggattaa tggaaattat ccaatccaga gacggaagga caaatccaga 2700
atccaaccac aactcaatca accaaagatt catggaagac aatgttcaaa acaatcaaat 2760
catggattct tgggaagagg gatcaggaga taaatcatct gacatctcat cggccctcga 2820
catcattgaa ttcatactca gcaccgactc ccaagagaac acggcagaca gcaatgaaat 2880
caacacagga accacaagac ttagcacgac aatctaccaa cctgaatcca aaacaacaga 2940
aacaagcaag gaaaatagtg gaccagctaa caaaaatcga cagtttgggg catcacacga 3000
acgtgccaca gagacaaaag atagaaatgt taatcaggag actgtacagg gaggatatag 3060
gagaggaagc agcccagata gtagaactga gactatggtc actcgaagaa tctccagaag 3120
cagcccagat cctaacaatg gaacccaaat ccaggaagat attgattaca atgaagttgg 3180
agagatggat aaggactcta ctaagaggga aatgcgacaa tttaaagatg ttccagtcaa 3240
ggtatcagga agtgatgcca ttcctccaac aaaacaagat ggagacggtg atgatggaag 3300
aggcctggaa tctatcagta catttgattc aggatatacc agtatagtga ctgccgcaac 3360
actagatgac gaagaagaac tccttatgaa gaacaacagg ccaagaaagt atcaatcaac 3420
accccagaac agtgacaagg gaattaaaaa aggggttgga aggccaaaag acacagacaa 3480
acaatcatca atattggact acgaactcaa cttcaaagga tcgaagaaga gccagaaaat 3540
cctcaaagcc agcacgaata caggagaacc aacaagacca cagaatggat cccaggggaa 3600
gagaatcaca tcctggaaca tcctcaacag cgagagcggc aatcgaacag aatcaacaaa 3660
ccaaacccat cagacatcaa cctcgggaca gaaccacaca atgggaccaa gcagaacaac 3720
ctccgaacca aggatcaaga cacaaaagac ggatggaaag gaaagagagg acacagaaga 3780
gagcactcga tttacagaaa gggcgattac attattacag aatcttggtg taatccaatc 3840
tgcagcaaaa ttagacctat accaagacaa gagagttgtg tgtgtggcga atgtcctaaa 3900
caatgcagat actgcatcaa agatagactt cctagcaggt ttgatgatag gagtgtcaat 3960
ggatcatgat accaaattaa atcagattca gaacgagata ttaagtttga aaactgatct 4020
taaaaagatg gatgaatcac atagaagact aattgagaat caaaaagaac aattatcact 4080
gatcacatca ttaatctcaa atcttaaaat tatgacagag agaggaggga agaaggacca 4140
accagaacct agcgggagga catccatgat caagacaaaa gcaaaagaag agaaaataaa 4200
gaaagtcagg tttgaccctc ttatggaaac acagggcatc gagaaaaaca tccctgacct 4260

```
ctatagatca atagagaaaa caccagaaaa cgacacacag atcaaatcag aaataaacag   4320
attgaatgat gaatccaatg ccactagatt agtacctaga agaataagca gtacaatgag   4380
atcattaata ataatcatta acaacagcaa tttatcatca aaagcaaagc aatcatacat   4440
caacgaactc aagctctgca agagtgacga ggaagtgtct gagttgatgg acatgttcaa   4500
tgaggatgtc agctcccagt aaaccgccaa ccaagggtca acaccaagaa aaccaatagc   4560
acaaaacagc caatcagaga ccaccccaat acaccaaacc aatcaacaca taacaaagat   4620
cgcggccgca tagatgatta agaaaaactt aggatgaaag gactaatcaa tcctccgaaa   4680
caatgagcat caccaactcc acaatctaca cattcccaga atcctctttc tccgagaatg   4740
gcaacataga gccgttacca ctcaaggtca atgaacagag aaaggccata cctcatatta   4800
gggttgtcaa gataggagat ccgcccaaac atggatccag atatctggat gtctttttac   4860
tgggcttctt tgagatggaa aggtcaaaag acaggtatgg gagcataagt gatctagatg   4920
atgatccaag ttacaaggtt tgtggctctg gatcattgcc acttgggttg gctagataca   4980
ccggaaatga tcaggaactc ctacaggctg caaccaagct cgatatagaa gtaagaagaa   5040
ctgtaaaggc tacggagatg atagtttaca ctgtacaaaa catcaaacct gaactatatc   5100
catggtccag tagattaaga aaagggatgt tatttgacgc taataaggtt gcacttgctc   5160
ctcaatgtct tccactagat agagggataa aattcagggt gatatttgtg aactgcacag   5220
caattggatc aataactcta ttcaaaatcc ctaagtccat ggcattgtta tcattgccta   5280
atacaatatc aataaatcta caagtacata tcaaaacagg agttcagaca gattccaaag   5340
gagtagttca gattctagat gaaaaaggtg aaaaatcact aaatttcatg gttcatctcg   5400
ggttgatcaa aaggaagatg ggcagaatgt actcagttga atattgtaag cagaagatcg   5460
agaagatgag attattattc tcattgggat tagttggagg gatcagcttc cacgtcaacg   5520
caactggctc tatatcaaag acattagcaa gtcaattagc attcaaaaga gaaatctgct   5580
atcccctaat ggatctgaat ccacacttaa attcagttat atgggcatca tcagttgaaa   5640
ttacaagggt agatgcagtt ctccagcctt cattacctgg cgaattcaga tactacccaa   5700
acatcatagc aaaaggggtc gggaaaatca gacagtaaaa tcaacaaccc tgatatccac   5760
cggtgtatta agccgaagca aataaaggat aatcaaaaac ttaggacaaa agaggtcaat   5820
accaacaact attagcagtc acactcgcaa gaataagaga gaagggacca aaaaagtcaa   5880
ataggagaaa tcaaaacaaa aggtacagaa caccagaaca acaaaatcaa aacatccaac   5940
tcactcaaaa caaaaattcc aaaagagacc ggcaacacaa caagcactga acacaatgcc   6000
aacttcaata ctgctaatta ttacaaccat gatcatggca tctttctgcc aaatagatat   6060
cacaaaacta cagcacgtag gtgtattggt caacagtccc aaagggatga agatatcaca   6120
aaactttgaa acaagatatc taattttgag cctcatacca aaaatagaag actctaactc   6180
ttgtggtgac caacagatca agcaatacaa gaagttattg gatagactga tcatcccttt   6240
atatgatgga ttaagattac agaaagatgt gatagtaacc aatcaagaat ccaatgaaaa   6300
cactgatccc agaacaaaac gattctttgg aggggtaatt ggaaccattg ctctgggagt   6360
agcaacctca gcacaaatta cagcggcagt tgctctggtt gaagccaagc aggcaagatc   6420
agacatcgaa aaactcaaag aagcaattag ggacacaaac aaagcagtgc agtcagttca   6480
gagctccata ggaaatttaa tagtagcaat taaatcagtc caggattatg ttaacaaaga   6540
aatcgtgcca tcgattgcga ggctaggttg tgaagcagca ggacttcaat taggaattgc   6600
```

-continued

```
attaacacag cattactcag aattaacaaa catatttggt gataacatag gatcgttaca   6660
agaaaaagga ataaaattac aaggtatagc atcattatac cgcacaaata tcacagaaat   6720
attcacaaca tcaacagttg ataaatatga tatctatgat ctgttattta cagaatcaat   6780
aaaggtgaga gttatagatg ttgacttgaa tgattactca atcaccctcc aagtcagact   6840
ccctttatta actaggctgc tgaacactca gatctacaaa gtagattcca tatcatataa   6900
catccaaaac agagaatggt atatccctct tcccagccat atcatgacga aaggggcatt   6960
tctaggtgga gcagacgtca aagaatgtat agaagcattc agcagctata tatgcccttc   7020
tgatccagga tttgtattaa accatgaaat agagagctgc ttatcaggaa acatatccca   7080
atgtccaaga acaacggtca catcagacat tgttccaaga tatgcatttg tcaatggagg   7140
agtggttgca aactgtataa caaccacctg tacatgcaac ggaattggta atagaatcaa   7200
tcaaccacct gatcaaggag taaaaattat aacacataaa gaatgtagta caataggtat   7260
caacggaatg ctgttcaata caaataaaga aggaactctt gcattctata caccaaatga   7320
tataacacta aacaattctg ttgcacttga tccaattgac atatcaatcg agctcaacaa   7380
ggccaaatca gatctagaag aatcaaaaga atggataaga aggtcaaatc aaaaactaga   7440
ttctattgga aattggcatc aatctagcac tacaatcata attattttga taatgatcat   7500
tatattgttt ataattaata taacgataat tacaattgca attaagtatt acagaattca   7560
aaagagaaat cgagtggatc aaaatgacaa gccatatgta ctaacaaaca aataacatat   7620
ctacagatca ttagatatta aaattataaa aaacttagga gtaaagttac gcaatccaac   7680
tctactcata taattgagga aggacccaat agacaaatcc aaattcgaga tggaatactg   7740
gaagcatacc aatcacggaa aggatgctgg taatgagctg gagacgtcta tggctactca   7800
tggcaacaag ctcactaata agataatata catattatgg acaataatcc tggtgttatt   7860
atcaatagtc ttcatcatag tgctaattaa ttccatcaaa agtgaaaagg cccacgaatc   7920
attgctgcaa gacataaata atgagtttat ggaaattaca gaaaagatcc aaatggcatc   7980
ggataatacc aatgatctaa tacagtcagg agtgaataca aggcttctta caattcagag   8040
tcatgtccag aattacatac caatatcatt gacacaacag atgtcagatc ttaggaaatt   8100
cattagtgaa attacaatta gaaatgataa tcaagaagtg ctgccacaaa gaataacaca   8160
tgatgtaggt ataaaacctt taaatccaga tgatttttgg agatgcacgt ctggtcttcc   8220
atctttaatg aaaactccaa aaataaggtt aatgccaggg ccgggattat tagctatgcc   8280
aacgactgtt gatggctgtg ttagaactcc gtctttagtt ataaatgatc tgatttatgc   8340
ttatacctca aatctaatta ctcgaggttg tcaggatata ggaaaatcat atcaagtctt   8400
acagataggg ataataactg taaactcaga cttggtacct gacttaaatc ctaggatctc   8460
tcataccttt aacataaatg acaataggaa gtcatgttct ctagcactcc taaatacaga   8520
tgtatatcaa ctgtgttcaa ctcccaaagt tgatgaaaga tcagattatg catcatcagg   8580
catagaagat attgtacttg atattgtcaa ttatgatggt tcaatctcaa caacaagatt   8640
taagaataat aacataagct ttgatcaacc atatgctgca ctatacccat ctgttggacc   8700
agggatatac tacaaaggca aaataatatt tctcgggtat ggaggtcttg aacatccaat   8760
aaatgagaat gtaatctgca acacaactgg gtgccccggg aaaacacaga gagactgtaa   8820
tcaagcatct catagtccat ggttttcaga taggaggatg gtcaactcca tcattgttgt   8880
tgacaaaggc ttaaactcaa ttccaaaatt gaaagtatgg acgatatcta tgcgacaaaa   8940
ttactggggg tcagaaggaa ggttacttct actaggtaac aagatctata tatatacaag   9000
```

atctacaagt tggcatagca agttacaatt aggaataatt gatattactg attacagtga 9060
tataaggata aaatggacat ggcataatgt gctatcaaga ccaggaaaca atgaatgtcc 9120
atggggacat tcatgtccag atggatgtat aacaggagta tatactgatg catatccact 9180
caatcccaca gggagcattg tgtcatctgt catattagac tcacaaaaat cgagagtgaa 9240
cccagtcata acttactcaa cagcaaccga aagagtaaac gagctggcca tcctaaacag 9300
aacactctca gctggatata caacaacaag ctgcattaca cactataaca aaggatattg 9360
ttttcatata gtagaaataa atcataaaag cttaaacaca tttcaaccca tgttgttcaa 9420
aacagagatt ccaaaaagct gcagttaatc ataattaacc ataatatgca tcaatctatc 9480
tataatacaa gtatatgata agtaatcagc aatcagacaa tagacgtacg gaaataataa 9540
aaaacttagg agaaaagtgt gcaagaaaaa tggacaccga gtcccacagc ggcacaacat 9600
ctgacattct gtaccctgaa tgtcacctca attctcctat agttaaagga aagatagcac 9660
aactgcatac aataatgagt ttgcctcagc cctacgatat ggatgatgat tcaatactga 9720
ttattactag acaaaaaatt aaactcaata aattagataa aagacaacgg tcaattagga 9780
aattaagatc agtcttaatg gaaagagtaa gtgatctagg taaatatacc tttatcagat 9840
atccagagat gtctagtgaa atgttccaat tatgtatacc cggaattaat aataaaaataa 9900
atgaattgct aagtaaagca agtaaaacat ataatcaaat gactgatgga ttaagagatc 9960
tatgggttac tatactatcg aagttagcat cgaaaaatga tggaagtaat tatgatatca 10020
atgaagatat tagcaatata tcaaatgttc acatgactta tcaatcagac aaatggtata 10080
atccattcaa gacatggttt actattaagt atgacatgag aagattacaa aaagccaaaa 10140
atgagattac attcaatagg cataaagatt ataatctatt agaagaccaa aagaatatat 10200
tgctgataca tccagaactc gtcttaatat tagataaaca aaattacaat gggtatataa 10260
tgactcctga attggtacta atgtattgtg atgtagttga agggaggtgg aatataagtt 10320
catgtgcaaa attggatcct aagttacaat caatgtatta taagggtaac aatttatggg 10380
aaataataga tggactattc tcgaccttag gagaaagaac atttgacata atatcactat 10440
tagaaccact tgcattatcg ctcattcaaa cttatgaccc ggttaaacag ctcagggggg 10500
ctttttaaa tcacgtgtta tcagaaatgg aattaatatt tgcagctgag tgtacaacag 10560
aggaaatacc taatgtggat tatatagata aaattttaga tgtgttcaaa gaatcaacaa 10620
tagatgaaat agcagaaatt ttctctttct tccgaacttt tggacaccct ccattagagg 10680
cgagtatagc agcagagaaa gttagaaagt atatgtatac tgagaaatgc ttgaaatttg 10740
atactatcaa taaatgtcat gctatttttt gtacaataat tataaatgga tatagagaaa 10800
gacatggtgg tcaatggcct ccagttacat tacctgtcca tgcacatgaa tttatcataa 10860
atgcatacgg atcaaattct gccatatcat atgagaatgc tgtagattat tataagagct 10920
tcataggaat aaaatttgac aagtttatag agcctcaatt ggatgaagac ttaactattt 10980
atatgaaaga taaagcatta tccccaaaga aatcaaactg ggacacagtc tatccagctt 11040
caaacctgtt ataccgcact aatgtgtctc atgattcacg aagattggtt gaagtattta 11100
tagcagatag taaatttgat ccccaccaag tattagatta cgtagaatca ggatattggc 11160
tggatgatcc tgaatttaat atctcatata gtttaaaaga gaaagaaata aaacaagaag 11220
gtagactttt tgcaaaaatg acatacaaga tgagggctac acaagtatta tcagaaacat 11280
tattggcgaa taatataggg aaattcttcc aagagaatgg gatggttaaa ggagaaattg 11340

-continued aattactcaa gagactaaca acaatatcta tgtctggagt tccgcggtat aatgaggtat 11400
acaataattc aaaaagtcac acagaagaac ttcaagctta taatgcaatt agcagttcca 11460
atttatcttc taatcagaag tcaaagaagt ttgaatttaa atctacagat atatacaatg 11520
atggatacga aaccgtaagc tgcttcttaa cgacagatct taaaaaatat tgtttaaatt 11580
ggaggtatga atcaacagct ttattcggtg atacttgtaa tcagatattt gggttaaagg 11640
aattatttaa ttggctgcac cctcgccttg aaaagagtac aatatatgtt ggagatcctt 11700
attgcccgcc atcagatatt gaacatttac cacttgatga ccatcctgat tcaggatttt 11760
atgttcataa tcctaaagga ggaatagaag ggttttgcca aaagttatgg acactcatat 11820
ctatcagtgc aatacattta gcagctgtca aaatcggtgt aagagttact gcaatggttc 11880
aaggggataa tcaagccata gctgttacca caagagtacc taataattat gattataaag 11940
ttaagaaaga gattgtttat aaagatgtgg taagattttt tgattccttg agagaggtga 12000
tggatgatct gggtcatgag ctcaaactaa atgaaactat aataagtagt aaaatgttta 12060
tatatagcaa aggatatac tatgacggaa gaatccttcc tcaggcatta aaagcattgt 12120
ctagatgtgt tttttggtct gaaacaatca tagatgagac aagatcagca tcctcaaatc 12180
tggctacatc gtttgcaaag gccattgaga atggctactc acctgtattg ggatatgtat 12240
gctcaatctt caaaaatatc caacagttgt atatagcgct tggaatgaat ataaacccaa 12300
ctataaccca aaatattaaa gatcaatatt tcaggaatat tcattggatg caatatgcct 12360
ccttaatccc tgctagtgtc ggaggattta attatatggc catgtcaagg tgttttgtca 12420
gaaacattgg agatcctaca gtcgctgcgt tagccgatat taaaagattt ataaaagcaa 12480
atttgttaga tcgaggtgtc ctttacagaa ttatgaatca agaaccaggc gagtcttctt 12540
ttttagactg ggcctcagat ccctattcat gtaacttacc acaatctcaa aatataacca 12600
ccatgataaa gaatataact gcaagaaatg tactacagga ctcaccaaac ccattactat 12660
ctggattatt tacaagtaca atgatagaag aggatgagga attagctgag ttcctaatgg 12720
acaggagaat aatcctccca agagttgcac atgacatttt agataattct cttactggaa 12780
ttaggaatgc tatagctggt atgttggata caacaaaatc actaattcga gtagggataa 12840
gcagaggagg attaacctat aacttattaa gaaagataag caactatgat cttgtacaat 12900
atgagacact tagtaaaact ttaagactaa tagtcagtga caagattaag tatgaagata 12960
tgtgctcagt agacctagcc atatcattaa gacaaaaaat gtggatgcat ttatcaggag 13020
gaagaatgat aaatggactt gaaactccag atcctttaga gttactgtct ggagtaataa 13080
taacaggatc tgaacattgt aggatatgtt attcaactga aggtgaaagc ccatatacat 13140
ggatgtattt accaggcaat cttaatatag gatcagctga gacaggaata gcatcattaa 13200
gggtccctta ctttggatca gttacagatg agagatctga agcacaatta gggtatatca 13260
aaaatctaag caaaccagct aaggctgcta taagaatagc aatgatatat acttgggcat 13320
ttgggaatga cgaaatatct tggatggaag catcacagat tgcacaaaca cgtgcaaact 13380
ttacattgga tagcttaaag attttgacac cagtgacaac atcaacaaat ctatcacaca 13440
ggttaaaaga tactgctact cagatgaaat tttctagtac atcacttatt agagtaagca 13500
ggttcatcac aatatctaat gataatatgt ctattaaaga agcaaatgaa actaaagata 13560
caaatcttat ttatcaacag gtaatgttaa caggattaag tgtatttgaa tatctattta 13620
ggttagagga gagtacagga cataacccta tggtcatgca tctacatata gaggatggat 13680
gttgtataaa agagagttac aatgatgagc atatcaatcc ggagtctaca ttagagttaa 13740

```
tcaaataccc tgagagtaat gaatttatat atgataagga ccctttaaag gatatagatc  13800
tatcaaaatt aatggttata agagatcatt cttatacaat tgacatgaat tactgggatg  13860
acacagatat tgtacatgca atatcaatat gtactgcagt tacaatagca gatacaatgt  13920
cgcagctaga tcgggataat cttaaggagc tggttgtgat tgcaaatgat gatgatatta  13980
acagtctgat aactgaattt ctgaccctag atatactagt gtttctcaaa acatttggag  14040
ggttactcgt gaatcaattt gcatataccc tttatggatt gaaaatagaa ggaagggatc  14100
ccatttggga ttatataatg agaacattaa aagacacctc acattcagta cttaaagtat  14160
tatctaatgc actatctcat ccaaaagtgt ttaagagatt ttgggattgt ggagttttga  14220
atcctattta tggtcctaat actgctagtc aagatcaagt taagcttgct ctctcgattt  14280
gcgagtactc cttggatcta tttatgagag aatggttgaa tggagcatca cttgagatct  14340
atatctgtga tagtgacatg gaaatagcaa atgacagaag acaagcattt ctctcaagac  14400
atcttgcctt tgtgtgttgt ttagcagaga tagcatcttt tggaccaaat ttattaaatc  14460
taacatatct agagagactt gatgaattaa aacaatactt agatctgaac atcaaagaag  14520
atcctactct taaatatgtg caagtatcag gactgttaat taaatcattc cctcaactg   14580
ttacgtatgt aaggaaaact gcgattaagt atctgaggat tcgtggtatt aatccgcctg  14640
aaacgattga agattgggat cccatagaag atgagaatat cttagacaat attgttaaaa  14700
ctgtaaatga caattgcagt gataatcaaa agagaaataa aagtagttat ttctggggat  14760
tagctctaaa gaattatcaa gtcgtgaaaa taagatccat aacgagtgat tctgaagtta  14820
atgaagcttc gaatgttact acacatggaa tgacacttcc tcagggagga agttatctat  14880
cacatcagct gaggttattt ggagtaaaca gtacaagttg tcttaaagct cttgaattat  14940
cacaaatctt aatgagggaa gttaaaaaag ataaagatag actcttttta ggagaaggag  15000
caggagctat gttagcatgt tatgatgcta cactcggtcc tgcaataaat tattataatt  15060
ctggtttaaa tattacagat gtaattggtc aacgggaatt aaaaatcttc ccatcagaag  15120
tatcattagt aggtaaaaaa ctaggaaatg taacacagat tcttaatcgg gtgagggtgt  15180
tatttaatgg gaatcccaat tcaacatgga taggaaatat ggaatgtgag agtttaatat  15240
ggagtgaatt aaatgataag tcaattggtt tagtacattg tgacatggag ggagcgatag  15300
gcaaatcaga agaaactgtt ctacatgaac attatagtat tattaggatt acatatttaa  15360
tcggggatga tgatgttgtc ctagtatcaa aaattatacc aactattact ccgaattggt  15420
ctaaaatact ctatctatac aagttgtatt ggaaggatgt aagtgtagtg tcccttaaaa  15480
catccaatcc tgcctcaaca gagctttatt taatttcaaa agatgcttac tgtactgtaa  15540
tggaacccag taatcttgtt ttatcaaaac ttaaaaggat atcatcaata gaagaaaata  15600
atctattaaa gtggataatc ttatcaaaaa ggaagaataa cgagtggtta cagcatgaaa  15660
tcaaagaagg agaaagggat tatgggataa tgaggccata tcatacagca ctgcaaattt  15720
ttggattcca aattaactta aatcacttag ctagagaatt tttatcaact cctgatttaa  15780
ccaacattaa taatataatt caaagtttta caagaacaat taaagatgtt atgttcgaat  15840
gggtcaatat cactcatgac aataaaagac ataaattagg aggaagatat aatctattcc  15900
cgcttaaaaa taaggggaaa ttaagattat tatcacgaag attagtacta agctggatat  15960
cattatcctt atcaaccaga ttactgacgg gccgttttcc agatgaaaaa tttgaaaata  16020
gggcacagac cggatatgta tcattggctg atattgattt agaatcctta aagttattat  16080
```

caagaaatat tgtcaaaaat tacaaagaac acataggatt aatatcatac tggtttttga 16140
ccaaagaggt caaaatacta atgaagctta taggaggagt caaactacta ggaattccta 16200
aacagtacaa agagttagag gatcgatcat ctcagggtta tgaatatgat aatgaatttg 16260
atattgatta atacataaaa acataaaata aaacacctat tcctcaccca ttcacttcca 16320
acaaaatgaa aagtaagaaa aacatgtaat atatatatac caaacagagt tttctcttg 16380 tttggt 16386

<210> SEQ ID NO 93
<211> LENGTH: 16362
<212> TYPE: DNA
<213> ORGANISM: Artificial Sequence
<220> FEATURE:
<223> OTHER INFORMATION: Recombinant rB/HPIV3 sequence

<400> SEQUENCE: 93
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180
ttattcccgg gcaaaaaaac actgtgtcta tatttgctct tggaccatca ataacagatg 240
acaatgataa aatgacattg gctcttctct tttgtctca ttctttagac aatgaaaagc 300
agcatgcgca aagagctgga tttttagttt ctctgttatc aatggcttat gccaacccag 360
aattatattt aacatcaaat ggtagtaatg cagatgttaa atatgttatc tacatgatag 420
agaaagaccc aggaagacag aaatatggtg ggtttgtcgt caagactaga gagatggttt 480
atgaaaagac aactgattgg atgttcggga gtgatcttga gtatgatcaa gacaatatgt 540
tgcaaaatgg tagaagcact tctacaatcg aggatcttgt tcatactttt ggatatccat 600
cgtgtcttgg agcccttata atccaagttt ggataatact tgttaaggct ataaccagta 660
tatcaggatt gaggaaagga ttctttactc ggttagaagc atttcgacaa gatggaacag 720
ttaaatccag tctagtgttg agcggtgatg cagtagaaca aattggatca attatgaggt 780
cccaacagag cttggtaaca ctcatggttg aaacactgat aacaatgaac acaggcagga 840
atgatctgac aacaatagaa aagaatatac agattgtagg aaactacatc agagatgcag 900
gtcttgcttc atttttcaac acaatcagat atggcattga gactagaatg gcagctctaa 960
ctctgtctac ccttagaccg gatatcaaca gactcaaggc actgatcgag ttatatctat 1020
caaaggggcc acgtgctcct tttatatgca ttttgagaga tcccgtgcat ggtgagtttg 1080
caccaggcaa ctatcctgcc ctctggagtt atgcgatggg tgtagcagtt gtacaaaaca 1140
aggccatgca acagtatgta acaggaaggt cttatctgga tattgaaatg ttccaacttg 1200
gtcaagcagt ggcacgtgat gccgagtcgc agatgagttc aatattagag gatgaactgg 1260
gggtcacaca agaagccaag caaagcttga agaaacacat gaagaacatc agcagttcag 1320
atacaacctt tcataagcct acagggggat cagccataga aatggcgata gatgaagaag 1380
cagggcagcc tgaatccaga ggagatcagg atcaaggaga tgagcctcgg tcatccatag 1440
ttccttatgc atgggcagac gaaaccggga atgacaatca aactgaatca actacagaaa 1500
ttgacagcat caaaactgaa caaagaaaca tcagagacag gctgaacaaa agactcaacg 1560
agaaaaggaa acagagtgac ccgagatcaa ctgacatcac aaacaacaca aatcaaactg 1620
aaatagatga tttgttcagt gcattcggaa gcaactagtc acaaagagat gaccaggcgc 1680
gccaagtaag aaaaacttag gattaatgga cctgcaggat ggaatattgg aaacacacaa 1740

```
acagcataaa taacaccaac aatgaaaccg aaacagccag aggcaaacat agtagcaagg   1800
ttacaaatat cataatgtac accttctgga caataacatt aacaatatta tcagtcattt   1860
ttataatgat attgacaaac ttaattaacc acaaagtcac accaacaact gcaatcatac   1920
aagatgcaac aagccagatc aagaacacaa ccccaacata cctcacccag aatcctcagc   1980
ttggaatcag tccctctaat ccgtctgaaa ttacatcaca aatcaccacc atactagctt   2040
caacaacacc aggagtcaag tcaaccctgc aatccacaac agtcaagacc aaaaacacaa   2100
caacaactca aacacaaccc agcaagccca ccacaaaaca acgccaaaac aaaccaccaa   2160
gcaaacccaa taatgatttt cactttgaag tgttcaactt tgtaccctgc agcatatgca   2220
gcaacaatcc aacctgctgg gctatctgca aaagaatacc aaacaaaaaa ccaggaaaga   2280
aaaccactac caagcccaca aaaaaaccaa ccctcaagac aaccaaaaaa gatcccaaac   2340
ctcaaaccac taaatcaaag gaagtaccca ccaccaagcc cacagaagag ccaaccatca   2400
acaccaccaa aacaaacatc ataactacac tactcacctc caacaccaca ggaaatccag   2460
aactcacaag tcaaatggaa accttccact caacttcctc cgaaggcaat ccaagccctt   2520
ctcaagtctc tacaacatcc gagtacccat cacaaccttc atctccaccc aacacaccac   2580
gccagtagtg atagctagcg gcgcgccagc aacaagtaag aaaaacttag gattaatgga   2640
aattatccaa tccagagacg gaaggacaaa tccagaatcc aaccacaact caatcaacca   2700
aagattcatg gaagacaatg ttcaaaacaa tcaaatcatg gattcttggg aagagggatc   2760
aggagataaa tcatctgaca tctcatcggc cctcgacatc attgaattca tactcagcac   2820
cgactcccaa gagaacacgg cagacagcaa tgaaatcaac acaggaacca caagacttag   2880
cacgacaatc taccaacctg aatccaaaac aacagaaaca agcaaggaaa atagtggacc   2940
agctaacaaa aatcgacagt ttggggcatc acacgaacgt gccacagaga caaaagatag   3000
aaatgttaat caggagactg tacagggagg atataggaga ggaagcagcc cagatagtag   3060
aactgagact atggtcactc gaagaatctc cagaagcagc ccagatccta acaatggaac   3120
ccaaatccag gaagatattg attacaatga agttggagag atggataagg actctactaa   3180
gagggaaatg cgacaattta aagatgttcc agtcaaggta tcaggaagtg atgccattcc   3240
tccaacaaaa caagatggag acggtgatga tggaagaggc ctggaatcta tcagtacatt   3300
tgattcagga tataccagta tagtgactgc cgcaacacta gatgacgaag aagaactcct   3360
tatgaagaac aacaggccaa gaaagtatca atcaacaccc cagaacagtg acaagggaat   3420
taaaaaaggg gttggaaggc caaaagacac agacaaacaa tcatcaatat tggactacga   3480
actcaacttc aaaggatcga agaagagcca gaaaatcctc aaagccagca cgaatacagg   3540
agaaccaaca agaccacaga atggatccca ggggaagaga atcacatcct ggaacatcct   3600
caacagcgag agcggcaatc gaacagaatc aacaaaccaa acccatcaga catcaacctc   3660
gggacagaac cacacaatgg gaccaagcag aacaacctcc gaaccaagga tcaagacaca   3720
aaagacggat ggaaaggaaa gagaggacac agaagagagc actcgattta cagaaagggc   3780
gattacatta ttacagaatc ttggtgtaat ccaatctgca gcaaaattag acctatacca   3840
agacaagaga gttgtgtgtg tggcgaatgt cctaaacaat gcagatactg catcaaagat   3900
agacttccta gcaggtttga tgataggagt gtcaatggat catgatacca aattaaatca   3960
gattcagaac gagatattaa gtttgaaaac tgatcttaaa aagatggatg aatcacatag   4020
aagactaatt gagaatcaaa aagaacaatt atcactgatc acatcattaa tctcaaatct   4080
```

-continued

```
taaaattatg acagagagag gagggaagaa ggaccaacca gaacctagcg ggaggacatc   4140
catgatcaag acaaaagcaa aagaagagaa aataaagaaa gtcaggtttg accctcttat   4200
ggaaacacag ggcatcgaga aaaacatccc tgacctctat agatcaatag agaaaacacc   4260
agaaaacgac acacagatca aatcagaaat aaacagattg aatgatgaat ccaatgccac   4320
tagattagta cctagaagaa taagcagtac aatgagatca ttaataataa tcattaacaa   4380
cagcaattta tcatcaaaag caaagcaatc atacatcaac gaactcaagc tctgcaagag   4440
tgacgaggaa gtgtctgagt tgatggacat gttcaatgag gatgtcagct cccagtaaac   4500
cgccaaccaa gggtcaacac caagaaaacc aatagcacaa aacagccaat cagagaccac   4560
cccaatacac caaaccaatc aacacataac aaagatcgcg gccgcataga tgattaagaa   4620
aaacttagga tgaaaggact aatcaatcct ccgaaacaat gagcatcacc aactccacaa   4680
tctacacatt cccagaatcc tctttctccg agaatggcaa catagagccg ttaccactca   4740
aggtcaatga acagagaaag gccatacctc atattagggt tgtcaagata ggagatccgc   4800
ccaaacatgg atccagatat ctggatgtct tttactgggg cttctttgag atggaaaggt   4860
caaaagacag gtatgggagc ataagtgatc tagatgatga tccaagttac aaggtttgtg   4920
gctctggatc attgccactt gggttggcta gatacaccgg aaatgatcag gaactcctac   4980
aggctgcaac caagctcgat atagaagtaa gaagaactgt aaaggctacg gagatgatag   5040
tttacactgt acaaaacatc aaacctgaac tatatccatg gtccagtaga ttaagaaaag   5100
ggatgttatt tgacgctaat aaggttgcac ttgctcctca atgtcttcca ctagatagag   5160
ggataaaatt cagggtgata tttgtgaact gcacagcaat tggatcaata actctattca   5220
aaatccctaa gtccatggca ttgttatcat tgcctaatac aatatcaata aatctacaag   5280
tacatatcaa aacaggagtt cagacagatt ccaaaggagt agttcagatt ctagatgaaa   5340
aaggtgaaaa atcactaaat ttcatggttc atctcgggtt gatcaaaagg aagatgggca   5400
gaatgtactc agttgaatat tgtaagcaga agatcgagaa gatgagatta ttattctcat   5460
tgggattagt tggagggatc agcttccacg tcaacgcaac tggctctata tcaaagacat   5520
tagcaagtca attagcattc aaaagagaaa tctgctatcc cctaatggat ctgaatccac   5580
acttaaattc agttatatgg gcatcatcag ttgaaattac aagggtagat gcagttctcc   5640
agccttcatt acctggcgaa ttcagatact acccaaacat catagcaaaa ggggtcggga   5700
aaatcagaca gtaaaatcaa caaccctgat atccaccggt gtattaagcc gaagcaaata   5760
aaggataatc aaaaacttag gacaaaagag gtcaatacca acaactatta gcagtcacac   5820
tcgcaagaat aagagagaag ggaccaaaaa agtcaaatag gagaaatcaa aacaaaaggt   5880
acagaacacc agaacaacaa aatcaaaaca tccaactcac tcaaaacaaa aattccaaaa   5940
gagaccggca acacaacaag cactgaacac aatgccaact tcaatactgc taattattac   6000
aaccatgatc atggcatctt tctgccaaat agatatcaca aaactacagc acgtaggtgt   6060
attggtcaac agtcccaaag ggatgaagat atcacaaaac tttgaaacaa gatatctaat   6120
tttgagcctc ataccaaaaa tagaagactc taactcttgt ggtgaccaac agatcaagca   6180
atacaagaag ttattggata gactgatcat cccttttatat gatggattaa gattacagaa   6240
agatgtgata gtaaccaatc aagaatccaa tgaaaacact gatcccagaa caaaacgatt   6300
ctttggaggg gtaattggaa ccattgctct gggagtagca acctcagcac aaattacagc   6360
ggcagttgct ctggttgaag ccaagcaggc aagatcagac atcgaaaaac tcaaagaagc   6420
aattagggac acaaacaaag cagtgcagtc agttcagagc tccataggaa atttaatagt   6480
```

-continued

```
agcaattaaa tcagtccagg attatgttaa caaagaaatc gtgccatcga ttgcgaggct   6540
aggttgtgaa gcagcaggac ttcaattagg aattgcatta acacagcatt actcagaatt   6600
aacaaacata tttggtgata acataggatc gttacaagaa aaggaataa aattacaagg    6660
tatagcatca ttataccgca caaatatcac agaaatattc acaacatcaa cagttgataa   6720
atatgatatc tatgatctgt tatttacaga atcaataaag gtgagagtta tagatgttga   6780
cttgaatgat tactcaatca ccctccaagt cagactccct ttattaacta ggctgctgaa   6840
cactcagatc tacaaagtag attccatatc atataacatc caaaacagag aatggtatat   6900
ccctcttccc agccatatca tgacgaaagg ggcatttcta ggtggagcag acgtcaaaga   6960
atgtatagaa gcattcagca gctatatatg cccttctgat ccaggatttg tattaaacca   7020
tgaaatagag agctgcttat caggaaacat atcccaatgt ccaagaacaa cggtcacatc   7080
agacattgtt ccaagatatg catttgtcaa tggaggagtg gttgcaaact gtataacaac   7140
cacctgtaca tgcaacggaa ttggtaatag aatcaatcaa ccacctgatc aaggagtaaa   7200
aattataaca cataaagaat gtagtacaat aggtatcaac ggaatgctgt tcaatacaaa   7260
taaagaagga actcttgcat tctatacacc aaatgatata acactaaaca attctgttgc   7320
acttgatcca attgacatat caatcgagct caacaaggcc aaatcagatc tagaagaatc   7380
aaaagaatgg ataagaaggt caaatcaaaa actagattct attggaaatt ggcatcaatc   7440
tagcactaca atcataatta ttttgataat gatcattata ttgtttataa ttaatataac   7500
gataattaca attgcaatta agtattacag aattcaaaag agaaatcgag tggatcaaaa   7560
tgacaagcca tatgtactaa caaacaaata acatatctac agatcattag atattaaaat   7620
tataaaaaac ttaggagtaa agttacgcaa tccaactcta ctcatataat tgaggaagga   7680
cccaatagac aaatccaaat tcgagatgga atactggaag cataccaatc acggaaagga   7740
tgctggtaat gagctggaga cgtctatggc tactcatggc aacaagctca ctaataagat   7800
aatatacata ttatggacaa taatcctggt gttattatca atagtcttca tcatagtgct   7860
aattaattcc atcaaaagtg aaaaggccca cgaatcattg ctgcaagaca taaataatga   7920
gtttatggaa attacagaaa agatccaaat ggcatcggat aataccaatg atctaataca   7980
gtcaggagtg aatacaaggc ttcttacaat tcagagtcat gtccagaatt acataccaat   8040
atcattgaca caacagatgt cagatcttag gaaattcatt agtgaaatta caattagaaa   8100
tgataatcaa gaagtgctgc cacaaagaat aacacatgat gtaggtataa aacctttaaa   8160
tccagatgat tttggagat gcacgtctgg tcttccatct ttaatgaaaa ctccaaaaat    8220
aaggttaatg ccagggccgg gattattagc tatgccaacg actgttgatg gctgtgttag   8280
aactccgtct ttagttataa atgatctgat ttatgcttat acctcaaatc taattactcg   8340
aggttgtcag gatataggaa aatcatatca agtcttacag atagggataa taactgtaaa   8400
ctcagacttg gtacctgact taaatcctag gatctctcat acctttaaca taaatgacaa   8460
taggaagtca tgttctctag cactcctaaa tacagatgta tatcaactgt gttcaactcc   8520
caaagttgat gaaagatcag attatgcatc atcaggcata gaagatattg tacttgatat   8580
tgtcaattat gatggttcaa tctcaacaac aagatttaag aataataaca taagctttga   8640
tcaaccatat gctgcactat acccatctgt tggaccaggg atatactaca aaggcaaaat   8700
aatatttctc gggtatggag gtcttgaaca tccaataaat gagaatgtaa tctgcaacac   8760
aactgggtgc cccgggaaaa cacagagaga ctgtaatcaa gcatctcata gtccatggtt   8820
```

-continued

```
ttcagatagg aggatggtca actccatcat tgttgttgac aaaggcttaa actcaattcc   8880
aaaattgaaa gtatggacga tatctatgcg acaaaattac tgggggtcag aaggaaggtt   8940
acttctacta ggtaacaaga tctatatata tacaagatct acaagttggc atagcaagtt   9000
acaattagga ataattgata ttactgatta cagtgatata aggataaaat ggacatggca   9060
taatgtgcta tcaagaccag gaaacaatga atgtccatgg ggacattcat gtccagatgg   9120
atgtataaca ggagtatata ctgatgcata tccactcaat cccacaggga gcattgtgtc   9180
atctgtcata ttagactcac aaaaatcgag agtgaaccca gtcataactt actcaacagc   9240
aaccgaaaga gtaaacgagc tggccatcct aaacagaaca ctctcagctg gatatacaac   9300
aacaagctgc attacacact ataacaaagg atattgtttt catatagtag aaataaatca   9360
taaaagctta aacacatttc aacccatgtt gttcaaaaca gagattccaa aaagctgcag   9420
ttaatcataa ttaaccataa tatgcatcaa tctatctata atacaagtat atgataagta   9480
atcagcaatc agacaataga cgtacggaaa taataaaaaa cttaggagaa aagtgtgcaa   9540
gaaaaatgga caccgagtcc cacagcggca caacatctga cattctgtac cctgaatgtc   9600
acctcaattc tcctatagtt aaaggaaaga tagcacaact gcatacaata atgagtttgc   9660
ctcagcccta cgatatggat gatgattcaa tactgattat tactagacaa aaaattaaac   9720
tcaataaatt agataaaaga caacggtcaa ttaggaaatt aagatcagtc ttaatggaaa   9780
gagtaagtga tctaggtaaa tataccttta tcagatatcc agagatgtct agtgaaatgt   9840
tccaattatg tatacccgga attaataata aaataaatga attgctaagt aaagcaagta   9900
aaacatataa tcaaatgact gatggattaa gagatctatg ggttactata ctatcgaagt   9960
tagcatcgaa aaatgatgga agtaattatg atatcaatga agatattagc aatatatcaa  10020
atgttcacat gacttatcaa tcagacaaat ggtataatcc attcaagaca tggtttacta  10080
ttaagtatga catgagaaga ttacaaaaag ccaaaaatga gattacattc aataggcata  10140
aagattataa tctattagaa gaccaaaaga atatattgct gatacatcca gaactcgtct  10200
taatattaga taaacaaaat tacaatgggt atataatgac tcctgaattg gtactaatgt  10260
attgtgatgt agttgaaggg aggtggaata taagttcatg tgcaaaattg gatcctaagt  10320
tacaatcaat gtattataag ggtaacaatt tatgggaaat aatagatgga ctattctcga  10380
ccttaggaga aagaacattt gacataatat cactattaga accacttgca ttatcgctca  10440
ttcaaactta tgacccggtt aaacagctca ggggggcttt tttaaatcac gtgttatcag  10500
aaatggaatt aatatttgca gctgagtgta caacagagga aatacctaat gtggattata  10560
tagataaaat tttagatgtg ttcaaagaat caacaataga tgaaatagca gaaattttct  10620
ctttcttccg aacttttgga caccctccat tagaggcgag tatagcagca gagaaagtta  10680
gaaagtatat gtatactgag aaatgcttga aatttgatac tatcaataaa tgtcatgcta  10740
ttttttgtac aataattata aatggatata gagaaagaca tggtggtcaa tggcctccag  10800
ttacattacc tgtccatgca catgaattta tcataaatgc atacggatca aattctgcca  10860
tatcatatga gaatgctgta gattattata agagcttcat aggaataaaa tttgacaagt  10920
ttatagagcc tcaattggat gaagacttaa ctatttatat gaaagataaa gcattatccc  10980
caaagaaatc aaactgggac acagtctatc cagcttcaaa cctgttatac cgcactaatg  11040
tgtctcatga ttcacgaaga ttggttgaag tatttatagc agatagtaaa tttgatcccc  11100
accaagtatt agattacgta gaatcaggat attggctgga tgatcctgaa tttaatatct  11160
catatagttt aaaagagaaa gaaataaaac aagaaggtag actttttgca aaaatgacat  11220
```

acaagatgag ggctacacaa gtattatcag aaacattatt ggcgaataat atagggaaat 11280
tcttccaaga gaatgggatg gttaaaggag aaattgaatt actcaagaga ctaacaacaa 11340
tatctatgtc tggagttccg cggtataatg aggtatacaa taattcaaaa agtcacacag 11400
aagaacttca agcttataat gcaattagca gttccaattt atcttctaat cagaagtcaa 11460
agaagtttga atttaaatct acagatatat acaatgatgg atacgaaacc gtaagctgct 11520
tcttaacgac agatcttaaa aaatattgtt taaattggag gtatgaatca acagctttat 11580
tcggtgatac ttgtaatcag atatttgggt taaaggaatt atttaattgg ctgcaccctc 11640
gccttgaaaa gagtacaata tatgttggag atccttattg cccgccatca gatattgaac 11700
atttaccact tgatgaccat cctgattcag gattttatgt tcataatcct aaaggaggaa 11760
tagaagggtt ttgccaaaag ttatggacac tcatatctat cagtgcaata catttagcag 11820
ctgtcaaaat cggtgtaaga gttactgcaa tggttcaagg ggataatcaa gccatagctg 11880
ttaccacaag agtacctaat aattatgatt ataaagttaa gaaagagatt gtttataaag 11940
atgtggtaag attttttgat tccttgagag aggtgatgga tgatctgggt catgagctca 12000
aactaaatga aactataata agtagtaaaa tgtttatata tagcaaaagg atatactatg 12060
acggaagaat ccttcctcag gcattaaaag cattgtctag atgtgttttt tggtctgaaa 12120
caatcataga tgagacaaga tcagcatcct caaatctggc tacatcgttt gcaaaggcca 12180
ttgagaatgg ctactcacct gtattgggat atgtatgctc aatcttcaaa aatatccaac 12240
agttgtatat agcgcttgga atgaatataa acccaactat aacccaaaat attaaagatc 12300
aatatttcag gaatattcat tggatgcaat atgcctcctt aatccctgct agtgtcggag 12360
gatttaatta tatggccatg tcaaggtgtt ttgtcagaaa cattggagat cctacagtcg 12420
ctgcgttagc cgatattaaa agatttataa aagcaaattt gttagatcga ggtgtccttt 12480
acagaattat gaatcaagaa ccaggcgagt cttctttttt agactgggcc tcagatccct 12540
attcatgtaa cttaccacaa tctcaaaata taaccaccat gataaagaat ataactgcaa 12600
gaaatgtact acaggactca ccaaacccat tactatctgg attatttaca agtacaatga 12660
tagaagagga tgaggaatta gctgagttcc taatggacag gagaataatc ctcccaagag 12720
ttgcacatga cattttagat aattctctta ctggaattag gaatgctata gctggtatgt 12780
tggatacaac aaaatcacta attcgagtag ggataagcag aggaggatta acctataact 12840
tattaagaaa gataagcaac tatgatcttg tacaatatga gacacttagt aaaactttaa 12900
gactaatagt cagtgacaag attaagtatg aagatatgtg ctcagtagac ctagccatat 12960
cattaagaca aaaaatgtgg atgcatttat caggaggaag aatgataaat ggacttgaaa 13020
ctccagatcc tttagagtta ctgtctggag taataataac aggatctgaa cattgtagga 13080
tatgttattc aactgaaggt gaaagcccat atacatggat gtatttacca ggcaatctta 13140
atataggatc agctgagaca ggaatagcat cattaagggt cccttacttt ggatcagtta 13200
cagatgagag atctgaagca caattagggt atatcaaaaa tctaagcaaa ccagctaagg 13260
ctgctataag aatagcaatg atatatactt gggcatttgg gaatgacgaa atatcttgga 13320
tggaagcatc acagattgca caaacacgtg caaactttac attggatagc ttaaagattt 13380
tgacaccagt gacaacatca acaaatctat cacacaggtt aaaagatact gctactcaga 13440
tgaaattttc tagtacatca cttattagag taagcaggtt catcacaata tctaatgata 13500
atatgtctat taaagaagca aatgaaacta aagatacaaa tcttatttat caacaggtaa 13560

-continued

```
tgttaacagg attaagtgta tttgaatatc tatttaggtt agaggagagt acaggacata  13620
accctatggt catgcatcta catatagagg atggatgttg tataaaagag agttacaatg  13680
atgagcatat caatccggag tctacattag agttaatcaa ataccctgag agtaatgaat  13740
ttatatatga taaggaccct ttaaaggata tagatctatc aaaattaatg gttataagag  13800
atcattctta tacaattgac atgaattact gggatgacac agatattgta catgcaatat  13860
caatatgtac tgcagttaca atagcagata caatgtcgca gctagatcgg gataatctta  13920
aggagctggt tgtgattgca aatgatgatg atattaacag tctgataact gaatttctga  13980
ccctagatat actagtgttt ctcaaaacat ttggagggtt actcgtgaat caatttgcat  14040
ataccccttta tggattgaaa atagaaggaa gggatcccat ttgggattat ataatgagaa  14100
cattaaaaga cacctcacat tcagtactta aagtattatc taatgcacta tctcatccaa  14160
aagtgtttaa gagattttgg gattgtggag ttttgaatcc tatttatggt cctaatactg  14220
ctagtcaaga tcaagttaag cttgctctct cgatttgcga gtactccttg gatctattta  14280
tgagagaatg gttgaatgga gcatcacttg agatctatat ctgtgatagt gacatggaaa  14340
tagcaaatga cagaagacaa gcatttctct caagacatct tgcctttgtg tgttgtttag  14400
cagagatagc atcttttgga ccaaatttat taaatctaac atatctagag agacttgatg  14460
aattaaaaca atacttagat ctgaacatca aagaagatcc tactcttaaa tatgtgcaag  14520
tatcaggact gttaattaaa tcattcccct caactgttac gtatgtaagg aaaactgcga  14580
ttaagtatct gaggattcgt ggtattaatc cgcctgaaac gattgaagat tgggatccca  14640
tagaagatga gaatatctta gacaatattg ttaaaactgt aaatgacaat tgcagtgata  14700
atcaaaagag aaataaaagt agttatttct ggggattagc tctaaagaat tatcaagtcg  14760
tgaaaataag atccataacg agtgattctg aagttaatga agcttcgaat gttactacac  14820
atggaatgac acttcctcag ggaggaagtt atctatcaca tcagctgagg ttatttggag  14880
taaacagtac aagttgtctt aaagctcttg aattatcaca aatcttaatg agggaagtta  14940
aaaaagataa agatagactc tttttaggag aaggagcagg agctatgtta gcatgttatg  15000
atgctacact cggtcctgca ataaattatt ataattctgg tttaaatatt acagatgtaa  15060
ttggtcaacg ggaattaaaa atcttcccat cagaagtatc attagtaggt aaaaaactag  15120
gaaatgtaac acagattctt aatcgggtga gggtgttatt taatgggaat cccaattcaa  15180
catggatagg aaatatggaa tgtgagagtt taatatggag tgaattaaat gataagtcaa  15240
ttggtttagt acattgtgac atggagggag cgataggcaa atcagaagaa actgttctac  15300
atgaacatta tagtattatt aggattacat atttaatcgg ggatgatgat gttgtcctag  15360
tatcaaaaat tataccaact attactccga attggtctaa aatactctat ctatacaagt  15420
tgtattggaa ggatgtaagt gtagtgtccc ttaaaacatc caatcctgcc tcaacagagc  15480
tttatttaat ttcaaaagat gcttactgta ctgtaatgga acccagtaat cttgttttat  15540
caaaacttaa aaggatatca tcaatagaag aaaataatct attaaagtgg ataatcttat  15600
caaaaaggaa gaataacgag tggttacagc atgaaatcaa agaaggagaa agggattatg  15660
ggataatgag gccatatcat acagcactgc aaatttttgg attccaaatt aacttaaatc  15720
acttagctag agaattttta tcaactcctg atttaaccaa cattaataat ataattcaaa  15780
gttttacaag aacaattaaa gatgttatgt tcgaatgggt caatatcact catgacaata  15840
aaagacataa attaggagga agatataatc tattcccgct taaaaataag ggaaattaa  15900
gattattatc acgaagatta gtactaagct ggatatcatt atccttatca accagattac  15960
```

tgacgggccg ttttccagat gaaaaatttg aaaatagggc acagaccgga tatgtatcat 16020
tggctgatat tgatttagaa tccttaaagt tattatcaag aaatattgtc aaaaattaca 16080
aagaacacat aggattaata tcatactggt ttttgaccaa agaggtcaaa atactaatga 16140
agcttatagg aggagtcaaa ctactaggaa ttcctaaaca gtacaaagag ttagaggatc 16200
gatcatctca gggttatgaa tatgataatg aatttgatat tgattaatac ataaaaacat 16260
aaaataaaac acctattcct cacccattca cttccaacaa aatgaaaagt aagaaaaaca 16320
tgtaatatat atataccaaa cagagttttt ctcttgtttg gt 16362

<210> SEQ ID NO 94
<211> LENGTH: 16368
<212> TYPE: DNA
<213> ORGANISM: Artificial Sequence
<220> FEATURE:
<223> OTHER INFORMATION: Recombinant rB/HPIV3 sequence

<400> SEQUENCE: 94
accaaacaag agaagagact ggtttgggaa tattaattca aataaaaatt aacttaggat 60
taaagaactt taccgaaagg taaggggaaa gaaatcctaa gagcttagcc atgttgagtc 120
tattcgacac attcagtgcg cgtaggcagg agaacataac gaaatcagct ggtggggctg 180
ttattcccgg gcaaaaaaac actgtgtcta tatttgctct tggaccatca ataacagatg 240
acaatgataa aatgacattg gctcttctct tttgtctcca ttctttagac aatgaaaagc 300
agcatgcgca aagagctgga tttttagttt ctctgttatc aatggcttat gccaacccag 360
aattatattt aacatcaaat ggtagtaatg cagatgttaa atatgttatc tacatgatag 420
agaaagaccc aggaagacag aaatatggtg ggtttgtcgt caagactaga gagatggttt 480
atgaaaagac aactgattgg atgttcggga gtgatcttga gtatgatcaa gacaatatgt 540
tgcaaaatgg tagaagcact tctacaatcg aggatcttgt tcatactttt ggatatccat 600
cgtgtcttgg agcccttata atccaagttt ggataatact tgttaaggct ataaccagta 660
tatcaggatt gaggaaagga ttctttactc ggttagaagc atttcgacaa gatggaacag 720
ttaaatccag tctagtgttg agcggtgatg cagtagaaca aattggatca attatgaggt 780
cccaacagag cttggtaaca ctcatggttg aaacactgat aacaatgaac acaggcagga 840
atgatctgac aacaatagaa aagaatatac agattgtagg aaactacatc agagatgcag 900
gtcttgcttc atttttcaac acaatcagat atggcattga gactagaatg gcagctctaa 960
ctctgtctac ccttagaccg gatatcaaca gactcaaggc actgatcgag ttatatctat 1020
caaaggggcc acgtgctcct tttatatgca ttttgagaga tcccgtgcat ggtgagtttg 1080
caccaggcaa ctatcctgcc ctctggagtt atgcgatggg tgtagcagtt gtacaaaaca 1140
aggccatgca acagtatgta acaggaaggt cttatctgga tattgaaatg ttccaacttg 1200
gtcaagcagt ggcacgtgat gccgagtcgc agatgagttc aatattagag gatgaactgg 1260
gggtcacaca agaagccaag caaagcttga agaaacacat gaagaacatc agcagttcag 1320
atacaacctt tcataagcct acagggggat cagccataga aatggcgata gatgaagaag 1380
cagggcagcc tgaatccaga ggagatcagg atcaaggaga tgagcctcgg tcatccatag 1440
ttccttatgc atgggcagac gaaaccggga atgacaatca aactgaatca actacagaaa 1500
ttgacagcat caaaactgaa caaagaaaca tcagagacag gctgaacaaa agactcaacg 1560
agaaaaggaa acagagtgac ccgagatcaa ctgacatcac aaacaacaca aatcaaactg 1620

-continued

```
aaatagatga tttgttcagt gcattcggaa gcaactagtc acaaagagat gaccaggcgc   1680
gccaagtaag aaaaacttag gattaatgga cctgcaggat ggaatattgg aaacacacaa   1740
acagcataaa taacaccaac aatgaaaccg aaacagccag aggcaaacat agtagcaagg   1800
ttacaaatgt agcacaaatc acattatcca ttctggcaat gataatctca acttcactta   1860
taattgcagc catcatattc atagcctcgg caaaccacaa agtcacacca acaactgcaa   1920
tcatacaaga tgcaacaagc cagatcaaga acacaacccc aacataccte acccagaatc   1980
ctcagcttgg aatcagtccc tctaatccgt ctgaaattac atcacaaatc accaccatac   2040
tagcttcaac aacaccagga gtcaagtcaa ccctgcaatc cacaacagtc aagaccaaaa   2100
acacaacaac aactcaaaca caacccagca agcccaccac aaaacaacgc caaaacaaac   2160
caccaagcaa acccaataat gattttcact ttgaagtgtt caactttgta ccctgcagca   2220
tatgcagcaa caatccaacc tgctgggcta tctgcaaaag aataccaaac aaaaaaccag   2280
gaaagaaaac cactaccaag cccacaaaaa aaccaaccct caagacaacc aaaaaagatc   2340
ccaaacctca aaccactaaa tcaaaggaag tacccaccac caagcccaca gaagagccaa   2400
ccatcaacac caccaaaaca aacatcataa ctacactact cacctccaac accacaggaa   2460
atccagaact cacaagtcaa atggaaacct tccactcaac ttcctccgaa ggcaatccaa   2520
gcccttctca agtctctaca acatccgagt acccatcaca accttcatct ccacccaaca   2580
caccacgcca gtagtgatag ctagcggcgc gccagcaaca agtaagaaaa acttaggatt   2640
aatggaaatt atccaatcca gagacggaag gacaaatcca gaatccaacc acaactcaat   2700
caaccaaaga ttcatggaag acaatgttca aaacaatcaa atcatggatt cttgggaaga   2760
gggatcagga gataaatcat ctgacatctc atcggccctc gacatcattg aattcatact   2820
cagcaccgac tcccaagaga acacggcaga cagcaatgaa atcaacacag gaaccacaag   2880
acttagcacg acaatctacc aacctgaatc caaaacaaca gaaacaagca aggaaaatag   2940
tggaccagct aacaaaaatc gacagtttgg ggcatcacac gaacgtgcca cagagacaaa   3000
agatagaaat gttaatcagg agactgtaca gggaggatat aggagaggaa gcagcccaga   3060
tagtagaact gagactatgg tcactcgaag aatctccaga agcagcccag atcctaacaa   3120
tggaacccaa atccaggaag atattgatta caatgaagtt ggagagatgg ataaggactc   3180
tactaagagg gaaatgcgac aatttaaaga tgttccagtc aaggtatcag gaagtgatgc   3240
cattcctcca acaaaacaag atggagacgg tgatgatgga agaggcctgg aatctatcag   3300
tacatttgat tcaggatata ccagtatagt gactgccgca acactagatg acgaagaaga   3360
actccttatg aagaacaaca ggccaagaaa gtatcaatca acaccccaga acagtgacaa   3420
gggaattaaa aaaggggttg gaaggccaaa agacacagac aaacaatcat caatattgga   3480
ctacgaactc aacttcaaag gatcgaagaa gagccagaaa atcctcaaag ccagcacgaa   3540
tacaggagaa ccaacaagac cacagaatgg atcccagggg aagagaatca catcctggaa   3600
catcctcaac agcgagagcg gcaatcgaac agaatcaaca aaccaaaccc atcagacatc   3660
aacctcggga cagaaccaca caatgggacc aagcagaaca acctccgaac caaggatcaa   3720
gacacaaaag acggatggaa aggaaagaga ggacacagaa gagagcactc gatttacaga   3780
aagggcgatt acattattac agaatcttgg tgtaatccaa tctgcagcaa aattagacct   3840
ataccaagac aagagagttg tgtgtgtggc gaatgtccta aacaatgcag atactgcatc   3900
aaagatagac ttcctagcag gtttgatgat aggagtgtca atggatcatg ataccaaatt   3960
aaatcagatt cagaacgaga tattaagttt gaaaactgat cttaaaaaga tggatgaatc   4020
```

acatagaaga ctaattgaga atcaaaaaga acaattatca ctgatcacat cattaatctc 4080
aaatcttaaa attatgacag agagaggagg gaagaaggac caaccagaac ctagcgggag 4140
gacatccatg atcaagacaa aagcaaaaga agagaaaata aagaaagtca ggtttgaccc 4200
tcttatggaa acacagggca tcgagaaaaa catccctgac ctctatagat caatagagaa 4260
aacaccagaa aacgacacac agatcaaatc agaaataaac agattgaatg atgaatccaa 4320
tgccactaga ttagtaccta gaagaataag cagtacaatg agatcattaa taataatcat 4380
taacaacagc aatttatcat caaaagcaaa gcaatcatac atcaacgaac tcaagctctg 4440
caagagtgac gaggaagtgt ctgagttgat ggacatgttc aatgaggatg tcagctccca 4500
gtaaaccgcc aaccaagggt caacaccaag aaaaccaata gcacaaaaca gccaatcaga 4560
gaccaccccca atacaccaaa ccaatcaaca cataacaaag atcgcggccg catagatgat 4620
taagaaaaac ttaggatgaa aggactaatc aatcctccga aacaatgagc atcaccaact 4680
ccacaatcta cacattccca gaatcctctt tctccgagaa tggcaacata gagccgttac 4740
cactcaaggt caatgaacag agaaaggcca tacctcatat tagggttgtc aagataggag 4800
atccgcccaa acatggatcc agatatctgg atgtcttttt actgggcttc tttgagatgg 4860
aaaggtcaaa agacaggtat gggagcataa gtgatctaga tgatgatcca agttacaagg 4920
tttgtggctc tggatcattg ccacttgggt tggctagata caccggaaat gatcaggaac 4980
tcctacaggc tgcaaccaag ctcgatatag aagtaagaag aactgtaaag gctacggaga 5040
tgatagttta cactgtacaa aacatcaaac ctgaactata tccatggtcc agtagattaa 5100
gaaaagggat gttatttgac gctaataagg ttgcacttgc tcctcaatgt cttccactag 5160
atagagggat aaaattcagg gtgatatttg tgaactgcac agcaattgga tcaataactc 5220
tattcaaaat ccctaagtcc atggcattgt tatcattgcc taatacaata tcaataaatc 5280
tacaagtaca tatcaaaaca ggagttcaga cagattccaa aggagtagtt cagattctag 5340
atgaaaaagg tgaaaaatca ctaaatttca tggttcatct cgggttgatc aaaaggaaga 5400
tgggcagaat gtactcagtt gaatattgta agcagaagat cgagaagatg agattattat 5460
tctcattggg attagttgga gggatcagct tccacgtcaa cgcaactggc tctatatcaa 5520
agacattagc aagtcaatta gcattcaaaa gagaaatctg ctatcccccta atggatctga 5580
atccacactt aaattcagtt atatgggcat catcagttga aattacaagg gtagatgcag 5640
ttctccagcc ttcattacct ggcgaattca gatactaccc aaacatcata gcaaaagggg 5700
tcgggaaaat cagacagtaa aatcaacaac cctgatatcc accggtgtat taagccgaag 5760
caaataaagg ataatcaaaa acttaggaca aaagaggtca ataccaacaa ctattagcag 5820
tcacactcgc aagaataaga gagaagggac caaaaaagtc aaataggaga aatcaaaaca 5880
aaaggtacag aacaccagaa caacaaaatc aaaacatcca actcactcaa aacaaaaatt 5940
ccaaaagaga ccggcaacac aacaagcact gaacacaatg ccaacttcaa tactgctaat 6000
tattacaacc atgatcatgg catctttctg ccaaatagat atcacaaaac tacagcacgt 6060
aggtgtattg gtcaacagtc ccaaagggat gaagatatca caaaactttg aaacaagata 6120
tctaattttg agcctcatac caaaaataga agactctaac tcttgtggtg accaacagat 6180
caagcaatac aagaagttat tggatagact gatcatccct ttatatgatg gattaagatt 6240
acagaaagat gtgatagtaa ccaatcaaga atccaatgaa aacactgatc ccagaacaaa 6300
acgattcttt ggaggggtaa ttggaaccat tgctctggga gtagcaacct cagcacaaat 6360

```
tacagcggca gttgctctgg ttgaagccaa gcaggcaaga tcagacatcg aaaaactcaa   6420
agaagcaatt agggacacaa acaaagcagt gcagtcagtt cagagctcca taggaaattt   6480
aatagtagca attaaatcag tccaggatta tgttaacaaa gaaatcgtgc catcgattgc   6540
gaggctaggt tgtgaagcag caggacttca attaggaatt gcattaacac agcattactc   6600
agaattaaca aacatatttg gtgataacat aggatcgtta caagaaaaag gaataaaatt   6660
acaaggtata gcatcattat accgcacaaa tatcacagaa atattcacaa catcaacagt   6720
tgataaatat gatatctatg atctgttatt tacagaatca ataaaggtga gagttataga   6780
tgttgacttg aatgattact caatcaccct ccaagtcaga ctccctttat taactaggct   6840
gctgaacact cagatctaca aagtagattc catatcatat aacatccaaa acagagaatg   6900
gtatatccct cttcccagcc atatcatgac gaaaggggca tttctaggtg gagcagacgt   6960
caaagaatgt atagaagcat tcagcagcta tatatgccct tctgatccag gatttgtatt   7020
aaaccatgaa atagagagct gcttatcagg aaacatatcc caatgtccaa gaacaacggt   7080
cacatcagac attgttccaa gatatgcatt tgtcaatgga ggagtggttg caaactgtat   7140
aacaaccacc tgtacatgca acggaattgg taatagaatc aatcaaccac ctgatcaagg   7200
agtaaaaatt ataacacata aagaatgtag tacaataggt atcaacggaa tgctgttcaa   7260
tacaaataaa gaaggaactc ttgcattcta tacaccaaat gatataacac taaacaattc   7320
tgttgcactt gatccaattg acatatcaat cgagctcaac aaggccaaat cagatctaga   7380
agaatcaaaa gaatggataa gaaggtcaaa tcaaaaacta gattctattg gaaattggca   7440
tcaatctagc actacaatca taattatttt gataatgatc attatattgt ttataattaa   7500
tataacgata attacaattg caattaagta ttacagaatt caaaagagaa atcgagtgga   7560
tcaaaatgac aagccatatg tactaacaaa caaataacat atctacagat cattagatat   7620
taaaattata aaaaacttag gagtaaagtt acgcaatcca actctactca tataattgag   7680
gaaggaccca atagacaaat ccaaattcga gatggaatac tggaagcata ccaatcacgg   7740
aaaggatgct ggtaatgagc tggagacgtc tatggctact catggcaaca agctcactaa   7800
taagataata tacatattat ggacaataat cctggtgtta ttatcaatag tcttcatcat   7860
agtgctaatt aattccatca aaagtgaaaa ggcccacgaa tcattgctgc aagacataaa   7920
taatgagttt atggaaatta cagaaaagat ccaaatggca tcggataata ccaatgatct   7980
aatacagtca ggagtgaata caaggcttct tacaattcag agtcatgtcc agaattacat   8040
accaatatca ttgacacaac agatgtcaga tcttaggaaa ttcattagtg aaattacaat   8100
tagaaatgat aatcaagaag tgctgccaca aagaataaca catgatgtag gtataaaacc   8160
tttaaatcca gatgattttt ggagatgcac gtctggtctt ccatctttaa tgaaaactcc   8220
aaaaataagg ttaatgccag ggccgggatt attagctatg ccaacgactg ttgatggctg   8280
tgttagaact ccgtctttag ttataaatga tctgatttat gcttatacct caaatctaat   8340
tactcgaggt tgtcaggata taggaaaatc atatcaagtc ttacagatag ggataataac   8400
tgtaaactca gacttggtac ctgacttaaa tcctaggatc tctcatacct ttaacataaa   8460
tgacaatagg aagtcatgtt ctctagcact cctaaataca gatgtatatc aactgtgttc   8520
aactcccaaa gttgatgaaa gatcagatta tgcatcatca ggcatagaag atattgtact   8580
tgatattgtc aattatgatg gttcaatctc aacaacaaga tttaagaata ataacataag   8640
ctttgatcaa ccatatgctg cactataccc atctgttgga ccagggatat actacaaagg   8700
caaaataata tttctcgggt atggaggtct tgaacatcca ataaatgaga atgtaatctg   8760
```

caacacaact gggtgccccg ggaaaacaca gagagactgt aatcaagcat ctcatagtcc 8820
atggttttca gataggagga tggtcaactc catcattgtt gttgacaaag gcttaaactc 8880
aattccaaaa ttgaaagtat ggacgatatc tatgcgacaa aattactggg ggtcagaagg 8940
aaggttactt ctactaggta acaagatcta tatatataca agatctacaa gttggcatag 9000
caagttacaa ttaggaataa ttgatattac tgattacagt gatataagga taaaatggac 9060
atggcataat gtgctatcaa gaccaggaaa caatgaatgt ccatggggac attcatgtcc 9120
agatggatgt ataacaggag tatatactga tgcatatcca ctcaatccca cagggagcat 9180
tgtgtcatct gtcatattag actcacaaaa atcgagagtg aacccagtca taacttactc 9240
aacagcaacc gaaagagtaa acgagctggc catcctaaac agaacactct cagctggata 9300
tacaacaaca agctgcatta cacactataa caaaggatat tgttttcata tagtagaaat 9360
aaatcataaa agcttaaaca catttcaacc catgttgttc aaaacagaga ttccaaaaag 9420
ctgcagttaa tcataattaa ccataaatatg catcaatcta tctataatac aagtatatga 9480
taagtaatca gcaatcagac aatagacgta cggaaataat aaaaaactta ggagaaaagt 9540
gtgcaagaaa aatggacacc gagtcccaca gcggcacaac atctgacatt ctgtaccctg 9600
aatgtcacct caattctcct atagttaaag gaaagatagc acaactgcat acaataatga 9660
gtttgcctca gccctacgat atggatgatg attcaatact gattattact agacaaaaaa 9720
ttaaactcaa taaattagat aaaagacaac ggtcaattag gaaattaaga tcagtcttaa 9780
tggaaagagt aagtgatcta ggtaaatata cctttatcag atatccagag atgtctagtg 9840
aaatgttcca attatgtata cccggaatta ataataaaat aaatgaattg ctaagtaaag 9900
caagtaaaac atataatcaa atgactgatg gattaagaga tctatgggtt actatactat 9960
cgaagttagc atcgaaaaat gatggaagta attatgatat caatgaagat attagcaata 10020
tatcaaatgt tcacatgact tatcaatcag acaaatggta taatccattc aagacatggt 10080
ttactattaa gtatgacatg agaagattac aaaaagccaa aaatgagatt acattcaata 10140
ggcataaaga ttataatcta ttagaagacc aaaagaatat attgctgata catccagaac 10200
tcgtcttaat attagataaa caaaattaca atgggtatat aatgactcct gaattggtac 10260
taatgtattg tgatgtagtt gaagggaggt ggaatataag ttcatgtgca aaattggatc 10320
ctaagttaca atcaatgtat tataagggta acaatttatg ggaaataata gatggactat 10380
tctcgacctt aggagaaaga acatttgaca taatatcact attagaacca cttgcattat 10440
cgctcattca aacttatgac ccggttaaac agctcagggg ggctttttta aatcacgtgt 10500
tatcagaaat ggaattaata tttgcagctg agtgtacaac agaggaaata cctaatgtgg 10560
attatataga taaaatttta gatgtgttca aagaatcaac aatagatgaa atagcagaaa 10620
ttttctcttt cttccgaact tttggacacc ctccattaga ggcgagtata gcagcagaga 10680
aagttagaaa gtatatgtat actgagaaat gcttgaaatt tgatactatc aataaatgtc 10740
atgctatttt ttgtacaata attataaatg gatatagaga aagacatggt ggtcaatggc 10800
ctccagttac attacctgtc catgcacatg aatttatcat aaatgcatac ggatcaaatt 10860
ctgccatatc atatgagaat gctgtagatt attataagag cttcatagga ataaaatttg 10920
acaagtttat agagcctcaa ttggatgaag acttaactat ttatatgaaa gataaagcat 10980
tatccccaaa gaaatcaaac tgggacacag tctatccagc ttcaaacctg ttataccgca 11040
ctaatgtgtc tcatgattca cgaagattgg ttgaagtatt tatagcagat agtaaatttg 11100

-continued atccccacca agtattagat tacgtagaat caggatattg gctggatgat cctgaattta 11160
atatctcata tagtttaaaa gagaaagaaa taaaacaaga aggtagactt tttgcaaaaa 11220
tgacatacaa gatgagggct acacaagtat tatcagaaac attattggcg aataatatag 11280
ggaaattctt ccaagagaat gggatggtta aaggagaaat tgaattactc aagagactaa 11340
caacaatatc tatgtctgga gttccgcggt ataatgaggt atacaataat tcaaaaagtc 11400
acacagaaga acttcaagct tataatgcaa ttagcagttc caatttatct tctaatcaga 11460
agtcaaagaa gtttgaattt aaatctacag atatatacaa tgatggatac gaaaccgtaa 11520
gctgcttctt aacgacagat cttaaaaaat attgtttaaa ttggaggtat gaatcaacag 11580
ctttattcgg tgatacttgt aatcagatat ttgggttaaa ggaattattt aattggctgc 11640
accctcgcct tgaaaagagt acaatatatg ttggagatcc ttattgcccg ccatcagata 11700
ttgaacattt accacttgat gaccatcctg attcaggatt ttatgttcat aatcctaaag 11760
gaggaataga agggttttgc caaaagttat ggacactcat atctatcagt gcaatacatt 11820
tagcagctgt caaaatcggt gtaagagtta ctgcaatggt tcaaggggat aatcaagcca 11880
tagctgttac cacaagagta cctaataatt atgattataa agttaagaaa gagattgttt 11940
ataaagatgt ggtaagattt tttgattcct tgagagaggt gatggatgat ctgggtcatg 12000
agctcaaact aaatgaaact ataataagta gtaaaatgtt tatatatagc aaaaggatat 12060
actatgacgg aagaatcctt cctcaggcat taaaagcatt gtctagatgt gttttttggt 12120
ctgaaacaat catagatgag acaagatcag catcctcaaa tctggctaca tcgtttgcaa 12180
aggccattga gaatggctac tcacctgtat tgggatatgt atgctcaatc ttcaaaaata 12240
tccaacagtt gtatatagcg cttggaatga atataaaccc aactataacc caaaatatta 12300
aagatcaata tttcaggaat attcattgga tgcaatatgc ctccttaatc cctgctagtg 12360
tcggaggatt taattatatg gccatgtcaa ggtgttttgt cagaaacatt ggagatccta 12420
cagtcgctgc gttagccgat attaaaagat ttataaaagc aaatttgtta gatcgaggtg 12480
tcctttacag aattatgaat caagaaccag gcgagtcttc ttttttagac tgggcctcag 12540
atccctattc atgtaactta ccacaatctc aaaatataac caccatgata aagaatataa 12600
ctgcaagaaa tgtactacag gactcaccaa acccattact atctggatta tttacaagta 12660
caatgataga agaggatgag gaattagctg agttcctaat ggacaggaga ataatcctcc 12720
caagagttgc acatgacatt ttagataatt ctcttactgg aattaggaat gctatagctg 12780
gtatgttgga tacaacaaaa tcactaattc gagtagggat aagcagagga ggattaacct 12840
ataacttatt aagaaagata agcaactatg atcttgtaca atatgagaca cttagtaaaa 12900
ctttaagact aatagtcagt gacaagatta agtatgaaga tatgtgctca gtagacctag 12960
ccatatcatt aagacaaaaa atgtggatgc atttatcagg aggaagaatg ataaatggac 13020
ttgaaactcc agatccttta gagttactgt ctggagtaat aataacagga tctgaacatt 13080
gtaggatatg ttattcaact gaaggtgaaa gcccatatac atggatgtat ttaccaggca 13140
atcttaatat aggatcagct gagacaggaa tagcatcatt aagggtccct tactttggat 13200
cagttacaga tgagagatct gaagcacaat tagggtatat caaaaatcta agcaaaccag 13260
ctaaggctgc tataagaata gcaatgatat atacttgggc atttgggaat gacgaaatat 13320
cttggatgga agcatcacag attgcacaaa cacgtgcaaa ctttacattg gatagcttaa 13380
agattttgac accagtgaca acatcaacaa atctatcaca caggttaaaa gatactgcta 13440
ctcagatgaa attttctagt acatcactta ttagagtaag caggttcatc acaatatcta 13500

```
atgataatat gtctattaaa gaagcaaatg aaactaaaga tacaaatctt atttatcaac  13560
aggtaatgtt aacaggatta agtgtatttg aatatctatt taggttagag gagagtacag  13620
gacataaccc tatggtcatg catctacata tagaggatgg atgttgtata aaagagagtt  13680
acaatgatga gcatatcaat ccggagtcta cattagagtt aatcaaatac cctgagagta  13740
atgaatttat atatgataag gaccctttaa aggatataga tctatcaaaa ttaatggtta  13800
taagagatca ttcttataca attgacatga attactggga tgacacagat attgtacatg  13860
caatatcaat atgtactgca gttacaatag cagatacaat gtcgcagcta gatcgggata  13920
atcttaagga gctggttgtg attgcaaatg atgatgatat taacagtctg ataactgaat  13980
ttctgaccct agatatacta gtgtttctca aaacatttgg agggttactc gtgaatcaat  14040
ttgcatatac cctttatgga ttgaaaatag aaggaaggga tcccatttgg gattatataa  14100
tgagaacatt aaaagacacc tcacattcag tacttaaagt attatctaat gcactatctc  14160
atccaaaagt gtttaagaga ttttgggatt gtggagtttt gaatcctatt tatggtccta  14220
atactgctag tcaagatcaa gttaagcttg ctctctcgat ttgcgagtac tccttggatc  14280
tatttatgag agaatggttg aatggagcat cacttgagat ctatatctgt gatagtgaca  14340
tggaaatagc aaatgacaga agacaagcat ttctctcaag acatcttgcc tttgtgtgtt  14400
gtttagcaga gatagcatct tttggaccaa atttattaaa tctaacatat ctagagagac  14460
ttgatgaatt aaaacaatac ttagatctga acatcaaaga agatcctact cttaaatatg  14520
tgcaagtatc aggactgtta attaaatcat tcccctcaac tgttacgtat gtaaggaaaa  14580
ctgcgattaa gtatctgagg attcgtggta ttaatccgcc tgaaacgatt gaagattggg  14640
atcccataga agatgagaat atcttagaca atattgttaa aactgtaaat gacaattgca  14700
gtgataatca aaagagaaat aaaagtagtt atttctgggg attagctcta aagaattatc  14760
aagtcgtgaa aataagatcc ataacgagtg attctgaagt taatgaagct tcgaatgtta  14820
ctacacatgg aatgacactt cctcagggag gaagttatct atcacatcag ctgaggttat  14880
ttggagtaaa cagtacaagt tgtcttaaag ctcttgaatt atcacaaatc ttaatgaggg  14940
aagttaaaaa agataaagat agactctttt taggagaagg agcaggagct atgttagcat  15000
gttatgatgc tacactcggt cctgcaataa attattataa ttctggttta aatattacag  15060
atgtaattgg tcaacgggaa ttaaaaatct tcccatcaga agtatcatta gtaggtaaaa  15120
aactaggaaa tgtaacacag attcttaatc gggtgagggt gttatttaat gggaatccca  15180
attcaacatg gataggaaat atggaatgtg agagtttaat atggagtgaa ttaaatgata  15240
agtcaattgg tttagtacat tgtgacatgg agggagcgat aggcaaatca gaagaaactg  15300
ttctacatga acattatagt attattagga ttacatattt aatcggggat gatgatgttg  15360
tcctagtatc aaaaattata ccaactatta ctccgaattg gtctaaaata ctctatctat  15420
acaagttgta ttggaaggat gtaagtgtag tgtcccttaa aacatccaat cctgcctcaa  15480
cagagcttta tttaatttca aaagatgctt actgtactgt aatggaaccc agtaatcttg  15540
ttttatcaaa acttaaaagg atatcatcaa tagaagaaaa taatctatta aagtggataa  15600
tcttatcaaa aaggaagaat aacgagtggt tacagcatga aatcaaagaa ggagaaaggg  15660
attatgggat aatgaggcca tatcatacag cactgcaaat ttttggattc caaattaact  15720
taaatcactt agctagagaa tttttatcaa ctcctgattt aaccaacatt aataatataa  15780
ttcaaagttt tacaagaaca attaaagatg ttatgttcga atgggtcaat atcactcatg  15840
```

-continued

```
acaataaaag acataaatta ggaggaagat ataatctatt cccgcttaaa aataagggga  15900

aattaagatt attatcacga agattagtac taagctggat atcattatcc ttatcaacca  15960

gattactgac gggccgtttt ccagatgaaa aatttgaaaa tagggcacag accggatatg  16020

tatcattggc tgatattgat ttagaatcct taaagttatt atcaagaaat attgtcaaaa  16080

attacaaaga acacatagga ttaatatcat actggttttt gaccaaagag gtcaaaatac  16140

taatgaagct tataggagga gtcaaactac taggaattcc taaacagtac aaagagttag  16200

aggatcgatc atctcagggt tatgaatatg ataatgaatt tgatattgat taatacataa  16260

aaacataaaa taaaacacct attcctcacc cattcacttc caacaaaatg aaaagtaaga  16320

aaaacatgta atatatatat accaaacaga gtttttctct tgtttggt              16368


<210> SEQ ID NO 95
<211> LENGTH: 897
<212> TYPE: DNA
<213> ORGANISM: Artificial Sequence
<220> FEATURE:
<223> OTHER INFORMATION: Recombinant RSV G protein

<400> SEQUENCE: 95

atgtctaaga caaaggatca gcggacagcc aaaacactgg aacggacatg ggataccctg     60

aatcacctcc tcttcatcag cagttgcctg tacaagctca atctgaagtc catcgcccag    120

atcactctct ccatccttgc catgatcatc tctacaagcc tcatcattgc cgcaattatc    180

ttcatcgcca gcgctaacca caaggtcacc cttaccacag ccattattca ggatgccacc    240

aaccagatca agaacacaac ccctacctac ctgacacaga accctcagct tggaatttca    300

ctgagcaacc tgtccgaaac cacatctaaa cctacaacca tcttggctct gaccacacca    360

aacgccgagt ccaccccaca aagtaccaca gtgaagacca aaaacaccac aaccacacag    420

attcagccaa gcaagcctac aactaagcaa aggcagaaca agccacagaa caaacccaac    480

aacgactttc actttgaggt gttcaacttt gtgccctgct ccatttgctc caacaaccct    540

acctgttggg ctatctgcaa gaggatcccc aacaagaagc ccggcaggaa gactactact    600

aagcctacta aacagccagc cattaagacc actaagaagg acccaaagcc acagacaacc    660

aagccaaagg aggtgctcac taccaagccc actgagaagc ccaccattaa caccactaaa    720

accaacatcc gcacaacatt gctgacatca aacattacag agaaccagga gcacacaagc    780

cagaaggaga cactgcatag cactacatcc gaaggcaatc ccagcccaag ccaggtctat    840

actacctcag agtacctgtc ccagagcctg agccctagca acactactag atggtag       897
```

RECOMBINANT CHIMERIC BOVINE/HUMAN PARAINFLUENZA VIRUS 3 EXPRESSING RSV G AND ITS USE

CROSS REFERENCE TO RELATED APPLICATIONS

This is the U.S. National Stage of International Application No. PCT/US2018/034848, filed on May 29, 2018, which was published in English under PCT Article 21(2), which in turn claims the benefit of U.S. Provisional Application No. 62/512,111, filed May 29, 2017. The provisional application is herein incorporated by reference in its entirety.

FIELD

This disclosure relates to recombinant chimeric bovine/human parainfluenza virus 3 (rB/HPIV3) vectors expressing Respiratory Syncytial Virus (RSV) G protein, or a recombinant RSV G protein, and use of the rB/HPIV3 vector, for example, to induce an immune response to RSV and HPIV3 in a subject.

PARTIES TO A JOINT RESEARCH AGREEMENT

This invention was made under Public Health Service Cooperative Research and Development Agreement (PHS-CRADA) No. 2013-0810 between the National Institute of Allergy and Infectious Disease at the National Institutes of Health and Sanofi Pasteur, Inc.

BACKGROUND

RSV is an enveloped non-segmented negative-strand RNA virus in the family Pneumoviridae, genus *Orthopneumovirus*. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite the burden of RSV infection in certain populations, development of an effective RSV vaccine remains elusive.

Parainfluenza viruses (PIV) are closely related enveloped non-segmented negative-strand RNA viruses that belong to the closely related family Paramyxoviridae. PIVs include members of the genus *Respirovirus* (including PIV1, PIV3, Sendai virus) and *Rubulavirus* (including PIV2, PIV4, PIV5). The human parainfluenza viruses (HPIVs, serotypes 1, 2, and 3) are second only to RSV in causing severe respiratory infections in infants and children worldwide, with HPIV3 being the most relevant of the HPIVs in terms of disease impact. The HPIV3 genome is approximately 15.5 kb, with a gene order of 3'-N-P-M-F-HN-L. Each gene encodes a separate mRNA that encodes a major protein: N, nucleoprotein; P, phosphoprotein; M, matrix protein; F, fusion glycoprotein; HN, hemagglutinin-neuramindase glycoprotein; L, large polymerase protein, with the P gene containing additional open reading frames encoding the accessory C and V proteins. Similar to RSV, development of an effective HPIV vaccine remains elusive.

Major challenges to developing pediatric vaccines against RSV and HPIV3 include the immaturity of the immune system during infancy, immune-suppression by maternal antibodies, inefficient immune protection at the superficial epithelium of the respiratory tract, and vaccine-induced enhanced disease that has been observed in studies with inactivated or subunit RSV and HPIV3 vaccines in virus-naïve recipients. Further, prior studies of a live-attenuated rB/HPIV3 vector expressing an RSV antigen (RSV F protein) revealed disappointing immunogenicity to RSV that was deemed insufficient for vaccine use.

Thus, despite substantial effort, a need remains for a safe and effective immunogen that induces a protective immune response to RSV and HPIV3, particularly in pediatric subjects.

SUMMARY

Recombinant chimeric bovine/human parainfluenza virus 3 (rB/HPIV3) vectors expressing RSV G or variants thereof ("rB/HPIV3-RSV G" vectors) are provided herein. The disclosed rB/HPIV3-RSV G vectors comprise a genome comprising, in a 3'-to-5' order, a 3' leader region, a BPIV3 N gene, a heterologous gene, BPIV3 P and M genes, HPIV3 F and HN genes, a BPIV3 L gene, and a 5' trailer region. The heterologous gene encodes one of: (a) a RSV G protein comprising an RSV G ectodomain, transmembrane domain, and cytoplasmic tail; (b) a recombinant RSV G protein comprising a RSV G ectodomain, a BPIV3 HN transmembrane domain, and a BPIV3 HN cytoplasmic tail; (c) a recombinant RSV G protein comprising a RSV G ectodomain, a HPIV3 HN transmembrane domain, and a HPIV3 HN cytoplasmic tail; or (d) a recombinant RSV G protein comprising a RSV G ectodomain, a HPIV1 HN transmembrane domain, and a HPIV1 HN cytoplasmic tail. The HPIV3 HN gene encodes a HPIV3 HN protein comprising 263T and 370P amino acid assignments. The rB/HPIV3 vectors disclosed herein are infectious, attenuated, and self-replicating, and can be used to induce an immune response to RSV and HPIV3.

In some embodiments, the heterologous gene encoding the wild-type (wt) RSV G protein or recombinant RSV G protein can be codon-optimized for expression in human cells.

Also provided herein are methods and compositions related to the expression of the disclosed viruses. For example, isolated polynucleotide molecules that include a nucleic acid sequence encoding the genome or antigenome of the described viruses are disclosed.

Immunogenic compositions including the rB/HPIV3-RSV G are also provided. The compositions can further include an adjuvant. Methods of eliciting an immune response in a subject by administering an effective amount of a disclosed rB/HPIV3-RSV G to the subject are also disclosed. In some embodiments, the subject is a human subject, for example, a human subject between 1 and 6 months of age, or between 1 and 12 months of age, or between 1 and 18 months of age, or older.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C. Map of the rB/HPIV3 genome and added RSV G gene of rB/HPIV3-RSV G vectors, and diagrams and features of modified RSV G proteins included in the vectors. (FIG. 1A) rB/HPIV3 gene map and G protein diagrams. The rB/HPIV3 gene map is shown at the top, and the second line shows the details of the sequence flanking the RSV strain A2 G gene inserted at the second gene position, between the vector N and P genes, using the indicated AscI sites (underlined). N GE: gene end signal from the BPIV3 N gene: P GS: gene start signal from the BPIV3 P gene; M48: AUG codon 48 of the RSV G open reading frame (ORF) that can serve as an alternative translational start site; CX3C (G amino acids 182-186): fractalkine motif, conserved among RSV strains; the TGA stop codon of the G ORF is emboldened and underlined. An additional TAG stop codon is underlined with * and was included in those G protein inserts indicated with *: this trinucleotide was added when needed to adjust the sequence length to conform to the "rule of six" (see Kolakofsky Virology 498:94-98, 2016). Several diagrams of RSV G protein structures are shown, including: (i) wt G, unmodified wild-type RSV G; (ii) mG, expressing only the transmembrane form of RSV G (mG) due to the M48I mutation that ablates expression of secreted G (sG); (iii) sG, expressing only sG, due to deletion of the first 47 codons, so that the ORF begins with the M48 codon; (iv) G_B3CT, with the cytoplasmic tail (CT) of RSV G replaced by the CT of BPIV3 HN; (v) G_B3TMCT, with the transmembrane domain (TM) and CT of RSV G replaced by the TM and CT of BPIV3 HN; (vi) G_dCX3C, with the C186R mutation ablating the CX3C motif (yielding CX3R); (vii) G_wCX4C, with the addition of A186 to ablate the CX3C motif (yielding CX3AC); (viii) G_dCX3C_B3CT, with the C186R mutation ablating the CX3C motif, and bearing the CT of BPIV3 HN; (ix) G_dCX3C_B3TMCT, with the C186R mutation ablating the CX3C motif, and bearing the TM and CT of BPIV3 HN; (x) wt G/GS-opt, GenScript codon-optimized wt G. (FIG. 1B) Amino acid sequences of the TM and CT domains of wt RSV G protein (top); and the following modified versions of RSV G: mG, sG, G_B3CT, and G_B3TMCT; and the wt BPIV3 HN (strain Kansas), and wt HPIV3 HN (strain JS). The sequences were aligned according to the beginning of the G ectodomain at amino acid 66. The presumed CT, TM, and ectodomains are demarcated with dashed lines, and BPIV3 HN sequences are boxed. Note that the N-terminus of sG is that of the primary translation product, which subsequently gets trimmed proteolytically to yield a predominant N-terminus at N66, or a secondary N-terminus at I75. (FIG. 1C) Sequence of the unmodified CX3C motif of wt G protein (top line, showing protein (SEQ ID NO: 41) and nucleotide (SEQ ID NO: 42) sequence), the dCX3C version in which the CX3C motif is disrupted by a C186R missense mutation (middle line, showing protein (SEQ ID NO: 43) and nucleotide (SEQ ID NO: 44) sequence), and the wCX4C version in which the CX3C motif is disrupted by the addition of an alanine codon following codon 185 (bottom line, showing protein (SEQ ID NO: 45) and nucleotide (SEQ ID NO: 46) sequence). The conserved cysteine residues are in bold; mutated nucleotides in dCX3C and wCX4C are underlined.

(FIG. 2A) Western blots of proteins from infected cells. Top panel: the bars to the left indicate fully and partially glycosylated forms of RSV G (upper and lower bars, respectively), lane 11 shows in addition the RSV N, P, M proteins expressed by wt RSV. Middle panel: BPIV3 N protein. Bottom panel: GAPDH protein used as loading control. (FIG. 2B) Relative levels of fully glycosylated (90-120 kDa) RSV G quantified from the experiment in part A by densitometry using the LiCor Image Studio software calibrated using the GAPDH signal and normalized to wt G (lane 2) set as 1.0. (FIG. 2C) Western blot of G protein in cell culture medium supernatants. (FIG. 2D) Relative levels of fully glycosylated G protein from FIG. 2C, normalized to wt G.

(FIG. 3A) Western blot showing expression of RSV G (top panel), BPIV3 N (middle panel), and GAPDH (bottom panel) as a loading control. (FIG. 3B) Relative levels of fully glycosylated (90-120 kDa) RSV G quantified from FIG. 3A and normalized to wt G (lane 2) as 1.0.

(FIG. 4A) Images of plaques that were probed with rabbit antisera raised separately against HPIV3 and RSV, and a goat hyperimmune serum to RSV (ab20531, Abcam): HPIV3 antigens alone were visualized as green, RSV G protein alone as red, and co-expression as yellow. (FIG. 4B) Images of plaques that were probed with the same HPIV3-specific rabbit hyperimmune serum and RSV G mAb 131-2G specific to the CX3C domain: HPIV3 antigens alone were visualized as green, RSV G containing the 131-2G epitope alone was red, and co-expression was yellow.

(FIG. 5A) Western blot of empty rB/HPIV3 vector (lane 1), vector expressing wt RSV G (lane 2), vectors expressing the indicated modified forms of RSV G (lanes 3-5), and wt RSV (lane 6). The upper panel was probed with polyclonal RSV antibodies, showing the fully-glycosylated 90-120 kDa form of G, evident in lane 5, and RSV structural proteins N, P, M, and G proteins including a smaller, broad band of G (~48-62 kDa) often observed with Vero cells (lane 6) as previously described (Corry et al. *J. Virol.* 90:1311-1320, 2015). The bottom panel shows the BPIV3 N protein. (FIG. 5B) RSV G packaging efficiency based on quantification of FIG. 5A and normalized to wt G (lane 2) as 1.0.

In FIG. 8A, a Student t-test was carried out between the two indicated groups (2 and 12), with the significance of the difference shown as a P value.

In FIGS. 9C and 9D, the RSV challenge virus titers for individual animals in the nasal turbinates (FIG. 9C) and lungs (FIG. 9D) were plotted versus the corresponding titers of complement-dependent serum RSV-neutralizing antibodies collected 28 days following vector immunization (from FIG. 8A). Pearson's linear regression model (statistical software Prism 7.0) was used to show the correlation of the neutralization titers (Log 2PRNT60) and viral titer (Log 10 PFU/g), shown by solid lines. The R squared values were 0.45 for NT and 0.51 for lungs: the R squared value indicates how well the data fit into the model (values range from 0 to 1, with a greater value indicating increased fit). The dotted lines indicate 95% confidence intervals.

SEQUENCE LISTING

Figure 1A:
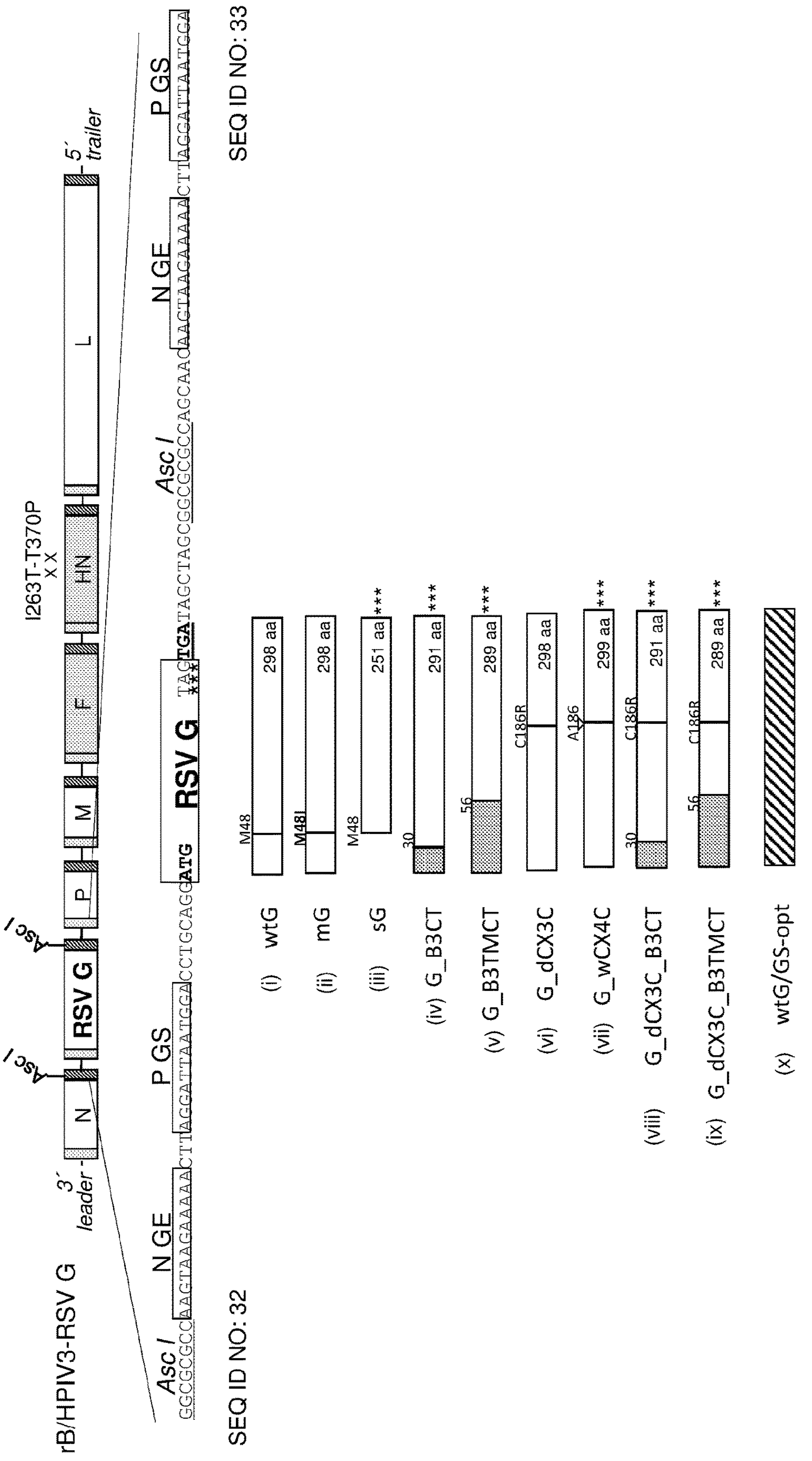

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file name "Sequence.txt' (~256 kb), which was created on Nov. 25, 2019, and which is incorporated by reference herein.

DETAILED DESCRIPTION

Major challenges to developing pediatric vaccines against RSV and HPIV3 include the immaturity of the immune system during infancy, immune-suppression by maternal antibodies, inefficient immune protection at the superficial epithelium of the respiratory tract, and vaccine-induced enhanced disease that has been observed in studies with inactivated or subunit RSV and HPIV3 vaccines in virus-naïve recipients (Kim et al., *Amer. J. Epidemiol.* 89:422-434, 1969; Ottolini et al., *Viral Immunol.* 13:231-236, 2000; Schneider-Ohrum et al., *J. Virol.* 91:e02180-16, 2017). Further, although immunization with a live-attenuated rB/HPIV3 vector expressing an RSV antigen (unmodified RSV F protein) did not prime vaccine-induced enhanced disease, clinical trial assessment revealed disappointing RSV immunogenicity (Bernstein, et al. 2012. Pediatric Infectious Disease Journal 31:109-114). Thus, despite substantial effort, a need remains for an effective immunogen that induces a protective immune response to RSV and/or HPIV3.

The present disclosure provides recombinant chimeric bovine/human parainfluenza virus 3 (rB/HPIV3) vectors expressing RSV G or variants thereof ("rB/HPIV3-RSV G" vectors) that meet the above-discussed need. For example, as described in the examples, of nine different rB/HPIV3-RSV G vectors, one vector (rB/HPIV3 comprising a heterologous gene encoding wt RSV G) produced an immune response to RSV in an animal model that provided titers of serum RSV-neutralizing antibodies assayed in the presence of complement that were not significantly different than those induced by wt RSV infection, even though the RSV was administered at a 10-fold higher dose, was not attenuated, and bears both the F and G neutralization antigens.

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the term "comprises" means "includes." Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. Adjuvants are described, for example, in Singh (ed.) Vaccine Adjuvants and Delivery Systems. Wiley-Interscience, 2007.

Administration: The introduction of a composition into a subject by a chosen route. Administration can be local or systemic. For example, if the chosen route is intranasal, the composition (such as a composition including a disclosed rB/HPIV3-RSV G vector) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid.

Attenuated: A virus that is "attenuated" or has an "attenuated phenotype" refers to a virus that has decreased virulence compared to a reference virus under similar conditions of infection. Attenuation usually is associated with decreased virus replication as compared to replication of a reference wild-type virus under similar conditions of infection, and thus "attenuation" and "restricted replication"

often are used synonymously. In some hosts (typically non-natural hosts, including experimental animals), disease is not evident during infection with a reference virus in question, and restriction of virus replication can be used as a surrogate marker for attenuation. In some embodiments, a disclosed rB/HPIV3-RSV G vector that is attenuated exhibits at least about 10-fold or greater decrease, such as at least about 100-fold or greater decrease in virus titer in the upper or lower respiratory tract of a mammal compared to non-attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceropithiecus aethiops*. An attenuated rB/HPIV3-RSV G vector may display different phenotypes including without limitation altered growth, temperature sensitive growth, host range restricted growth, or plaque size alteration.

Cytoplasmic Tail (CT): A contiguous region of a transmembrane protein that includes a terminus (either N- or C-terminus) of the protein and extends into the cytoplasm of a cell or enveloped virus from the cytoplasmic surface of the cell membrane or viral envelope. In the case of a type I transmembrane protein, the CT includes the C-terminus of the protein. In the case of a type II transmembrane protein, the CT includes the N-terminus of the protein.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Gene: A nucleic acid sequence that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

A "gene" of a rB/HPIV3 vector as described herein refers to a portion of the rB/HPIV3 genome encoding an mRNA and typically begins at the upstream (3') end with a gene-start (GS) signal and ends at the downstream (5') end with the gene-end (GE) signal. In this context, the term gene also embraces what is referred to as a "translational open reading frame", or ORF, particularly in the case where a protein, such as C, is expressed from an additional ORF rather than from a unique mRNA. To construct a disclosed rB/HPIV3 vector, one or more genes or genome segments may be deleted, inserted or substituted in whole or in part.

Heterologous: Originating from a different genetic source. A heterologous gene included in a recombinant genome is a gene that does not originate from that genome. In one specific, non-limiting example, a heterologous gene encoding an ectodomain of a RSV G protein is included in the genome of a rB/HPIV3 vector as described herein.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Infectious and Self-Replicating Virus: A virus that is capable of entering and replicating in a cultured cell or cell of an animal or human host to produce progeny virus capable of the same activity.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic composition: A preparation of immunogenic material capable of stimulating an immune response, which in some examples can be administered for the prevention, amelioration, or treatment of infectious or other types of disease. The immunogenic material may include attenuated or killed microorganisms (such as bacteria or viruses), or antigenic proteins, peptides or DNA derived from them. Immunogenic compositions comprise an antigen (such as a virus) that induces a measurable T cell response against the antigen, or induces a measurable B cell response (such as production of antibodies) against the antigen. In one example, an immunogenic composition comprises a disclosed rB/HPIV3-RSV G that induces a measurable CTL response against RSV and HPIV3, or induces a measurable B cell response (such as production of antibodies) against RSV and HPIV3, when administered to a subject. For in vivo use, the immunogenic composition will typically include a recombinant virus in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% pure, such as at least 75%, 80%, 90%, 95%, 98%, 99%, or even 99.9% pure.

Linker: A bi-functional molecule that can be used to link two molecules into one contiguous molecule. Non-limiting examples of peptide linkers include glycine-serine linkers.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "polynucleotide." A nucleic acid molecule is usually at least 10 bases in length, unless otherwise specified. The term includes single- and double-stranded forms of DNA. A nucleic acid molecule may include either or both naturally occurring and modified nucleotides linked together by naturally occurring and/or non-naturally occurring nucleotide linkages.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Parainfluenza virus (PIV): A number of enveloped non-segmented negative-sense single-stranded RNA viruses from family Paramyxoviridae that are descriptively grouped together. This includes all of the members of genus *Respirovirus* (e.g., HPIV1, HPIV3) and a number of members of genus *Rubulavirus* (e.g. HPIV2, HPIV4, PIV5). PIVs are made up of two structural modules: (1) an internal ribonucleoprotein core, or nucleocapsid, containing the viral genome, and (2) an outer, roughly spherical lipoprotein envelope. The PIV genome is approximately 15,000 nucleotides in length and encodes at least eight polypeptides. These proteins include the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins. The gene order is 3'-N-P-M-F-HN-L-5', and each gene encodes a separate protein encoding mRNA, with the P gene containing one or more additional open reading frames (ORFs) encoding accessory proteins.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Recombinant: A recombinant nucleic acid molecule or protein is one that has a sequence that is not naturally occurring: for example, includes one or more nucleic acid substitutions, deletions or insertions, and/or has a sequence that is made by an artificial combination of two otherwise separated segments of sequence. This artificial combination can be accomplished, for example, by chemical synthesis, targeted mutation of a naturally occurring nucleic acid molecule or protein, or, artificial manipulation of isolated segments of nucleic acids, for example, by genetic engineering techniques. A recombinant virus is one that includes a genome that includes a recombinant nucleic acid molecule.

Recombinant chimeric bovine/human parainfluenza virus 3 (rB/HPIV3): A chimeric PIV3 comprising a genome comprising a combination of BPIV3 and HPIV3 genes that together make up the full complement of PIV3 genes in the PIV3 genome (N, P, M, F, HN, and L genes). The disclosed rB/HPIV3 vectors are based on a BPIV3 genome having F and HN genes replaced with the corresponding genes from HPIV3 (one example of which is discussed in Schmidt A C et al., *J. Virol.* 74:8922-8929, 2000). The structural and functional genetic elements that control gene expression, such as gene start and gene end sequences and genome and anti-genome promoters, are BPIV3 structural and functional genetic elements. The rB/HPIV3 vectors described herein are infectious, self-replicating, and attenuated.

In some embodiments, a heterologous gene encoding RSV G protein or variant thereof is inserted between the N and P genes of the rB/HPIV3 genome to generate a "rB/HPIV3-RSV G" vector. The disclosed rB/HPIV3-RSV G vectors are infectious, self-replicating, and attenuated, and can be used to induce a bivalent immune response to RSV and HPIV3 in a subject.

Respiratory Syncytial Virus (RSV): An enveloped non-segmented negative-sense single-stranded RNA virus of the family Pneumoviridae, genus *Orthopneumovirus*. The RSV genome is ~15,000 nucleotides in length and includes 10 genes encoding 11 proteins, including the glycoproteins SH, G and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Several animal models of infection by human RSV and closely-related animal counterparts are available, including model organisms infected with human RSV, as well as model organisms infected with species-specific RSV, such as use of bRSV infection in cattle (see, e.g., Bern et al., *Am J. Physiol. Lung Cell Mol. Physiol.,* 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV G protein: An RSV envelope glycoprotein that is a type II membrane protein and facilitates attachment of RSV to host cell membranes.

The RSV G protein is expressed during RSV infection in two forms. One is the full-length transmembrane form (mG), which is expressed on the cell surface and is packaged into the virus particle. The other form is an N-terminally-truncated, secreted form, sG. The full-length G protein (mG) is a type II protein that has an N-terminal cytoplasmic tail (CT, predicted to comprise amino acids 1-37 in strain A2, see FIG. 1B), a hydrophobic transmembrane domain (TM, comprising approximately amino acids 38-65, see FIG. 1B), and an ectodomain (comprising approximately amino acids 66-298). The sG form is relatively abundant in RSV-infected cell cultures, and is produced by alternative translation initiation at the second AUG codon (M48) in the ORF, whose corresponding position in the protein lies within the TM domain (see FIG. 1B). The N-terminus is then subjected to intracellular proteolytic trimming that creates a new N-terminus at N66 (FIG. 1B).

The ectodomain of RSV G protein comprises two large divergent domains that flank a short central conserved region at amino acids 164-186. The divergent domains have a high content of proline, alanine, threonine, and serine amino acids, and (for strain A2) an estimated four N-linked and 24-25 O-linked carbohydrate side chains. The central conserved domain contains a cysteine noose (i.e., a tight turn stabilized by two disulfide bonds) that bears a conserved CX3C motif (CWAIC, amino acids 182-186 of the A2 strain). The mG and sG forms are believed to be essentially the same with regard to glycosylation and protein structure except that mG forms a multimer that probably is a trimer or tetramer, whereas sG remains a monomer.

An exemplary RSV G protein sequence is provided herein as SEQ ID NO: 22.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

When determining sequence identity between two sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci.* USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

In one examples, once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Homologs and variants of a polypeptide (such as a RSV G ectodomain) are typically characterized by possession of at least about 75%, for example at least about 80%, 85%, 90%, 91%, 92%, 93%, 94%, 95%, 96%, 97%, 98% or 99% sequence identity counted over the full-length alignment with the amino acid sequence of interest. As used herein, reference to "at least 90% identity" or similar language refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals. In an example, a subject is a human. In a particular example, the subject is a newborn infant. In an additional example, a subject is selected that is in need of inhibiting an RSV infection and/or a HPIV3 infection. For example, the subject is either uninfected and at risk of RSV infection and/or HPIV3 infection or is infected in need of treatment.

Transmembrane domain (TM): An amino acid sequence that spans a lipid bilayer, such as the lipid bilayer of a cell or virus or virus-like particle.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. An inactivated (killed) vaccine is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

II. rB/HPIV3-RSV G Vectors

Recombinant chimeric viral vectors comprising a BPIV3 genome with the encoding sequences of the BPIV3 HN and F genes replaced by encoding sequences of the corresponding HPIV3 HN and F gene, and further comprising a heterologous gene encoding a RSV G protein (such as a wild-type RSV G protein) or a variant thereof are provided herein. These recombinant chimeric viral vectors are referred as "rB/HPIV3-RSV G" vectors.

The rB/HPIV3-RSV G genome contains a full complement of PIV3 genes. Therefore, the rB/HPIV3-RSV G vectors are infectious and replication-competent, but are attenuated in rhesus monkeys and humans due to the BPIV3 backbone, and the presence of the heterologous gene.

The genome of the rB/HPIV3-RSV G vectors comprises the heterologous gene encoding RSV G or a variant thereof, HPIV3 F and HN genes, BPIV3 N, P, M, and L genes, and BPIV3 genomic promoter (3' leader region) and 5' trailer region, with the order of 3'-leader region—BPIV3 N, heterologous gene, BPIV3 P, BPIV3 M, HPIV3 F, HPIV3 HN, BPIV3 L—5'-trailer. Exemplary nucleic acid sequences of these genes and proteins encoded thereby are provided herein, as are structural and functional genetic elements that control gene expression, such as gene start and gene end sequences and genome and anti-genome promoters.

An exemplary BPIV3 genome sequence (Kansas stain) is provided as GenBank Acc. No. AF178654.1, which is incorporated by reference herein in its entirety. An exemplary HPIV3 JS strain genome sequence is provided as GenBank Acc. No. Z11575.1, which is incorporated by reference herein in its entirety. In some embodiments, sequences from these strains can be used to construct the rB/HPIV3 aspect of the rB/HPIV3-RSV G vector, for example, as described in Schmidt et al., (*J. Virol.* 74:8922-8929, 2000). In some such embodiments, the HN protein encoded by the HPIV3 HN gene can be modified to have threonine and proline residues at positions 263 and 370, respectively.

In some embodiments, the rB/HPIV3-RSV G vector comprises a genome comprising HPIV3 F and HN genes and BPIV3 N, P, M, and L genes encoding HPIV3 F and HN proteins and BPIV3 N, P, C, V, M, and L proteins as set forth below, or encoding HPIV3 F and HN proteins and BPIV3 N, P, C, V, M, and L proteins individually having at least 90% (such as at least 95% or at least 98%) sequence identity to the corresponding HPIV3 F and HN protein or BPIV3 N, P, C, V, M, and L protein set forth below:

BPIV3 N (GenBank Acc. No.: AAF28254.1, encoded by nucleotides 111-1658 of GenBank No. AF178654.1)

(SEQ ID NO: 1)

```
MLSLFDTFSARRQENITKSAGGAVIPGQKNTVSIFALGPSITDDNDKMTLALLFLSHSLDNEKQHAQRAGFLVSLLSMAY

ANPELYLTSNGSNADVKYVIYMIEKDPGRQKYGGFVVKTREMVYEKTTDWMFGSDLEYDQDNMLQNGRSTSTIEDLVHTF

GYPSCLGALIIQVWIILVKAITSISGLRKGFFTRLEAFRQDGTVKSSLVLSGDAVEQIGSIMRSQQSLVTLMVETLITMN

TGRNDLTTIEKNIQIVGNYIRDAGLASFFNTIRYGIETRMAALTLSTLRPDINRLKALIELYLSKGPRAPFICILRDPVH

GEFAPGNYPALWSYAMGVAVVQNKAMQQYVTGRSYLDIEMFQLGQAVARDAESQMSSILEDELGVTQEAKQSLKKHMKNI

SSSDTTFHKPTGGSAIEMAIDEEAGQPESRGDQDQGDEPRSSIVPYAWADETGNDNQTESTTEIDSIKTEQRNIRDRLNK

RLNEKRKQSDPRSTDITNNTNQTEIDDLFSAFGSN
```

BPIV3 P (GenBank Acc. No.: AAF28255, encoded by nucleotides 1784-3574 of GenBank No. AF178654)

(SEQ ID NO: 2)

```
MEDNVQNNQIMDSWEEGSGDKSSDISSALDIIEFILSTDSQENTADSNEINTGTTRLSTTIYQPESKTTETSKENSGPAN

KNRQFGASHERATETKDRNVNQETVQGGYRRGSSPDSRTETMVTRRISRSSPDPNNGTQIQEDIDYNEVGEMDKDSTKRE

MRQFKDVPVKVSGSDAIPPTKQDGDGDDGRGLESISTFDSGYTSIVTAATLDDEEELLMKNNRPRKYQSTPQNSDKGIKK

GVGRPKDTDKQSSILDYELNFKGSKKSQKILKASTNTGEPTRPQNGSQGKRITSWNILNSESGNRTESTNQTHQTSTSGQ

NHTMGPSRTTSEPRIKTQKTDGKEREDTEESTRFTERAITLLQNLGVIQSAAKLDLYQDKRVVCVANVLNNADTASKIDF

LAGLMIGVSMDHDTKLNQIQNEILSLKTDLKKMDESHRRLIENQKEQLSLITSLISNLKIMTERGGKKDQPEPSGRTSMI

KTKAKEEKIKKVRFDPLMETQGIEKNIPDLYRSIEKTPENDTQIKSEINRLNDESNATRLVPRRISSTMRSLIIIINNSN

LSSKAKQSYINELKLCKSDEEVSELMDMFNEDVSSQ
```

BPIV3 C (encoded by nucleotide 1794-2399 of GenBank No. AF178654)

(SEQ ID NO: 3)

```
MFKTIKSWILGKRDQEINHLTSHRPSTSLNSYSAPTPKRTRQTAMKSTQEPQDLARQSTNLNPKQQKQARKIVDQLTKID

SLGHHTNVPQRQKIEMLIRRLYREDIGEEAAQIVELRLWSLEESPEAAQILTMEPKSRKILITMKLERWIRTLLRGKCDN

LKMFQSRYQEVMPFLQQNKMETVMMEEAWNLSVHLIQDIPV
```

-continued

BPIV3 V (encoded by nucleotide 1784-3018 of GenBank No. AF178654 with an inserted nucleotide g between nucleotide 2505-2506 at a gene editing site located at nucleotide 2500-2507)

(SEQ ID NO: 4)

MEDNVQNNQIMDSWEEGSGDKSSDISSALDIIEFILSTDSQENTADSNEINTGTTRLSTTIYQPESKTTETSKENSGPAN

KNRQFGASHERATETKDRNVNQETVQGGYRRGSSPDSRTETMVTRRISRSSPDPNNGTQIQEDIDYNEVGEMDKDSTKRE

MRQFKDVPVKVSGSDAIPPTKQDGDGDDGRGLESISTFDSGYTSIVTAATLDDEEELLMKNNRPRKYQSTPQNSDKGIKK

GGWKAKRHRQTIINIGLRTQLQRIEEEPENPQSQHEYRRTNKTTEWIPGEENHILEHPQQRERQSNRINKPNPSDINLGT

EPHNGTKQNNLRTKDQDTKDGWKGKRGHRREHSIYRKGDYIITESWCNPICSKIRPIPRQESCVCGECPKQCRYCIKDRL

PSRFDDRSVNGS

BPIV3 M (GenBank Acc. No.: AAF28256, encoded by nucleotides 3735-4790 of GenBank No. AF178654)

(SEQ ID NO: 5)

MSITNSTIYTFPESSFSENGNIEPLPLKVNEQRKAIPHIRVVKIGDPPKHGSRYLDVFLLGFFEMERSKDRYGSISDLDD

DPSYKVCGSGSLPLGLARYTGNDQELLQAATKLDIEVRRTVKATEMIVYTVQNIKPELYPWSSRLRKGMLFDANKVALAP

QCLPLDRGIKFRVIFVNCTAIGSITLFKIPKSMALLSLPNTISINLQVHIKTGVQTDSKGVVQILDEKGEKSLNFMVHLG

LIKRKMGRMYSVEYCKQKIEKMRLLFSLGLVGGISFHVNATGSISKTLASQLAFKREICYPLMDLNPHLNSVIWASSVEI

TRVDAVLQPSLPGEFRYYPNIIAKGVGKIRQ

HPIV3 F (encoded by nucleotides 5072-6691 of GenBank No. Z11575)

(SEQ ID NO: 6)

MPTSILLIITTMIMASFCQIDITKLQHVGVLVNSPKGMKISQNFETRYLILSLIPKIEDSNSCGDQQIKQYKKLLDRLII

PLYDGLRLQKDVIVTNQESNENTDPRTKRFFGGVIGTIALGVATSAQITAAVALVEAKQARSDIEKLKEAIRDTNKAVQS

VQSSIGNLIVAIKSVQDYVNKEIVPSIARLGCEAAGLQLGIALTQHYSELTNIFGDNIGSLQEKGIKLQGIASLYRTNIT

EIFTTSTVDKYDIYDLLFTESIKVRVIDVDLNDYSITLQVRLPLLTRLLNTQIYKVDSISYNIQNREWYIPLPSHIMTKG

AFLGGADVKECIEAFSSYICPSDPGFVLNHEIESCLSGNISQCPRTTVTSDIVPRYAFVNGGVVANCITTTCTCNGIGNR

INQPPDQGVKIITHKECSTIGINGMLFNTNKEGTLAFYTPNDITLNNSVALDPIDISIELNKAKSDLEESKEWIRRSNQK

LDSIGNWHQSSTTIIIILIMIIILFIINITIITIAIKYYRIQKRNRVDQNDKPYVLTNK

HPIV3 wt HN (encoded by nucleotides 6806-8524 of GenBank No. Z11575)

(SEQ ID NO: 7)

MEYWKHTNHGKDAGNELETSMATHGNKLTNKIIYILWTIILVLLSIVFIIVLINSIKSEKAHESLLQDINNEFMEITEKI

QMASDNTNDLIQSGVNTRLLTIQSHVQNYIPISLTQQMSDLRKFISEITIRNDNQEVLPQRITHDVGIKPLNPDDFWRCT

SGLPSLMKTPKIRLMPGPGLLAMPTTVDGCVRTPSLVINDLIYAYTSNLITRGCQDIGKSYQVLQIGIITVNSDLVPDLN

PRISHTFNINDNRKSCSLALLNTDVYQLCSTPKVDERSDYASSGIEDIVLDIVNYDGSISTTRFKNNNISFDQPYAALYP

SVGPGIYYKGKIIFLGYGGLEHPINENVICNTTGCPGKTQRDCNQASHSPWFSDRRMVNSIIVVDKGLNSIPKLKVWTIS

MRQNYWGSEGRLLLLGNKIYIYTRSTSWHSKLQLGIIDITDYSDIRIKWTWHNVLSRPGNNECPWGHSCPDGCITGVYTD

AYPLNPTGSIVSSVILDSQKSRVNPVITYSTATERVNELAILNRTLSAGYTTTSCITHYNKGYCFHIVEINHKSLNTFQP

MLFKTEIPKSCS

In some embodiments, the HPIV3 HN gene in rB/HPIV3 vector encodes a HPIV3 HN protein comprising the amino acid sequence set forth as:

(SEQ ID NO: 8)

MEYWKHTNHGKDAGNELETSMATHGNKLTNKIIYILWTIILVLLSIVFI

IVLINSIKSEKAHESLLQDINNEFMEITEKIQMASDNTNDLIQSGVNTR

LLTIQSHVQNYIPISLTQQMSDLRKFISEITIRNDNQEVLPQRITHDVG

IKPLNPDDFWRCTSGLPSLMKTPKIRLMPGPGLLAMPTTVDGCVRTPSL

VINDLIYAYTSNLITRGCQDIGKSYQVLQIGIITVNSDLVPDLNPRISH

-continued

TFNINDNRKSCSLALLNIDVYQLCSTPKVDERSDYASSGIEDIVLDIVN

YDGSISTTRFKNNNISFDQPYAALYPSVGPGIYYKGKIIFLGYGGLEHP

INENVICNTTGCPGKTQRDCNQASHSTWFSDRRMVNSIIVVDKGLNSIP

KLKVWTISMRQNYWGSEGRLLLLGNKIYIYTRSTSWHSKLQLGIIDITD

YSDIRIKWTWHNVLSRPGNNECPWGHSCPDGCITGVYTDAYPLNPTGSI

VSSVILDSQKSRVNPVITYSTATERVNELAILNRTLSAGYTTTSCITHY

NKGYCFHIVEINHKSLNTFQPMLFKTEIPKSCS

The HN protein shown as SEQ ID NO: 7 comprises 263T and 370P amino acid assignments. As discussed in the examples, rB/HPIV3-RSV G including an HN protein with 263T and 370P amino acid assignments can be recovered and passaged with substantially reduced occurrence of adventitious mutations, which increases the efficiency of virus production, analysis, and manufacture. Any of the rB/HPIV3-RSV G vectors provided herein can comprise a HPIV3 HN gene encoding HN protein with 263T and 370P amino acid assignments (for example, introduced into the HN protein by I263T and T370P amino acid substitutions). An exemplary DNA sequence encoding SEQ ID NO: 7 is provided as follows:

(SEQ ID NO: 9)

atggaatactggaagcataccaatcacggaaaggatgctggtaatgagc tggagacgtctatggctactcatggcaacaagctcactaataagataat atacatattatggacaataatcctggtgttattatcaatagtcttcatc atagtgctaattaattccatcaaaagtgaaaaggcccacgaatcattgc tgcaagacataaataatgagtttatggaaattacagaaaagatccaaat ggcatcggataataccaatgatctaatacagtcaggagtgaatacaagg cttcttacaattcagagtcatgtccagaattacataccaatatcattga cacaacagatgtcagatcttaggaaattcattagtgaaattacaattag aaatgataatcaagaagtgctgccacaaagaataacacatgatgtaggt ataaaacctttaaatccagatgatttttggagatgcacgtctggtcttc catctttaatgaaaactccaaaaataaggttaatgccagggccgggatt attagctatgccaacgactgttgatggctgtgttagaactccgtcttta gttataaatgatctgatttatgcttatacctcaaatctaattactcgag gttgtcaggatataggaaaatcatatcaagtcttacagatagggataat aactgtaaactcagacttggtacctgacttaaatcctaggatctctcat acctttaacataaatgacaataggaagtcatgttctctagcactcctaa atatagatgtatatcaactgtgttcaactcccaaagttgatgaaagatc agattatgcatcatcaggcatagaagatattgtacttgatattgtcaat tatgatggttcaatctcaacaacaagatttaagaataataacataagct ttgatcaaccatatgctgcactatacccatctgttggaccagggatata ctacaaaggcaaaataatatttctcgggtatggaggtcttgaacatcca ataaatgagaatgtaatctgcaacacaactgggtgccccgggaaaacac agagagactgtaatcaagcatctcatagtacttggttttcagataggag gatggtcaactccatcattgttgttgacaaaggcttaaactcaattcca aaattgaaagtatggacgatatctatgcgacaaaattactgggggtcag aaggaaggttacttctactaggtaacaagatctatatatatacaagatc tacaagttggcatagcaagttacaattaggaataattgatattactgat tacagtgatataaggataaaatggacatggcataatgtgctatcaagac caggaaacaatgaatgtccatggggacattcatgtccagatggatgtat aacaggagtatatactgatgcatatccactcaatcccacagggagcatt gtgtcatctgtcatattagactcacaaaaatcgagagtgaacccagtca -continued taacttactcaacagcaaccgaaagagtaaacgagctggccatcctaaa cagaacactctcagctggatatacaacaacaagctgcattacacactat aacaaaggatattgttttcatatagtagaaataaatcataaaagcttaa acacatttcaacccatgttgttcaaaacagagattccaaaaagctgcag ttaa BPIV3 L (GenBank Acc. No.: AAF28259, encoded by nucleotides 8640-15341 of GenBank No. AF178654)

(SEQ ID NO: 10)

MDTESHSGTTSDILYPECHLNSPIVKGKIAQLHTIMSLPQPYDMDDDSI

LIITRQKIKLNKLDKRQRSIRKLRSVLMERVSDLGKYTFIRYPEMSSEM

FQLCIPGINNKINELLSKASKTYNQMTDGLRDLWVTILSKLASKNDGSN

YDINEDISNISNVHMTYQSDKWYNPFKTWFTIKYDMRRLQKAKNEITFN

RHKDYNLLEDQKNILLIHPELVLILDKQNYNGYIMTPELVLMYCDVVEG

RWNISSCAKLDPKLQSMYYKGNNLWEIIDGLFSTLGERTFDIISLLEPL

ALSLIQTYDPVKQLRGAFLNHVLSEMELIFAAECTTEEIPNVDYIDKIL

DVFKESTIDEIAEIFSFFRTFGHPPLEASIAAEKVRKYMYTEKCLKFDT

INKCHAIFCTIIINGYRERHGGQWPPVTLPVHAHEFIINAYGSNSAISY

ENAVDYYKSFIGIKFDKFIEPQLDEDLTIYMKDKALSPKKSNWDTVYPA

SNLLYRTNVSHDSRRLVEVFIADSKFDPHQVLDYVESGYWLDDPEFNIS

YSLKEKEIKQEGRLFAKMTYKMRATQVLSETLLANNIGKFFQENGMVKG

EIELLKRLTTISMSGVPRYNEVYNNSKSHTEELQAYNAISSSNLSSNQK

SKKFEFKSTDIYNDGYETVSCFLTTDLKKYCLNWRYESTALFGDTCNQI

FGLKELFNWLHPRLEKSTIYVGDPYCPPSDIEHLPLDDHPDSGFYVHNP

KGGIEGFCQKLWTLISISAIHLAAVKIGVRVTAMVQGDNQAIAVTTRVP

NNYDYKVKKEIVYKDVVRFFDSLREVMDDLGHELKLNETIISSKMFIYS

KRIYYDGRILPQALKALSRCVFWSETIIDETRSASSNLATSFAKAIENG

YSPVLGYVCSIFKNIQQLYIALGMNINPTITQNIKDQYFRNIHWMQYAS

LIPASVGGFNYMAMSRCFVRNIGDPTVAALADIKRFIKANLLDRGVLYR

IMNQEPGESSFLDWASDPYSCNLPQSQNITTMIKNITARNVLQDSPNPL

LSGLFTSTMIEEDEELAEFLMDRRIILPRVAHDILDNSLTGIRNAIAGM

LDTTKSLIRVGISRGGLTYNLLRKISNYDLVQYETLSKTLRLIVSDKIK

YEDMCSVDLAISLRQKMWMHLSGGRMINGLETPDPLELLSGVIITGSEH

CRICYSTEGESPYTWMYLPGNLNIGSAETGIASLRVPYFGSVTDERSEA

QLGYIKNLSKPAKAAIRIAMIYTWAFGNDEISWMEASQIAQTRANFTLD

SLKILTPVTTSTNLSHRLKDTATQMKFSSTSLIRVSRFITISNDNMSIK

EANETKDTNLIYQQVMLTGLSVFEYLFRLEESTGHNPMVMHLHIEDGCC

IKESYNDEHINPESTLELIKYPESNEFIYDKDPLKDIDLSKLMVIRDHS

YTIDMNYWDDTDIVHAISICTAVTIADTMSQLDRDNLKELVVIANDDDI

NSLITEFLTLDILVFLKTFGGLLVNQFAYTLYGLKIEGRDPIWDYIMRT

LKDTSHSVLKVLSNALSHPKVFKRFWDCGVLNPIYGPNTASQDQVKLAL

SICEYSLDLFMREWLNGASLEIYICDSDMEIANDRRQAFLSRHLAFVCC

LAEIASFGPNLLNLTYLERLDELKQYLDLNIKEDPTLKYVQVSGLLIKS

-continued

FPSTVTYVRKTAIKYLRIRGINPPETIEDWDPIEDENILDNIVKTVNDN

CSDNQKRNKSSYFWGLALKNYQVVKIRSITSDSEVNEASNVTTHGMTLP

QGGSYLSHQLRLFGVNSTSCLKALELSQILMREVKKDKDRLFLGEGAGA

MLACYDATLGPAINYYNSGLNITDVIGQRELKIFPSEVSLVGKKLGNVT

QILNRVRVLFNGNPNSTWIGNMECESLIWSELNDKSIGLVHCDMEGAIG

KSEETVLHEHYSIIRITYLIGDDDVVLVSKIIPTITPNWSKILYLYKLY

WKDVSVVSLKTSNPASTELYLISKDAYCTVMEPSNLVLSKLKRISSIEE

NNLLKWIILSKRKNNEWLQHEIKEGERDYGIMRPYHTALQIFGFQINLN

HLAREFLSTPDLTNINNIIQSFTRTIKDVMFEWVNITHDNKRHKLGGRY

NLFPLKNKGKLRLLSRRLVLSWISLSLSTRLLTGRFPDEKFENRAQTGY

VSLADIDLESLKLLSRNIVKNYKEHIGLISYWFLTKEVKILMKLIGGVK

LLGIPKQYKELEDRSSQGYEYDNEFDID

The encoding sequences of the HPIV3 F and HN genes and the BPIV3 N, P, M, and L genes in the rB/HPIV3-RSV G vector are flanked by appropriate gene start and gene-end sequences to facilitate expression from the viral genome. For example, in some embodiments, the encoding sequences of the HPIV3 F and HN genes and the BPIV3 N, P, M, and L genes can be flanked by BPIV3 gene-start and gene end sequences as follows:

| Gene | Gene start | SEQ ID | Gene end | SEQ ID |
|---|---|---|---|---|
| N | aggattaaagac | 11 | aaataagaaaaa | 16 |
| P | aggattaaag | 12 | aaataagaaaaa | 17 |
| M | aggattaaag | 12 | aaataaaggataatcaaaaa | 18 |
| F | aggacaaaag | 13 | aattataaaaaa | 19 |
| HN | aggagtaaag | 14 | aaatataaaaaa | 20 |
| L | aggagcaaag | 15 | aaagtaagaaaaa | 21 |

Further, the rB/HPIV3-RSV G vector comprises appropriate genome and anti-genome promoters, such as those of the BPIV3 Kansas strain as set forth in GenBank Acc. No. AF178654, which provides genomic promoter as nucleotides 1-96 and the antigenomic promoter as nucleotides 15361-15456.

The genome of the rB/HPIV3-RSV G comprises a heterologous gene encoding a native RSV G protein or a variant thereof, such as a recombinant RSV G protein comprising BPIV3 HN transmembrane and/or cytoplasmic tail sequences in place of the native RSV G transmembrane and/or cytoplasmic tail sequences. Human RSV can be classified into two groups: A and B. Groups A and B include subgroups A1, A2, B1, and B2, based mainly on sequence variability of the attachment (G) and fusion (F) proteins. The heterologous gene included in the genome of the rB/HPIV3-RSV G can encode a RSV G protein and/or an RSV G ectodomain from (or derived from) any human RSV group (such as Group A or Group B) or subgroup of human RSV (such as subgroup A1, A2, B1, or B2).

An exemplary human RSV G protein sequence from subgroup A2 is set forth below:

(SEQ ID NO: 22)

MSKNKDQRTAKTLERTWDTLNHLLFISSCLYKLNLKSVAQITLSILAMI

ISTSLIIAAIIFIASANHKVTPTTAIIQDATSQIKNTTPTYLTQNPQLG

ISPSNPSEITSQITTILASTTPGVKSTLQSTTVKTKNTTTTQTQPSKPT

TKQRQNKPPSKPNNDFHFEVFNFVPCSICSNNPTCWAICKRIPNKKPGK

KTTTKPTKKPTLKTTKKDPKPQTTKSKEVPTTKPTEEPTINTTKTNIIT

TLLTSNTTGNPELTSQMETFHSTSSEGNPSPSQVSTTSEYPSQPSSPPN

TPRQ

In some embodiments, the heterologous gene included in the genome of the rB/HPIV3-RSV G encodes a RSV G protein comprising or consisting of the amino acid sequence set forth as SEQ ID NO: 22, or an amino acid sequence at least 90% (such as at least 95% or at least 98%) identical to SEQ ID NO: 22

An exemplary human RSV G ectodomain sequence from subgroup A2 is set forth below:

(SEQ ID NO: 23)

NHKVTPTTAIIQDATSQIKNTTPTYLTQNPQLGISPSNPSEITSQITTI

LASTTPGVKSTLQSTTVKTKNTTTTQTQPSKPTTKQRQNKPPSKPNNDF

HFEVFNFVPCSICSNNPTCWAICKRIPNKKPGKKTTTKPTKKPTLKTTK

KDPKPQTTKSKEVPTTKPTEEPTINTTKTNIITTLLTSNTTGNPELTSQ

METFHSTSSEGNPSPSQVSTTSEYPSQPSSPPNTPRQ

In some embodiments, the heterologous gene encodes a recombinant RSV G ectodomain comprising or consisting of the amino acid sequence set forth as SEQ ID NO: 23, or an amino acid sequence at least 90% (such as at least 95% or at least 98%) identical to SEQ ID NO: 23. The ectodomain is linked to appropriate transmembrane domain and cytoplasmic tail sequences, such as those set forth herein.

An exemplary human RSV G protein sequence from RSV A/Maryland/001/11 is set forth below:

(SEQ ID NO: 47)

MSKTKDQRTAKTLERTWDTLNHLLFISSCLYKLNLKSIAQITLSILAMI

ISTSLIIAAIIFIASANHKVTLTTAIIQDATNQIKNTTPTYLTQNPQLG

ISLSNLSETTSKPTTILALTTPNAESTPQSTTVKTKNTTTTQIQPSKPT

TKQRQNKPQNKPNNDFHFEVFNFVPCSICSNNPTCWAICKRIPNKKPGR

KTTTKPTKQPAIKTTKKDPKPQTTKPKEVLTTKPTEKPTINTTKTNIRT

TLLTSNITENQEHTSQKETLHSTTSEGNPSPSQVYTTSEYLSQSLSPSN

TTRW

In some embodiments, the heterologous gene included in the genome of the rB/HPIV3-RSV G encodes a RSV G protein comprising or consisting of the amino acid sequence set forth as SEQ ID NO: 47, or an amino acid sequence at least 90% (such as at least 95% or at least 98%) identical to SEQ ID NO: 47.

An exemplary human RSV G ectodomain sequence from RSV A/Maryland/001/11 is set forth below:

(SEQ ID NO: 48)
NHKVTLTTAIIQDATNQIKNTTPTYLTQNPQLGISLSNLSETTSKPTTI

LALTTPNAESTPQSTTVKTKNTTTTQIQPSKPTTKQRQNKPQNKPNNDF

HFEVFNFVPCSICSNNPTCWAICKRIPNKKPGRKTTTKPTKQPAIKTTK

KDPKPQTTKPKEVLTTKPTEKPTINTTKTNIRTTLLTSNITENQEHTSQ

KETLHSTTSEGNPSPSQVYTTSEYLSQSLSPSNTTRW

In some embodiments, the heterologous gene encodes a recombinant RSV G ectodomain comprising or consisting of the amino acid sequence set forth as SEQ ID NO: 48, or an amino acid sequence at least 90% (such as at least 95% or at least 98%) identical to SEQ ID NO: 48. The ectodomain is linked to appropriate transmembrane domain and cytoplasmic tail sequences, such as those set forth herein.

An exemplary human RSV G protein sequence from Subgroup B (B1, AAB82435.1, see Karron et al., Proc. Natl. Acad. Sci. U.S.A. 94, 13961-6, 1997) is set forth below:

(SEQ ID NO: 49)
MSKHKNQRTARTLEKTWDTLNHLIVISSCLYRLNLKSIAQIALSVLAMI

ISTSLIIAAIIFIISANHKVTLTTVTVQTIKNHTEKNITTYLTQVPPER

VSSSKQPTTTSPIHTNSATTSPNTKSETHHTTAQTKGRTTTSTQTNKPS

TKPRLKNPPKKPKDDYHFEVFNFVPCSICGNNQLCKSICKTIPSNKPKK

KPTIKPTNKPTTKTTNKRDPKTPAKTTKKETTTNPTKKPTLTTTERDTS

TSQSTVLDTTTLEHTIQQQSLHSTTPENTPNSTQTPTASEPSTSNSTQN

TQSHA

In some embodiments, the heterologous gene included in the genome of the rB/HPIV3-RSV G encodes a RSV G protein comprising or consisting of the amino acid sequence set forth as SEQ ID NO: 49, or an amino acid sequence at least 90% (such as at least 95% or at least 98%) identical to SEQ ID NO: 49.

An exemplary human RSV G ectodomain sequence from Subgroup B (B1, AAB82435.1) is set forth below:

(SEQ ID NO: 50)
NHKVILTIVIVQTIKNHTEKNITTYLTQVPPERVSSSKQPITTSPIHTN

SATTSPNIKSETHHTTAQTKGRITTSTQINKPSTKPRLKNPPKKPKDDY

HFEVFNFVPCSICGNNQLCKSICKTIPSNKPKKKPTIKPINKPTIKTIN

KRDPKTPAKTIKKETTINPIKKPTLITTERDTSTSQSTVLDTTTLEHTI

QQQSLHSTTPENTPNSTQTPTASEPSTSNSTQNTQSHA

In some embodiments, the heterologous gene encodes a recombinant RSV G ectodomain comprising or consisting of the amino acid sequence set forth as SEQ ID NO: 50, or an amino acid sequence at least 90% (such as at least 95% or at least 98%) identical to SEQ ID NO: 50. The ectodomain is linked to appropriate transmembrane domain and cytoplasmic tail sequences, such as those set forth herein.

An exemplary human RSV G protein sequence from Subgroup A (genotype ON1; ON67-1210A, AEQ98758.1, Eshagi A. et al., Plos One 7(3):e32807, 2012 is set forth below:

(SEQ ID NO: 51)
MSKTKDQRTAKTLERTWDTLNHLLFISSCLYKLNLKSIAQITLSILAMI

ISTSLIIAAIIFIASANHKVTLTTAIIQDATNQIKNTTPTYLTQNPQLG

ISFSNLSGTTSQSTTILASTTPSAESTPQSTTVKIKNTTTTQILPSKPT

TKQRQNKPQNKPNNDFHFEVFNFVPCSICSNNPTCWAICKRIPNKKPGK

KTTTKPTKKPTLKTTKKDPKPQTTKPKEVLTTKPTGKPTINTTKTNIRT

TLLTSNTKGNPEHTSQEETLHSTTSEGYLSPSQVYTTSGQEETLHSTTS

EGYLSPSQVYTTSEYLSQSLSSSNTTK

In some embodiments, the heterologous gene included in the genome of the rB/HPIV3-RSV G encodes a RSV G protein comprising or consisting of the amino acid sequence set forth as SEQ ID NO: 51, or an amino acid sequence at least 90% (such as at least 95% or at least 98%) identical to SEQ ID NO: 51.

An exemplary human RSV G ectodomain sequence from Subgroup A (genotype ON1; ON67-1210A, AEQ98758.1, Eshagi A. et al., Plos One 7(3):e32807, 2012) is set forth below:

(SEQ ID NO: 52)
NHKVTLTTAIIQDATNQIKNTTPTYLTQNPQLGISFSNLSGTTSQSTTI

LASTTPSAESTPQSTTVKIKNTTTTQILPSKPTTKQRQNKPQNKPNNDF

HFEVFNFVPCSICSNNPTCWAICKRIPNKKPGKKTTTKPTKKPTLKTTK

KDPKPQTTKPKEVLTTKPTGKPTINTTKTNIRTTLLTSNTKGNPEHTSQ

EETLHSTTSEGYLSPSQVYTTSGQEETLHSTTSEGYLSPSQVYTTSEYL

SQSLSSSNTTK

In some embodiments, the heterologous gene encodes a recombinant RSV G ectodomain comprising or consisting of the amino acid sequence set forth as SEQ ID NO: 52, or an amino acid sequence at least 90% (such as at least 95% or at least 98%) identical to SEQ ID NO: 52. The ectodomain is linked to appropriate transmembrane domain and cytoplasmic tail sequences, such as those set forth herein.

An exemplary human RSV G protein sequence from Subgroup B (genotype BA1; BA4128/99B, AAQ16179.1, Trento A. et al., J. Gen. Virol. 84, 3115-3120, 2003) is set forth below:

(SEQ ID NO: 53)
MSKNKNQRTARTLEKTWDTLNHLIVISSCLYKLNLKSIAQIALSVLAMI

ISTSLIIAAIIFIISANHKVTLTTVTVQTIKNHTEKNITTYLTQVSPER

VSPSKQLTTTPPIYTNSATISPNTKSETHHTTAQTKGRTTTPTQNNKPS

TKPRPKNPPKKPKDDYHFEVFNFVPCSICGNNQLCKSICKTIPSNKPKK

KPTIKPTNKPPTKTTNKRDPKKLAKTLKKETTINPTKKPTPKTTERDTS

TSQSTVLDTTTSKHTERDTSTSQSTVLDTTTSKHTIQQQSLHSTTPENT

PNSTQTPTASEPSTSNSTQKL

In some embodiments, the heterologous gene included in the genome of the rB/HPIV3-RSV G encodes a RSV G protein comprising or consisting of the amino acid sequence set forth as SEQ ID NO: 53, or an amino acid sequence at least 90% (such as at least 95% or at least 98%) identical to SEQ ID NO: 53.

An exemplary human RSV G ectodomain sequence from Subgroup B (genotype BA1; BA4128/99B, AAQ16179.1, Trento A. et al., J. Gen. Virol. 84, 3115-20, 2003) is set forth below:

```
                                        (SEQ ID NO: 54)
NHKVTLTTVTVQTIKNHTEKNITTYLTQVSPERVSPSKQLTTTPPIYTN

SATISPNTKSETHHTTAQTKGRTTTPTQNNKPSTKPRPKNPPKKPKDDY

HFEVFNFVPCSICGNNQLCKSICKTIPSNKPKKKPTIKPTNKPPTKTTN

KRDPKKLAKTLKKETTINPTKKPTPKTTERDTSTSQSTVLDTTTSKHTE

RDTSTSQSTVLDTTTSKHTIQQQSLHSTTPENTPNSTQTPTASEPSTSN

STQKL
```

In some embodiments, the heterologous gene encodes a recombinant RSV G ectodomain comprising or consisting of the amino acid sequence set forth as SEQ ID NO: 54, or an amino acid sequence at least 90% (such as at least 95% or at least 98%) identical to SEQ ID NO: 54. The ectodomain is linked to appropriate transmembrane domain and cytoplasmic tail sequences, such as those set forth herein.

In some embodiments, the heterologous gene encodes a recombinant RSV G protein comprising an RSV G ectodomain and transmembrane domain linked to a cytoplasmic tail of a BPIV3 HN protein, a HPIV3 HN protein, or a HPIV1 HN protein. In some embodiments, the heterologous gene encodes a recombinant RSV G protein comprising an RSV G ectodomain linked to a transmembrane domain and cytoplasmic tail of a BPIV3 HN protein, a HPIV3 HN protein, or a HPIV1 HN protein. As discussed in the Examples, swapping the PIV HN transmembrane and cytoplasmic tail protein sequences with the RSV G transmembrane and cytoplasmic tail protein sequences promotes membrane insertion and packaging of the type-II membrane protein into the virion envelope. It is believed that an increase in the amount of RSV G ectodomain exposed on the surface of the virion envelope leads to a corresponding increase in the immune response to the RSV G ectodomain.

The transmembrane domain and cytoplasmic tail of an exemplary RSV G sequence from RSV A2 are set forth as follows:

```
RSV G CT:
                                         SEQ ID NO: 24
MSKNKDQRTAKTLERTWDTLNHLLFISSCLYKLNLKS,

RSV G TM:
                                         SEQ ID NO: 25
VAQITLSILAMIISTSLIIAAIIFIASA.

RSV G TM + CT:
                                         SEQ ID NO: 26
MSKNKDQRTAKTLERTWDTLNHLLFISSCLYKLNLKSVAQITLSILAMI
ISTSLIIAAIIFIASA,
```

Further, the cytoplasmic tail and transmembrane domain of an exemplary BPIV3 HN protein are set forth as follows:

```
BPIV3 HN CT:
                                         SEQ ID NO: 27
MEYWKHTNSINNTNNETETARGKHSSKVTN,

BPIV3 HN TM:
                                         SEQ ID NO: 28
IIMYTFWTITLTILSVIFIMILTNLI,
```

-continued

```
BPIV3 HN TM + CT:
                                         SEQ ID NO: 29
MEYWKHTNSINNTNNETETARGKHSSKVTNIIMYTFWTITLTILSVIFIM
ILTNLI,
```

Further, the cytoplasmic tail and transmembrane domain of an exemplary HPIV3 HN protein are set forth as follows:

```
HPIV3 HN CT:
                                         SEQ ID NO: 55
MEYWKHTNHGKDAGNELETSMATHGNKLTNK,

HPIV3 HN TM:
                                         SEQ ID NO: 56
IIYILWTIILVLLSIVFIIVLINSI,

HPIV3 HN TM + CT:
                                         SEQ ID NO: 57
MEYWKHTNHGKDAGNELETSMATHGNKLTNKIIYILWTIILVLLSIVFII
VLINSI,
```

Further, the cytoplasmic tail and transmembrane domain of an exemplary HPIV1 HN protein are set forth as follows:

```
HPIV1 HN CT:
                                         SEQ ID NO: 58
MAEKGKTNSSYWSTTRNDNSTVNTHINTPAGRTHW,

HPIV1 HN TM:
                                         SEQ ID NO: 59
ILLIATTMHTVLSFIIMILCIDLII,

HPIV1 HN TM + CT:
                                         SEQ ID NO: 60
MAEKGKTNSSYWSTTRNDNSTVNTHINTPAGRTHWILLIATTMHTVLSFI
IMILCIDLII,
```

The human RSV G, BPIV3 HN, HPIV3 HN, and HPIV1 HN proteins exhibit remarkable sequence conservation across corresponding viral subgroups. Accordingly, the cytoplasmic tail and transmembrane domain sequences of an RSV G protein can readily be identified and swapped for the corresponding sequences of a BPIV3, HPIV3, or HPIV1 HN protein as needed when constructing the heterologous gene included in the rB/HPIV3-RSV G vector.

An exemplary amino acid sequence of a recombinant RSV G comprising a RSV G ectodomain and transmembrane domain from RSV A2, and a BPIV3 HN cytoplasmic tail is provided below:

```
                                        (SEQ ID NO: 30)
MEYWKHTNSINNTNNETETARGKHSSKVTNVAQITLSILAMIISTSLII

AAIIFIASANHKVTPTTAIIQDATSQIKNTTPTYLTQNPQLGISPSNPS

EITSQITTILASTTPGVKSTLQSTTVKTKNTTTTQTQPSKPTTKQRQNK

PPSKPNNDFHFEVFNFVPCSICSNNPTCWAICKRIPNKKPGKKTTTKPT

KKPTLKTTKKDPKPQTTKSKEVPTTKPTEEPTINTTKTNIITTLLTSNT

TGNPELTSQMETFHSTSSEGNPSPSQVSTTSEYPSQPSSPPNTPRQ
```

In some embodiments, the heterologous gene encodes a recombinant RSV G comprising or consisting of the amino acid sequence set forth as SEQ ID NO: 30, or an amino acid sequence at least 90% (such as at least 95% or at least 98%) identical to SEQ ID NO: 30.

An exemplary amino acid sequence of a recombinant RSV G comprising the RSV G ectodomain from RSV A2 and BPIV3 HN transmembrane domain and cytoplasmic tail is provided below:

(SEQ ID NO: 31)

```
MEYWKHTNSINNTNNETETARGKHSSKVTNIIMYTFWTITLTILSVIFI
MILTNLINHKVTPTTAIIQDATSQIKNTTPTYLTQNPQLGISPSNPSEI
TSQITTILASTTPGVKSTLQSTTVKTKNTTTTQTQPSKPTTKQRQNKPP
SKPNNDFHFEVFNFVPCSICSNNPTCWAICKRIPNKKPGKKTTTKPTKK
PTLKTTKKDPKPQTTKSKEVPTTKPTEEPTINTTKTNIITTLLTSNTTG
NPELTSQMETFHSTSSEGNPSPSQVSTTSEYPSQPSSPPNTPRQ
```

In some embodiments, the heterologous gene encodes a recombinant RSV G comprising or consisting of the amino acid sequence set forth as SEQ ID NO: 31, or an amino acid sequence at least 90% (such as at least 95% or at least 98%) identical to SEQ ID NO: 31.

An exemplary amino acid sequence of a recombinant RSV G comprising a RSV G ectodomain and transmembrane domain from RSV B (B1, GenBank AAB82435.1), and a BPIV3 HN cytoplasmic tail is provided below:

(SEQ ID NO: 61)

```
MEYWKHTNSINNTNNETETARGKHSSKVTNIAQIALSVLAMIISTSLII
AAIIFIISANHKVTLTTVTVQTIKNHTEKNITTYLTQVPPERVSSSKQP
TTTSPIHTNSATTSPNTKSETHHTTAQTKGRTTTSTQTNKPSTKPRLKN
PPKKPKDDYHFEVFNFVPCSICGNNQLCKSICKTIPSNKPKKKPTIKPT
NKPTTKTTNKRDPKTPAKTTKKETTTNPTKKPTLTTTERDTSTSQSTVL
DTTTLEHTIQQQSLHSTTPENTPNSTQTPTASEPSTSNSTQNTQSHA
```

In some embodiments, the heterologous gene encodes a recombinant RSV G comprising or consisting of the amino acid sequence set forth as SEQ ID NO: 61, or an amino acid sequence at least 90% (such as at least 95% or at least 98%) identical to SEQ ID NO: 61.

An exemplary amino acid sequence of a recombinant RSV G comprising the RSV G ectodomain from RSV B (B1, GenBank AAB82435.1) and BPIV3 HN transmembrane domain and cytoplasmic tail is provided below:

(SEQ ID NO: 62)

```
MEYWKHTNSINNTNNETETARGKHSSKVTNIIMYTFWTITLTILSVIFI
MILTNLINHKVTLTTVTVQTIKNHTEKNITTYLTQVPPERVSSSKQPTT
TSPIHTNSATTSPNTKSETHHTTAQTKGRTTTSTQTNKPSTKPRLKNPP
KKPKDDYHFEVFNFVPCSICGNNQLCKSICKTIPSNKPKKKPTIKPTNK
PTTKTTNKRDPKTPAKTTKKETTTNPTKKPTLTTTERDTSTSQSTVLDT
TTLEHTIQQQSLHSTTPENTPNSTQTPTASEPSTSNSTQNTQSHA
```

In some embodiments, the heterologous gene encodes a recombinant RSV G comprising or consisting of the amino acid sequence set forth as SEQ ID NO: 62, or an amino acid sequence at least 90% (such as at least 95% or at least 98%) identical to SEQ ID NO: 62.

An exemplary amino acid sequence of a recombinant RSV G comprising a RSV G ectodomain and transmembrane domain from RSV A/Maryland/001/11, and a BPIV3 HN cytoplasmic tail is provided below:

(SEQ ID NO: 63)

```
MEYWKHENSINNTNNETETARGKHSSKVENIAQIELSILAMIISTSLII
AAIIFIASANHKVELTTAIIQDATNQIKNETPTYLTQNPQLGISLSNLS
ETTSKPTTILALTTPNAESTPQSTTVKTKNETTTQIQPSKPETKQRQNK
PQNKPNNDFHFEVFNFVPCSICSNNPTCWAICKRIPNKKPGRKETTKPT
KQPAIKTEKKDPKPQTTKPKEVLETKPTEKPTINTEKTNIRTTLLTSNI
TENQEHTSQKETLHSTESEGNPSPSQVYTTSEYLSQSLSPSNETRW
```

In some embodiments, the heterologous gene encodes a recombinant RSV G comprising or consisting of the amino acid sequence set forth as SEQ ID NO: 63, or an amino acid sequence at least 90% (such as at least 95% or at least 98%) identical to SEQ ID NO: 63.

An exemplary amino acid sequence of a recombinant RSV G comprising the RSV G ectodomain from RSV A/Maryland/001/11 and BPIV3 HN transmembrane domain and cytoplasmic tail is provided below:

(SEQ ID NO: 64)

```
MEYWKHTNSINNTNNETETARGKHSSKVTNIIMYTFWTITLTILSVIFI
MILTNLINHKVTLTTAIIQDATNQIKNTTPTYLTQNPQLGISLSNLSET
TSKPTTILALTTPNAESTPQSTTVKTKNTTTTQIQPSKPTTKQRQNKPQ
NKPNNDFHFEVFNFVPCSICSNNPTCWAICKRIPNKKPGRKTTTKPTKQ
PAIKTTKKDPKPQTTKPKEVLTTKPTEKPTINTTKTNIRTTLLTSNITE
NQEHTSQKETLHSTTSEGNPSPSQVYTTSEYLSQSLSPSNTTRW
```

In some embodiments, the heterologous gene encodes a recombinant RSV G comprising or consisting of the amino acid sequence set forth as SEQ ID NO: 64, or an amino acid sequence at least 90% (such as at least 95% or at least 98%) identical to SEQ ID NO: 64.

An exemplary amino acid sequence of a recombinant RSV G comprising a RSV G ectodomain and transmembrane domain from RSV ON1, and a BPIV3 HN cytoplasmic tail is provided below:

(SEQ ID NO: 65)

```
MEYWKHTNSINNTNNETETARGKHSSKVTNIAQITLSILAMIISTSLII
AAIIFIASANHKVTLTTAIIQDATNQIKNTTPTYLTQNPQLGISFSNLS
GTTSQSTTILASTTPSAESTPQSTTVKIKNTTTTQILPSKPTTKQRQNK
PQNKPNNDFHFEVFNFVPCSICSNNPTCWAICKRIPNKKPGKKTTTKPT
KKPTLKTTKKDPKPQTTKPKEVLTTKPTGKPTINTTKTNIRTTLLTSNT
KGNPEHTSQEETLHSTTSEGYLSPSQVYTTSGQEETLHSTTSEGYLSPS
QVYTTSEYLSQSLSSSNTTK
```

In some embodiments, the heterologous gene encodes a recombinant RSV G comprising or consisting of the amino acid sequence set forth as SEQ ID NO: 65, or an amino acid sequence at least 90% (such as at least 95% or at least 98%) identical to SEQ ID NO: 65.

An exemplary amino acid sequence of a recombinant RSV G comprising the RSV G ectodomain from RSV ON1, and BPIV3 HN transmembrane domain and cytoplasmic tail is provided below:

(SEQ ID NO: 66)
MEYWKHTNSINNTNNETETARGKHSSKVTNIIMYTFWTITLTILSVIFI

MILTNLINHKVTLTTAIIQDATNQIKNTTPTYLTQNPQLGISFSNLSGT

TSQSTTILASTTPSAESTPQSTTVKIKNTTTTQILPSKPTTKQRQNKPQ

NKPNNDFHFEVFNFVPCSICSNNPTCWAICKRIPNKKPGKKTTTKPTKK

PTLKTTKKDPKPQTTKPKEVLTTKPTGKPTINTTKTNIRTTLLTSNTKG

NPEHTSQEETLHSTTSEGYLSPSQVYTTSGQEETLHSTTSEGYLSPSQV

YTTSEYLSQSLSSSNTTK

In some embodiments, the heterologous gene encodes a recombinant RSV G comprising or consisting of the amino acid sequence set forth as SEQ ID NO: 66, or an amino acid sequence at least 90% (such as at least 95% or at least 98%) identical to SEQ ID NO: 66.

An exemplary amino acid sequence of a recombinant RSV G comprising a RSV G ectodomain and transmembrane domain from RSV BA1, and a BPIV3 HN cytoplasmic tail is provided below:

(SEQ ID NO: 67)
MEYWKHTNSINNTNNETETARGKHSSKVTNIAQIALSVLAMIISTSLII

AAIIFIISANHKVTLTTVTVQTIKNHTEKNITTYLTQVSPERVSPSKQL

TTTPPIYTNSATISPNTKSETHHTTAQTKGRTTTPTQNNKPSTKPRPKN

PPKKPKDDYHFEVFNFVPCSICGNNQLCKSICKTIPSNKPKKKPTIKPT

NKPPTKTTNKRDPKKLAKTLKKETTINPTKKPTPKTTERDTSTSQSTVL

DTTTSKHTERDTSTSQSTVLDTTTSKHTIQQQSLHSTTPENTPNSTQTP

TASEPSTSNSTQKL

In some embodiments, the heterologous gene encodes a recombinant RSV G comprising or consisting of the amino acid sequence set forth as SEQ ID NO: 67, or an amino acid sequence at least 90% (such as at least 95% or at least 98%) identical to SEQ ID NO: 67.

An exemplary amino acid sequence of a recombinant RSV G comprising the RSV G ectodomain from RSV BA1, and BPIV3 HN transmembrane domain and cytoplasmic tail is provided below:

(SEQ ID NO: 68)
MEYWKHTNSINNTNNETETARGKHSSKVTNIIMYTFWTITLTILSVIFI

MILTNLINHKVTLTTVTVQTIKNHTEKNITTYLTQVSPERVSPSKQLTT

TPPIYTNSATISPNTKSETHHTTAQTKGRTTTPTQNNKPSTKPRPKNPP

KKPKDDYHFEVFNFVPCSICGNNQLCKSICKTIPSNKPKKKPTIKPTNK

PPTKTTNKRDPKKLAKTLKKETTINPTKKPTPKTTERDTSTSQSTVLDT

TTSKHTERDTSTSQSTVLDTTTSKHTIQQQSLHSTTPENTPNSTQTPTA

SEPSTSNSTQKL

In some embodiments, the heterologous gene encodes a recombinant RSV G comprising or consisting of the amino acid sequence set forth as SEQ ID NO: 68, or an amino acid sequence at least 90% (such as at least 95% or at least 98%) identical to SEQ ID NO: 68.

An exemplary amino acid sequence of a recombinant RSV G comprising a RSV G ectodomain and transmembrane domain from RSV A2, and a HPIV3 HN cytoplasmic tail is provided below:

(SEQ ID NO: 69)
MEYWKHTNHGKDAGNELETSMATHGNKLTNKVAQITLSILAMIISTSLI

IAAIIFIASANHKVTPTTAIIQDATSQIKNTTPTYLTQNPQLGISPSNP

SEITSQITTILASTTPGVKSTLQSTTVKTKNTTTTQTQPSKPTTKQRQN

KPPSKPNNDFHFEVFNFVPCSICSNNPTCWAICKRIPNKKPGKKTTTKP

TKKPTLKTTKKDPKPQTTKSKEVPTTKPTEEPTINTTKTNIITTLLTSN

TTGNPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 69, or an amino acid sequence at least 90% (such as at least 95% or at least 98%) identical to SEQ ID NO: 69.

An exemplary amino acid sequence of a recombinant RSV G comprising the RSV G ectodomain from RSV A2 and HPIV3 HN transmembrane domain and cytoplasmic tail is provided below:

(SEQ ID NO: 70)
MEYWKHTNHGKDAGNELETSMATHGNKLTNKIIYILWTIILVLLSIVFI

IVLINSINHKVTPTTAIIQDATSQIKNTTPTYLTQNPQLGISPSNPSEI

TSQITTILASTTPGVKSTLQSTTVKTKNTTTTQTQPSKPTTKQRQNKPP

SKPNNDFHFEVFNFVPCSICSNNPTCWAICKRIPNKKPGKKTTTKPTKK

PTLKTTKKDPKPQTTKSKEVPTTKPTEEPTINTTKTNIITTLLTSNTTG

NPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 70, or an amino acid sequence at least 90% (such as at least 95% or at least 98%) identical to SEQ ID NO: 70.

An exemplary amino acid sequence of a recombinant RSV G comprising a RSV G ectodomain and transmembrane domain from RSV B (B1, GenBank AAB82435.1), and a HPIV3 HN cytoplasmic tail is provided below:

(SEQ ID NO: 71)
MEYWKHTNHGKDAGNELETSMATHGNKLTNKIAQIALSVLAMIISTSLI

IAAIIFIISANHKVTLTTVTVQTIKNHTEKNITTYLTQVPPERVSSSKQ

PTTTSPIHTNSATTSPNTKSETHHTTAQTKGRTTTSTQTNKPSTKPRLK

NPPKKPKDDYHFEVFNFVPCSICGNNQLCKSICKTIPSNKPKKKPTIKP

TNKPTTKTTNKRDPKTPAKTTKKETTTNPTKKPTLTTTERDTSTSQSTV

LDTTTLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 71, or an amino acid sequence at least 90% (such as at least 95% or at least 98%) identical to SEQ ID NO: 71.

An exemplary amino acid sequence of a recombinant RSV G comprising the RSV G ectodomain from RSV B (B1, GenBank AAB82435.1) and HPIV3 HN transmembrane domain and cytoplasmic tail is provided below:

(SEQ ID NO: 72)

MEYWKHTNHGKDAGNELETSMATHGNKLTNKIIYILWTIILVLLSIVFI

IVLINSINHKVTLTTVTVQTIKNHTEKNITTYLTQVPPERVSSSKQPTT

TSPIHTNSATTSPNTKSETHHTTAQTKGRTTTSTQTNKPSTKPRLKNPP

KKPKDDYHFEVFNFVPCSICGNNQLCKSICKTIPSNKPKKKPTIKPTNK

PTTKTTNKRDPKTPAKTTKKETTTNPTKKPTLTTTERDTSTSQSTVLDT

TTLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 72, or an amino acid sequence at least 90% (such as at least 95% or at least 98%) identical to SEQ ID NO: 72.

An exemplary amino acid sequence of a recombinant RSV G comprising a RSV G ectodomain and transmembrane domain from RSV A/Maryland/001/11, and a HPIV3 HN cytoplasmic tail is provided below:

(SEQ ID NO: 73)

MEYWKHTNHGKDAGNELETSMATHGNKLTNKIAQITLSILAMIISTSLI

IAAIIFIASANHKVTLTTAIIQDATNQIKNTTPTYLTQNPQLGISLSNL

SETTSKPTTILALTTPNAESTPQSTTVKTKNTTTTQIQPSKPTTKQRQN

KPQNKPNNDFHFEVFNFVPCSICSNNPTCWAICKRIPNKKPGRKTTTKP

TKQPAIKTTKKDPKPQTTKPKEVLTTKPTEKPTINTTKTNIRTTLLTSN

ITENQEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 73, or an amino acid sequence at least 90% (such as at least 95% or at least 98%) identical to SEQ ID NO: 73.

An exemplary amino acid sequence of a recombinant RSV G comprising the RSV G ectodomain from RSV A/Maryland/001/11 and HPIV3 HN transmembrane domain and cytoplasmic tail is provided below:

(SEQ ID NO: 74)

MEYWKHTNHGKDAGNELETSMATHGNKLTNKIIYILWTIILVLLSIVFI

IVLINSINHKVTLTTAIIQDATNQIKNTTPTYLTQNPQLGISLSNLSET

TSKPTTILALTTPNAESTPQSTTVKTKNTTTTQIQPSKPTTKQRQNKPQ

NKPNNDFHFEVFNFVPCSICSNNPTCWAICKRIPNKKPGRKTTTKPTKQ

PAIKTTKKDPKPQTTKPKEVLTTKPTEKPTINTTKTNIRTTLLTSNITE

NQEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 74, or an amino acid sequence at least 90% (such as at least 95% or at least 98%) identical to SEQ ID NO: 74.

An exemplary amino acid sequence of a recombinant RSV G comprising a RSV G ectodomain and transmembrane domain from RSV ON1, and a HPIV3 HN cytoplasmic tail is provided below:

(SEQ ID NO: 75)

MEYWKHTNHGKDAGNELETSMATHGNKLTNKIAQITLSILAMIISTSLI

IAAIIFIASANHKVTLTTAIIQDATNQIKNTTPTYLTQNPQLGISFSNL

SGTTSQSTTILASTTPSAESTPQSTTVKIKNTTTTQILPSKPTTKQRQN

KPQNKPNNDFHFEVFNFVPCSICSNNPTCWAICKRIPNKKPGKKTTTKP

TKKPTLKTTKKDPKPQTTKPKEVLTTKPTGKPTINTTKTNIRTTLLTSN

TKGNPEHTSQEETLHSTTSEGYLSPSQVYTTSGQEETLHSTTSEGYLSP

SQVYTTSEYLSQSLSSSNTTK

In some embodiments, the heterologous gene encodes a recombinant RSV G comprising or consisting of the amino acid sequence set forth as SEQ ID NO: 75, or an amino acid sequence at least 90% (such as at least 95% or at least 98%) identical to SEQ ID NO: 75.

An exemplary amino acid sequence of a recombinant RSV G comprising the RSV G ectodomain from RSV ON1, and HPIV3 HN transmembrane domain and cytoplasmic tail is provided below:

(SEQ ID NO: 76)

MEYWKHTNHGKDAGNELETSMATHGNKLTNKIIYILWTIILVLLSIVFI

IVLINSINHKVTLTTAIIQDATNQIKNTTPTYLTQNPQLGISFSNLSGT

TSQSTTILASTTPSAESTPQSTTVKIKNTTTTQILPSKPTTKQRQNKPQ

NKPNNDFHFEVFNFVPCSICSNNPTCWAICKRIPNKKPGKKTTTKPTKK

PTLKTTKKDPKPQTTKPKEVLTTKPTGKPTINTTKTNIRTTLLTSNTKG

NPEHTSQEETLHSTTSEGYLSPSQVYTTSGQEETLHSTTSEGYLSPSQV

YTTSEYLSQSLSSSNTTK

In some embodiments, the heterologous gene encodes a recombinant RSV G comprising or consisting of the amino acid sequence set forth as SEQ ID NO: 76, or an amino acid sequence at least 90% (such as at least 95% or at least 98%) identical to SEQ ID NO: 76.

An exemplary amino acid sequence of a recombinant RSV G comprising a RSV G ectodomain and transmembrane domain from RSV BA1, and a HPIV3 HN cytoplasmic tail is provided below:

(SEQ ID NO: 77)

MEYWKHTNHGKDAGNELETSMATHGNKLTNKIAQIALSVLAMIISTSLI

IAAIIFIISANHKVTLTTVTVQTIKNHTEKNITTYLTQVSPERVSPSKQ

LTTTPPIYTNSATISPNTKSETHHTTAQTKGRTTTPTQNNKPSTKPRPK

NPPKKPKDDYHFEVFNFVPCSICGNNQLCKSICKTIPSNKPKKKPTIKP

TNKPPTKTTNKRDPKKLAKTLKKETTINPTKKPTPKTTERDTSTSQSTV

LDTTTSKHTERDTSTSQSTVLDTTTSKHTIQQQSLHSTTPENTPNSTQT

PTASEPSTSNSTQKL

In some embodiments, the heterologous gene encodes a recombinant RSV G comprising or consisting of the amino acid sequence set forth as SEQ ID NO: 77, or an amino acid sequence at least 90% (such as at least 95% or at least 98%) identical to SEQ ID NO: 77.

An exemplary amino acid sequence of a recombinant RSV G comprising the RSV G ectodomain from RSV BA1, and HPIV3 HN transmembrane domain and cytoplasmic tail is provided below:

(SEQ ID NO: 78

MEYWKHTNHGKDAGNELETSMATHGNKLTNKIIYILWTIILVLLSIVFII

VLINSINHKVTLTTVTVQTIKNHTEKNITTYLTQVSPERVSPSKQLTTTP

PIYTNSATISPNTKSETHHTTAQTKGRTTTPTQNNKPSTKPRPKNPPKKP

KDDYHFEVFNFVPCSICGNNQLCKSICKTIPSNKPKKKPTIKPTNKPPTK

TTNKRDPKKLAKTLKKETTINPTKKPTPKTTERDTSTSQSTVLDTTTSKH

TERDTSTSQSTVLDTTTSKHTIQQQSLHSTTPENTPNSTQTPTASEPSTS

NSTQKL

In some embodiments, the heterologous gene encodes a recombinant RSV G comprising or consisting of the amino acid sequence set forth as SEQ ID NO: 78, or an amino acid sequence at least 90% (such as at least 95% or at least 98%) identical to SEQ ID NO: 78.

An exemplary amino acid sequence of a recombinant RSV G comprising a RSV G ectodomain and transmembrane domain from RSV A2, and a HPIV1 HN cytoplasmic tail is provided below:

(SEQ ID NO: 79)

MAEKGKTNSSYWSTTRNDNSTVNTHINTPAGRTHWVAQITLSILAMIIST

SLIIAAIIFIASANHKVTPTTAIIQDATSQIKNTTPTYLTQNPQLGISPS

NPSEITSQITTILASTTPGVKSTLQSTTVKTKNTTTTQTQPSKPTTKQRQ

NKPPSKPNNDFHFEVFNFVPCSICSNNPTCWAICKRIPNKKPGKKTTTKP

TKKPTLKTTKKDPKPQTTKSKEVPTTKPTEEPTINTTKTNIITTLLTSNT

TGNPELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 79, or an amino acid sequence at least 90% (such as at least 95% or at least 98%) identical to SEQ ID NO: 79.

An exemplary amino acid sequence of a recombinant RSV G comprising the RSV G ectodomain from RSV A2 and HPIV1 HN transmembrane domain and cytoplasmic tail is provided below:

(SEQ ID NO: 80)

MAEKGKTNSSYWSTTRNDNSTVNTHINTPAGRTHWILLIATTMHTVLSFI

IMILCIDLIINHKVTPTTAIIQDATSQIKNTTPTYLTQNPQLGISPSNPS

EITSQITTILASTTPGVKSTLQSTTVKTKNTTTTQTQPSKPTTKQRQNKP

PSKPNNDFHFEVFNFVPCSICSNNPTCWAICKRIPNKKPGKKTTTKPTKK

PTLKTTKKDPKPQTTKSKEVPTTKPTEEPTINTTKTNIITTLLTSNTTGN

PELTSQMETFHSTSSEGNPSPSQVSTTSEYPSQPSSPPNTPRQ

In some embodiments, the heterologous gene encodes a recombinant RSV G comprising or consisting of the amino acid sequence set forth as SEQ ID NO: 80, or an amino acid sequence at least 90% (such as at least 95% or at least 98%) identical to SEQ ID NO: 80.

An exemplary amino acid sequence of a recombinant RSV G comprising a RSV G ectodomain and transmembrane domain from RSV B (B1, GenBank AAB82435.1), and a HPIV1 HN cytoplasmic tail is provided below:

(SEQ ID NO: 81)

MAEKGKTNSSYWSTTRNDNSTVNTHINTPAGRTHWIAQIALSVLAMIIST

SLIIAAIIFIISANHKVTLTTVTVQTIKNHTEKNITTYLTQVPPERVSSS

KQPTTTSPIHTNSATTSPNTKSETHHTTAQTKGRTTTSTQTNKPSTKPRL

KNPPKKPKDDYHFEVFNFVPCSICGNNQLCKSICKTIPSNKPKKKPTIKP

TNKPTTKTTNKRDPKTPAKTTKKETTTNPTKKPTLTTTERDTSTSQSTVL

DTTTLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 81, or an amino acid sequence at least 90% (such as at least 95% or at least 98%) identical to SEQ ID NO: 81.

An exemplary amino acid sequence of a recombinant RSV G comprising the RSV G ectodomain from RSV B (B1, GenBank AAB82435.1) and HPIV1 HN transmembrane domain and cytoplasmic tail is provided below:

(SEQ ID NO: 82)

MAEKGKTNSSYWSTTRNDNSTVNTHINTPAGRTHWILLIATTMHTVLSFI

IMILCIDLIINHKVTLTTVTVQTIKNHTEKNITTYLTQVPPERVSSSKQP

TTTSPIHTNSATTSPNTKSETHHTTAQTKGRTTTSTQTNKPSTKPRLKNP

PKKPKDDYHFEVFNFVPCSICGNNQLCKSICKTIPSNKPKKKPTIKPTNK

PTTKTTNKRDPKTPAKTTKKETTTNPTKKPTLTTTERDTSTSQSTVLDTT

TLEHTIQQQSLHSTTPENTPNSTQTPTASEPSTSNSTQNTQSHA

In some embodiments, the heterologous gene encodes a recombinant RSV G comprising or consisting of the amino acid sequence set forth as SEQ ID NO: 82, or an amino acid sequence at least 90% (such as at least 95% or at least 98%) identical to SEQ ID NO: 82.

An exemplary amino acid sequence of a recombinant RSV G comprising a RSV G ectodomain and transmembrane domain from RSV A/Maryland/001/11, and a HPIV1 HN cytoplasmic tail is provided below:

(SEQ ID NO: 83)

MAEKGKINSSYWSTTRNDNSTVNTHINTPAGRTHWIAQITLSILAMIIST

SLIIAAIIFIASANHKVILTTAIIQDATNQIKNTTPTYLTQNPQLGISLS

NLSETTSKPITILALTTPNAESTPQSTIVKTKNITTTQIQPSKPITKQRQ

NKPQNKPNNDFHFEVFNFVPCSICSNNPTCWAICKRIPNKKPGRKTITKP

TKQPAIKTTKKDPKPQTTKPKEVLITKPTEKPTINTTKINIRTILLTSNI

TENQEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 83, or an amino acid sequence at least 90% (such as at least 95% or at least 98%) identical to SEQ ID NO: 83.

An exemplary amino acid sequence of a recombinant RSV G comprising the RSV G ectodomain from RSV A/Maryland/001/11 and HPIV1 HN transmembrane domain and cytoplasmic tail is provided below:

(SEQ ID NO: 84)
MAEKGKTNSSYWSTTRNDNSTVNTHINTPAGRTHWILLIATTMHTVLSFI

IMILCIDLIINHKVTLTTAIIQDATNQIKNTTPTYLTQNPQLGISLSNLS

ETTSKPTTILALTTPNAESTPQSTTVKTKNTTTTQIQPSKPTTKQRQNKP

QNKPNNDFHFEVFNFVPCSICSNNPTCWAICKRIPNKKPGRKTTTKPTKQ

PAIKTTKKDPKPQTTKPKEVLTTKPTEKPTINTTKTNIRTTLLTSNITEN

QEHTSQKETLHSTTSEGNPSPSQVYTTSEYLSQSLSPSNTTRW

In some embodiments, the heterologous gene encodes a recombinant RSV G comprising or consisting of the amino acid sequence set forth as SEQ ID NO: 84, or an amino acid sequence at least 90% (such as at least 95% or at least 98%) identical to SEQ ID NO: 84.

An exemplary amino acid sequence of a recombinant RSV G comprising a RSV G ectodomain and transmembrane domain from RSV ON1, and a HPIV1 HN cytoplasmic tail is provided below:

(SEQ ID NO: 85)
MAEKGKTNSSYWSTTRNDNSTVNTHINTPAGRTHWIAQITLSILAMIIST

SLIIAAIIFIASANHKVTLTTAIIQDATNQIKNTTPTYLTQNPQLGISFS

NLSGTTSQSTTILASTTPSAESTPQSTTVKIKNTTTTQILPSKPTTKQRQ

NKPQNKPNNDFHFEVFNFVPCSICSNNPTCWAICKRIPNKKPGKKTTTKP

TKKPTLKTTKKDPKPQTTKPKEVLTTKPTGKPTINTTKTNIRTTLLTSNT

KGNPEHTSQEETLHSTTSEGYLSPSQVYTTSGQEETLHSTTSEGYLSPSQ

VYTTSEYLSQSLSSSNTTK

In some embodiments, the heterologous gene encodes a recombinant RSV G comprising or consisting of the amino acid sequence set forth as SEQ ID NO: 85, or an amino acid sequence at least 90% (such as at least 95% or at least 98%) identical to SEQ ID NO: 85.

An exemplary amino acid sequence of a recombinant RSV G comprising the RSV G ectodomain from RSV ON1, and HPIV1 HN transmembrane domain and cytoplasmic tail is provided below:

(SEQ ID NO: 86)
MAEKGKTNSSYWSTTRNDNSTVNTHINTPAGRTHWILLIATTMHTVLSFI

IMILCIDLIINHKVTLTTAIIQDATNQIKNTTPTYLTQNPQLGISFSNLS

GTTSQSTTILASTTPSAESTPQSTTVKIKNTTTTQILPSKPTTKQRQNKP

QNKPNNDFHFEVFNFVPCSICSNNPTCWAICKRIPNKKPGKKTTTKPTKK

PTLKTTKKDPKPQTTKPKEVLTTKPTGKPTINTTKTNIRTTLLTSNTKGN

PEHTSQEETLHSTTSEGYLSPSQVYTTSGQEETLHSTTSEGYLSPSQVYT

TSEYLSQSLSSSNTTK

In some embodiments, the heterologous gene encodes a recombinant RSV G comprising or consisting of the amino acid sequence set forth as SEQ ID NO: 86, or an amino acid sequence at least 90% (such as at least 95% or at least 98%) identical to SEQ ID NO: 86.

An exemplary amino acid sequence of a recombinant RSV G comprising a RSV G ectodomain and transmembrane domain from RSV BA1, and a HPIV1 HN cytoplasmic tail is provided below:

(SEQ ID NO: 87)
MAEKGKTNSSYWSTTRNDNSTVNTHINTPAGRTHWIAQIALSVLAMIIST

SLIIAAIIFIISANHKVTLTTVTVQTIKNHTEKNITTYLTQVSPERVSPS

KQLTTTPPIYTNSATISPNTKSETHHTTAQTKGRTTTPTQNNKPSTKPRP

KNPPKKPKDDYHFEVFNFVPCSICGNNQLCKSICKTIPSNKPKKKPTIKP

TNKPPTKTTNKRDPKKLAKTLKKETTINPTKKPTPKTTERDTSTSQSTVL

DTTTSKHTERDTSTSQSTVLDTTTSKHTIQQQSLHSTTPENTPNSTQTPT

ASEPSTSNSTQKL

In some embodiments, the heterologous gene encodes a recombinant RSV G comprising or consisting of the amino acid sequence set forth as SEQ ID NO: 87, or an amino acid sequence at least 90% (such as at least 95% or at least 98%) identical to SEQ ID NO: 87.

An exemplary amino acid sequence of a recombinant RSV G comprising the RSV G ectodomain from RSV BA1, and HPIV1 HN transmembrane domain and cytoplasmic tail is provided below:

(SEQ ID NO: 88)
MAEKGKENSSYWSTERNDNSTVNTHINTPAGRTHWILLIATTMHTVLSFI

IMILCIDLIINHKVTLETVEVQTIKNHTEKNITTYLTQVSPERVSPSKQL

ETTPPIYENSATISPNEKSETHHTTAQTKGRETTPTQNNKPSTKPRPKNP

PKKPKDDYHFEVFNFVPCSICGNNQLCKSICKTIPSNKPKKKPTIKPENK

PPEKTENKRDPKKLAKTLKKETTINPTKKPTPKTTERDTSTSQSTVLDTT

ESKHTERDTSTSQSTVLDTTTSKHTIQQQSLHSTTPENTPNSTQTPTASE

PSTSNSTQKL

In some embodiments, the heterologous gene encodes a recombinant RSV G comprising or consisting of the amino acid sequence set forth as SEQ ID NO: 88, or an amino acid sequence at least 90% (such as at least 95% or at least 98%) identical to SEQ ID NO: 88.

In additional embodiments, the heterologous gene of the rB/HPIV3-RSV G comprises a sequence encoding a wild-type RSV G or variant thereof that has been codon-optimized for expression in a human cell. For example, the encoding sequence of the heterologous gene can be codon-optimized for human expression using a GeneArt (GA), DNA2.0 (D2), or GenScript (GS) optimization algorithm. Non-limiting examples of nucleic acid sequences encoding the RSV G protein that have been codon-optimized for expression in a human cell are provided as follows:

"GS" codon optimized DNA coding sequence for wt G from RSV A2:
(SEQ ID NO: 89)
atgtcaaagaacaaggatcagagaactgccaagaccctggaaagaacctg ggacaccctgaaccacctgctgtttatctcaagctgcctgtacaagctga atctgaaaagtgtggcccagatcaccctgtcaattctggctatgatcatt tcaacaagcctgatcattgccgctatcattttcatcgcaagcgccaacca caaggtcacccccaccacagctatcattcaggacgcaacatcccagatta agaacactacccccacctatctgacacagaatcctcagctgggaatctcc ccatctaacccctcagagattaccagccagatcacaactattctggcctc -continued caccacacctggcgtgaagtccactctgcagtctactaccgtcaagacca aaaatacaactaccacacagacacagccttctaagccaactaccaaacag cggcagaataagcccctagtaaaccaaacaatgacttccattttgaggt gttcaactttgtcccatgcagcatctgttccaacaatcccacctgctggg ccatctgtaagagaattccaaacaagaaacccggcaagaagaccactacc aaacctactaagaaaccaaccctgaagacaactaagaaagatcctaaacc acagaccacaaagtctaaagaagtgcccactaccaagcctacagaggaac caactatcaacacaactaagactaacatcatcaccacactgctgacaagc aacactaccggcaatcccgagctgaccagccagatggaaacctttcactc cacaagctccgaggggaatcccagtccttcacaggtgtctacaactagtg aataccccagccagccttctagtccacccaacacccctaggcagtga Codon optimized (Biobasic) DNA coding sequence for wt G from RSV A/Maryland/001/11:

(SEQ ID NO: 95)

atgtctaagacaaaggatcagcggacagccaaaacactggaacggacatg ggataccctgaatcacctcctcttcatcagcagttgcctgtacaagctca atctgaagtccatcgcccagatcactctctccatccttgccatgatcatc tctacaagcctcatcattgccgcaattatcttcatcgccagcgctaacca caaggtcaccctaccacagccattattcaggatgccaccaaccagatca agaacacaacccctacctacctgacacagaaccctcagcttggaatttca ctgagcaacctgtccgaaaccacatctaaacctacaaccatcttggctct gaccacaccaaacgccgagtccaccccacaaagtaccacagtgaagacca aaaacaccacaaccacacagattcagccaagcaagcctacaactaagcaa aggcagaacaagccacagaacaaacccaacaacgactttcactttgaggt gttcaactttgtgccctgctccatttgctccaacaaccctacctgttggg ctatctgcaagaggatccccaacaagaagcccggcaggaagactactact aagcctactaaacagccagccattaagaccactaagaaggacccaaagcc acagacaaccaagccaaaggaggtgctcactaccaagcccactgagaagc ccaccattaacaccactaaaaccaacatccgcacaacattgctgacatca aacattacagagaaccaggagcacacaagccagaaggagacactgcatag cactacatccgaaggcaatcccagcccaagccaggtctatactacctcag agtacctgtcccagagcctgagccctagcaacactactagatggtag Codon optimized (Biobasic) DNA coding sequence for wt G from RSV B1:

(SEQ ID NO: 90)

agtctaaacacaagaatcagcggaccgcccggaccttggaaaagacttgg gatacccttaaccaccttatcgtgatttcctcctgcctgtaccgcctcaa cctcaagagcattgctcagatcgcgctctcagtgctggccatgataatct ccacttccttgataattgccgccattatcttcattatttctgcaaaccac aaagtcaccctgaccaccgttaccgtgcaaaccattaaaaaccacacgga gaagaacatcactacatacctgactcaggttcccccggagcgagtgagca gctccaagcagcccacaacaacaagccctatccatacaaattcagcaaca acaagtccaaacacaaagtctgaaacgcatcacacaaccgctcagacgaa -continued aggcaggaccacaacatccacccagactaataaacccagtactaagccta gactgaagaaccctcccaagaaacctaaggacgactatcatttcgaggtg tttaattttgtaccttgcagcatctgtggcaacaatcagctctgcaaaag catctgtaagaccatcccgtctaataagccaaagaagaagcccacgataa aaccaacaaataaaccaactaccaagacaacaaataagagggacccaaag acccccgctaaaactaccaagaaggagactaccaccaacccgacaaagaa acccaccctgacgactactgagagagatacttcaacttcacaaagcaccg tcctggatacaactaccctggagcacacaatccagcaacagagcctgcat agtactacgcctgaaaacactccaaactctacccagacgcccacagcctc agaaccttctacctccaatagtacccaaaatacccagagtcatgcatag In some embodiments, the genome of the rB/HPIV3-RSV G vector comprises an antigenomic cDNA sequence set forth as any one of SEQ ID NOs: 85-88.

Non-limiting examples of methods of generating a recombinant parainfluenza virus (such as a 50 rB/HPIV3) including a heterologous gene, methods of attenuating the viruses (e.g., by recombinant or chemical means), as well as viral sequences and reagents for use in such methods are provided in US Patent Publications 2012/0045471, 2010/0119547, 2009/0263883, 2009/0017517, 7632508, 7622123, 7250171, 7208161, 7201907, 7192593, PCT Pub. No. WO 2016/118642, Liang et al. (J. Virol, 88(8): 4237-4250, 2014), and Tang et al. (J Virol, 77(20):10819-10828, 2003), each of which is incorporated by reference herein. In some embodiments, these methods can be modified as needed using the description provided herein to construct a disclosed rB/HPIV3-RSV G vector.

The genome of the rB/HPIV3-RSV G vector can include one or more variations (for example, mutations that cause an amino acid deletion, substitution, or insertion) as long as the resulting the rB/HPIV3-RSV G retains the desired biological function, such as a level of attenuation or immunogenicity. These variations in sequence can be naturally occurring variations or they can be engineered through the use of genetic engineering technique.

Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the −3 position) of a selected viral gene is modified, alone or in combination with introduction of an upstream start codon, to modulate gene expression by specifying up- or down-regulation of translation.

Alternatively, or in combination with other modifications disclosed herein, gene expression can be modulated by altering a transcriptional GS signal of a selected gene(s) of the virus. In additional embodiments, modifications to a transcriptional GE signal can be incorporated into the viral genome.

In addition to the above described modifications to rB/HPIV3-RSV G, different or additional modifications to the genome can be made to facilitate manipulations, such as the insertion of unique restriction sites in various intergenic regions (e.g., a unique Asc I site between the N and P genes) or elsewhere. Nontranslated gene sequences can be removed to increase capacity for inserting foreign sequences.

Introduction of the foregoing modifications into rB/HPIV3-RSV G can be achieved by a variety of well-known methods. Examples of such techniques are found in see, e.g., Sambrook et al. (Molecular Cloning: A Laboratory Manual, 4$^{th}$ ed., Cold Spring Harbor, N.Y., 2012) and Ausubel et al. (In Current Protocols in Molecular Biology, John Wiley & Sons, New York, through supplement 104, 2013). Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

The disclosed embodiments of rB/HPIV3-RSV G are self-replicating, that is they are capable of replicating following infection of an appropriate host cell, and have an attenuated phenotype, for example when administered to a human subject. Preferably, the rB/HPIV3-RSV G is attenuated about 3- to 500-fold or more in the upper respiratory tract and about 100 to 5000 fold or more in the lower respiratory tract in a mammal compared to control HPIV3. In some embodiments, it is preferred that the level of viral replication in vitro is sufficient to provide for production of virus for use on a wide spread scale. In some embodiments, it is preferred that the level of viral replication of attenuated paramyxovirus in vitro is at least $10^6$, more preferably at least $10^7$, and most preferably at least $10^8$ per ml.

In some embodiments, the rB/HPIV3-RSV G vectors can be produced using the reverse genetics recombinant DNA-based technique (Collins, et al. 1995. *Proc Natl Acad Sci USA* 92:11563-11567). This system allows de novo recovery of infectious virus entirely from cDNA in a qualified cell substrate under defined conditions. Reverse genetics provides a means to introduce predetermined mutations into the rB/HPIV3-RSV G genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the virus does not contain recombinant DNA from the original recovery.

To propagate rB/HPIV3-RSV G vectors for immunization and other purposes, a number of cell lines which allow for viral growth may be used. Parainfluenza virus grows in a variety of human and animal cells. Preferred cell lines for propagating attenuated rB/HPIV3-RSV G virus for immunization include HEp-2 cells, FRhL-DBS2 cells, LLC-MK2 cells, MRC-5 cells, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by standard clarification procedures, e.g., centrifugation, and may be further purified as desired using known procedures.

The rB/HPIV3-RSV G vectors can be tested in various well known and generally accepted in vitro and in vivo models to confirm adequate attenuation, resistance to phenotypic reversion, and immunogenicity. In in vitro assays, the modified virus is tested for temperature sensitivity of virus replication or "ts phenotype," and for the small plaque phenotype. Modified virus also may be evaluated in an in vitro human airway epithelium (HAE) model, which appears to provide a means of ranking viruses in the order of their relative attenuation in non-human primates and humans (Zhang et al., 2002 J Virol 76:5654-5666; Schaap-Nutt et al., 2010 *Vaccine* 28:2788-2798; Ilyushina et al., 2012 J Virol 86:11725-11734). Modified viruses are further tested in animal models of HPIV3 or RSV infection. A variety of animal models (e.g., murine, cotton rat, and primate) are available.

Immunogenicity of a rB/HPIV3-RSV G vector can be assessed in an animal model (such as a non-human primate, for example an African green monkey), for example, by determining the number of animals that form antibodies to RSV and HPIV3 after one immunization and after a second immunization, and by measuring the magnitude of that response. In some embodiments, a rB/HPIV3-RSV G has sufficient immunogenicity if about 60 to 80% of the animals develop antibodies after the first immunization and about 80 to 100% of the animals develop antibodies after the second immunization. Preferably, the immune response protects against infection by both RSV and HPIV3.

Also provided are isolated polynucleotides comprising or consisting of the genome or antigenome of a disclosed rB/HPIV3-RSV G vector, vectors comprising the polynucleotides, and host cells comprising the polynucleotides or vectors.

IV. Immunogenic Compositions

Immunogenic compositions comprising a disclosed rB/HPIV3-RSV G vector and a pharmaceutically acceptable carrier are also provided. Such compositions can be administered to a subject by a variety of modes, for example, by an intranasal route. Standard methods for preparing administrable immunogenic compositions are described, for example, in such publications as *Remingtons Pharmaceutical Sciences,* 19$^{th}$ Ed., Mack Publishing Company, Easton, Pa., 1995.

Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

The immunogenic composition can contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic composition can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the recombinant virus, and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998*, Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the immunogenic composition can include a rB/HPIV3-RSV G encoding an RSV G ectodomain from one particular RSV subgroup or strain and also a recombinant rB/HPIV3-RSV G encoding an RSV G ectodomain from a different RSV subgroup or strain. For example, the composition can include rB/HPIV3-RSV G including recombinant RSV G proteins from subtype A and subtype B RSV. The different viruses can be in an admixture and administered simultaneously, or administered separately. Due to the phenomenon of cross-protection among certain strains of RSV, immunization with one rB/HPIV3-RSV G encoding a RSV G ectodomain from a first strain may protect against several different strains of the same or different subgroup.

In some instances it may be desirable to combine the immunogenic composition including the rB/HPIV3-RSV G, with other pharmaceutical products (e.g., vaccines) which induce protective responses to other viral agents, particularly those causing other childhood illnesses. For example, a composition including a rB/HPIV3-RSV G as described herein can also include other vaccines recommended by the Advisory Committee on Immunization Practices (ACIP; cdc.gov/vaccines/acip/index.html) for the targeted age group (e.g., infants from approximately one to six months of age). These additional vaccines include, but are not limited to, IN-administered vaccines. As such, a rB/HPIV3-RSV G as described herein may be administered simultaneously with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the immunogenic composition can be provided in unit dosage form for use to induce an immune response in a subject, for example, to prevent HPIV3 and/or RSV infection in the subject. A unit dosage form contains a suitable single preselected dosage for administration to a subject, or suitable marked or measured multiples of two or more preselected unit dosages, and/or a metering mechanism for administering the unit dose or multiples thereof.

V. Methods of Eliciting an Immune Response

Provided herein are methods of eliciting an immune response in a subject by administering an immunogenic composition containing a disclosed rB/HPIV3-RSV G to the subject. Upon immunization, the subject responds by producing antibodies specific for one or more of RSV G protein and HPIV3 HN and F proteins. In addition, innate and cell-mediated immune responses are induced, which can provide antiviral effectors as well as regulating the immune response. As a result of the immunization the host becomes at least partially or completely immune to HPIV3 and/or RSV infection, or resistant to developing moderate or severe HPIV3 and/or RSV disease, particularly of the lower respiratory tract.

Because nearly all humans are infected with RSV and HPIV3 by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV, HPIV3, and/or HPIV1 specific antibodies. In additional embodiments, the subject is no more than one year old, such as no more than 6 months old, no more than 3 months, or no more than 1 month old.

Subjects at greatest risk of RSV and/or HPIV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. In some embodiments, these subjects can be selected for administration of a disclosed rB/HPIV3-RSV G.

The immunogenic compositions containing the rB/HPIV3-RSV G are administered to a subject susceptible to or otherwise at risk of RSV and/or HPIV3 infection in an "effective amount" which is sufficient to induce or enhance the individual's immune response capabilities against RSV and/or HPIV3. The immunogenic composition may be administered by any suitable method, including but not limited to, via injection, aerosol delivery, nasal spray, nasal droplets, oral inoculation, or topical application. In a preferred embodiment, the attenuated virus is administered according to established human intranasal administration protocols (e.g., as discussed in Karron et al. JID 191:1093-104, 2005). Briefly, adults or children are inoculated intranasally via droplet with an effective amount of the rB/HPIV3-RSV G, typically in a volume of 0.5 ml of a physiologically acceptable diluent or carrier. This has the advantage of simplicity and safety compared to parenteral immunization with a non-replicating virus. It also provides direct stimulation of local respiratory tract immunity, which plays a major role in resistance to RSV and HPIV3. Further, this mode of vaccination effectively bypasses the immunosuppressive effects of HPIV3- and RSV-specific maternally-derived serum antibodies, which typically are found in the very young. Also, while the parenteral administration of RSV antigens can sometimes be associated with immunopathologic complications, this has not been observed with a live virus.

In all subjects, the precise amount of immunogen administered and the timing and repetition of administration will be determined by various factors, including the patient's state of health and weight, the mode of administration, the nature of the formulation, etc. Dosages will generally range from about 3.0 $\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more later. In another embodiment, young infants could be given a dose of about 5.0 $\log_{10}$ to 6.0 $\log_{10}$ PFU per patient at approximately 2, 4, and 6 months of age, which is the recommended time of administration of a number of other childhood vaccines. In yet another embodiment, an additional booster dose could be administered at approximately 10-15 months of age.

The embodiments of rB/HPIV3-RSV G described herein, and immunogenic compositions thereof, are administered to a subject in an amount effective to induce or enhance an immune response against the HPIV3 and RSV antigens included in the rB/HPIV3-RSV G in the subject. An effective amount will allow some growth and proliferation of the virus, in order to produce the desired immune response, but will not produce viral-associated symptoms or illnesses. Based on the guidance provided herein and knowledge in the art, the proper amount of rB/HPIV3-RSV G to use for immunization cane determined.

A desired immune response is to inhibit subsequent infection with RSV and/or HPIV3. The RSV and/or HPIV3infection does not need to be completely inhibited for the method to be effective. For example, administration of an effective amount of a disclosed rB/HPIV3-RSV G can decrease subsequent RSV and/or HPIV3infection (for example, as measured by infection of cells, or by number or percentage of subjects infected by RSV and/or HPIV3) by a desired amount, for example by at least 10%, at least 20%, at least 50%, at least 60%, at least 70%, at least 80%, at least 90%, at least 95%, at least 98%, or even at least 100% (prevention of detectable RSV and/or HPIV3infection), as compared to a suitable control.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, hamster, cotton rat, bovine, ovine, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease).

Administration of the rB/HPIV3-RSV G to a subject can elicit the production of an immune response that is protective against serious lower respiratory tract disease, such as pneumonia and bronchiolitis, or croup, when the subject is subsequently infected or re-infected with a wild-type RSV or HPIV3. While the naturally circulating virus is still capable of causing infection, particularly in the upper respiratory tract, there is a reduced possibility of rhinitis as a result of the immunization and a possible boosting of resistance by subsequent infection by wild-type virus. Following immunization, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be immunized with multiple immunogenic compositions that together comprise rB/HPIV3-RSV G with genomes encoding a RSV G proteins from at least one predominant strain of both RSV subgroups A and B.

An immunogenic composition including one or more of the disclosed rB/HPIV3-RSV G viruses can be used in coordinate (or prime-boost) immunization protocols or combinatorial formulations. It is contemplated that there can be several boosts, and that each boost can be a different disclosed immunogen. It is also contemplated in some examples that the boost may be the same immunogen as another boost, or the prime. In certain embodiments, novel combinatorial immunogenic compositions and coordinate immunization protocols employ separate immunogens or formulations, each directed toward eliciting an anti-viral immune response, such as an immune response to RSV and HPIV3 proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness.

EXAMPLES

The following examples are provided to illustrate particular features of certain embodiments, but the scope of the claims should not be limited to those features exemplified.

Example 1

Identification of rB/HPIV3 Vectors Expressing RSV G or Variants Thereof for Induction of a Protective Immune Response to RSV and HPIV3

This example describes development, production, and evaluation of a rB/HPIV3 vector to express wt G protein of RSV A2 strain, and variants thereof, from the second gene position, between the vector N and P genes.

The vector backbone used in this example is a chimera of bovine PIV3 (Kansas strain) and human PIV3 (JS strain), called rB/HPIV3 (Schmidt et al., 2000, *J. Virol.* 74:8922-8929). This vector consists of BPIV3 in which the genes encoding the F and HN glycoproteins (the two PIV3 neutralization antigens and major protective antigens) have been replaced by their counterparts from HPIV3. HPIV3 and BPIV3 are very closely-related viruses, and the rB/HPIV3 chimera contains all of the PIV3 genes and is fully replication-competent, but is attenuated in rhesus monkeys and humans due to the BPIV3 backbone (Karron et al., 2012, Vaccine 30:3975-3981).

A version of the rB/HPIV3 with the wild type (wt) RSV F gene inserted in the second gene position (N-P), called MEDI-534, previously was evaluated in HPIV3- and RSV-seronegative infants and children (Bernstein et al., *Ped. Infect. Dis., J.* 31:109-114, 2012). MEDI-534 was attenuated and well-tolerated (as was the empty rB/HPIV3 vector in a different study in seronegative children, Karron et al., 2012, Vaccine 30:3975-3981). However, while all vaccine recipients seroconverted against HPIV3, only half developed detectable serum RSV-neutralizing antibodies analyzed by a micro-neutralization assay in the absence of added complement. There also was loss of RSV F protein expression by substantial proportions of vector that had been recovered in nasal washes from vaccinees (Yang et al., Vaccine 31:2822-2827, 2013). An advantage of the rB/HPIV3 vector system is that, because rB/HPIV3 expressing RSV wt F protein was shown to be safe and well-tolerated in seronegative children, as noted above (Bernstein et al., 2012, Pediatr. Infect. Dis. J. 31:109-114), versions with improved RSV inserts can be anticipated to be similarly well-tolerated, putting them on a fast track for clinical development.

Figure 1B:
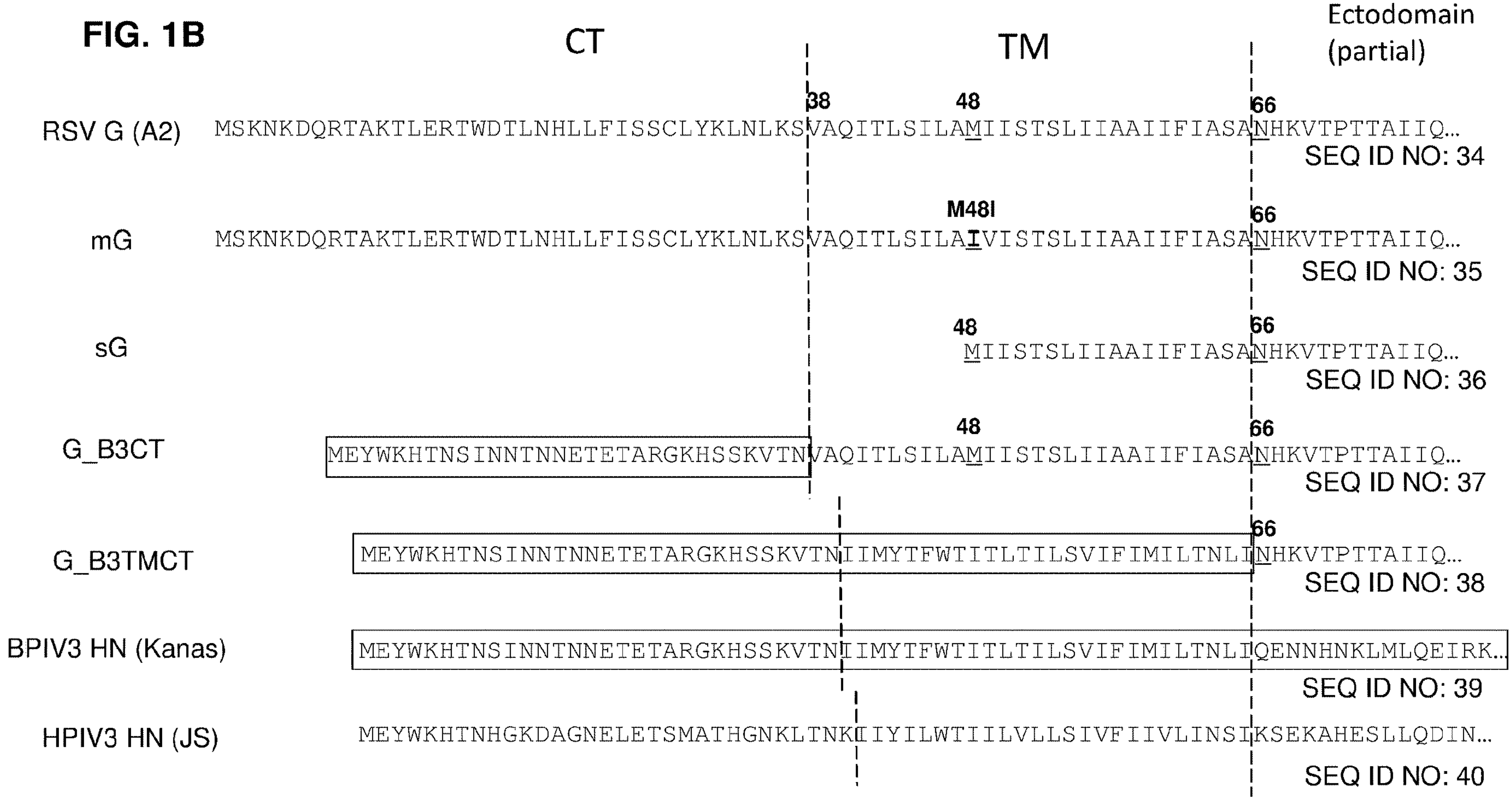

The rB/HPIV3-RSV G vectors were designed so that the RSV G gene was flanked by BPIV3 transcription regulatory elements including a gene end (GE) signal copied from the N gene, a gene start (GS) signal copied from the P gene, and CTT trinucleotide intergenic regions (FIG. 1A). Additionally, the HN gene of the rB/HPIV3 includes 263T and 370P amino acid assignments, which results in virus that could be recovered and passaged with substantially reduced appearance of adventitious mutations to increase the efficiency of virus production, analysis, and manufacture.

RSV G and RSV G Variants

The RSV G protein is expressed during RSV infection in two forms. One is the full-length transmembrane form (mG), which is expressed on the cell surface and is packaged into the virus particle. The other form is an N-terminally-truncated, secreted form, sG. The full-length G protein (mG) is a type II protein that has an N-terminal cytoplasmic tail (CT, predicted to comprise amino acids 1-37 in strain A2, see FIG. 1B), a hydrophobic transmembrane domain (TM, comprising approximately amino acids 38-65, see FIG. 1B), and an ectodomain (comprising approximately amino acids 66-298). The sG form is produced by alternative translation initiation at the second AUG codon (M48) in the ORF, whose corresponding position in the protein lies within the TM domain (see FIG. 1B). The N-terminus is then subjected to intracellular proteolytic trimming that creates a new N-terminus at N66 (FIG. 1B).

The ectodomain of G consists of two large divergent domains that flank a short central conserved region at amino acids 164-186. The divergent domains have a high content of proline, alanine, threonine, and serine amino acids, and (for strain A2) an estimated four N-linked and 24-25 O-linked carbohydrate side chains. The central conserved domain contains a cysteine noose (i.e., a tight turn stabilized by two disulfide bonds) that bears a conserved CX3C motif (CWAIC, 182-186 aa of the A2 strain). The mG and sG forms are believed to be essentially the same with regard to glycosylation and protein structure except that mG forms a multimer that probably is a trimer or tetramer, whereas sG remains a monomer.

A CX3C domain also occurs in the chemokine called fractalkine (FIG. 1C), and the sequences flanking the CX3C domains in RSV G and fractalkine also share sequence relatedness (Tripp et al., *Nature Immunol.* 2:732-738[[m]], 2001). The G protein has been shown to mimic fractalkine in the ability to induce leukocyte chemotaxis in vitro (Tripp et al., 2001, *Nature Immunol* 2:732-738), and also binds to the fractalkine receptor CX3CR1, which can initiate RSV infection (Tripp et al., 2001, *Nature Immunol* 2:732-738; Johnson et al., 2015, *PLoS Pathog.* 11:e1005318). Like the G protein, fractalkine is expressed as a full-length transmembrane form and a truncated secreted form. For fractalkine, the full-length transmembrane form acts as an adhesion molecule that interacts with the fractalkine receptor CX3CR1 expressed on T cells, NK cells, and monocytes; and the secreted form acts as a chemoattractant for the same cell types. The role of the CX3C domain in RSV attachment seems straight-forward (i.e., allowing the virus to bind to cells expressing CX3CR1), but the effects of the CX3C domain and sG on host immunity remain unclear. In principle, ablation of the CX3C domain and/or the expression of sG would be expected to reduce the chemotactic influx of immune cells and might reduce disease, and this is supported by several studies with mutant RSVs (e.g., Maher et al., 2004, *Microbes Infect.* 6:1049-1055; Boyoglu-Barnum et al., 2017, *J. Virol.,* 91(10): e02059-16), although there also are contradictory data (e.g. Harcourt et al., 2006, *J. Immunol.* 176:1600-1608). Other effects of G also have been described: e.g., sG was shown to act as an antigen decoy to reduce neutralization by antibodies, and also appeared to interfere with clearance of RSV by macrophages and complement (Bukreyev et al., *J. Virol.,* 86(19): 10880-4, 2012). As another example, in vitro, the G protein interfered with human dendritic cell activation (Johnson et al., 2012, *J. Virol.* 86:1339-1347). In addition, the binding of RSV to CX3CR1 expressed on human neonatal regulatory B cells lead to a Th2-polarized response (Zhivaki et al., 2017, *Immunity* 46:301-314). Thus, the effects of the G protein, including its sG form and CX3C motif, on host immunity are incompletely understood and likely are complex.

RSV G and nine derivatives thereof are shown in FIG. 1A (constructs (i)-(x)), which are described below:

Constructs (i) is wt RSV G. The wt RSV G used in this example is from subgroup A2 and has the amino acid sequence set forth as:

(SEQ ID NO: 22)

```
MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVPCSICSNNPTCWAICKRIPNKKPGKKTTT

KPTKKPTLKTTKKDPKPQTTKSKEVPTTKPTEEPTINTTKTNIITTLLTS

NTTGNPELTSQMETFHSTSSEGNPSPSQVSTTSEYPSQPSSPPNTPRQ
```

Constructs (ii) and (iii) in FIG. 1A encode the mG and sG forms of G protein. The mG construct was made by ablating expression of sG by a M48I mutation (FIG. 1B), and the sG construct was made by deletion of the first 47 codons of the G ORF so that codon M48 initiates the ORF (FIG. 1B); as described previously, the protein subsequently gets trimmed intracellularly to a major product with an N-terminus of N66 (Roberts et al., *J. Virol.,* 68(7): 4538-4546, 1994, Teng et al., *J. Virol.* 289:283-296, 2001).

Constructs (iv) and (v) in FIG. 1A (G_B3CT and G_B3TMCT) are chimeric proteins that have the CT and TMCT of wt G replaced by those of the vector BPIV3 HN protein (see FIG. 1B) to promote efficient packaging of RSV G into the vector particles. It is believed that the presence in RSV G of CT or TMCT domains from the vector HN protein would promote homologous interactions with internal vector proteins such as M and N to facilitate the incorporation of RSV G into the viral particle. Identification of the sequence boundaries of the TM and CT of BPIV3 HN was determined by inspection and alignment with HPIV3 HN (FIG. 1B).

Constructs (vi) and (vii) in FIG. 1A (G_dCX3C and G_wCX4C) have mutations that ablate the CX3C motif in the G protein: specifically, G_dCX3C has a C186R mutation that changes the assignment of the second cysteine residue in the CX3C motif (FIG. 1C), and G_wCX4C has the insertion of an alanine residue between positions 185 and 186 that disrupts the spacing of the motif (FIG. 1C).

In constructs (viii) and (ix) in FIG. 1A, the C186R mutation also was made in combination with the B3CT and B3TMCT substitutions (G_dCX3C_B3CT and G_dCX3C_B3TMCT).

In addition, a construct encoding wt G was codon-optimized for human expression by GenScript (wt G/GS-opt, FIG. 1A, form x).

The range of RSV G variants allowed assessment of the effects of sG, the CX3C motif, the CT and TMCT mutations, and codon optimization on the immunogenicity of the RSV G protein. In addition, possible effects on the immune response to the rB/HPIV3 vector could also be assessed. In this context, PIV3 is a suitable surrogate for RSV because it is a related respiratory virus that has general similarities in epidemiology, tissue tropism, and disease. In addition, the RSV G insert is not needed for replication of the PIV vector, removing this confounding factor. Thus, effects on vector immunogenicity, as well as possible changes in immunologic restriction of vector replication, were assessed.

Full antigenomic cDNA sequences for rB/HPIV3-RSV wtG (construct (i)), rB/HPIV3-RSV wt G/GS-opt (construct (x)), rB/HPIV3-RSV G_B3TMCT (construct (v)), rB/HPIV3-RSV G_B3CT (construct (iv)) are provided in the exemplary sequences section below.

Virus Replication and RSV G Expression

The rB/HPIV3 vectors expressing various forms of RSV G replicated efficiently in LLC-MK2 cells (7.6-8.6 $\log_{10}$ $TCID_{50}$/ml). No growth defect was observed with any construct.

The intracellular expression of RSV G by the various constructs was evaluated in Vero (FIGS. 2A and 2B) and LLC-MK2 (FIG. 3) cells by Western blot analysis. Cells were infected with each vector at a multiplicity of infection (MOI) of 10 $TCID_{50}$ (50% tissue culture infection doses) per cell, or by wt RSV at MOI of 3 plaque formation units (PFU) per cell. Cells were harvested at 24 h post-infection (p.i.) and cell lysates were prepared, subjected to gel electrophoresis under denaturing and reducing conditions, and analyzed by Western blotting using polyclonal antibodies against RSV and HPIV3.

Figures 2A, 2B, 2C, 2D:
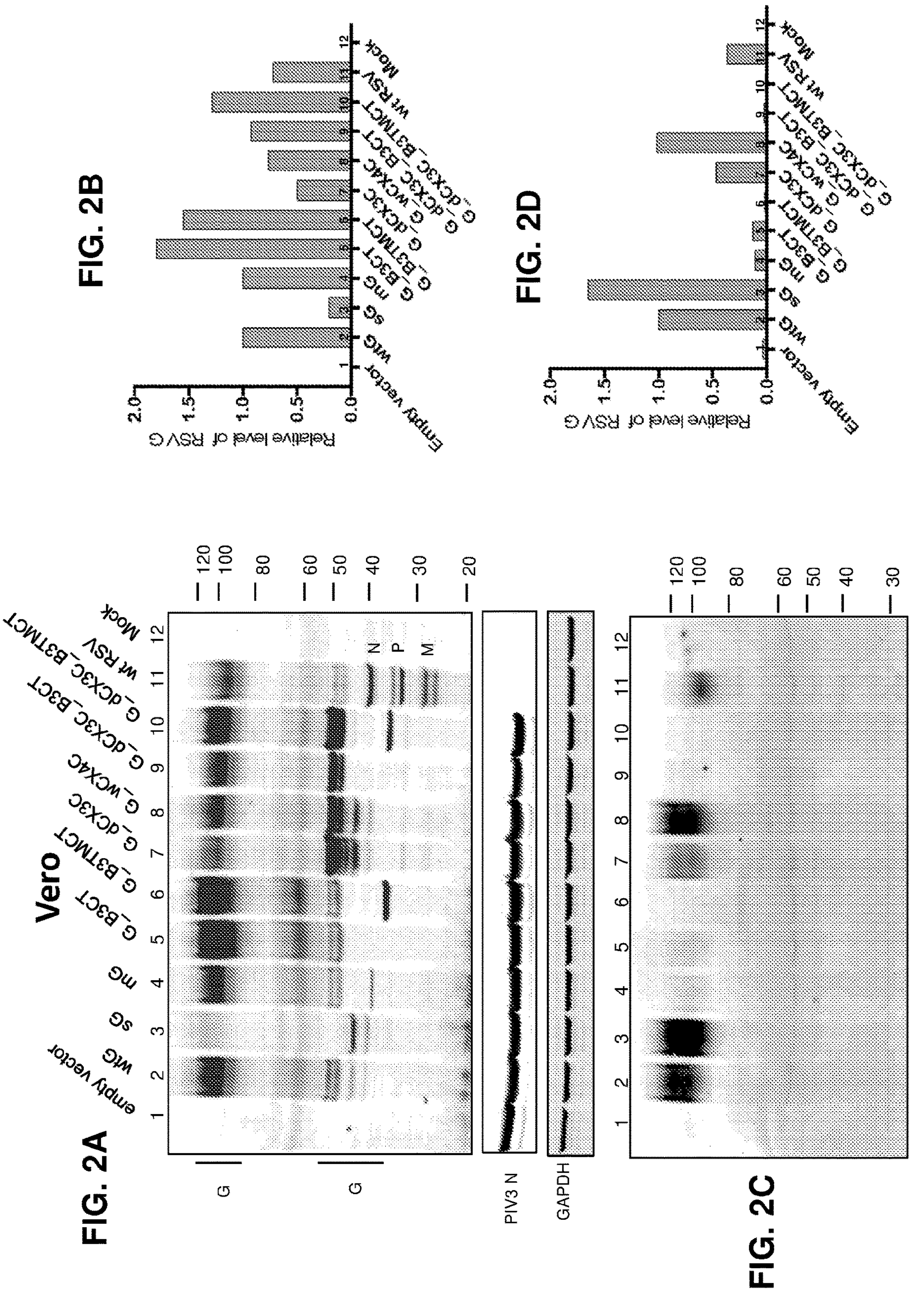
FIGS. 2A-2D. Western blot analysis of modified RSV G proteins expressed in Vero cells from the rB/HPIV3-RSV G vectors. Vero cells were infected with the indicated rB/HPIV3-RSV G vector or wt RSV at an MOI of 10 $TCID_{50}$ or 3 PFU per cell, respectively. At 24 hours post-infection (h.p.i.), the cells were harvested for analysis, and at 48 h.p.i., the overlying cell culture medium supernatants from duplicate cultures were harvested for analysis. The cells and medium supernatants were analyzed separately by gel electrophoresis under denaturing and reducing conditions followed by Western blotting with antisera raised separately against RSV and HPIV3, followed by secondary antibodies conjugated with infrared fluorescent dyes, and the relative levels of the large predominant band of fully glycosylated, 90-120 kDa RSV G protein were quantified densitometric analysis using an Odyssey imaging system (LiCor).
Figure 3B:
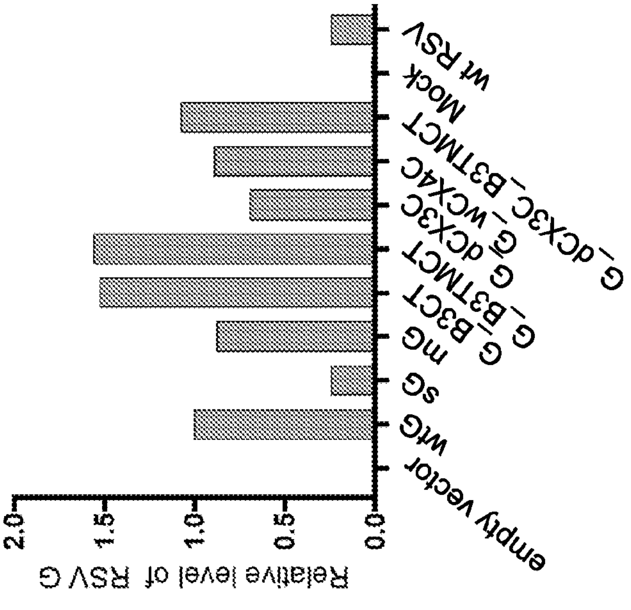
FIGS. 3A and 3B. Western blot analysis of RSV G expression from rB/HPIV3-RSV G vectors in LLC-MK2 cells. LLC-MK2 cells were infected with the indicated rB/HPIV3-RSV G constructs or wt RSV as described in FIG. 2A. Cells were harvested at 24 h.p.i. processed, and subjected to by Western blot analysis with antisera raised separately against RSV and HPIV3 as described in FIGS. 2A and 2B.
Figure 3A:
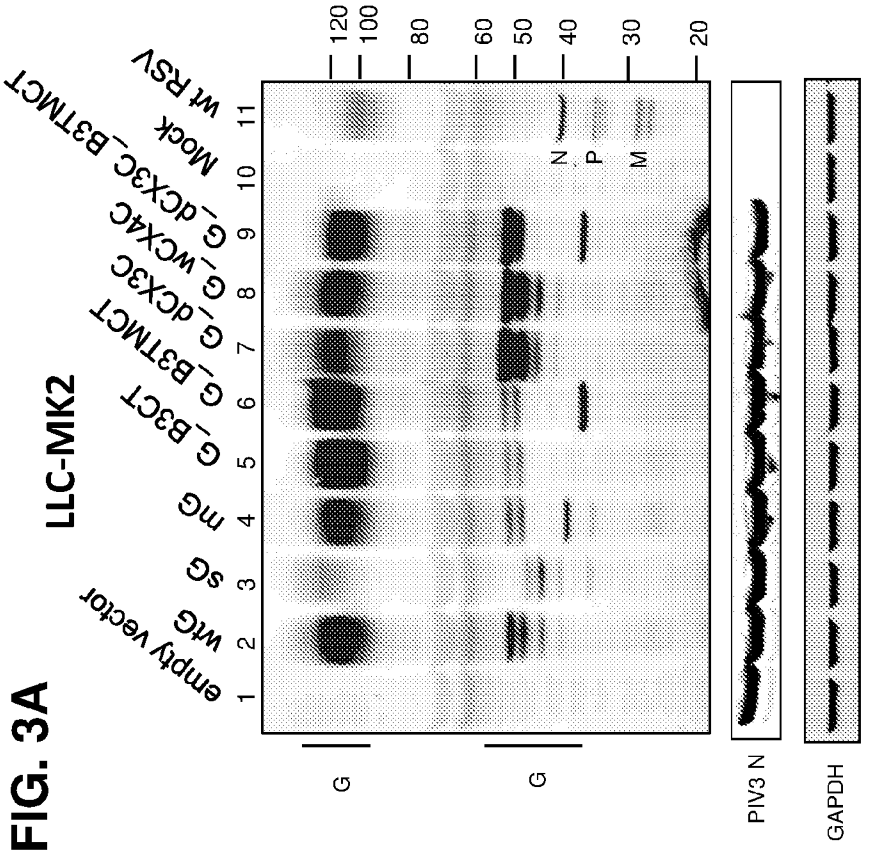

Intracellular RSV G expressed by the rB/HPIV3 vector expressing wt RSV G (FIG. 2A, lane 2) and by wt RSV (lane 11) was detected as a predominant diffuse band of 90-120 kD (FIG. 2A), which corresponds to the fully glycosylated form, and as less abundant bands of 35-50 kD that represent processing intermediates of the G protein with incomplete O-glycosylation. Expression of the various G protein species described above by the mG construct was essentially the same as for wt G (FIGS. 2A and 2B, lane 4 versus 2). In contrast, the sG construct had only a trace amount of the large diffuse band, consistent with efficient secretion. The sG construct also had versions of the incompletely-glycosylated bands of the G protein that were reduced in size due to the N-terminal truncation. The CT and TMCT substitutions increased expression of the large G band by 50-80%, an effect that is unexplained (FIGS. 2A and 2B, lanes 5 and 6 versus 2). In contrast, CX3C ablation reduced the accumulation of the large G band by 20-50% percent, which appeared to be due at least in part to an increase in the accumulation of the 35-50 kD incompletely-glycosylated forms (FIGS. 2A and 2B, lanes 7 and 8 versus 2). The reduction in accumulation of the large G band associated with the CX3C mutations was compensated for when combined with the B3CT and B3TMCT substitutions (FIGS. 2A and 2B, lanes 9 and 10). There were no significant differences in the expression of the BPIV3 N protein between the constructs, including the empty vector (FIG. 2A), suggesting that none of the forms of the RSV G had much effect on vector gene expression in vitro. Intracellular expression of the RSV G and BPIV3 N protein in LLC-MK2 cells (FIGS. 3A and 3B) followed similar patterns as their expression in Vero cells.

Secretion of RSV G was evaluated from Vero cell cultures that were infected in parallel as described above and incubated for 48 h (FIG. 2C, 2D). The overlying medium was collected and clarified by centrifugation at 10,000×g for 60 min in order to remove debris as well as rB/HPIV3 virions. The clarified supernatants were then subjected to Western blot analysis with polyclonal antibodies against RSV and HPIV3. In the case of cells infected with rB/HPIV3 expressing wt G (FIG. 2C, lane 2) or infected with RSV (lane 11), the only form of G protein that was detected in the clarified, virus-depleted medium was the large, diffuse 90-120 kD species, indicating only the completely glycosylated form of G was secreted into medium (FIG. 2C, lanes 2 and 11). As expected, very little G protein was detected in the medium from cells infected with the mG construct (FIGS. 2C and 2D, lane 4), while sG protein produced by the sG construct was 70% more abundant than with the wt G construct (FIGS. 2C and 2D, lane 3 versus 2). Ablation of the CX3C by either mutation appeared to slightly decrease the expression of sG protein (FIGS. 2C and 2D, lanes 7 and 8), which likely was due to the overall reduced expression (FIGS. 2A and 2B, lanes 7 and 8). The B3CT and B3TMCT substitution completely abrogated the expression of sG protein (FIGS. 2C and 2D, lanes 5-6 and 9-10). This perhaps was not surprising in the case of B3TMCT, since the native M48 codon that normally is used to initiate synthesis of sG protein is located in the TM domain of G that was replaced with the TM domain from HPIV3 HN protein (although two other AUG codons are present in the HPIV3 HN TM domain that apparently were not utilized, FIG. 1B). In the case of the B3CT substitution, the native TM with its M48 codon is present, and it is not known why it was not utilized. One possibility is that the nucleotide sequence upstream of this region influences initiation at the M48 codon.

Figure 4A:
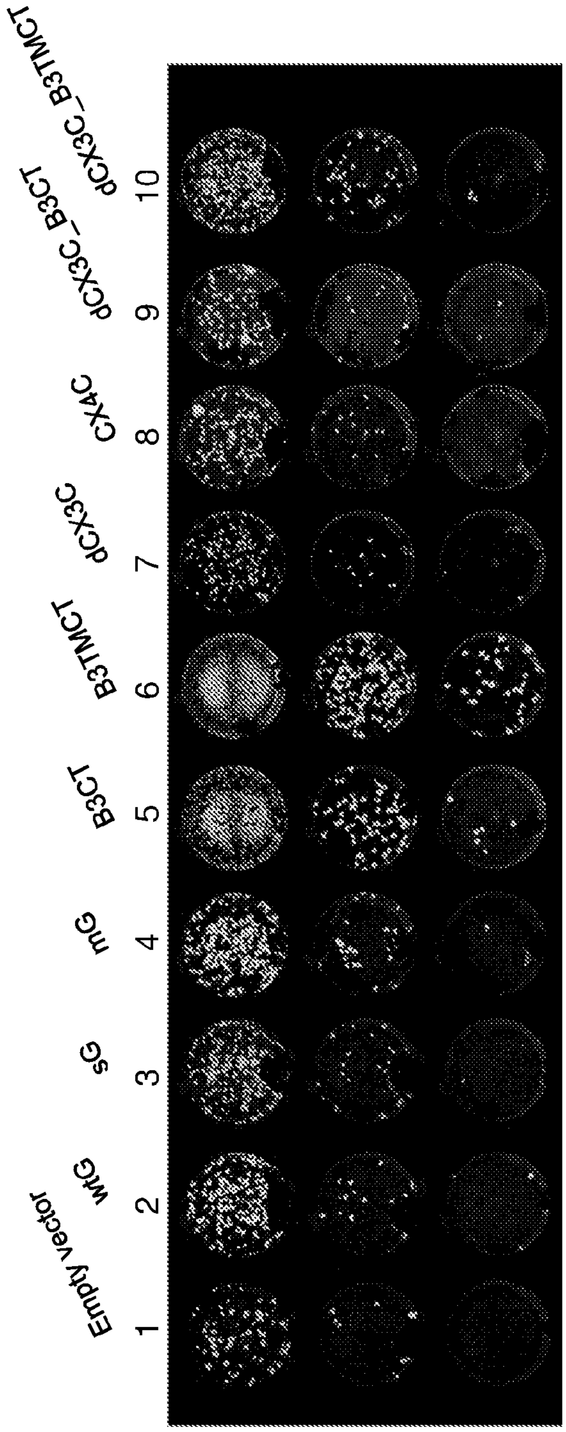
FIGS. 4A and 4B. Double-staining plaque assays characterizing expression of modified forms of RSV G protein from rB/HPIV3-RSV G. rB/HPIV3 constructs expressing the indicated modified G proteins were inoculated in 10-fold dilution series on Vero cell monolayers in 24-well plates and incubated under methyl cellulose overlay for 6 days. The monolayers were fixed with 80% methanol and analyzed with the indicated primary antibodies followed by secondary antibodies conjugated to infrared dye.

The stability of RSV G expression by the rB/HPIV3 constructs following passage in vitro was determined by a double-staining plaque assay (FIG. 4A), similar to assays described previously for rB/HPIV3 constructs expressing the RSV F protein (Liang et al., *J. Virol.,* 89(18): 9499-9510, 2015). Briefly, Vero cells were infected with 10-fold serially diluted viral stocks and incubated under methyl cellulose overlay until plaques formed. Plaques were fixed and stained with primary rabbit anti-HPIV3 or goat anti-RSV antibodies followed by species-specific secondary antibodies conjugated to infrared dye (PIV3, green; RSV, red) (FIG. 4A). Co-expression of HPIV3 antigens and RSV G by a single PFU was visualized as yellow. All of the vector stocks expressing RSV G were found to have almost 100% of PFU expressing RSV G, with the exception that this could not be determined in the case of the sG construct because the rapid secretion of G into the medium precluded staining of the plaques for this protein (FIG. 4A, column 3).

Figure 4B:
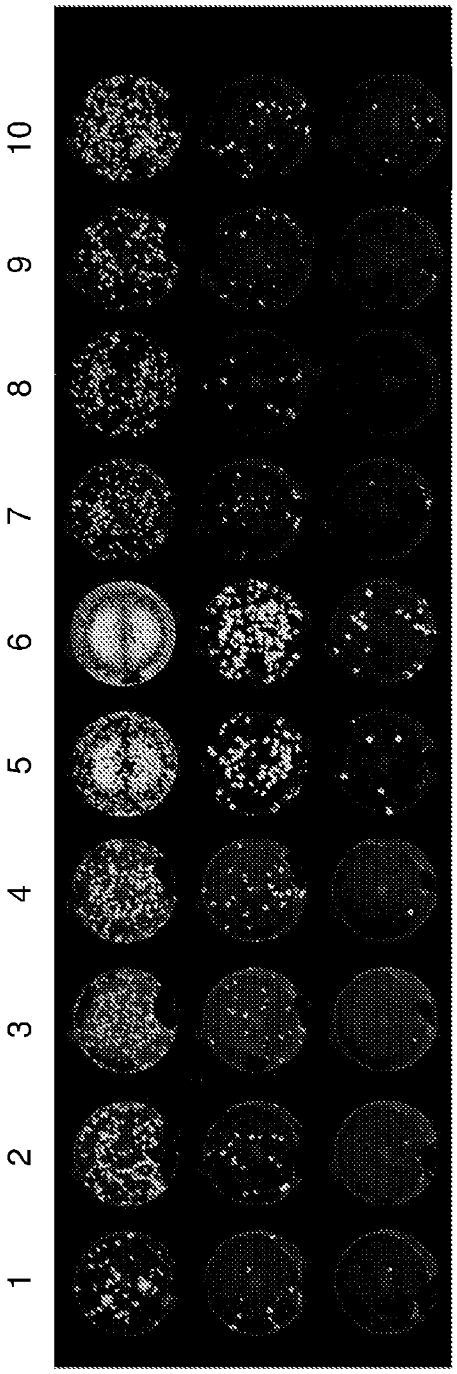

Additionally, a double-plaque assay was performed using an RSV G MAb (131-2G) that is specific to the CX3C domain (FIG. 4B). This antibody bound to plaques for all of the versions of G in which the CX3C motif was intact (FIG. 4B lanes 2, 4, 5, 6) except for sG (lane 3), but did not bind to the versions with mutations in the CX3C motif (FIG. 4B, lanes 7-10). This indicated that ablation of CX3C motif disrupted the 131-2G binding epitope on RSV G, and was confirmation of the absence of an intact CX3C motif in these mutants.

RSV G Packaging

Figure 5B:
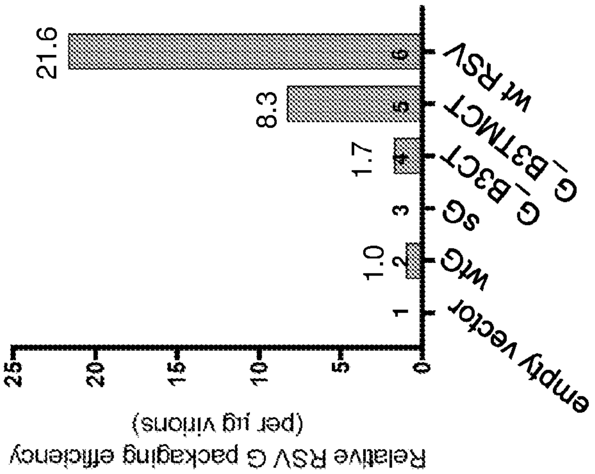
FIGS. 5A and 5B. Quantification of RSV G packaging efficiency by Western blot analysis of purified rB/HPIV3-RSV G particles. LLC-MK2 and Vero cells were infected with, respectively, 0.01 $TCID_{50}$ of the indicated rB/HPIV3-RSV G construct or 0.1 PFU of wt RSV. The cultures were harvested on day 4 and clarified cell culture medium supernatants were subjected to centrifugation on discontinuous 30%/60% w/v sucrose gradients. Purified virions were harvested from the sucrose interface and pelleted by centrifugation. Approximately 4 g of each virus were subjected to gel electrophoresis under denaturing and reducing conditions. Western blots were prepared and analyzed with antisera raised separately against RSV and HPIV3.
Figure 5A:
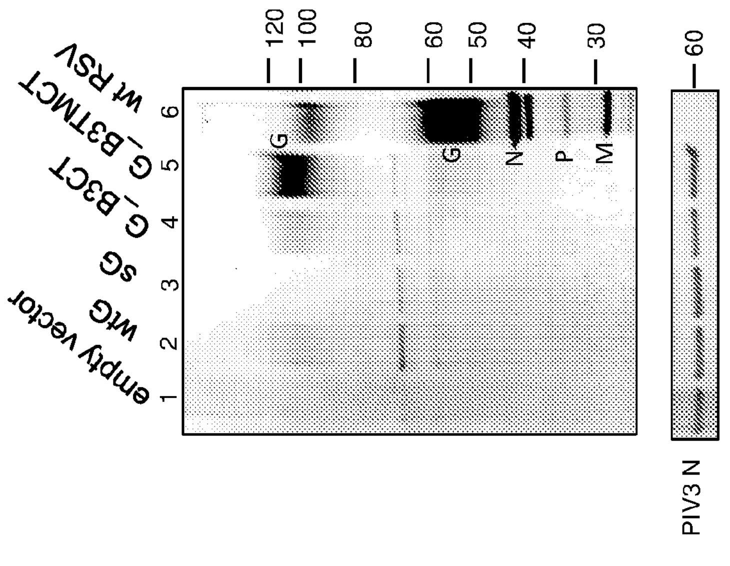
Figure 6A:
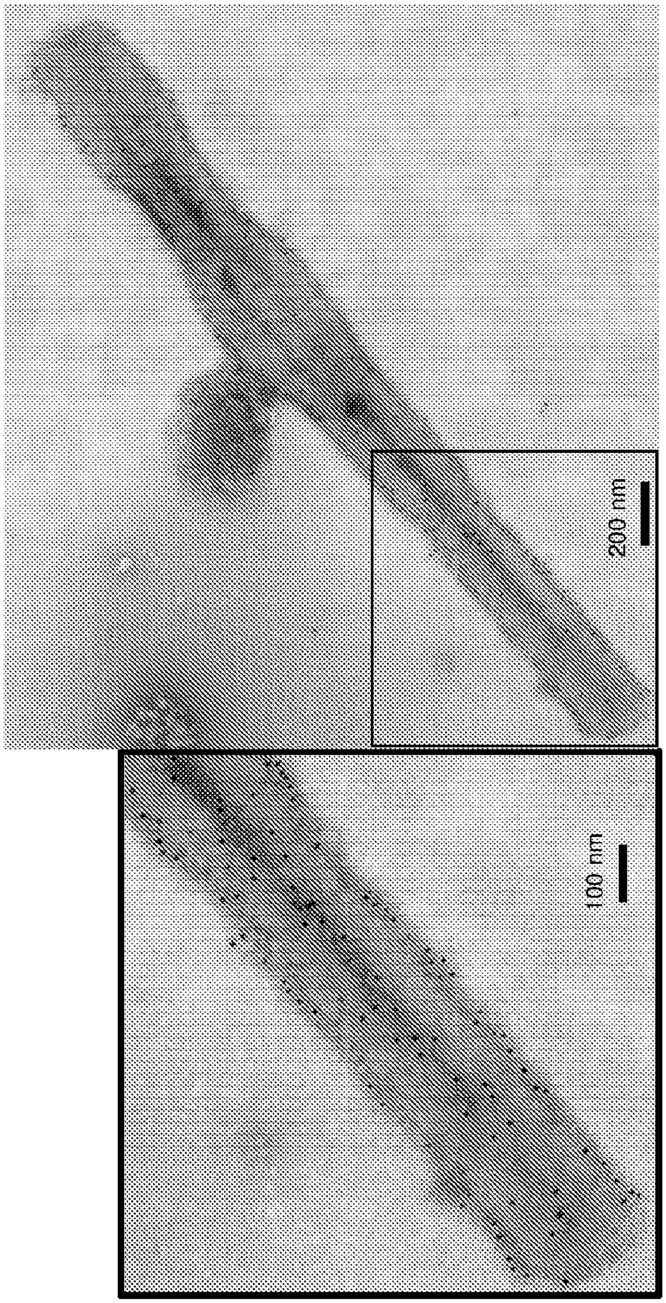
FIGS. 6A-6L. Imaging of packaged RSV G in virions by transmission electron microscopy (TEM) with immune-gold labeling. Purified virions from the preparations described in FIG. 5 were incubated with G-specific mouse MAb 131-2G (specific to the CX3C domain) and polyclonal goat anti-mouse secondary antibodies conjugated with 10 nm gold particles. Selected representative virion images are shown for: wt RSV (FIGS. 6A and 6B), rB/HPIV3 vector expressing wt RSV G (FIGS. 6C and 6D), rB/HPIV3 vector expressing only sG (FIGS. 6E and 6F), rB/HPIV3 vector expressing chimeric RSV G with CT of BPIV3 HN (FIGS. 6G and 6H), rBHPIV3 vector expressing chimeric RSV G with TM and CT of BPIV3 HN (FIGS. I and 6J), and empty rB/HPIV3 vector (FIGS. 6K and 6L).
Figure 6B:
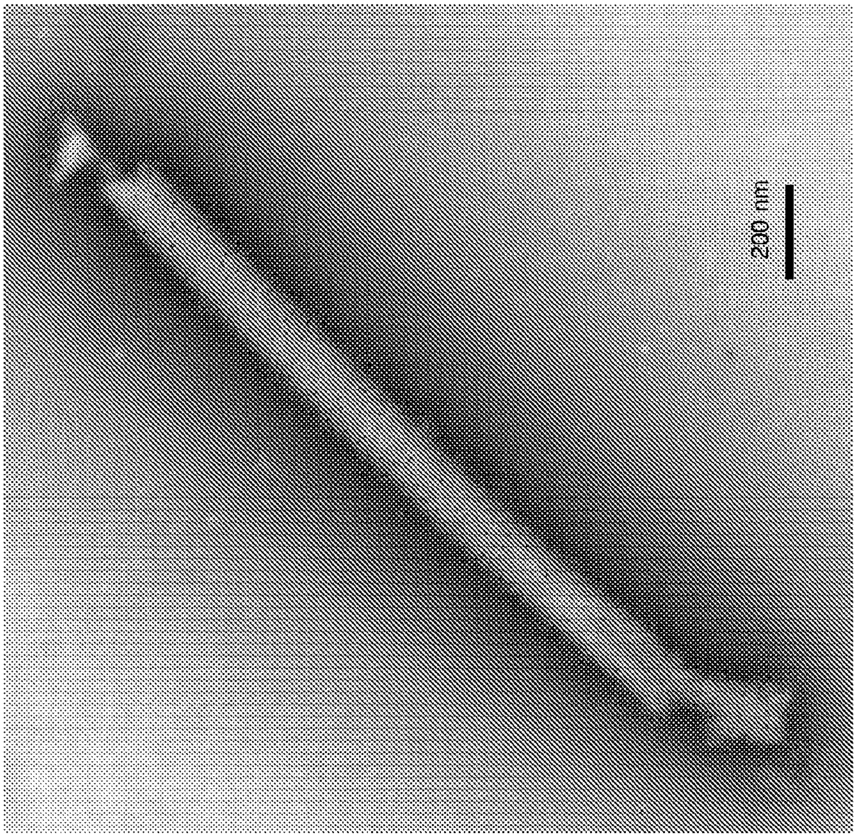
Figure 6C:
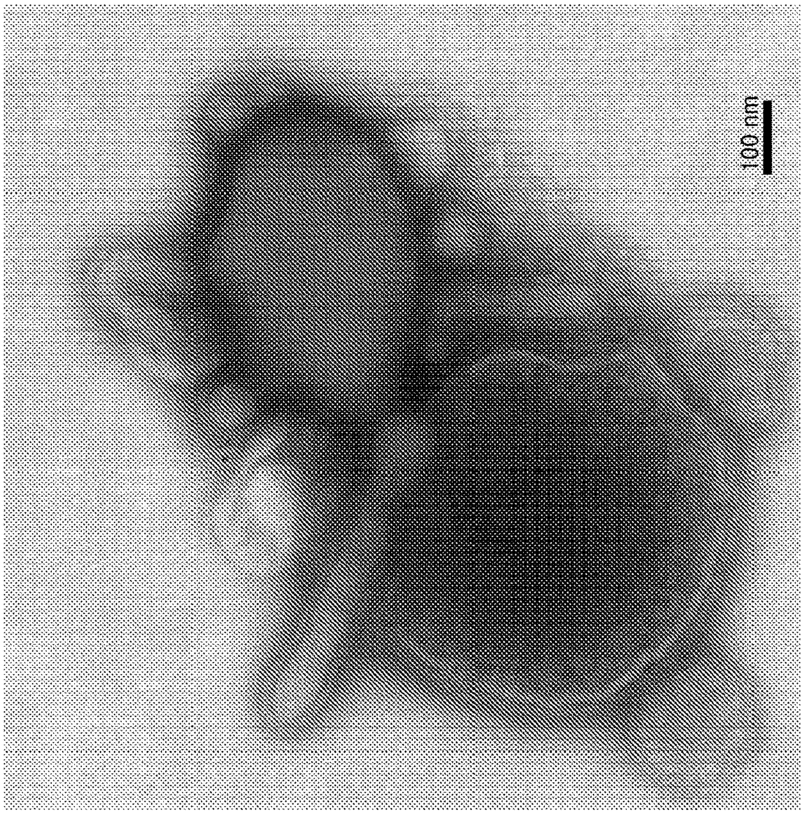
Figure 6D:
Figure 6E:
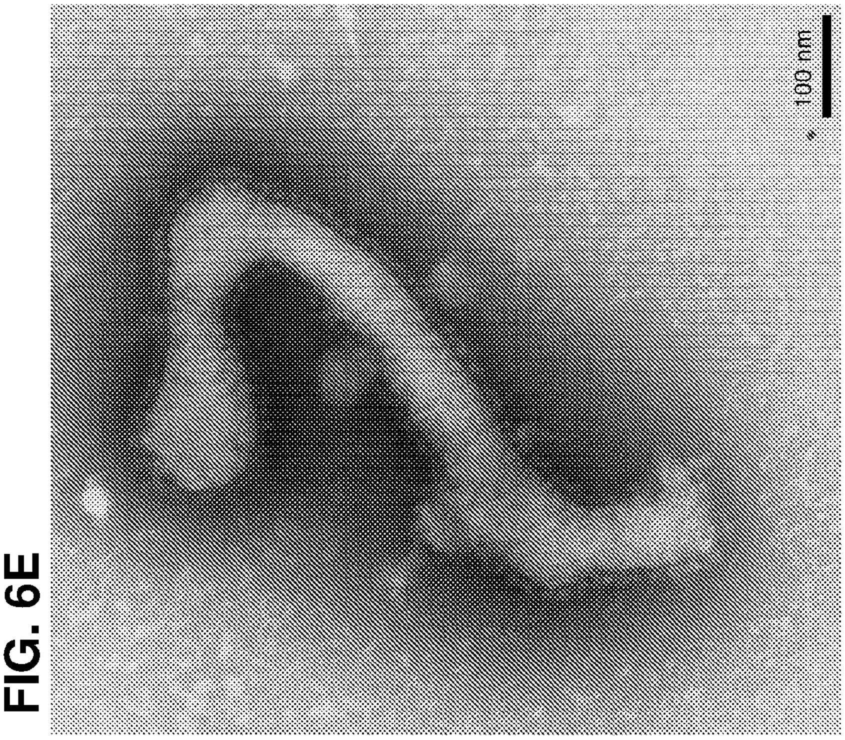
Figure 6F:
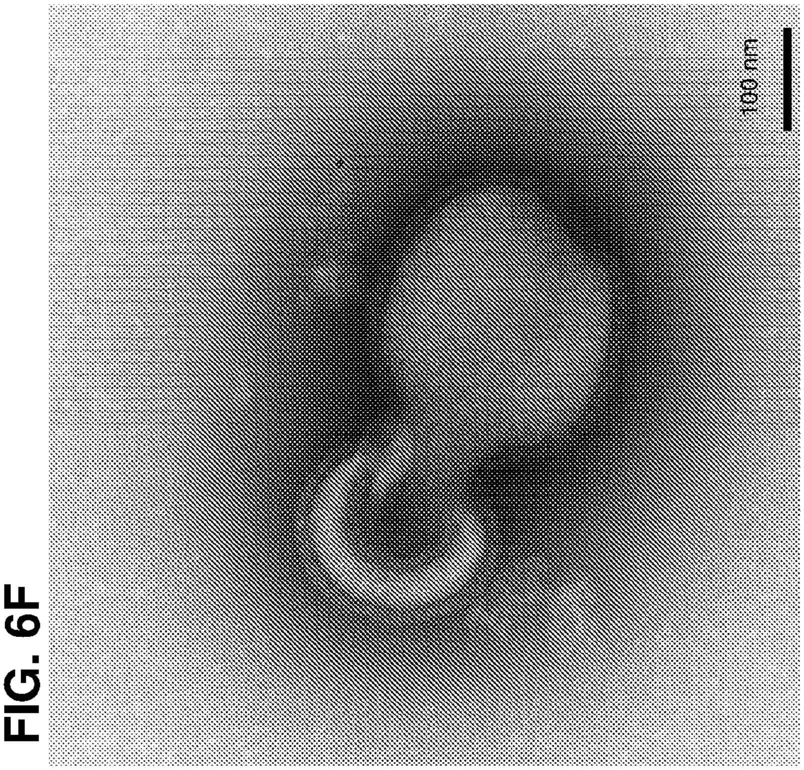
Figure 6G:
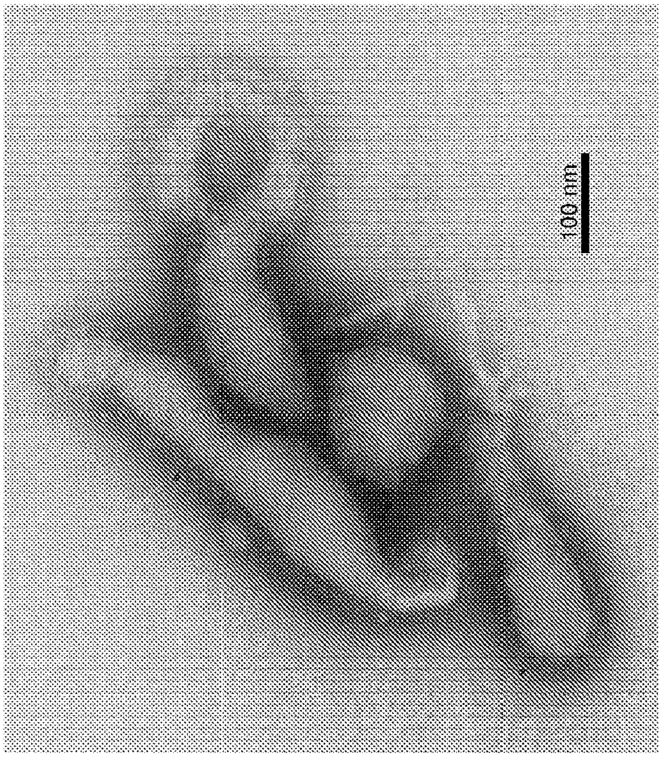
Figure 6H:
Figure 6J:
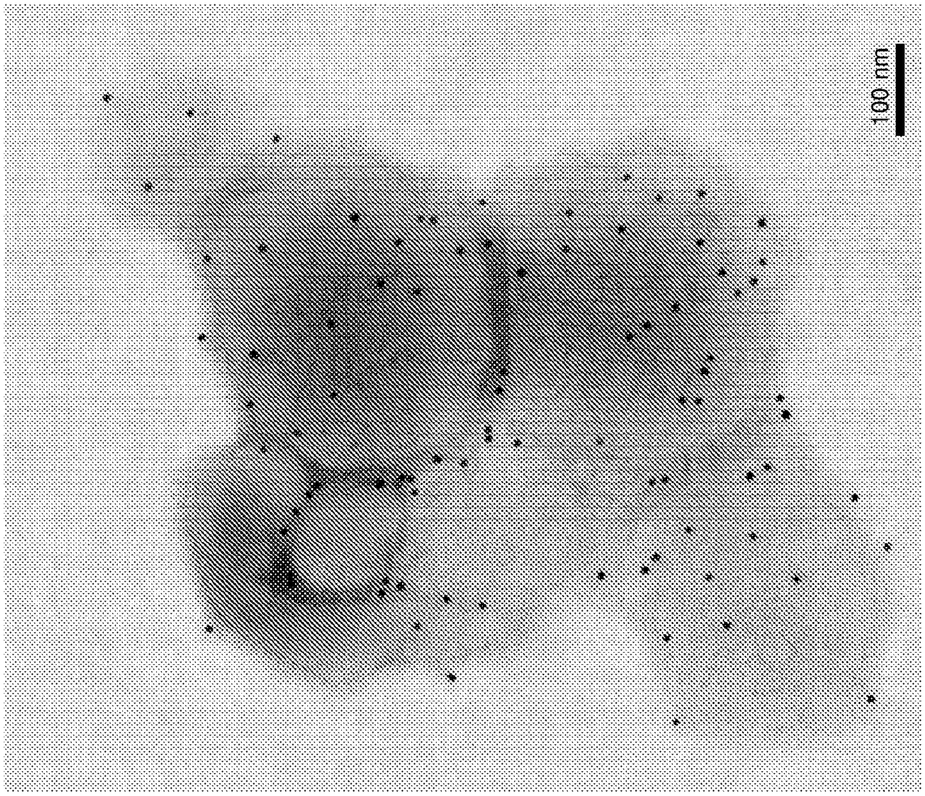
Figure 6I:
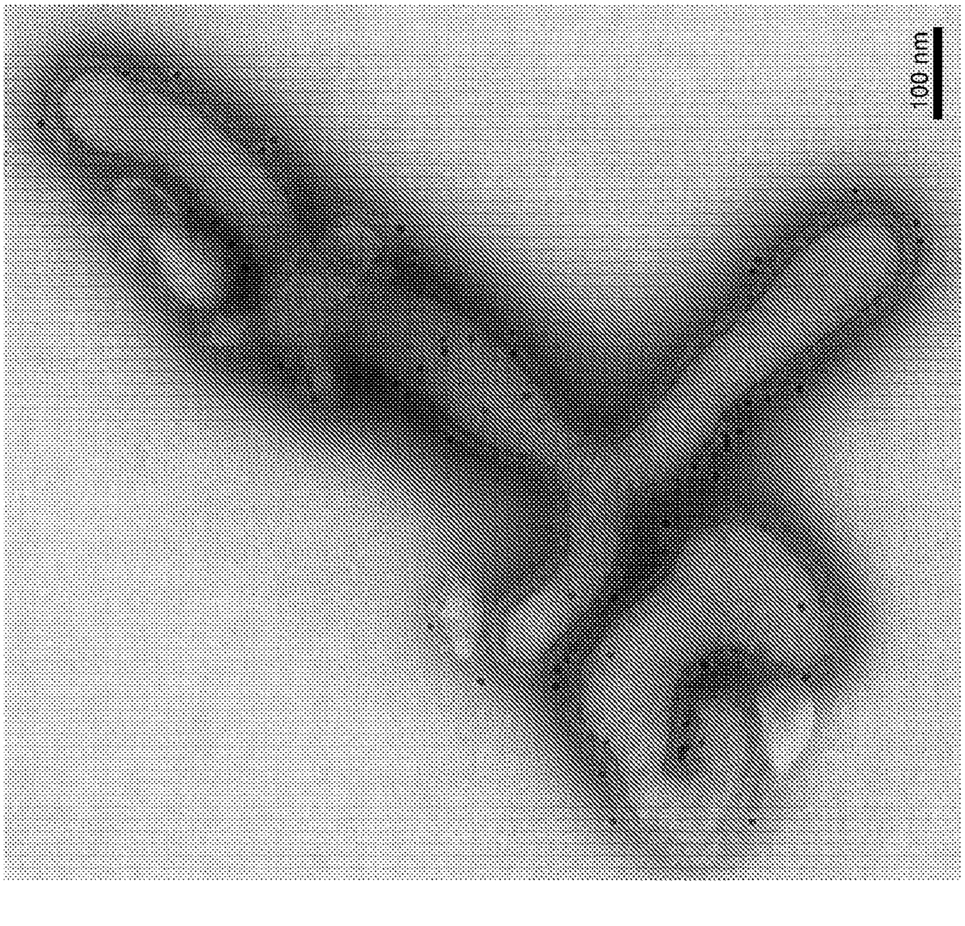
Figure 6L:
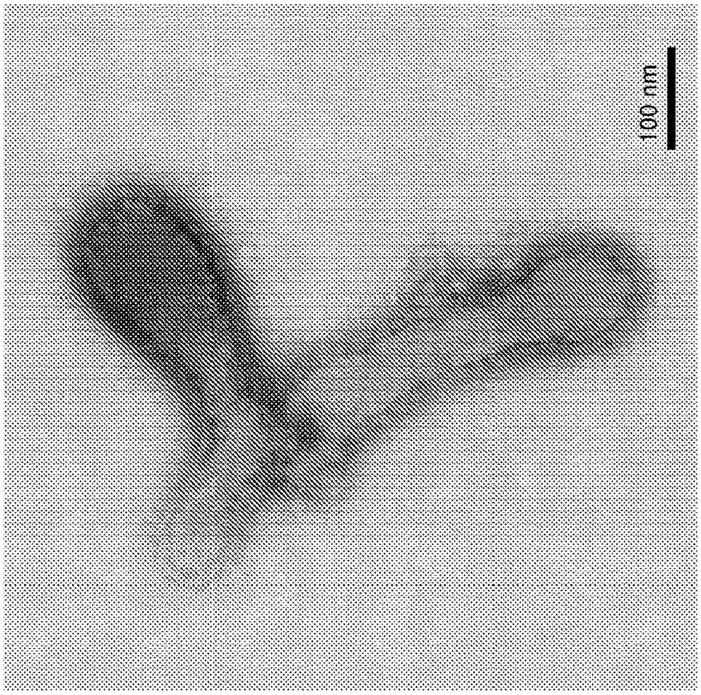
Figure 6K:

To evaluate the packaging efficiency of RSV G into rB/HPIV3 virions, empty vector and various vectors expressing versions of RSV G were propagated in LLC-MK2, and wt RSV was propagated in Vero cells. The medium overlying the cells was harvested, clarified by low speed centrifugation, and subjected to centrifugation on 30%-60% discontinuous sucrose gradients. For each construct, four micrograms of purified virus were analyzed by Western blot (FIG. 5A) and were quantified and normalized relative to wt G as 1.0. This showed that the unmodified wt G was detectable in vector virions as a very faint band (FIG. 5A, lane 2), and its packaging efficiency was less than 5% per μg of virion protein that of wt RSV (FIGS. 5A and 5B, lanes 2 and 6). Note that most of the G protein that was packaged in RSV virions grown in Vero cells had a lower molecular weight (50-60 kD) than the normally predominant 90-120 kD form. This was previously shown to arise due to cleavage by the cellular protease cathepsin L during long incubations in that particular cell line (Corry et al., 2015*, J. Virol.* 90:1311-1320). In the quantitation shown in FIG. 5B, both forms were quantified for wt RSV. The TMCT substitution from the BPIV3 HN protein enhanced the packaging efficiency of RSV G by 8.3-fold (FIGS. 5A and B, lanes 2 and 5), and the same magnitude of effect also was observed for the G_dCX3C_B3TMCT construct. The BPIV3 HN CT substitution alone only marginally increased the packaging of RSV G into vector virions (FIGS. 5A and 5B, lanes 2 and 4). As expected, sG protein was not packaged in the vector (FIG. 5A, lane 3).

The packaging of RSV G was also visualized by immunegold labeling and transmission electron microscopy (TEM, FIG. 6). Purified virions prepared as described above (FIG. 5) were labeled by incubation with MAb 131-2G followed by anti-mouse IgG conjugated with gold particles. The specimens were imaged by TEM as previously described (Liang et al., *J. Virol.,* 90(21): 10022-10038, 2016). The results showed that wt RSV virions had extensive antibody staining, indicative of a high density of packaging of the RSV G protein (FIGS. 6A and 6B). In contrast, virions of rB/HPIV3-wt G had only sporadic labeling (FIGS. 6C and 6D), and many virions had no detectable G. There was essentially no antibody binding to virions of vector expressing the sG protein (FIGS. 6E and 6F). The B3CT substitution appeared to slightly increase antibody binding (FIGS. 6G and 6H), while the B3TMCT substitution greatly improved the efficiency of antibody binding (FIGS. 6I and 6J). Empty vector virions were not labeled with the immunegold particles (FIGS. 6K and 6L). Thus, the densities of RSV G displayed in TEM analysis were in agreement with the efficiency of G packaging quantified by Western blot.

In Vivo Replication, Immunogenicity and Protection

Figure 7A:
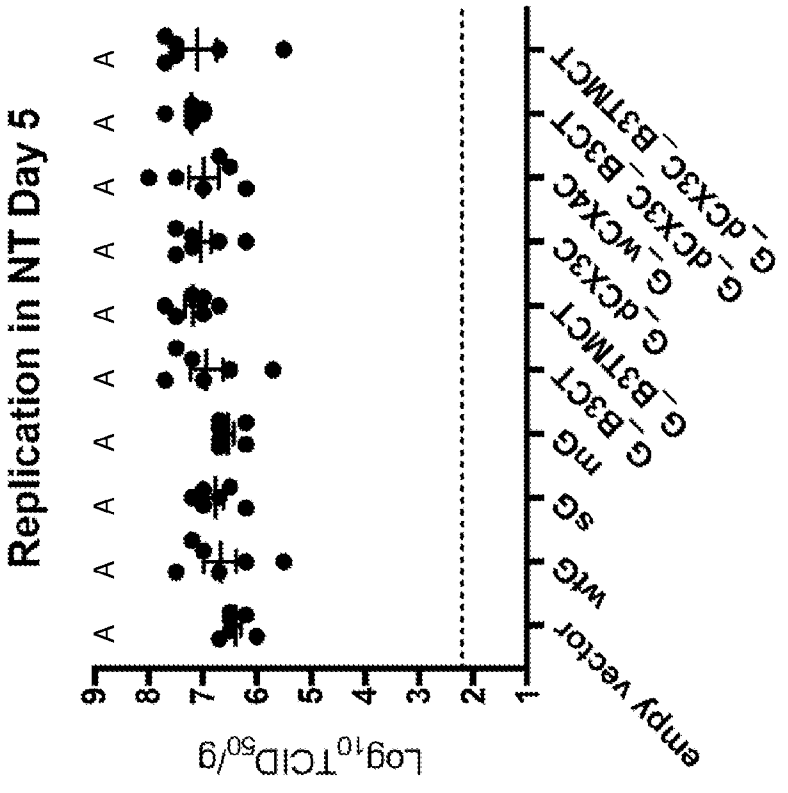
FIGS. 7A and 7B. Replication of rB/HPIV3-RSV G vectors in the upper and lower respiratory tracts of hamsters. Hamsters in groups of six were infected intranasally (IN) with $10^5$ $TCID_{50}$ of vector or $10^6$ PFU of wt RSV. Nasal turbinates and lungs were collected on day 5 post-immunization and homogenized. Titers of vectors in nasal turbinates (FIG. 7A) and lungs (FIG. 7B) were determined by $TCID_{50}$ hemadsorption assays on LLC-MK2 cells. The limit of detection of $TCID_{50}$ is indicated as dashed line. Mean titer and standard error of the mean (SEM) are shown as horizontal line with error bars. The statistical significance of differences in mean titers among all groups in the present study was analyzed using one-way ANOVA followed by Tukey-Kramer test. The mean titers of any two groups designated with a same letter (A, or B) are not statistically different.
Figure 7B:
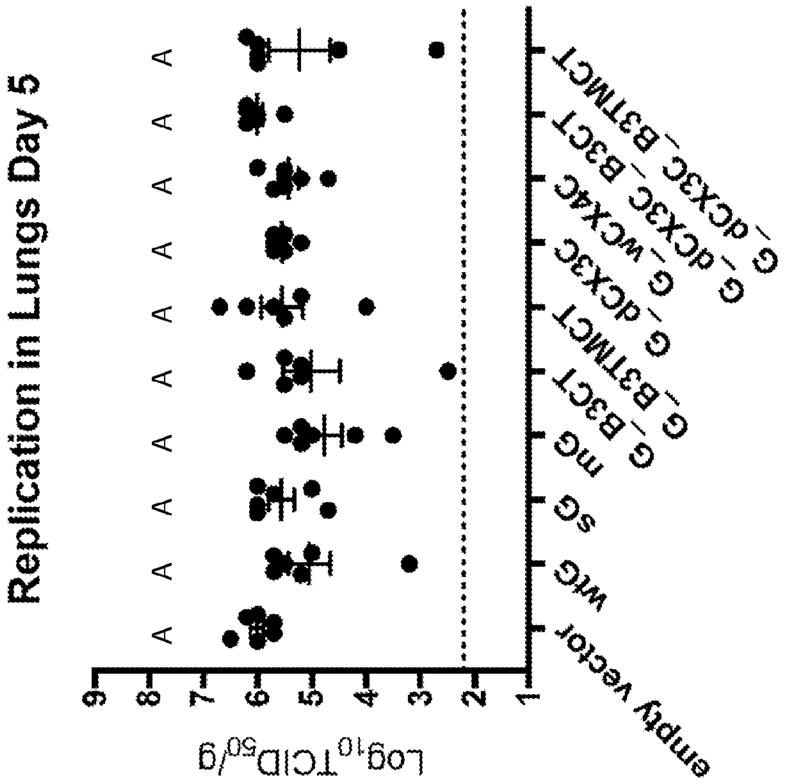

The replication, immunogenicity, and protective efficacy of the vectors were evaluated in a hamster model (FIGS. 7-9, respectively). To evaluate replication, hamsters in groups of six were immunized IN with $10^5$ $TCID_{50}$ of the indicated vector or $10^6$ PFU of wt RSV. Lungs and nasal turbinates were collected on day 5 after immunization, and the titers of the rB/HPIV3 vectors were determined by $TCID_{50}$ hemadsorption assays on LLC-MK2 cell monolayers, whereas RSV titers were determined by plaque assay on Vero monolayers. In the nasal turbinates, all of the vectors bearing an RSV G insert replicated to similar titers as the empty rB/HPIV3 vector (FIG. 7A), whereas in the lungs the vectors bearing an RSV G insert all were slightly more attenuated than the empty vector, although the differences were not significant (FIG. 7B). There were no significant differences between the replication of the various vectors expressing various forms of RSV G. Thus, for example, the expression of sG, or lack of expression of sG, or presence of the CX3C motif, or the absence of this motif, did not have an impact on the immunobiological milieu of the hamster lung sufficient to affect the replication of the rB/HPIV3 vector, which has the same tissue tropism as RSV (Zhang et al., *J. Virol.* 76:5654-5666, 2002; Zhang et al., *J. Virol.* 79:1113-1124, 2005) and shares many similarities in biology.

To evaluate immunogenicity, hamsters were immunized with vectors and wt RSV as described above, and sera were collected on days 0 and 28 post-immunization, In vitro 60% plaque reduction neutralization assays were carried out to quantify the serum RSV- and HPIV3-neutralizing antibody titers (FIG. 8).

Serum RSV-neutralizing antibody titers were determined in vitro on Vero cells by a 60%-plaque reduction neutralization titer ($PRNT_{60}$) assay using recombinant RSV that expresses the green fluorescent protein (RSV-GFP, Munir et al., *J. Virol.* 82:8780-8796, 2008). Assays were done in the presence or absence of added complement. The presence of complement can confer virus-lysis and steric-hindrance capabilities that give neutralization activity to otherwise non-neutralizing antibodies, and that can enhance the neutralization activity of poorly-neutralizing antibodies, whereas neutralization in the absence of complement depends on the direct capability of the antibodies (Yoder et al. 2004, J. Med. Virol. 72:688-694). Thus, assays done without complement provide a more stringent evaluation, and detect only those antibodies that can directly neutralize RSV (Liang et al., *J. Virol.,* 89(18): 9499-9510, 2015).

Figure 8A:
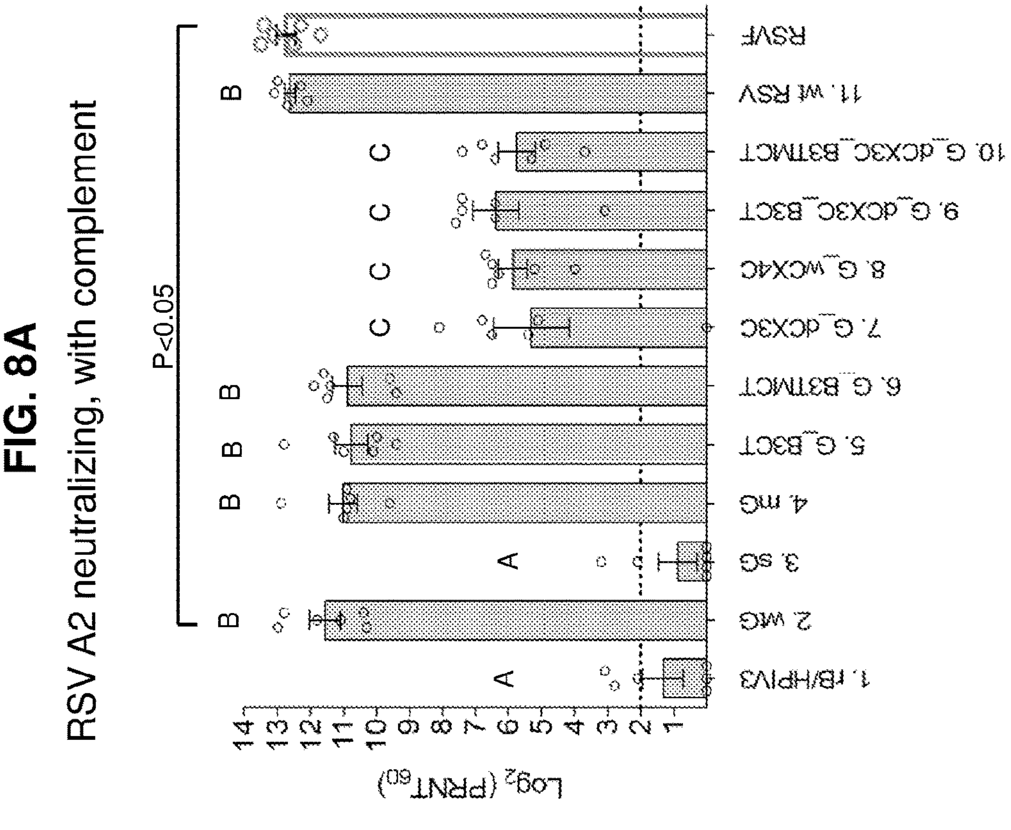
FIGS. 8A-8E. RSV- and HPIV3-neutralizing serum antibody titers induced by rB/HPIV3-RSV G vectors and wt RSV in immunized hamsters. Hamsters in groups of six were infected IN by $10^5$ $TCID_{50}$ of the indicated rB/HPIV3-RSV G vector or $10^6$PFU of wt RSV. Sera were collected on day 28 post-immunization. The serum neutralization titers were determined by 60% plaque reduction neutralization assay ($PRNT_{60}$) on Vero cell monolayers. For comparison, sera from a group of hamsters immunized with the same dose of vector expressing unmodified wt RSV F (from a separate experiment performed in essentially the same way) were included in RSV neutralization assays. Neutralization titers against: wt RSV, with complement (FIG. 8A), HPIV3, with complement (FIG. 8B), RSV B1, of subgroup B, with complement (FIG. 8C), RSV CX3C mutant (CWAIS), with complement (FIG. 8D), and wt RSV, without complement (FIG. 8E), are shown. The limit of detection is indicated with a dashed line. Each dot represents the titer of an individual animal. The bars indicate the mean titers of the groups; and error bars represent the SEM. The statistical significance of differences in mean titers among all groups in each assay was analyzed using one-way ANOVA followed by Tukey-Kramer test. Mean titers designated with the same letter (A, B, C or D) are not statistically different.

When serum RSV-neutralizing antibody titers were evaluated by a neutralization assay performed with added complement, vectors expressing wt G, mG, G_B3CT and G_B3TMCT were shown to induce similarly high titers (>1:1024) that are not statistically different from that induced by a 10-fold higher ($10^6$ PFU) of wt (i.e., not attenuated) RSV (FIG. 8A, lanes 2, 4-6 versus 11). In contrast, the sG construct did not induce detectable serum RSV neutralization antibodies (FIG. 8A, lane 3), despite its robust secretory expression (FIG. 2C, lane 3). Interestingly, CX3C ablation drastically reduced the RSV serum neutralization titers (FIG. 8A, lanes 7-10), indicating the role of the CX3C motif for the induction of RSV-neutralizing antibodies. Thus, ablating the expression of sG, or ablating the CX3C motif, did not increase the immunogenicity of the G protein, as would have been expected if these features interfered significantly with host immunity. On the contrary, the CX3C motif contributed substantially to inducing a strong RSV-neutralizing antibody response. To compare G-versus F-induced neutralization activity, sera of hamsters immunized with the same dose of rB/HPIV3 expressing unmodified wild-type (wt) RSV F from a previous study (Liang et al., *J. Virol.,* 89(18): 9499-9510, 2015) were assayed in parallel (FIG. 8A, lane 12). The wt G induced slightly lower titers of RSV serum neutralization antibodies than wt F, but the difference was not statistically significant (FIG. 8A, lanes 2 and 12).

Figure 8B:
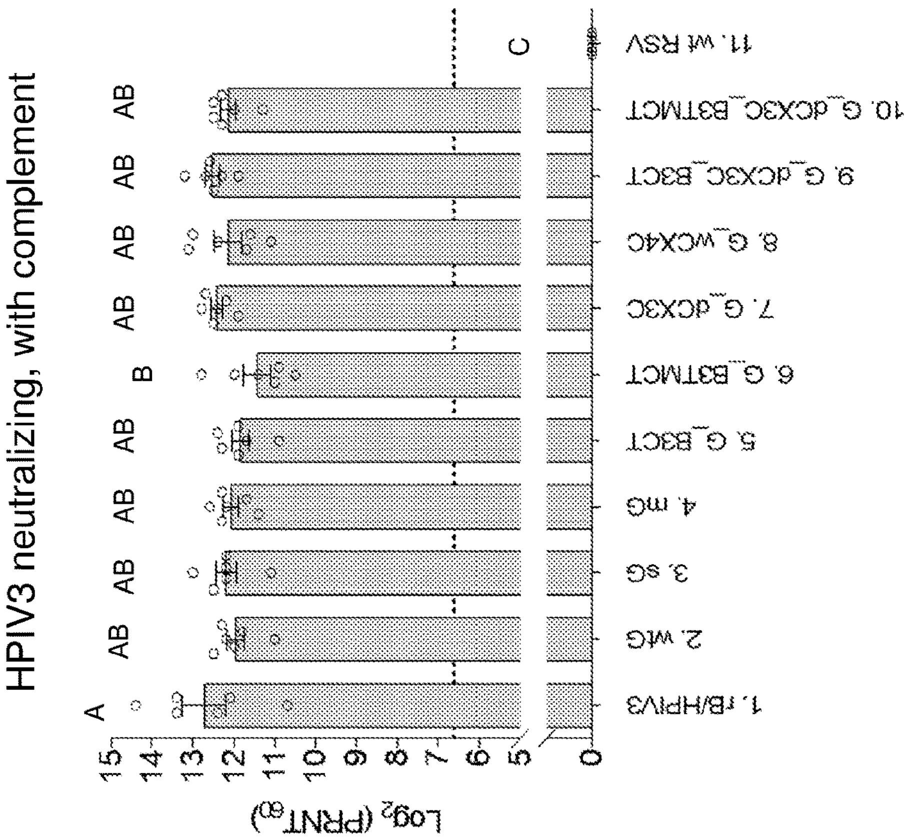

When serum HPIV3-neutralizing antibody titers (i.e., against the vector) were evaluated by an assay with added complement, all of the vectors expressing various forms of RSV G were similarly immunogenic (FIG. 8B, lanes 2-10), with the exception of the G_B3TMCT construct which induced a slightly but significantly lower level of serum HPIV3-neutralizing antibodies than the empty vector (FIG. 8B, lanes 1 and 6). The lower titer induced by the G_B3TMCT construct suggested that the enhanced packaging of RSV G by its TMCT substitution interfered with vector replication efficiency in vivo, perhaps by reducing the packaging of vector HN protein. Thus, the presence or absence of the sG protein or the CX3C motif in the expressed G protein did not have a significant effect on the antibody response against the vector.

Hamster sera were also assayed for neutralizing serum antibodies against a subgroup B strain of RSV (B1). While the neutralization activity against the B1 strain remained similarly high for wt RSV and wt F sera (FIG. 8C, lanes 11-12), the B1 cross-neutralization activities induced by RSV G constructs were substantially reduced (FIG. 8C, lanes 2 and 4-6), and disruption of the CX3C motif almost completely abolished the neutralization activity (FIG. 8C, lanes 7-10). This indicates that the G protein of RSV G A2 induced moderate titers of cross-subgroup neutralizing antibodies; furthermore, this was highly dependent upon the presence of CX3C motif.

Figure 8D:
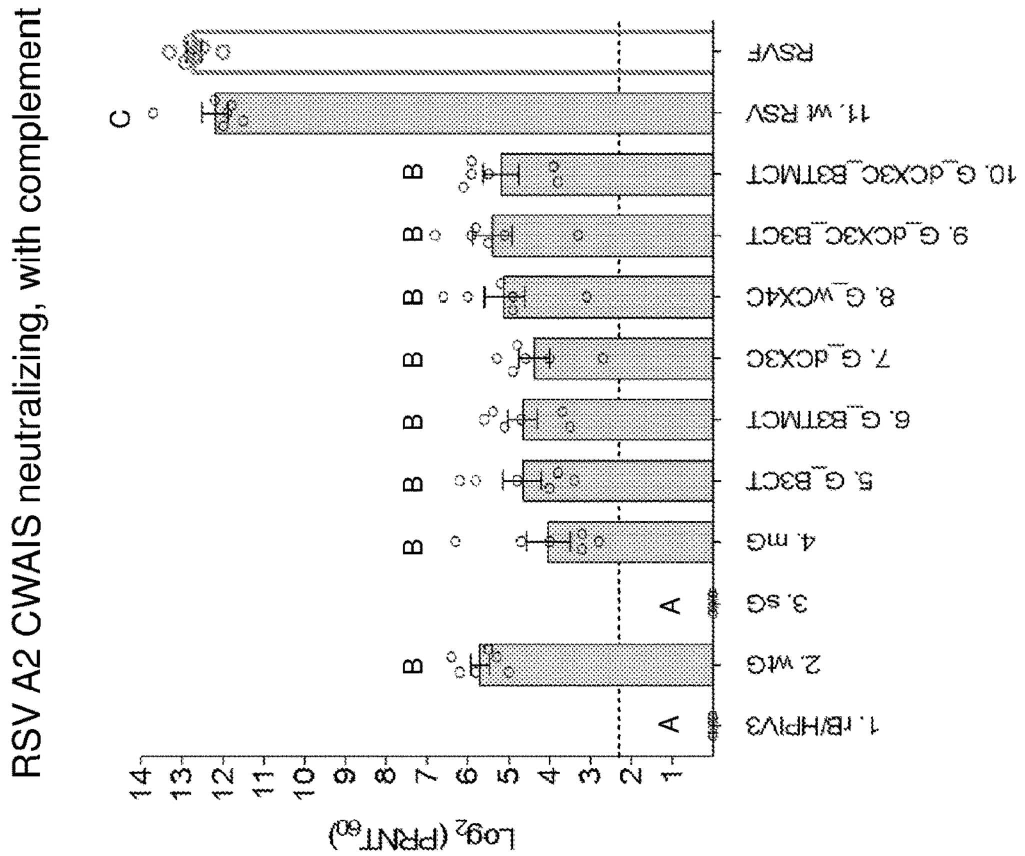
Figure 8C:
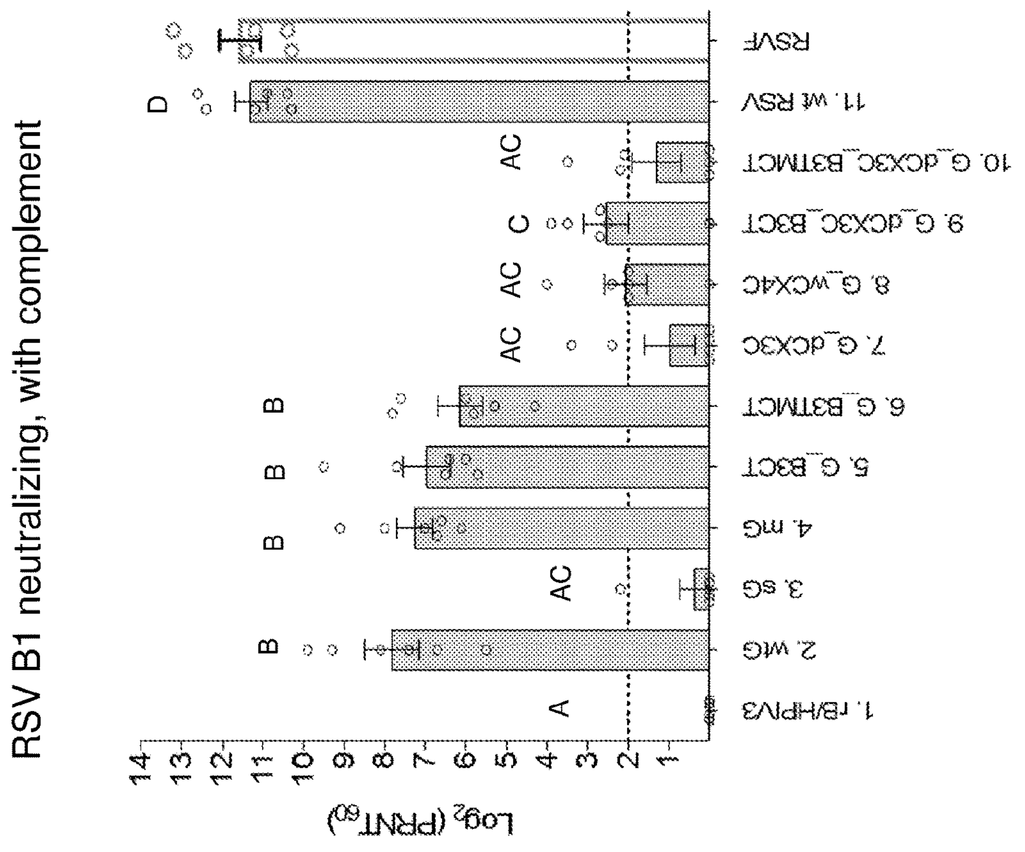

To further characterize the role of the CX3C motif in the induction of RSV-neutralizing antibodies, an A2 RSV strain bearing a mutated CX3C (CWAIS) of G was used to analyze the serum RSV-neutralizing titers in the presence of added complement (FIG. 8D). While the serum neutralizing activity against the CX3C-mutated RSV induced by the four CX3C-ablation mutants (FIG. 8D, lanes 7-10) remained relatively low compared to wt RSV and vector expressing wt F (FIG. 8D, lanes 11 and 12), the neutralization activity in sera of wt G, mG, G_B3CT and G_B3TMCT against this CWAIS mutant were equally low (FIG. 8D, lanes 2 and 4-6). This was further confirmation that the CX3C domain is a major neutralization epitope of the G protein.

The titers of serum neutralizing antibodies, measured in the presence of complement, against wt RSV A2 (from FIG. 8A), wt RSV B1 (from FIG. 8C), and RSV A2 CWAIS (from FIG. 8D) are shown in Table 1. This further illustrates that ablation of sG (resulting in mG) did not result in increased immunogenicity; that packaging of G into the vector particle did not increase immunogenicity; and that ablation of the CX3C motif strongly reduced immunogenicity.

TABLE 1

The relative mean RSV serum neutralization titers induced by $10^5$ $TCID_{50}$ vectors compared to that induced by $10^6$ PFU wt RSV A2 in hamsters. All titers were determined in the presence of complement.

| Viruses for immunization | Strains of RSV used in neutralization assays: RSV A2 | RSV B1 | RSV A2 CWAIS |
|---|---|---|---|
| Empty vector | <4 | <4 | <4 |
| sG | <4 | <4 | <4 |
| wtG | 3040 | 226 | 52 |
| mG | 2077 | 152 | 16 |
| G_B3CT | 1746 | 125 | 25 |
| G_B3TMCT | 1911 | 70 | 25 |
| G_dCX3C | 40 | <4 | 21 |
| G_wCX4C | 58 | 4 | 35 |
| G_dCX3C_B3CT | 83 | 6 | 42 |
| G_dCX3C_B3TMCT | 54 | <4 | 36 |
| wt RSV A2 | 6339 | 2521 | 4640 |
| RSV F | 6889 | 3040 | 6654 |

Figure 8E:
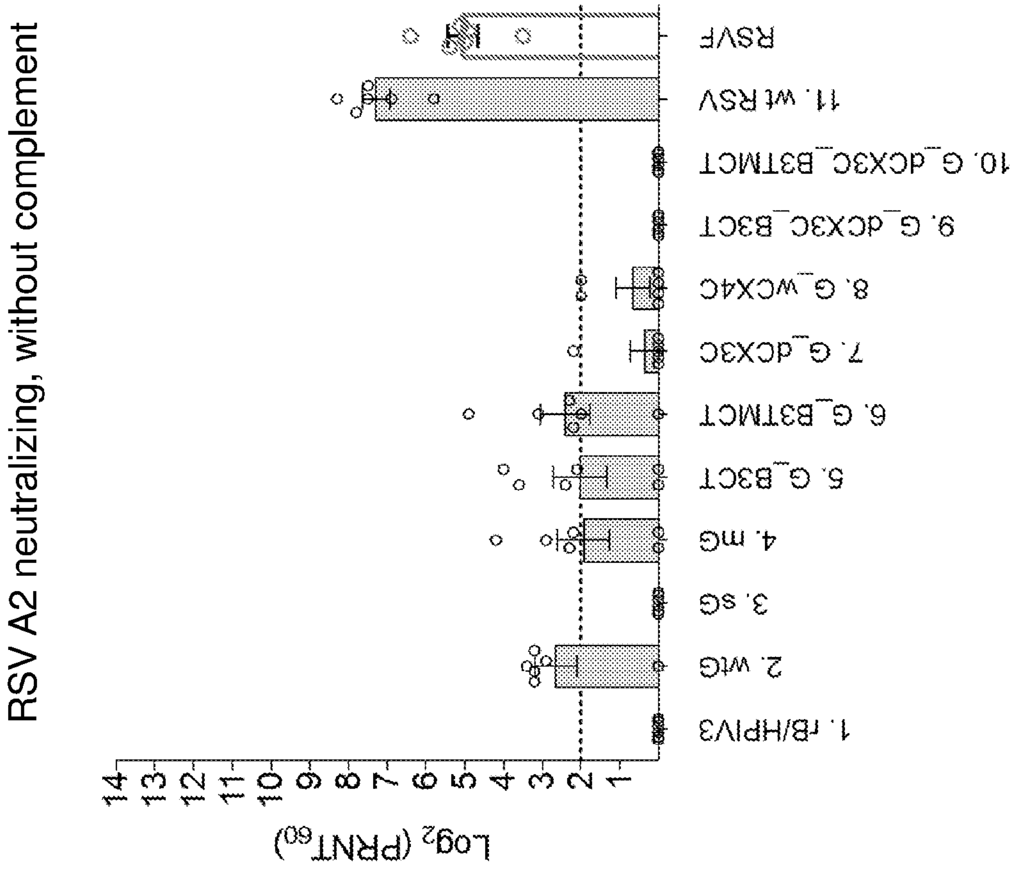

Serum RSV-neutralizing antibody titers were also evaluated by a neutralization assay performed in the absence of added complement (FIG. 8E) which provides a more stringent assessment of neutralization activity. The complement-independent assay showed that, while both wt RSV and vector-expressed wt F induced moderate titers of complement-independent serum RSV-neutralizing antibodies (FIG. 8E, lanes 11 and 12), the G constructs induced relatively low titers of serum antibodies capable of neutralizing RSV in the absence of complement in vitro (FIG. 8E, lanes 2-10). This result is offered with the caveat that Vero cells are deficient in the CX3CR1 receptor that may play a significant role in attachment in vivo (Johnson S M et al., 2015, PLoS Pathog., 11:e1005318), and therefore this Vero-based assay may fail to detect G-specific neutralizing antibodies. This may be resolved by a neutralization assay using an in vitro model of mucociliary human airway epithelium (HAE), which does express the CX3CR1 receptor (Johnson S M et al., 2015, PLoS Pathog., 11:e1005318), although HAE cultures are not very amenable to in vitro neutralization assays.

Figure 9A:
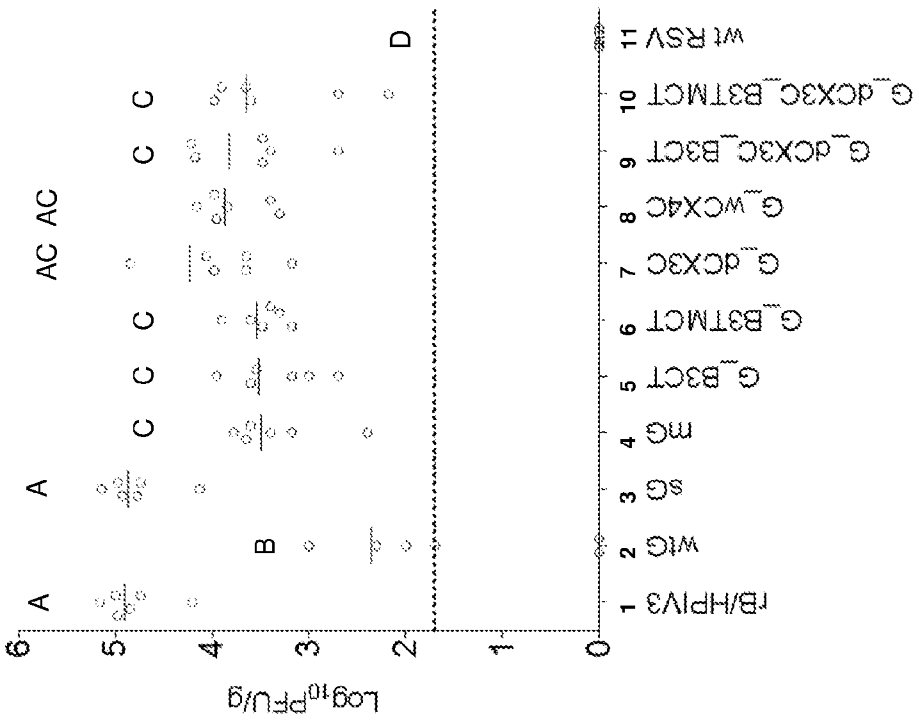
FIGS. 9A-9D. Protection of immunized hamsters against wt RSV A2 challenge. Hamsters in groups of six were immunized IN with $10^5$ $TCID_{50}$ of the indicated rB/HPIV3-RSV G vector or $10^6$PFU of wt RSV as described in FIG. 8 and 31 days later were challenged IN by $10^6$ PFU of wt RSV. On day 3 post-challenge, animals were sacrificed and viral titers were determined in homogenates of the (FIG. 9A) nasal turbinates (NT) and (FIG. 9B) lungs by plaque assay in Vero cells. The limit of detection is indicated with a dashed line. Each dot represents the titer of an individual animal. Mean titers are indicated as short horizontal bars. The statistical significance of differences in mean titers among all groups was analyzed using one-way ANOVA followed by Tukey-Kramer test. Mean titers of groups designated with a same letter (A, B, C or D) are not statistically different.

To measure protective efficacy, the hamsters that were immunized in the experiment in FIG. 8 were challenged IN with $10^6$ PFU of wt RSV on day 31 post-immunization. Hamsters were sacrificed 3 days later. Nasal turbinates and lungs were collected and homogenized for RSV plaque assay titration (FIG. 9). In the nasal turbinates, vector expressing wt G (FIG. 9A, lane 2) was significantly more protective than any of the other G constructs (lanes 3-10). In contrast, the sG construct was not protective (FIG. 9A, lane 3), correlating with its inability to induce RSV-neutralizing antibody (FIG. 9A, lane 3). Constructs mG, G_B3CT and G_B3TMCT induced substantial protection (FIG. 9A, lanes 4-6); while CX3C ablation (lanes 7 and 8) drastically reduced the protection compared to the unmodified wt G (lane 2), to a level that was not statistically different from sG and the empty vector (lanes 1 and 3). Enhanced packaging of the dCX3C mutant by B3CT and B3TMCT (FIG. 9A, lanes 9 and 10) appeared to slightly improve the protective efficacy to the level that was significantly better than sG and the empty vector (lanes 1 and 3). Only the wt RSV inoculation achieved complete protection in the nasal turbinates (FIG. 9A, lane 11). Superior protection with wt RSV was not unexpected, since it was administered at a 10-fold higher dose, it is not attenuated, it bears both the F and G neutralization antigens, and it expresses all of the viral antigens and thus would induce a broader cellular immune response. In studies with PIVs in hamsters, internal proteins in chimeric viruses have been shown to induce protection in a short term (1-2 month) challenge, but this wanes by four months (Tao T et al., 2000, *Vaccine* 18:1359-1366).

Figure 9B:
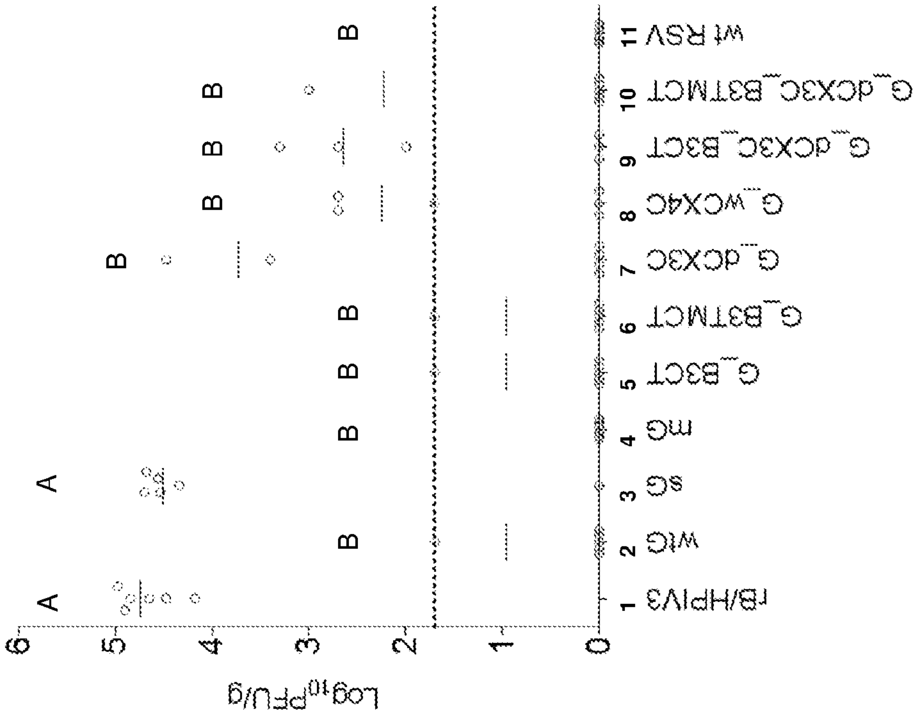

Vector-induced protection against RSV was much better in the lungs than in the nasal turbinates. The vectors expressing wt G, mG, G_B3CT, and B_B3TMCT conferred almost complete protection (FIG. 9B, lanes 2 and 4-6). But the vectors expressing any of the four CXC3 ablation mutants were less protective, with 1-3 hamsters per group not completely protected (FIG. 9B, lanes 7-10). As was observed in the nasal turbinates, the TMCT substitution exhibited some improvement of protection with the dCX3C construct (FIG. 9B, lane 10).

Figure 9D:
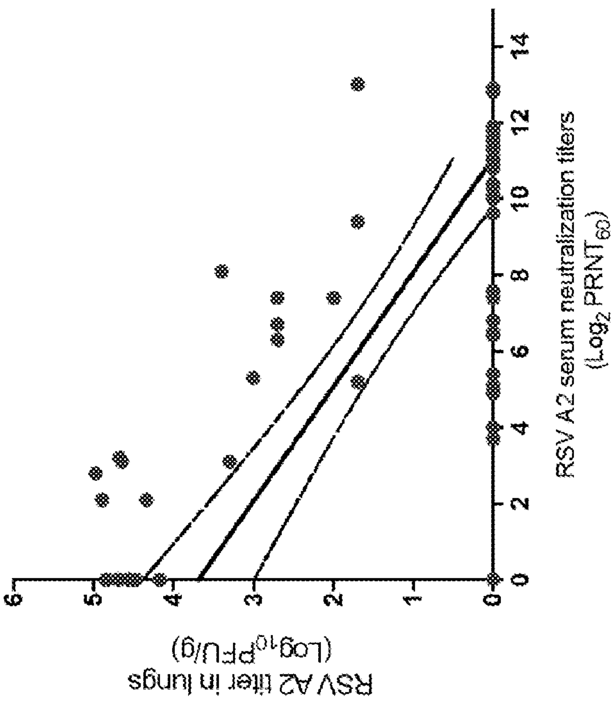
Figure 9C:
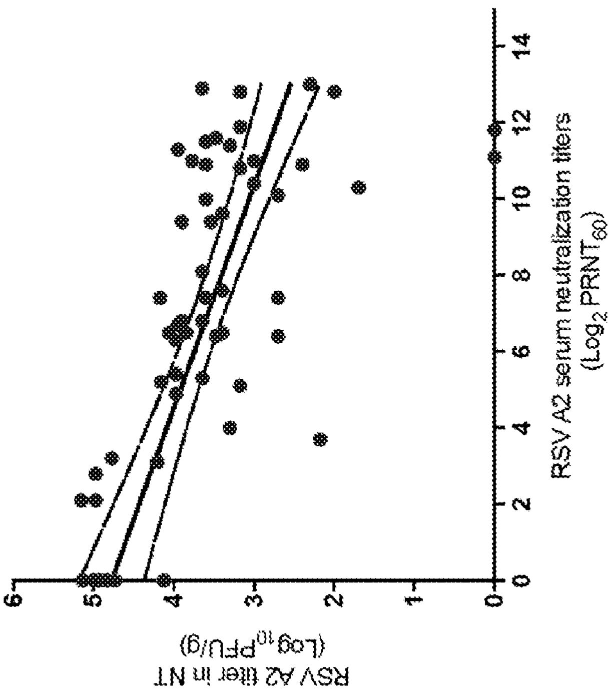

The titers of serum RSV-neutralizing antibodies on day 28 following the initial immunization (measured for individual animals in the presence of added complement, from FIG. 8A), were plotted versus the titers of challenge RSV in the nasal turbinates (from FIG. 9A) and lungs (from FIG. 9B) of the same individuals, resulting in the plots shown in FIGS. 9C and 9D, respectively. This showed that protection against challenge RSV replication in either the nasal turbinates or lungs, indicated by a reduction in challenge virus titer, was strongly correlated with the titer of serum complement-dependent RSV neutralizing antibodies (FIGS. 9C and D, respectively).

Codon-Optimized G ORF (wtG/GS-Opt)

Figure 10A:
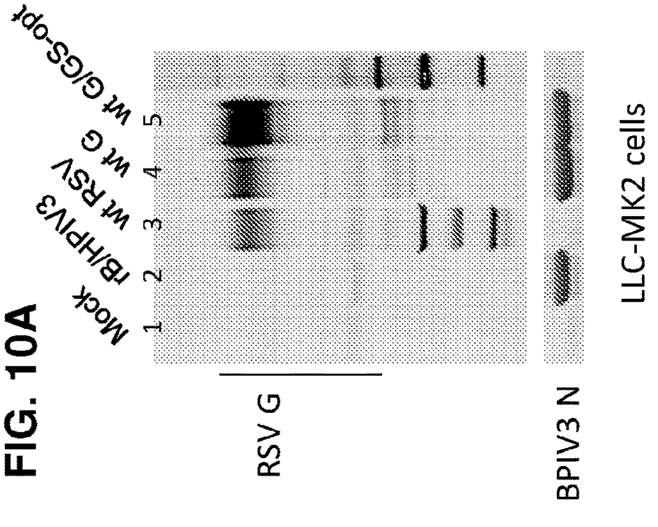
FIGS. 10A-10D. Expression of G protein from a B/HPIV3 vector bearing a G ORF that was codon-optimized for human translation (construct (x) in FIG. 1A, or wt G/GS-opt). The accumulation of G protein in LLC-MK2 and Vero cells infected with rB/HPIV3 vectors expressing wt G or wt G/GS-opt was evaluated by Western blot analysis (FIGS. 10A and 10B). The LLC-MK2 (10A) and Vero (10B) cells were infected with the indicated rB/HPIV3-RSV-G vector or wt RSV at an MOI of 10 $TCID_{50}$ or 3 PFU per cell, respectively. At 24 hours post-infection, the cells were harvested and lysates prepared and analyzed by gel electrophoresis under denaturing and reducing conditions followed by Western blotting with antisera raised against RSV, followed by secondary antibodies conjugated with infrared fluorescent dyes, and the bound antibodies were visualized using an Odyssey imaging system (LiCor). Quantification of band intensities in Western blot analysis indicated that there was 2.3-fold increase of RSV G expression by codon-optimization in LLC-MK2 cells (FIG. 10C) and 2.2-fold increase in Vero cells (FIG. 10D).
Figure 10B:
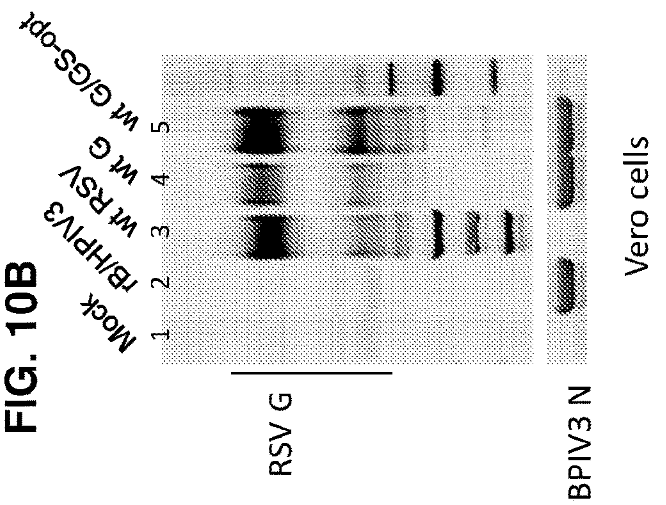
Figure 10C:
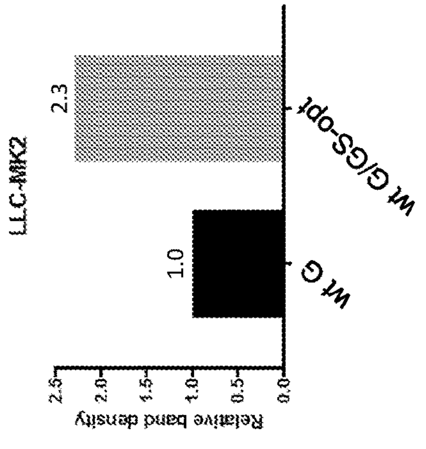
Figure 10D:
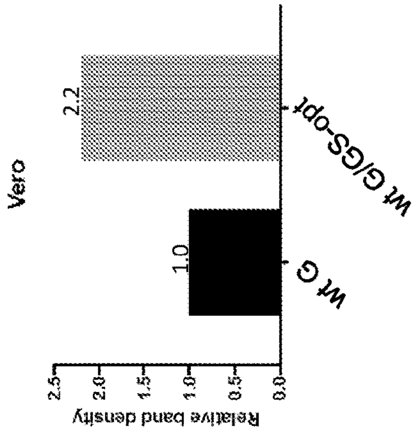

A rB/HPIV3 construct expressing a RSV G ORF that was codon-optimized for human expression (GenScript), with no changes to amino acid coding (wtG/GS-opt, construct (x) in FIG. 1A), replicated in Vero and LLCMK-2 cells with a high level of efficiency similar to that of the other vectors. The intracellular expression of G protein by construct wtG/GS-opt in LLC-MK2 cells and Vero cells was evaluated by Western blot analysis. The LLC-MK2 and Vero cells were infected with rB/HPIV3 expressing wtG/GS-opt or wtG at a MOI of 10 $TCID_{50}$ per cell, or with wt RSV at an MOI of 3 PFU per cell. Cells were harvested at 24 hours post infection and cell lysates were prepared, subjected to gel electrophoresis under denaturing and reducing conditions, and analyzed by Western blotting using polyclonal antibodies against RSV (FIGS. 10A and B). This showed that the codon-optimized version was expressed approximately 2.2- to 2.3-fold more efficiently than the non-optimized wt ORF (FIGS. 10C and D.

Figure 11:
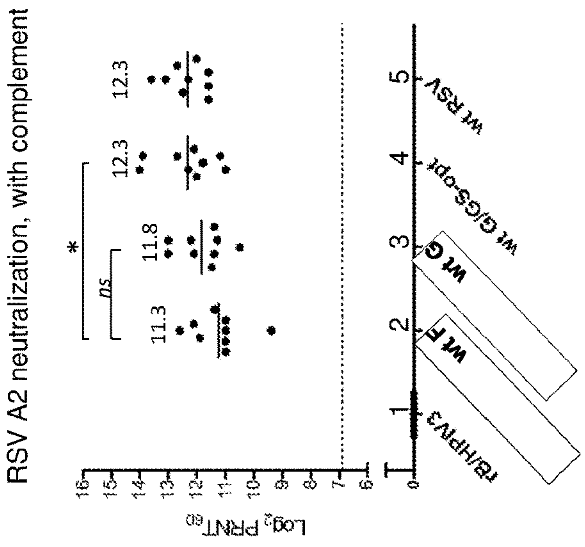
FIG. 11 RSV-neutralizing serum antibody titers induced by rB/HPIV3-RSV-G vectors expressing codon-optimized or non-optimized G ORFs in immunized hamsters. Hamsters in groups of nine were infected IN by $10^4$ $TCID_{50}$ of the indicated rB/HPIV3-RSV G vectors (lanes 1-4) or $10^6$ PFU of wt RSV (lane 5). Sera were collected on day 28 post-immunization. The serum neutralization titers were determined by 60% plaque reduction neutralization assay ($PRNT_{60}$) on Vero cell monolayers in the presence of added complement. Neutralization titers against wt RSV, with added complement are shown. Lane 1, empty rB/HPIV3 vector; lane 2, wt F, unmodified wild-type RSV F, specifically the "Non-HEK/non-opt" construct that was described in a patent application (PCT/US2016/014154) and a previous publication (Liang, et al., *J. Virol.* 89: 9499-9510, 2015); lane 3, wt G, wild-type RSV G of A2 strain; lane 4, wt G/GS-opt, a GenScript optimized wild-type G of A2 strain, having the same amino acid sequence as the wt G construct in lane 3; lane 5, wt RSV, wild-type RSV A2 as control. The limit of detection is indicated with a dashed line. Each dot represents the titer of an individual animal. The horizontal lines indicate the mean titers of the groups. The statistical significance of differences in mean titers among all groups in each assay was analyzed using unpaired two-tailed student t-test: * indicates $P<0.05$; ns=not significant.
Figure 12A:
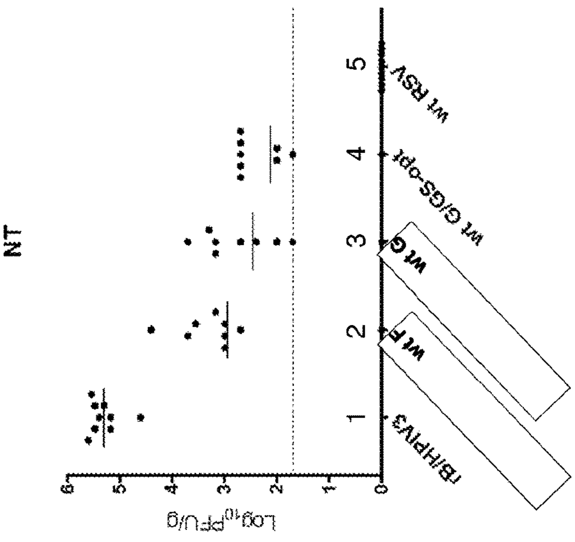
FIGS. 12A-12B Replication of wt RSV challenge in hamsters previously infected with the indicated rB/HPIV3-RSV-G or RSV-F vector or wt RSV. Hamsters infected in FIG. 11 were challenged intranasally 30 days later with $10^6$ PFU of wt RSV in total volume of 100 ul in both nostrils. Nasal turbinates (NT) and lungs were collected on day 3 after challenge and homogenized. Titers of RSV in nasal turbinates (FIG. 12A) and lungs (FIG. 12B) were determined by plaque assays in Vero monolayers. The horizontal lines indicate the mean value of titers in that group. Limit of detected is shown by a dashed line.
Figure 12B:
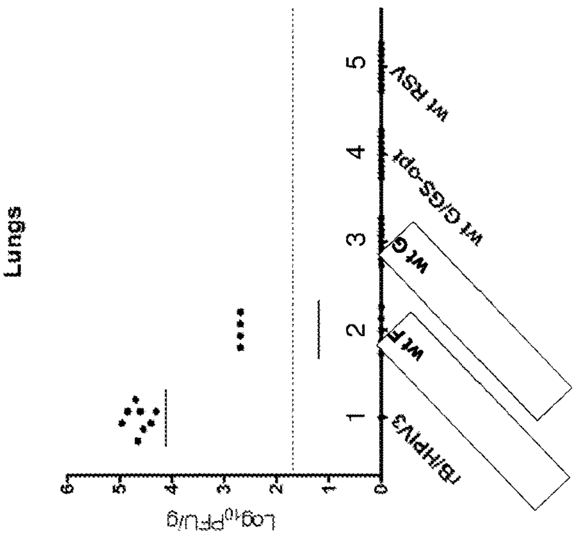

The in vivo replication and immunogenicity of rB/HPIV3 expressing the codon-optimized G ORF was evaluated in parallel with rB/HPIV3 expressing the unmodified wt G ORF. Following the methods described in FIG. 7, hamsters in groups of nine were immunized IN with $10^4$ $TCID_{50}$ of the indicated vector or $10^6$ PFU of wt RSV. Sera were collected on day 28 after immunization. Hamsters were challenged intranasally on day 30 with $10^6$ PFU of wt RSV. Lungs and nasal turbinates were collected on day 3 after challenge. The titers of challenge RSV replication were determined by plaque assay on Vero monolayers. Serum RSV-neutralizing antibody titers were evaluated by plaque reduction neutralization in the presence of complement (FIG. 11). The serum RSV-neutralizing antibody titer induced by wild-type G (wt G) was slightly higher than that induced by wild-type F (wt F), although the difference was not significant (FIG. 11, lanes 2 and 3). But the codon-optimized wild-type G (wtG/GS-opt) induced a 2-fold higher titer of serum RSV-neutralizing antibodies than the wt F, which was statistically significant (FIG. 11, lanes 2 and 4). This indicated that GS codon-optimization of RSV G enhanced the immunogenicity of the rB/HPIV3-RSV G vector. Similar to their trend in the induction of serum RSV-neutralizing antibodies, the wt G and wt G/GS-opt conferred increased protection against RSV challenge in the nasal turbinates compared to wt F (FIG. 12A). In the lungs, wt G and wtG/GS-opt conferred complete protection, as with the wt RSV (FIG. 12B, lanes 3-5), while wt F was only partially protective (FIG. 12B, lane 2). These results indicated that rB/HPIV3 expressing wt G was more immunogenic and protective than rB/HPIV3 expressing wt F in hamsters; and the GenScript codon-optimization of RSV G enhanced its immunogenicity and protective efficacy.

Blocking RSV Infection of Ciliated Airway Epithelial Cells by RSV G-Induced Serum Antibodies Vero cells are known to be deficient in the CX3CR1 surface protein that has been identified as a major receptor for G-mediated attachment in vivo (Johnson S M et al., 2015, PLoS Pathog., 11:e1005318). Thus, an important component of virus neutralization by G-induced antibodies might be missed by neutralization assays in Vero cells. To better evaluate the neutralization activity of G-induced serum antibodies, we performed a serum neutralization assay using an in vitro model of differentiated mucociliary human airway epithelium (HAE) that has been shown to be a close facsimile of in vivo HAE, and which does express CX3CR1 (Johnson S M et al., 2015, PLoS Pathog., 11:e1005318).

Figure 13:
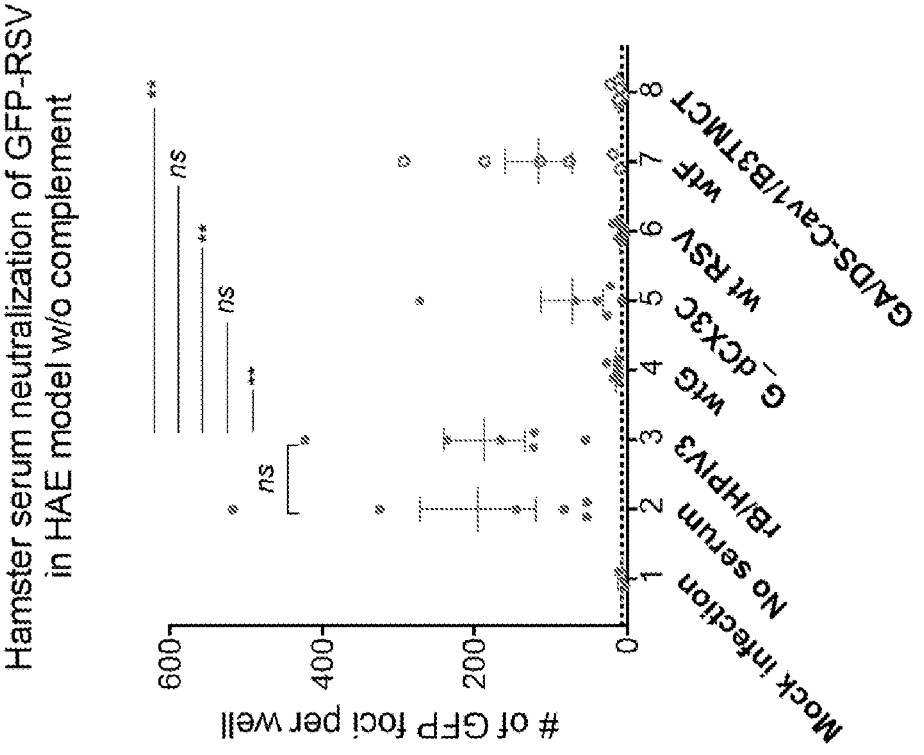
FIG. 13. Evaluation of the ability of serum RSV-neutralizing antibodies to block RSV-GFP infection in an in vitro model of primary differentiated mucociliary human airway epithelial (HAE) tissue. Aliquots of RSV-GFP were incubated for 30 min at 37° C. with the indicated hamster serum in the absence of added complement, from the experiment shown in FIGS. 7 and 8, and were then inoculated onto HAE cultures (one well per sample). After 60 min at 37° C., the inoculum was removed and the cultures were incubated for 48 hours. The GFP foci of infected cells were imaged and quantified, and the mean of each set of duplicates was calculated. Significant differences were identified by an unpaired t test: ** indicates $P<0.01$; ns=not significant.

HAE cells were differentiated in culture at an air-liquid interface. Full differentiation was verified by the formation of ciliated cells and tight junctions imaged by confocal microscopy. Sera of immunized hamsters from the experiment shown in FIG. 8 were tested for the ability to block RSV infection in the HAE model. Equal aliquots of RSV-GFP (A2 strain) were pre-incubated with hamster serum in the absence of added complement, and then used to infect HAE cultures. The inocula was removed after infection and cells were cultured at the air-liquid interface. At 48 hours post infection, the GFP foci of infected cells were visualized and quantified (FIG. 13). In the uninfected culture, there was a background of approximately 6 foci per culture insert (FIG. 13, lane 1), likely due to autofluorescent cells. In the RSV-GFP infected culture, an average of approximately 200 (ranging from 53 to 518) GFP fluorescent foci were detected (FIG. 13, lane 2). Pre-incubation of RSV-GFP with sera from hamsters infected with the empty vector had no effect in RSV infection in HAE cells (FIG. 13, lane 3). Remarkably, the sera from hamsters immunized with wt G or wt RSV almost completely prevented the infection (FIG. 13, lanes 4 and 6). Surprisingly, the sera from hamsters immunized by the vector expressing wt RSV F displayed little inhibitory activity in this model; but the sera from hamsters immunized by the vector expressing a stabilized prefusion F (from a previous study and used here as a positive control for high-quality neutralizing antibody response) completed blocked the RSV infection (FIG. 13, lane 8). Interestingly, the sera of hamsters infected with the G_dCX3C construct were only partially protective compared with sera with wt G (FIG. 13, lanes 4 and 5). These results indicated that the wt RSV G induced high-quality neutralizing antibodies that can effectively prevent RSV infection in HAE in the absence of added complement. In addition, the integrity of the CX3C motif was important for the induction of serum neutralization antibodies by RSV G. Unexpectedly, in this assay, the neutralizing activity of sera raised against wt G was greater than for wt F, likely reflecting an effect on attachment. These results indicate antibodies to RSV G are particularly effective in neutralization of RSV in an in vitro model of HAE that closely resembles authentic HAE, and therefore the G protein may be an effective antigen to include in an RSV vaccine.

CONCLUSION

A number of studies have provided data indicating that the CX3C motif in the RSV G protein and expression of the soluble form of RSV G (sG) has various deleterious effects on host immune responses to RSV infection. This has been reported to include reduced dendritic cell activation (Johnson et al., 2012, *J. Virol.* 86:1339-1347), augmented inflammatory responses (Johnson et al., 1998, *J. Virol.* 72:2871-2880), inhibition of innate immunity (Shingai et al., 2008, *Int. Immunol.* 20:1169-1180; Polack et a12005, *Proc. Natl. Acad. Sci. USA* 102:8996-9001), and inhibition of immune cell responses (Chirkova et al., 2013, *J. Virol.* 87:13466-13479), among other activities. Based on these studies, it was expected that ablation of the CX3C motif and/or sG should make a safer, more immunogenic vaccine (e.g., Boyoglu-Barnum et al., "Mutating the CX3C Motif in the G Protein Should Make a Live Respiratory Syncytial Virus Vaccine Safer and More Effective," *J. Virol.,* 91(10): e02059-16, 2017; Chirkova et al., 2013, *J. Virol.* 87:13466-13479).

Surprisingly, data provided in the present example indicate that the mG construct (construct (ii), FIG. 1A), from which expression of sG was ablated, was modestly less immunogenic and protective than wt G protein, when expressed from the rB/HPIV3 vector. The finding that ablation of expression of the sG protein did not increase immunogenicity and protection was contrary to the postulated role of sG in impairing immune responses. Furthermore, the enhanced expression of sG on its own did not affect vector replication or vector immunogenicity. This was evident in comparing wtG (that expresses sG) with mG (that does not), and evaluating the effects of expression of sG protein alone (construct (iii), FIG. 1A), none of which affected vector replication or immunogenicity. Thus, there was no evidence that sG affected the host immune response in a manner that significantly affected RSV G immunogenicity and protective efficacy, or vector replication and immunogenicity.

Additionally, ablation of the CX3C motif greatly reduced the immunogenicity of RSV G (whether assayed with or without complement) and protective efficacy against RSV. Thus, contrary to the studies discussed above, this region of RSV G provides a positive effect on RSV immunogenicity and protective efficacy. Ablating the CX3C domain also did not significantly affect vector replication or immunogenicity. Thus, this motif did not alter the pulmonary immune milieu sufficient to affect vector replication or immunogenicity.

This example shows that features of the RSV G protein such as sG protein and the CX3C motif do not impair the immunogenicity and protective efficacy of the G protein expressed from a rB/HPIV3 vector. rB/HPIV3-based immunogens expressing wt G ectodomain were identified as preferred for inducing an immune response to RSV G. Surprisingly, the wt G construct induced titers of serum RSV-neutralizing antibodies assayed in the presence of complement that were not significantly different than those induced by wt RSV, even though RSV was administered at a 10-fold higher dose, is not attenuated, and bears both the F and G neutralization antigens. Additionally, the HAE assay (FIG. 13) showed that antibodies induced by wt G completely blocked infection in a model that closely mimics in vivo HAE, the predominant site of RSV replication in vivo, whereas antibodies induced by wt F did not. The RSV G protein is often considered to be a secondary neutralization and protective antigen compared to F. The present data revise this view and indicate that the G protein can improve neutralization (and likely protection). This suggests that the inclusion of vector expressing RSV G to an RSV immunization protocol improved neutralization and protection, a contribution that is not appreciated by conventional neutralization assays that do not involve the CX3CR receptor for RSV.

```
Exemplary antigenomic cDNA sequences:
rB/HPIV3- RSV wt G (SEQ ID NO: 91):
accaaacaagagaagagactggtttgggaatattaattcaaataaaaattaacttaggattaaagaactttaccgaaagg

taaggggaaagaaatcctaagagcttagccatgttgagtctattcgacacattcagtgcgcgtaggcaggagaacataac

gaaatcagctggtggggctgttattcccgggcaaaaaaacactgtgtctatatttgctcttggaccatcaataacagatg

acaatgataaaatgacattggctcttctctttttgtctcattctttagacaatgaaaagcagcatgcgcaaagagctgga

tttttagtttctctgttatcaatggcttatgccaacccagaattatatttaacatcaaatggtagtaatgcagatgttaa

atatgttatctacatgatagagaaagacccaggaagacagaaatatggtgggtttgtcgtcaagactagagagatggttt

atgaaaagacaactgattggatgttcgggagtgatcttgagtatgatcaagacaatatgttgcaaaatggtagaagcact

tctacaatcgaggatcttgttcatacttttggatatccatcgtgtcttggagcccttataatccaagtttggataatact

tgttaaggctataaccagtatatcaggattgaggaaaggattctttactcggttagaagcatttcgacaagatggaacag

ttaaatccagtctagtgttgagcggtgatgcagtagaacaaattggatcaattatgaggtcccaacagagcttggtaaca

ctcatggttgaaacactgataacaatgaacacaggcaggaatgatctgacaacaatagaaaagaatatacagattgtagg
```

-continued aaactacatcagagatgcaggtcttgcttcatttttcaacacaatcagatatggcattgagactagaatggcagctctaa ctctgtctacccttagaccggatatcaacagactcaaggcactgatcgagttatatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatgtccaaaaacaaggaccaacgcaccgctaagacattagaa aggacctgggacactctcaatcatttattattcatatcatcgtgcttatataagttaaatcttaaatctgtagcacaaat cacattatccattctggcaatgataatctcaacttcacttataattgcagccatcatattcatagcctcggcaaaccaca aagtcacaccaacaactgcaatcatacaagatgcaacaagccagatcaagaacacaaccccaacatacctcacccagaat cctcagcttggaatcagtccctctaatccgtctgaaattacatcacaaatcaccaccatactagcttcaacaacaccagg agtcaagtcaaccctgcaatccacaacagtcaagaccaaaaacacaacaacaactcaaacacaacccagcaagcccacca caaaacaacgccaaaacaaaccaccaagcaaacccaataatgattttcactttgaagtgttcaactttgtaccctgcagc atatgcagcaacaatccaacctgctgggctatctgcaaaagaataccaaacaaaaaaccaggaaagaaaaccactaccaa gcccacaaaaaaaccaaccctcaagacaaccaaaaaagatcccaaacctcaaaccactaaatcaaaggaagtacccacca ccaagcccacagaagagccaaccatcaacaccaccaaaacaaacatcataactacactactcacctccaacaccacagga aatccagaactcacaagtcaaatggaaaccttccactcaacttcctccgaaggcaatccaagcccttctcaagtctctac aacatccgagtacccatcacaaccttcatctccacccaacacaccacgccagtgatagctagcggcgcgccagcaacaag taagaaaaacttaggattaatggaaattatccaatccagagacggaaggacaaatccagaatccaaccacaactcaatca accaaagattcatggaagacaatgttcaaaacaatcaaatcatggattcttgggaagagggatcaggagataaatcatct gacatctcatcggccctcgacatcattgaattcatactcagcaccgactcccaagagaacacggcagacagcaatgaaat caacacaggaaccacaagacttagcacgacaatctaccaacctgaatccaaaacaacagaaacaagcaaggaaaatagtg gaccagctaacaaaaatcgacagtttggggcatcacacgaacgtgccacagagacaaaagatagaaatgttaatcaggag actgtacagggaggatataggagaggaagcagcccagatagtagaactgagactatggtcactcgaagaatctccagaag cagcccagatcctaacaatggaacccaaatccaggaagatattgattacaatgaagttggagagatggataaggactcta ctaagagggaaatgcgacaatttaaagatgttccagtcaaggtatcaggaagtgatgccattcctccaacaaaacaagat ggagacggtgatgatggaagaggcctggaatctatcagtacatttgattcaggatataccagtatagtgactgccgcaac actagatgacgaagaagaactccttatgaagaacaacaggccaagaaagtatcaatcaacaccccagaacagtgacaagg gaattaaaaaaggggttggaaggccaaaagacacagacaaacaatcatcaatattggactacgaactcaacttcaaagga tcgaagaagagccagaaaatcctcaaagccagcacgaatacaggagaaccaacaagaccacagaatggatcccaggggaa gagaatcacatcctggaacatcctcaacagcgagagcggcaatcgaacagaatcaacaaaccaaacccatcagacatcaa cctcgggacagaaccacacaatgggaccaagcagaacaacctccgaaccaaggatcaagacacaaaagacggatggaaag gaaagagaggacacagaagagagcactcgatttacagaaagggcgattacattattacagaatcttggtgtaatccaatc tgcagcaaaattagacctataccaagacaagagagttgtgtgtgtggcgaatgtcctaaacaatgcagatactgcatcaa agatagacttcctagcaggtttgatgataggagtgtcaatggatcatgataccaaattaaatcagattcagaacgagata ttaagtttgaaaactgatcttaaaaagatggatgaatcacatagaagactaattgagaatcaaaaagaacaattatcact gatcacatcattaatctcaaatcttaaaattatgacagagagaggagggaagaaggaccaaccagaacctagcgggagga -continued catccatgatcaagacaaaagcaaaagaagagaaaataaagaaagtcaggtttgaccctcttatggaaacacagggcatc gagaaaaacatccctgacctctatagatcaatagagaaaacaccagaaaacgacacacagatcaaatcagaaataaacag attgaatgatgaatccaatgccactagattagtacctagaagaataagcagtacaatgagatcattaataataatcatta acaacagcaatttatcatcaaaagcaaagcaatcatacatcaacgaactcaagctctgcaagagtgacgaggaagtgtct gagttgatggacatgttcaatgaggatgtcagctcccagtaaaccgccaaccaagggtcaacaccaagaaaaccaatagc acaaaacagccaatcagagaccaccccaatacaccaaaccaatcaacacataacaaagatcgcggccgcatagatgatta agaaaaacttaggatgaaaggactaatcaatcctccgaaacaatgagcatcaccaactccacaatctacacattcccaga atcctctttctccgagaatggcaacatagagccgttaccactcaaggtcaatgaacagagaaaggccatacctcatatta gggttgtcaagataggagatccgcccaaacatggatccagatatctggatgtctttttactgggcttctttgagatggaa aggtcaaaagacaggtatgggagcataagtgatctagatgatgatccaagttacaaggtttgtggctctggatcattgcc acttgggttggctagatacaccggaaatgatcaggaactcctacaggctgcaaccaagctcgatatagaagtaagaagaa ctgtaaaggctacggagatgatagtttacactgtacaaaacatcaaacctgaactatatccatggtccagtagattaaga aaagggatgttatttgacgctaataaggttgcacttgctcctcaatgtcttccactagatagagggataaaattcagggt gatatttgtgaactgcacagcaattggatcaataactctattcaaaatccctaagtccatggcattgttatcattgccta atacaatatcaataaatctacaagtacatatcaaaacaggagttcagacagattccaaaggagtagttcagattctagat gaaaaaggtgaaaaatcactaaatttcatggttcatctcgggttgatcaaaaggaagatgggcagaatgtactcagttga atattgtaagcagaagatcgagaagatgagattattattctcattgggattagttggagggatcagcttccacgtcaacg caactggctctatatcaaagacattagcaagtcaattagcattcaaaagagaaatctgctatcccctaatggatctgaat ccacacttaaattcagttatatgggcatcatcagttgaaattacaagggtagatgcagttctccagccttcattacctgg cgaattcagatactacccaaacatcatagcaaaaggggtcgggaaaatcagacagtaaaatcaacaaccctgatatccac cggtgtattaagccgaagcaaataaaggataatcaaaaacttaggacaaaagaggtcaataccaacaactattagcagtc acactcgcaagaataagagagaagggaccaaaaaagtcaaataggagaaatcaaaacaaaaggtacagaacaccagaaca acaaaatcaaaacatccaactcactcaaaacaaaaattccaaaagagaccggcaacacaacaagcactgaacacaatgcc aacttcaatactgctaattattacaaccatgatcatggcatctttctgccaaatagatatcacaaaactacagcacgtag gtgtattggtcaacagtcccaaagggatgaagatatcacaaaactttgaaacaagatatctaattttgagcctcatacca aaaatagaagactctaactcttgtggtgaccaacagatcaagcaatacaagaagttattggatagactgatcatcccttt atatgatggattaagattacagaaagatgtgatagtaaccaatcaagaatccaatgaaaacactgatcccagaacaaaac gattctttggaggggtaattggaaccattgctctgggagtagcaacctcagcacaaattacagcggcagttgctctggtt gaagccaagcaggcaagatcagacatcgaaaaactcaaagaagcaattagggacacaaacaaagcagtgcagtcagttca gagctccataggaaatttaatagtagcaattaaatcagtccaggattatgttaacaaagaaatcgtgccatcgattgcga ggctaggttgtgaagcagcaggacttcaattaggaattgcattaacacagcattactcagaattaacaaacatatttggt gataacataggatcgttacaagaaaaaggaataaaattacaaggtatagcatcattataccgcacaaatatcacagaaat attcacaacatcaacagttgataaatatgatatctatgatctgttatttacagaatcaataaaggtgagagttatagatg ttgacttgaatgattactcaatcaccctccaagtcagactccctttattaactaggctgctgaacactcagatctacaaa gtagattccatatcatataacatccaaaacagagaatggtatatccctcttcccagccatatcatgacgaaaggggcatt tctaggtggagcagacgtcaaagaatgtatagaagcattcagcagctatatatgcccttctgatccaggatttgtattaa accatgaaatagagagctgcttatcaggaaacatatcccaatgtccaagaacaacggtcacatcagacattgttccaaga tatgcatttgtcaatggaggagtggttgcaaactgtataacaaccacctgtacatgcaacggaattggtaatagaatcaa tcaaccacctgatcaaggagtaaaaattataacacataaagaatgtagtacaataggtatcaacggaatgctgttcaata caaataaagaaggaactcttgcattctatacaccaaatgatataacactaaacaattctgttgcacttgatccaattgac -continued atatcaatcgagctcaacaaggccaaatcagatctagaagaatcaaaagaatggataagaaggtcaaatcaaaaactaga ttctattggaaattggcatcaatctagcactacaatcataattattttgataatgatcattatattgtttataattaata taacgataattacaattgcaattaagtattacagaattcaaaagagaaatcgagtggatcaaaatgacaagccatatgta ctaacaaacaaataacatatctacagatcattagatattaaaattataaaaaacttaggagtaaagttacgcaatccaac tctactcatataattgaggaaggacccaatagacaaatccaaattcgagatggaatactggaagcataccaatcacggaa aggatgctggtaatgagctggagacgtctatggctactcatggcaacaagctcactaataagataatatacatattatgg acaataatcctggtgttattatcaatagtcttcatcatagtgctaattaattccatcaaaagtgaaaaggcccacgaatc attgctgcaagacataaataatgagtttatggaaattacagaaaagatccaaatggcatcggataataccaatgatctaa tacagtcaggagtgaatacaaggcttcttacaattcagagtcatgtccagaattacataccaatatcattgacacaacag atgtcagatcttaggaaattcattagtgaaattacaattagaaatgataatcaagaagtgctgccacaaagaataacaca tgatgtaggtataaaacctttaaatccagatgattttggagatgcacgtctggtcttccatctttaatgaaaactccaa aaataaggttaatgccagggccgggattattagctatgccaacgactgttgatggctgtgttagaactccgtctttagtt ataaatgatctgatttatgcttatacctcaaatctaattactcgaggttgtcaggatataggaaaatcatatcaagtctt acagatagggataataactgtaaactcagacttggtacctgacttaaatcctaggatctctcatacctttaacataaatg acaataggaagtcatgttctctagcactcctaaatacagatgtatatcaactgtgttcaactcccaaagttgatgaaaga tcagattatgcatcatcaggcatagaagatattgtacttgatattgtcaattatgatggttcaatctcaacaacaagatt taagaataataacataagctttgatcaaccatatgctgcactatacccatctgttggaccagggatatactacaaaggca aaataatatttctcgggtatggaggtcttgaacatccaataaatgagaatgtaatctgcaacacaactgggtgccccggg aaaacacagagagactgtaatcaagcatctcatagtccatggttttcagataggaggatggtcaactccatcattgttgt tgacaaaggcttaaactcaattccaaaattgaaagtatggacgatatctatgcgacaaaattactgggggtcagaaggaa ggttacttctactaggtaacaagatctatatatatacaagatctacaagttggcatagcaagttacaattaggaataatt gatattactgattacagtgatataaggataaaatggacatggcataatgtgctatcaagaccaggaaacaatgaatgtcc atggggacattcatgtccagatggatgtataacaggagtatatactgatgcatatccactcaatcccacagggagcattg tgtcatctgtcatattagactcacaaaaatcgagagtgaacccagtcataacttactcaacagcaaccgaaagagtaaac gagctggccatcctaaacagaacactctcagctggatatacaacaacaagctgcattacacactataacaaaggatattg ttttcatatagtagaaataaatcataaaagcttaaacacatttcaacccatgttgttcaaaacagagattccaaaaagct gcagttaatcataattaaccataatatgcatcaatctatctataatacaagtatatgataagtaatcagcaatcagacaa tagacgtacggaaataataaaaaacttaggagaaaagtgtgcaagaaaaatggacaccgagtcccacagcggcacaacat ctgacattctgtaccctgaatgtcacctcaattctcctatagttaaaggaaagatagcacaactgcatacaataatgagt ttgcctcagccctacgatatggatgatgattcaatactgattattactagacaaaaaattaaactcaataaattagataa aagacaacggtcaattaggaaattaagatcagtcttaatggaaagagtaagtgatctaggtaaatatacctttatcagat atccagagatgtctagtgaaatgttccaattatgtatacccggaattaataataaaataaatgaattgctaagtaaagca agtaaaacatataatcaaatgactgatggattaagagatctatgggttactatactatcgaagttagcatcgaaaaatga tggaagtaattatgatatcaatgaagatattagcaatatatcaaatgttcacatgacttatcaatcagacaaatggtata atccattcaagacatggtttactattaagtatgacatgagaagattacaaaaagccaaaaatgagattacattcaatagg cataaagattataatctattagaagaccaaaagaatatattgctgatacatccagaactcgtcttaatattagataaaca aaattacaatgggtatataatgactcctgaattggtactaatgtattgtgatgtagttgaagggaggtggaatataagtt catgtgcaaaattggatcctaagttacaatcaatgtattataagggtaacaatttatgggaaataatagatggactattc tcgaccttaggagaaagaacatttgacataatatcactattagaaccacttgcattatcgctcattcaaacttatgaccc ggttaaacagctcagggggctttttaaatcacgtgttatcagaaatggaattaatatttgcagctgagtgtacaacag aggaaatacctaatgtggattatatagataaaatttagatgtgttcaaagaatcaacaatagatgaaatagcagaaatt -continued ttctctttcttccgaacttttggacaccctccattagaggcgagtatagcagcagagaaagttagaaagtatatgtatac tgagaaatgcttgaaatttgatactatcaataaatgtcatgctatttttgtacaataattataaatggatatagagaaa gacatggtggtcaatggcctccagttacattacctgtccatgcacatgaatttatcataaatgcatacggatcaaattct gccatatcatatgagaatgctgtagattattataagagcttcataggaataaaatttgacaagtttatagagcctcaatt ggatgaagacttaactatttatatgaaagataaagcattatccccaaagaaatcaaactgggacacagtctatccagctt caaacctgttataccgcactaatgtgtctcatgattcacgaagattggttgaagtatttatagcagatagtaaatttgat ccccaccaagtattagattacgtagaatcaggatattggctggatgatcctgaatttaatatctcatatagtttaaaaga gaaagaaataaaacaagaaggtagacttttgcaaaaatgacatacaagatgagggctacacaagtattatcagaaacat tattggcgaataatatagggaaattcttccaagagaatgggatggttaaaggagaaattgaattactcaagagactaaca acaatatctatgtctggagttccgcggtataatgaggtatacaataattcaaaaagtcacacagaagaacttcaagctta taatgcaattagcagttccaatttatcttctaatcagaagtcaaagaagtttgaatttaaatctacagatatatacaatg atggatacgaaaccgtaagctgcttcttaacgacagatcttaaaaaatattgtttaaattggaggtatgaatcaacagct ttattcggtgatacttgtaatcagatatttgggttaaaggaattatttaattggctgcaccctcgccttgaaaagagtac aatatatgttggagatccttattgcccgccatcagatattgaacatttaccacttgatgaccatcctgattcaggatttt atgttcataatcctaaaggaggaatagaagggttttgccaaaagttatggacactcatatctatcagtgcaatacattta gcagctgtcaaaatcggtgtaagagttactgcaatggttcaaggggataatcaagccatagctgttaccacaagagtacc taataattatgattataaagttaagaaagagattgtttataaagatgtggtaagatttttgattccttgagagaggtga tggatgatctgggtcatgagctcaaactaaatgaaactataataagtagtaaaatgtttatatatagcaaaaggatatac tatgacggaagaatccttcctcaggcattaaaagcattgtctagatgtgtttttggtctgaaacaatcatagatgagac aagatcagcatcctcaaatctggctacatcgtttgcaaaggccattgagaatggctactcacctgtattgggatatgtat gctcaatcttcaaaaatatccaacagttgtatatagcgcttggaatgaatataaacccaactataacccaaaatattaaa gatcaatatttcaggaatattcattggatgcaatatgcctccttaatccctgctagtgtcggaggatttaattatatggc catgtcaaggtgttttgtcagaaacattggagatcctacagtcgctgcgttagccgatattaaaagatttataaaagcaa atttgttagatcgaggtgtcctttacagaattatgaatcaagaaccaggcgagtcttctttttagactgggcctcagat ccctattcatgtaacttaccacaatctcaaaatataaccaccatgataaagaatataactgcaagaaatgtactacagga ctcaccaaacccattactatctggattatttacaagtacaatgatagaagaggatgaggaattagctgagttcctaatgg acaggagaataatcctcccaagagttgcacatgacattttagataattctcttactggaattaggaatgctatagctggt atgttggatacaacaaaatcactaattcgagtagggataagcagaggaggattaacctataacttattaagaaagataag caactatgatcttgtacaatatgagacacttagtaaaactttaagactaatagtcagtgacaagattaagtatgaagata tgtgctcagtagacctagccatatcattaagacaaaaaatgtggatgcatttatcaggaggaagaatgataaatggactt gaaactccagatcctttagagttactgtctggagtaataataacaggatctgaacattgtaggatatgttattcaactga aggtgaaagcccatatacatggatgtatttaccaggcaatcttaatataggatcagctgagacaggaatagcatcattaa gggtcccttactttggatcagttacagatgagagatctgaagcacaattagggtatatcaaaaatctaagcaaaccagct aaggctgctataagaatagcaatgatatatacttgggcatttgggaatgacgaaatatcttggatggaagcatcacagat tgcacaaacacgtgcaaactttacattggatagcttaaagattttgacaccagtgacaacatcaacaaatctatcacaca ggttaaaagatactgctactcagatgaaattttctagtacatcacttattagagtaagcaggttcatcacaatatctaat gataatatgtctattaaagaagcaaatgaaactaaagatacaaatcttatttatcaacaggtaatgttaacaggattaag tgtatttgaatatctatttaggttagaggagagtacaggacataaccctatggtcatgcatctacatatagaggatggat gttgtataaaagagagttacaatgatgagcatatcaatccggagtctacattagagttaatcaaataccctgagagtaat gaatttatatatgataaggaccctttaaaggatatagatctatcaaaattaatggttataagagatcattcttatacaat -continued tgacatgaattactgggatgacacagatattgtacatgcaatatcaatatgtactgcagttacaatagcagatacaatgt cgcagctagatcgggataatcttaaggagctggttgtgattgcaaatgatgatgatattaacagtctgataactgaattt ctgaccctagatatactagtgtttctcaaaacatttggagggttactcgtgaatcaatttgcatataccctttatggatt gaaaatagaaggaagggatcccatttgggattatataatgagaacattaaaagacacctcacattcagtacttaaagtat tatctaatgcactatctcatccaaaagtgtttaagagattttgggattgtggagttttgaatcctatttatggtcctaat actgctagtcaagatcaagttaagcttgctctctcgatttgcgagtactccttggatctatttatgagagaatggttgaa tggagcatcacttgagatctatatctgtgatagtgacatggaaatagcaaatgacagaagacaagcatttctctcaagac atcttgcctttgtgtgttgtttagcagagatagcatcttttggaccaaatttattaaatctaacatatctagagagactt gatgaattaaaacaatacttagatctgaacatcaaagaagatcctactcttaaatatgtgcaagtatcaggactgttaat taaatcattcccctcaactgttacgtatgtaaggaaaactgcgattaagtatctgaggattcgtggtattaatccgcctg aaacgattgaagattgggatcccatagaagatgagaatatcttagacaatattgttaaaactgtaaatgacaattgcagt gataatcaaaagagaaataaaagtagttatttctggggattagctctaaagaattatcaagtcgtgaaaataagatccat aacgagtgattctgaagttaatgaagcttcgaatgttactacacatggaatgacacttcctcagggaggaagttatctat cacatcagctgaggttatttggagtaaacagtacaagttgtcttaaagctcttgaattatcacaaatcttaatgagggaa gttaaaaaagataaagatagactctttttaggagaaggagcaggagctatgttagcatgttatgatgctacactcggtcc tgcaataaattattataattctggtttaaatattacagatgtaattggtcaacgggaattaaaaatcttcccatcagaag tatcattagtaggtaaaaaactaggaaatgtaacacagattcttaatcgggtgagggtgttatttaatgggaatcccaat tcaacatggataggaaatatggaatgtgagagtttaatatggagtgaattaaatgataagtcaattggtttagtacattg tgacatggagggagcgataggcaaatcagaagaaactgttctacatgaacattatagtattattaggattacatatttaa tcggggatgatgatgttgtcctagtatcaaaaaattataccaactattactccgaattggtctaaaatactctatctatac aagttgtattggaaggatgtaagtgtagtgtcccttaaaacatccaatcctgcctcaacagagctttatttaatttcaaa agatgcttactgtactgtaatggaacccagtaatcttgttttatcaaaacttaaaaggatatcatcaatagaagaaaata atctattaaagtggataatcttatcaaaaaggaagaataacgagtggttacagcatgaaatcaaagaaggagaaagggat tatgggataatgaggccatatcatacagcactgcaaatttttggattccaaattaacttaaatcacttagctagagaatt tttatcaactcctgatttaaccaacattaataatataattcaaagttttacaagaacaattaaagatgttatgttcgaat gggtcaatatcactcatgacaataaaagacataaattaggaggaagatataatctattcccgcttaaaaataaggggaaa ttaagattattatcacgaagattagtactaagctggatatcattatccttatcaaccagattactgacgggccgttttcc agatgaaaaatttgaaaatagggcacagaccggatatgtatcattggctgatattgatttagaatccttaaagttattat caagaaatattgtcaaaaattacaaagaacacataggattaatatcatactggtttttgaccaaagaggtcaaaatacta atgaagcttataggaggagtcaaactactaggaattcctaaacagtacaaagagttagaggatcgatcatctcagggtta tgaatatgataatgaatttgatattgattaatacataaaaacataaaataaaacacctattcctcacccattcacttcca acaaaatgaaaagtaagaaaaacatgtaatatatatataccaaacagagtttttctcttgtttggt rB/HPIV3-RSV wt G/GS-opt (SEQ ID NO: 92):
accaaacaagagaagagactggtttgggaatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaacactgtgtctatatttgctcttggaccatcaataacagatg acaatgataaaatgacattggctcttctctttttgtctcattctttagacaatgaaaagcagcatgcgcaaagagctgga tttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact -continued tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcatttttcaacacaatcagatatggcattgagactagaatggcagctctaa ctctgtctacccttagaccggatatcaacagactcaaggcactgatcgagttatatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatgtcaaagaacaaggatcagagaactgccaagaccctggaa agaacctgggacaccctgaaccacctgctgtttatctcaagctgcctgtacaagctgaatctgaaaagtgtggcccagat caccctgtcaattctggctatgatcatttcaacaagcctgatcattgccgctatcattttcatcgcaagcgccaaccaca aggtcacccccaccacagctatcattcaggacgcaacatcccagattaagaacactacccccacctatctgacacagaat cctcagctgggaatctccccatctaacccctcagagattaccagccagatcacaactattctggcctccaccacacctgg cgtgaagtccactctgcagtctactaccgtcaagaccaaaaatacaactaccacacagacacagccttctaagccaacta ccaaacagcggcagaataagcccccctagtaaaccaaacaatgacttccattttgaggtgttcaactttgtcccatgcagc atctgttccaacaatcccacctgctgggccatctgtaagagaattccaaacaagaaacccggcaagaagaccactaccaa acctactaagaaaccaaccctgaagacaactaagaaagatcctaaaccacagaccacaaagtctaaagaagtgcccacta ccaagcctacagaggaaccaactatcaacacaactaagactaacatcatcaccacactgctgacaagcaacactaccggc aatcccgagctgaccagccagatggaaacctttcactccacaagctccgaggggaatcccagtccttcacaggtgtctac aactagtgaataccccagccagccttctagtccacccaacacccctaggcagtgatagctagcggcgcgccagcaacaag taagaaaaacttaggattaatggaaattatccaatccagagacggaaggacaaatccagaatccaaccacaactcaatca accaaagattcatggaagacaatgttcaaaacaatcaaatcatggattcttgggaagagggatcaggagataaatcatct gacatctcatcggccctcgacatcattgaattcatactcagcaccgactcccaagagaacacggcagacagcaatgaaat caacacaggaaccacaagacttagcacgacaatctaccaacctgaatccaaaacaacagaaacaagcaaggaaaatagtg gaccagctaacaaaaatcgacagtttggggcatcacacgaacgtgccacagagacaaaagatagaaatgttaatcaggag actgtacagggaggatataggagaggaagcagcccagatagtagaactgagactatggtcactcgaagaatctccagaag cagcccagatcctaacaatggaacccaaatccaggaagatattgattacaatgaagttggagagatggataaggactcta ctaagagggaaatgcgacaatttaaagatgttccagtcaaggtatcaggaagtgatgccattcctccaacaaaacaagat ggagacggtgatgatggaagaggcctggaatctatcagtacatttgattcaggatataccagtatagtgactgccgcaac actagatgacgaagaagaactccttatgaagaacaacaggccaagaaagtatcaatcaacaccccagaacagtgacaagg gaattaaaaaaggggttggaaggccaaaagacacagacaaacaatcatcaatattggactacgaactcaacttcaaagga tcgaagaagagccagaaaatcctcaaagccagcacgaatacaggagaaccaacaagaccacagaatggatcccaggggaa gagaatcacatcctggaacatcctcaacagcgagagcggcaatcgaacagaatcaacaaaccaaacccatcagacatcaa cctcgggacagaaccacacaatgggaccaagcagaacaacctccgaaccaaggatcaagacacaaaagacggatggaaag gaaagagaggacacagaagagagcactcgatttacagaaagggcgattacattattacagaatcttggtgtaatccaatc tgcagcaaaattagacctataccaagacaagagagttgtgtgtgtggcgaatgtcctaaacaatgcagatactgcatcaa -continued agatagacttcctagcaggtttgatgataggagtgtcaatggatcatgataccaaattaaatcagattcagaacgagata
ttaagtttgaaaactgatcttaaaaagatggatgaatcacatagaagactaattgagaatcaaaaagaacaattatcact
gatcacatcattaatctcaaatcttaaaattatgacagagagaggagggaagaaggaccaaccagaacctagcgggagga
catccatgatcaagacaaaagcaaaagaagagaaaataaagaaagtcaggtttgaccctcttatggaaacacagggcatc
gagaaaaacatccctgacctctatagatcaatagagaaaacaccagaaaacgacacacagatcaaatcagaaataaacag
attgaatgatgaatccaatgccactagattagtacctagaagaataagcagtacaatgagatcattaataataatcatta
acaacagcaatttatcatcaaaagcaaagcaatcatacatcaacgaactcaagctctgcaagagtgacgaggaagtgtct
gagttgatggacatgttcaatgaggatgtcagctcccagtaaaccgccaaccaagggtcaacaccaagaaaaccaatagc
acaaaacagccaatcagagaccaccccaatacaccaaaccaatcaacacataacaaagatcgcggccgcatagatgatta
agaaaaacttaggatgaaaggactaatcaatcctccgaaacaatgagcatcaccaactccacaatctacacattcccaga
atcctctttctccgagaatggcaacatagagccgttaccactcaaggtcaatgaacagagaaaggccatacctcatatta
gggttgtcaagataggagatccgcccaaacatggatccagatatctggatgtctttttactgggcttctttgagatggaa
aggtcaaaagacaggtatgggagcataagtgatctagatgatgatccaagttacaaggtttgtggctctggatcattgcc
acttgggttggctagatacaccggaaatgatcaggaactcctacaggctgcaaccaagctcgatatagaagtaagaagaa
ctgtaaaggctacggagatgatagtttacactgtacaaaacatcaaacctgaactatatccatggtccagtagattaaga
aaagggatgttatttgacgctaataaggttgcacttgctcctcaatgtcttccactagatagagggataaaattcagggt
gatatttgtgaactgcacagcaattggatcaataactctattcaaaatccctaagtccatggcattgttatcattgccta
atacaatatcaataaatctacaagtacatatcaaaacaggagttcagacagattccaaaggagtagttcagattctagat
gaaaaaggtgaaaaatcactaaatttcatggttcatctcgggttgatcaaaaggaagatgggcagaatgtactcagttga
atattgtaagcagaagatcgagaagatgagattattattctcattgggattagttggagggatcagcttccacgtcaacg
caactggctctatatcaaagacattagcaagtcaattagcattcaaaagagaaatctgctatcccctaatggatctgaat
ccacacttaaattcagttatatgggcatcatcagttgaaattacaagggtagatgcagttctccagccttcattacctgg
cgaattcagatactacccaaacatcatagcaaaaggggtcgggaaaatcagacagtaaaatcaacaaccctgatatccac
cggtgtattaagccgaagcaaataaaggataatcaaaaacttaggacaaaagaggtcaataccaacaactattagcagtc
acactcgcaagaataagagagaagggaccaaaaaagtcaaataggagaaatcaaaacaaaaggtacagaacaccagaaca
acaaaatcaaaacatccaactcactcaaaacaaaaattccaaaagagaccggcaacacaacaagcactgaacacaatgcc
aacttcaatactgctaattattacaaccatgatcatggcatctttctgccaaatagatatcacaaaactacagcacgtag
gtgtattggtcaacagtcccaaagggatgaagatatcacaaaactttgaaacaagatatctaattttgagcctcatacca
aaaatagaagactctaactcttgtggtgaccaacagatcaagcaatacaagaagttattggatagactgatcatcccttt
atatgatggattaagattacagaaagatgtgatagtaaccaatcaagaatccaatgaaaacactgatcccagaacaaaac
gattctttggaggggtaattggaaccattgctctgggagtagcaacctcagcacaaattacagcggcagttgctctggtt
gaagccaagcaggcaagatcagacatcgaaaaactcaaagaagcaattagggacacaaacaaagcagtgcagtcagttca
gagctccataggaaatttaatagtagcaattaaatcagtccaggattatgttaacaaagaaatcgtgccatcgattgcga
ggctaggttgtgaagcagcaggacttcaattaggaattgcattaacacagcattactcagaattaacaaacatatttggt
gataacataggatcgttacaagaaaaaggaataaaattacaaggtatagcatcattataccgcacaaatatcacagaaat
attcacaacatcaacagttgataaatatgatatctatgatctgttatttacagaatcaataaaggtgagagttatagatg
ttgacttgaatgattactcaatcaccctccaagtcagactccctttattaactaggctgctgaacactcagatctacaaa
gtagattccatatcatataacatccaaaacagagaatggtatatccctcttcccagccatatcatgacgaaaggggcatt
tctaggtggagcagacgtcaaagaatgtatagaagcattcagcagctatatatgcccttctgatccaggatttgtattaa
accatgaaatagagagctgcttatcaggaaacatatcccaatgtccaagaacaacggtcacatcagacattgttccaaga -continued tatgcatttgtcaatggaggagtggttgcaaactgtataacaaccacctgtacatgcaacggaattggtaatagaatcaa tcaaccacctgatcaaggagtaaaaattataacacataaagaatgtagtacaataggtatcaacggaatgctgttcaata caaataaagaaggaactcttgcattctatacaccaaatgatataacactaaacaattctgttgcacttgatccaattgac atatcaatcgagctcaacaaggccaaatcagatctagaagaatcaaaagaatggataagaaggtcaaatcaaaaactaga ttctattggaaattggcatcaatctagcactacaatcataattattttgataatgatcattatattgtttataattaata taacgataattacaattgcaattaagtattacagaattcaaaagagaaatcgagtggatcaaaatgacaagccatatgta ctaacaaacaaataacatatctacagatcattagatattaaaattataaaaaacttaggagtaaagttacgcaatccaac tctactcatataattgaggaaggacccaatagacaaatccaaattcgagatggaatactggaagcataccaatcacggaa aggatgctggtaatgagctggagacgtctatggctactcatggcaacaagctcactaataagataatatacatattatgg acaataatcctggtgttattatcaatagtcttcatcatagtgctaattaattccatcaaaagtgaaaaggcccacgaatc attgctgcaagacataaataatgagtttatggaaattacagaaaagatccaaatggcatcggataataccaatgatctaa tacagtcaggagtgaatacaaggcttcttacaattcagagtcatgtccagaattacataccaatatcattgacacaacag atgtcagatcttaggaaattcattagtgaaattacaattagaaatgataatcaagaagtgctgccacaaagaataacaca tgatgtaggtataaaacctttaaatccagatgatttttggagatgcacgtctggtcttccatctttaatgaaaactccaa aaataaggttaatgccagggccgggattattagctatgccaacgactgttgatggctgtgttagaactccgtctttagtt ataaatgatctgatttatgcttatacctcaaatctaattactcgaggttgtcaggatataggaaaatcatatcaagtctt acagatagggataataactgtaaactcagacttggtacctgacttaaatcctaggatctctcatacctttaacataaatg acaataggaagtcatgttctctagcactcctaaatacagatgtatatcaactgtgttcaactcccaaagttgatgaaaga tcagattatgcatcatcaggcatagaagatattgtacttgatattgtcaattatgatggttcaatctcaacaacaagatt taagaataataacataagctttgatcaaccatatgctgcactatacccatctgttggaccagggatatactacaaaggca aaataatatttctcgggtatggaggtcttgaacatccaataaatgagaatgtaatctgcaacacaactgggtgccccggg aaaacacagagagactgtaatcaagcatctcatagtccatggttttcagataggaggatggtcaactccatcattgttgt tgacaaaggcttaaactcaattccaaaattgaaagtatggacgatatctatgcgacaaaattactgggggtcagaaggaa ggttacttctactaggtaacaagatctatatatatacaagatctacaagttggcatagcaagttacaattaggaataatt gatattactgattacagtgatataaggataaaatggacatggcataatgtgctatcaagaccaggaaacaatgaatgtcc atggggacattcatgtccagatggatgtataacaggagtatatactgatgcatatccactcaatcccacagggagcattg tgtcatctgtcatattagactcacaaaaatcgagagtgaacccagtcataacttactcaacagcaaccgaaagagtaaac gagctggccatcctaaacagaacactctcagctggatatacaacaacaagctgcattacacactataacaaaggatattg ttttcatatagtagaaataaatcataaaagcttaaacacatttcaacccatgttgttcaaaacagagattccaaaaagct gcagttaatcataattaaccataatatgcatcaatctatctataatacaagtatatgataagtaatcagcaatcagacaa tagacgtacggaaataataaaaaacttaggagaaaagtgtgcaagaaaaatggacaccgagtcccacagcggcacaacat ctgacattctgtaccctgaatgtcacctcaattctcctatagttaaaggaaagatagcacaactgcatacaataatgagt ttgcctcagccctacgatatggatgatgattcaatactgattattactagacaaaaaattaaactcaataaattagataa aagacaacggtcaattaggaaattaagatcagtcttaatggaaagagtaagtgatctaggtaaatatacctttatcagat atccagagatgtctagtgaaatgttccaattatgtatacccggaattaataataaaataaatgaattgctaagtaaagca agtaaaacatataatcaaatgactgatggattaagagatctatgggttactatactatcgaagttagcatcgaaaaatga tggaagtaattatgatatcaatgaagatattagcaatatatcaaatgttcacatgacttatcaatcagacaaatggtata atccattcaagacatggtttactattaagtatgacatgagaagattacaaaaagccaaaaatgagattacattcaatagg cataaagattataatctattagaagaccaaaagaatatattgctgatacatccagaactcgtcttaatattagataaaca aaattacaatgggtatataatgactcctgaattggtactaatgtattgtgatgtagttgaagggaggtggaatataagtt catgtgcaaaattggatcctaagttacaatcaatgtattataagggtaacaatttatgggaaataatagatggactattc -continued tcgaccttaggagaaagaacatttgacataatatcactattagaaccacttgcattatcgctcattcaaacttatgaccc ggttaaacagctcagggggctttttaaatcacgtgttatcagaaatggaattaatatttgcagctgagtgtacaacag aggaaatacctaatgtggattatatagataaaattttagatgtgttcaaagaatcaacaatagatgaaatagcagaaatt ttctctttcttccgaacttttggacaccctccattagaggcgagtatagcagcagagaaagttagaaagtatatgtatac tgagaaatgcttgaaatttgatactatcaataaatgtcatgctatttttttgtacaataattataaatggatatagagaaa gacatggtggtcaatggcctccagttacattacctgtccatgcacatgaatttatcataaatgcatacggatcaaattct gccatatcatatgagaatgctgtagattattataagagcttcataggaataaaatttgacaagtttatagagcctcaatt ggatgaagacttaactatttatatgaaagataaagcattatccccaaagaaatcaaactgggacacagtctatccagctt caaacctgttataccgcactaatgtgtctcatgattcacgaagattggttgaagtatttatagcagatagtaaatttgat ccccaccaagtattagattacgtagaatcaggatattggctggatgatcctgaatttaatatctcatatagtttaaaaga gaaagaaataaaacaagaaggtagacttttgcaaaaatgacatacaagatgagggctacacaagtattatcagaaacat tattggcgaataatatagggaaattcttccaagagaatgggatggttaaaggagaaattgaattactcaagagactaaca acaatatctatgtctggagttccgcggtataatgaggtatacaataattcaaaaagtcacacagaagaacttcaagctta taatgcaattagcagttccaatttatcttctaatcagaagtcaaagaagtttgaatttaaatctacagatatatacaatg atggatacgaaaccgtaagctgcttcttaacgacagatcttaaaaaatattgtttaaattggaggtatgaatcaacagct ttattcggtgatacttgtaatcagatatttgggttaaaggaattatttaattggctgcaccctcgccttgaaaagagtac aatatatgttggagatccttattgcccgccatcagatattgaacatttaccacttgatgaccatcctgattcaggatttt atgttcataatcctaaaggaggaatagaagggttttgccaaaagttatggacactcatatctatcagtgcaatacattta gcagctgtcaaaatcggtgtaagagttactgcaatggttcaaggggataatcaagccatagctgttaccacaagagtacc taataattatgattataaagttaagaaagagattgtttataaagatgtggtaagatttttttgattccttgagagaggtga tggatgatctgggtcatgagctcaaactaaatgaaactataataagtagtaaaatgtttatatatagcaaaaggatatac tatgacggaagaatccttcctcaggcattaaaagcattgtctagatgtgtttttttggtctgaaacaatcatagatgagac aagatcagcatcctcaaatctggctacatcgtttgcaaaggccattgagaatggctactcacctgtattgggatatgtat gctcaatcttcaaaaatatccaacagttgtatatagcgcttggaatgaatataaacccaactataacccaaaatattaaa gatcaatatttcaggaatattcattggatgcaatatgcctccttaatccctgctagtgtcggaggatttaattatatggc catgtcaaggtgttttgtcagaaacattggagatcctacagtcgctgcgttagccgatattaaaagatttataaaagcaa atttgttagatcgaggtgtcctttacagaattatgaatcaagaaccaggcgagtcttcttttttagactgggcctcagat ccctattcatgtaacttaccacaatctcaaaatataaccaccatgataaagaatataactgcaagaaatgtactacagga ctcaccaaacccattactatctggattatttacaagtacaatgatagaagaggatgaggaattagctgagttcctaatgg acaggagaataatcctcccaagagttgcacatgacattttagataattctcttactggaattaggaatgctatagctggt atgttggatacaacaaaatcactaattcgagtagggataagcagaggaggattaacctataacttattaagaaagataag caactatgatcttgtacaatatgagacacttagtaaaactttaagactaatagtcagtgacaagattaagtatgaagata tgtgctcagtagacctagccatatcattaagacaaaaaatgtggatgcatttatcaggaggaagaatgataaatggactt gaaactccagatcctttagagttactgtctggagtaataataacaggatctgaacattgtaggatatgttattcaactga aggtgaaagcccatatacatggatgtatttaccaggcaatcttaatataggatcagctgagacaggaatagcatcattaa gggtcccttactttggatcagttacagatgagagatctgaagcacaattagggtatatcaaaaatctaagcaaaccagct aaggctgctataagaatagcaatgatatatacttgggcatttgggaatgacgaaatatcttggatggaagcatcacagat tgcacaaacacgtgcaaactttacattggatagcttaaagattttgacaccagtgacaacatcaacaaatctatcacaca ggttaaaagatactgctactcagatgaaattttctagtacatcacttattagagtaagcaggttcatcacaatatctaat gataatatgtctattaaagaagcaaatgaaactaaagatacaaatcttatttatcaacaggtaatgttaacaggattaag -continued tgtatttgaatatctatttaggttagaggagagtacaggacataaccctatggtcatgcatctacatatagaggatggat gttgtataaaagagagttacaatgatgagcatatcaatccggagtctacattagagttaatcaaataccctgagagtaat gaatttatatatgataaggaccctttaaaggatatagatctatcaaaattaatggttataagagatcattcttatacaat tgacatgaattactgggatgacacagatattgtacatgcaatatcaatatgtactgcagttacaatagcagatacaatgt cgcagctagatcgggataatcttaaggagctggttgtgattgcaaatgatgatgatattaacagtctgataactgaattt ctgaccctagatatactagtgtttctcaaaacatttggagggttactcgtgaatcaatttgcatataccctttatggatt gaaaatagaaggaagggatcccatttgggattatataatgagaacattaaaagacacctcacattcagtacttaaagtat tatctaatgcactatctcatccaaaagtgtttaagagattttgggattgtggagttttgaatcctatttatggtcctaat actgctagtcaagatcaagttaagcttgctctctcgatttgcgagtactccttggatctatttatgagagaatggttgaa tggagcatcacttgagatctatatctgtgatagtgacatggaaatagcaaatgacagaagacaagcatttctctcaagac atcttgcctttgtgtgttgtttagcagagatagcatcttttggaccaaatttattaaatctaacatatctagagagactt gatgaattaaaacaatacttagatctgaacatcaaagaagatcctactcttaaatatgtgcaagtatcaggactgttaat taaatcattcccctcaactgttacgtatgtaaggaaaactgcgattaagtatctgaggattcgtggtattaatccgcctg aaacgattgaagattgggatcccatagaagatgagaatatcttagacaatattgttaaaactgtaaatgacaattgcagt gataatcaaaagagaaataaaagtagttatttctggggattagctctaaagaattatcaagtcgtgaaaataagatccat aacgagtgattctgaagttaatgaagcttcgaatgttactacacatggaatgacacttcctcagggaggaagttatctat cacatcagctgaggttatttggagtaaacagtacaagttgtcttaaagctcttgaattatcacaaatcttaatgagggaa gttaaaaaagataaagatagactctttttaggagaaggagcaggagctatgttagcatgttatgatgctacactcggtcc tgcaataaattattataattctggtttaaatattacagatgtaattggtcaacgggaattaaaaatcttcccatcagaag tatcattagtaggtaaaaaactaggaaatgtaacacagattcttaatcgggtgagggtgttatttaatgggaatcccaat tcaacatggataggaaatatggaatgtgagagtttaatatggagtgaattaaatgataagtcaattggtttagtacattg tgacatggagggagcgataggcaaatcagaagaaactgttctacatgaacattatagtattattaggattacatatttaa tcggggatgatgatgttgtcctagtatcaaaaaattataccaactattactccgaattggtctaaaatactctatctatac aagttgtattggaaggatgtaagtgtagtgtcccttaaaacatccaatcctgcctcaacagagctttatttaatttcaaa agatgcttactgtactgtaatggaacccagtaatcttgttttatcaaaacttaaaaggatatcatcaatagaagaaaata atctattaaagtggataatcttatcaaaaaggaagaataacgagtggttacagcatgaaatcaaagaaggagaaagggat tatgggataatgaggccatatcatacagcactgcaaattttggattccaaattaacttaaatcacttagctagagaatt tttatcaactcctgatttaaccaacattaataatataattcaaagttttacaagaacaattaaagatgttatgttcgaat gggtcaatatcactcatgacaataaaagacataaattaggaggaagatataatctattcccgcttaaaaataaggggaaa ttaagattattatcacgaagattagtactaagctggatatcattatccttatcaaccagattactgacgggccgttttcc agatgaaaaatttgaaaatagggcacagaccggatatgtatcattggctgatattgatttagaatccttaaagttattat caagaaatattgtcaaaaattacaaagaacacataggattaatatcatactggtttttgaccaaagaggtcaaaatacta atgaagcttataggaggagtcaaactactaggaattcctaaacagtacaaagagttagaggatcgatcatctcagggtta tgaatatgataatgaatttgatattgattaatacataaaaacataaaataaaacacctattcctcacccattcacttcca acaaaatgaaaagtaagaaaaaacatgtaatatatatataccaaacagagtttttctcttgtttggt rB/HPIV3- RSV G_B3TMCT (SEQ ID NO: 93):

accaaacaagagaagagactggtttgggaatattaattcaaataaaaattaacttaggattaaagaactttaccgaaagg taaggggaaagaaatcctaagagcttagccatgttgagtctattcgacacattcagtgcgcgtaggcaggagaacataac gaaatcagctggtggggctgttattcccgggcaaaaaaacactgtgtctatatttgctcttggaccatcaataacagatg acaatgataaaatgacattggctcttctctttttgtctcattctttagacaatgaaaagcagcatgcgcaaagagctgga tttttagtttctctgttatcaatggcttatgccaacccagaattatatttaacatcaaatggtagtaatgcagatgttaa -continued atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcatttttcaacacaatcagatatggcattgagactagaatggcagctctaa ctctgtctacccttagaccggatatcaacagactcaaggcactgatcgagttatatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatggaatattggaaacacacaaacagcataaataacaccaac aatgaaaccgaaacagccagaggcaaacatagtagcaaggttacaaatatcataatgtacaccttctggacaataacatt aacaatattatcagtcatttttataatgatattgacaaacttaattaaccacaaagtcacaccaacaactgcaatcatac aagatgcaacaagccagatcaagaacacaaccccaacatacctcacccagaatcctcagcttggaatcagtccctctaat ccgtctgaaattacatcacaaatcaccaccatactagcttcaacaacaccaggagtcaagtcaaccctgcaatccacaac agtcaagaccaaaaacacaacaacaactcaaacacaacccagcaagcccaccacaaaacaacgccaaaacaaaccaccaa gcaaacccaataatgattttcactttgaagtgttcaactttgtaccctgcagcatatgcagcaacaatccaacctgctgg gctatctgcaaaagaataccaaacaaaaaaccaggaaagaaaaccactaccaagcccacaaaaaaaccaaccctcaagac aaccaaaaaagatcccaaacctcaaaccactaaatcaaaggaagtacccaccaccaagcccacagaagagccaaccatca acaccaccaaaacaaacatcataactacactactcacctccaacaccacaggaaatccagaactcacaagtcaaatggaa accttccactcaacttcctccgaaggcaatccaagcccttctcaagtctctacaacatccgagtacccatcacaaccttc atctccacccaacacaccacgccagtagtgatagctagcggcgcgccagcaacaagtaagaaaaacttaggattaatgga aattatccaatccagagacggaaggacaaatccagaatccaaccacaactcaatcaaccaaagattcatggaagacaatg ttcaaaacaatcaaatcatggattcttgggaagagggatcaggagataaatcatctgacatctcatcggccctcgacatc attgaattcatactcagcaccgactcccaagagaacacggcagacagcaatgaaatcaacacaggaaccacaagacttag cacgacaatctaccaacctgaatccaaaacaacagaaacaagcaaggaaaatagtggaccagctaacaaaaatcgacagt ttggggcatcacacgaacgtgccacagagacaaaagatagaaatgttaatcaggagactgtacagggaggatataggaga ggaagcagcccagatagtagaactgagactatggtcactcgaagaatctccagaagcagcccagatcctaacaatggaac ccaaatccaggaagatattgattacaatgaagttggagagatggataaggactctactaagagggaaatgcgacaattta aagatgttccagtcaaggtatcaggaagtgatgccattcctccaacaaaacaagatggagacggtgatgatggaagaggc ctggaatctatcagtacatttgattcaggatataccagtatagtgactgccgcaacactagatgacgaagaagaactcct tatgaagaacaacaggccaagaaagtatcaatcaacaccccagaacagtgacaagggaattaaaaaaggggttggaaggc caaaagacacagacaaacaatcatcaatattggactacgaactcaacttcaaaggatcgaagaagagccagaaaatcctc aaagccagcacgaatacaggagaaccaacaagaccacagaatggatcccaggggaagagaatcacatcctggaacatcct caacagcgagagcggcaatcgaacagaatcaacaaaccaaacccatcagacatcaacctcgggacagaaccacacaatgg -continued gaccaagcagaacaacctccgaaccaaggatcaagacacaaaagacggatggaaaggaaagagaggacacagaagagagc actcgatttacagaaagggcgattacattattacagaatcttggtgtaatccaatctgcagcaaaattagacctatacca agacaagagagttgtgtgtgtggcgaatgtcctaaacaatgcagatactgcatcaaagatagacttcctagcaggtttga tgataggagtgtcaatggatcatgataccaaattaaatcagattcagaacgagatattaagtttgaaaactgatcttaaa aagatggatgaatcacatagaagactaattgagaatcaaaaagaacaattatcactgatcacatcattaatctcaaatct taaaattatgacagagagaggagggaagaaggaccaaccagaacctagcgggaggacatccatgatcaagacaaaagcaa aagaagagaaaataaagaaagtcaggtttgaccctcttatggaaacacagggcatcgagaaaaacatccctgacctctat agatcaatagagaaaacaccagaaaacgacacacagatcaaatcagaaataaacagattgaatgatgaatccaatgccac tagattagtacctagaagaataagcagtacaatgagatcattaataataatcattaacaacagcaatttatcatcaaaag caaagcaatcatacatcaacgaactcaagctctgcaagagtgacgaggaagtgtctgagttgatggacatgttcaatgag gatgtcagctcccagtaaaccgccaaccaagggtcaacaccaagaaaaccaatagcacaaaacagccaatcagagaccac cccaatacaccaaaccaatcaacacataacaaagatcgcggccgcatagatgattaagaaaaacttaggatgaaaggact aatcaatcctccgaaacaatgagcatcaccaactccacaatctacacattcccagaatcctctttctccgagaatggcaa catagagccgttaccactcaaggtcaatgaacagagaaaggccatacctcatattagggttgtcaagataggagatccgc ccaaacatggatccagatatctggatgtctttttactgggcttctttgagatggaaaggtcaaaagacaggtatgggagc ataagtgatctagatgatgatccaagttacaaggtttgtggctctggatcattgccacttgggttggctagatacaccgg aaatgatcaggaactcctacaggctgcaaccaagctcgatatagaagtaagaagaactgtaaaggctacggagatgatag tttacactgtacaaaacatcaaacctgaactatatccatggtccagtagattaagaaaagggatgttatttgacgctaat aaggttgcacttgctcctcaatgtcttccactagatagagggataaaattcagggtgatatttgtgaactgcacagcaat tggatcaataactctattcaaaatccctaagtccatggcattgttatcattgcctaatacaatatcaataaatctacaag tacatatcaaaacaggagttcagacagattccaaaggagtagttcagattctagatgaaaaaggtgaaaaatcactaaat ttcatggttcatctcgggttgatcaaaaggaagatgggcagaatgtactcagttgaatattgtaagcagaagatcgagaa gatgagattattattctcattgggattagttggagggatcagcttccacgtcaacgcaactggctctatatcaaagacat tagcaagtcaattagcattcaaaagagaaatctgctatcccctaatggatctgaatccacacttaaattcagttatatgg gcatcatcagttgaaattacaagggtagatgcagttctccagccttcattacctggcgaattcagatactacccaaacat catagcaaaaggggtcgggaaaatcagacagtaaaatcaacaaccctgatatccaccggtgtattaagccgaagcaaata aaggataatcaaaaacttaggacaaaagaggtcaataccaacaactattagcagtcacactcgcaagaataagagagaag ggaccaaaaaagtcaaataggagaaatcaaaacaaaaggtacagaacaccagaacaacaaaatcaaaacatccaactcac tcaaaacaaaaattccaaaagagaccggcaacacaacaagcactgaacacaatgccaacttcaatactgctaattattac aaccatgatcatggcatctttctgccaaatagatatcacaaaactacagcacgtaggtgtattggtcaacagtcccaaag ggatgaagatatcacaaaactttgaaacaagatatctaattttgagcctcataccaaaaatagaagactctaactcttgt ggtgaccaacagatcaagcaatacaagaagttattggatagactgatcatccctttatatgatggattaagattacagaa agatgtgatagtaaccaatcaagaatccaatgaaaacactgatcccagaacaaaacgattctttggaggggtaattggaa ccattgctctgggagtagcaacctcagcacaaattacagcggcagttgctctggttgaagccaagcaggcaagatcagac atcgaaaaactcaaagaagcaattagggacacaaacaaagcagtgcagtcagttcagagctccataggaaatttaatagt agcaattaaatcagtccaggattatgttaacaaagaaatcgtgccatcgattgcgaggctaggttgtgaagcagcaggac ttcaattaggaattgcattaacacagcattactcagaattaacaaacatatttggtgataacataggatcgttacaagaa aaaggaataaaattacaaggtatagcatcattataccgcacaaatatcacagaaatattcacaacatcaacagttgataa atatgatatctatgatctgttatttacagaatcaataaaggtgagagttatagatgttgacttgaatgattactcaatca ccctccaagtcagactccctttattaactaggctgctgaacactcagatctacaaagtagattccatatcatataacatc -continued

```
caaaacagagaatggtatatccctcttcccagccatatcatgacgaaaggggcatttctaggtggagcagacgtcaaaga
atgtatagaagcattcagcagctatatatgcccttctgatccaggatttgtattaaaccatgaaatagagagctgcttat
caggaaacatatcccaatgtccaagaacaacggtcacatcagacattgttccaagatatgcatttgtcaatggaggagtg
gttgcaaactgtataacaaccacctgtacatgcaacggaattggtaatagaatcaatcaaccacctgatcaaggagtaaa
aattataacacataaagaatgtagtacaataggtatcaacggaatgctgttcaatacaaataaagaaggaactcttgcat
tctatacaccaaatgatataacactaaacaattctgttgcacttgatccaattgacatatcaatcgagctcaacaaggcc
aaatcagatctagaagaatcaaaagaatggataagaaggtcaaatcaaaaactagattctattggaaattggcatcaatc
tagcactacaatcataattattttgataatgatcattatattgtttataattaatataacgataattacaattgcaatta
agtattacagaattcaaaagagaaatcgagtggatcaaaatgacaagccatatgtactaacaaacaaataacatatctac
agatcattagatattaaaattataaaaaacttaggagtaaagttacgcaatccaactctactcatataattgaggaagga
cccaatagacaaatccaaattcgagatggaatactggaagcataccaatcacggaaaggatgctggtaatgagctggaga
cgtctatggctactcatggcaacaagctcactaataagataatatacatattatggacaataatcctggtgttattatca
atagtcttcatcatagtgctaattaattccatcaaaagtgaaaaggcccacgaatcattgctgcaagacataaataatga
gtttatggaaattacagaaaagatccaaatggcatcggataataccaatgatctaatacagtcaggagtgaatacaaggc
ttcttacaattcagagtcatgtccagaattacataccaatatcattgacacaacagatgtcagatcttaggaaattcatt
agtgaaattacaattagaaatgataatcaagaagtgctgccacaaagaataacacatgatgtaggtataaaacctttaaa
tccagatgattttggagatgcacgtctggtcttccatctttaatgaaaactccaaaaataaggttaatgccagggccgg
gattattagctatgccaacgactgttgatggctgtgttagaactccgtctttagttataaatgatctgatttatgcttat
acctcaaatctaattactcgaggttgtcaggatataggaaaatcatatcaagtcttacagatagggataataactgtaaa
ctcagacttggtacctgacttaaatcctaggatctctcatacctttaacataaatgacaataggaagtcatgttctctag
cactcctaaatacagatgtatatcaactgtgttcaactcccaaagttgatgaaagatcagattatgcatcatcaggcata
gaagatattgtacttgatattgtcaattatgatggttcaatctcaacaacaagatttaagaataataacataagctttga
tcaaccatatgctgcactatacccatctgttggaccagggatatactacaaaggcaaaataatatttctcgggtatggag
gtcttgaacatccaataaatgagaatgtaatctgcaacacaactgggtgccccgggaaaacacagagagactgtaatcaa
gcatctcatagtccatggttttcagataggaggatggtcaactccatcattgttgttgacaaaggcttaaactcaattcc
aaaattgaaagtatggacgatatctatgcgacaaaattactggggtcagaaggaaggttacttctactaggtaacaaga
tctatatatatacaagatctacaagttggcatagcaagttacaattaggaataattgatattactgattacagtgatata
aggataaaatggacatggcataatgtgctatcaagaccaggaaacaatgaatgtccatggggacattcatgtccagatgg
atgtataacaggagtatatactgatgcatatccactcaatcccacagggagcattgtgtcatctgtcatattagactcac
aaaaatcgagagtgaacccagtcataacttactcaacagcaaccgaaagagtaaacgagctggccatcctaaacagaaca
ctctcagctggatatacaacaacaagctgcattacacactataacaaaggatattgttttcatatagtagaaataaatca
taaaagcttaaacacatttcaacccatgttgttcaaaacagagattccaaaaagctgcagttaatcataattaaccataa
tatgcatcaatctatctataatacaagtatatgataagtaatcagcaatcagacaatagacgtacggaaataataaaaaa
cttaggagaaaagtgtgcaagaaaaatggacaccgagtcccacagcggcacaacatctgacattctgtaccctgaatgtc
acctcaattctcctatagttaaaggaaagatagcacaactgcatacaataatgagtttgcctcagccctacgatatggat
gatgattcaatactgattattactagacaaaaaattaaactcaataaattagataaaagacaacggtcaattaggaaatt
aagatcagtcttaatggaaagagtaagtgatctaggtaaatatacctttatcagatatccagagatgtctagtgaaatgt
tccaattatgtatacccggaattaataataaaataaatgaattgctaagtaaagcaagtaaaacatataatcaaatgact
gatggattaagagatctatgggttactatactatcgaagttagcatcgaaaaatgatggaagtaattatgatatcaatga
agatattagcaatatatcaaatgttcacatgacttatcaatcagacaaatggtataatccattcaagacatggtttacta
ttaagtatgacatgagaagattacaaaaagccaaaaatgagattacattcaataggcataaagattataatctattagaa
```

-continued gaccaaaagaatatattgctgatacatccagaactcgtcttaatattagataaacaaaattacaatgggtatataatgac tcctgaattggtactaatgtattgtgatgtagttgaagggaggtggaatataagttcatgtgcaaaattggatcctaagt tacaatcaatgtattataagggtaacaatttatgggaaataatagatggactattctcgaccttaggagaaagaacattt gacataatatcactattagaaccacttgcattatcgctcattcaaacttatgacccggttaaacagctcaggggggcttt tttaaatcacgtgttatcagaaatggaattaatatttgcagctgagtgtacaacagaggaaatacctaatgtggattata tagataaaatttagatgtgttcaaagaatcaacaatagatgaaatagcagaaattttctctttcttccgaacttttgga caccctccattagaggcgagtatagcagcagagaaagttagaaagtatatgtatactgagaaatgcttgaaatttgatac tatcaataaatgtcatgctatttttttgtacaataattataaatggatatagagaaagacatggtggtcaatggcctccag ttacattacctgtccatgcacatgaatttatcataaatgcatacggatcaaattctgccatatcatatgagaatgctgta gattattataagagcttcataggaataaaatttgacaagtttatagagcctcaattggatgaagacttaactatttatat gaaagataaagcattatccccaaagaaatcaaactgggacacagtctatccagcttcaaacctgttataccgcactaatg tgtctcatgattcacgaagattggttgaagtatttatagcagatagtaaatttgatccccaccaagtattagattacgta gaatcaggatattggctggatgatcctgaatttaatatctcatatagtttaaaagagaaagaaataaaacaagaaggtag actttttgcaaaaatgacatacaagatgagggctacacaagtattatcagaaacattattggcgaataatatagggaaat tcttccaagagaatgggatggttaaaggagaaattgaattactcaagagactaacaacaatatctatgtctggagttccg cggtataatgaggtatacaataattcaaaaagtcacacagaagaacttcaagcttataatgcaattagcagttccaattt atcttctaatcagaagtcaaagaagtttgaatttaaatctacagatatatacaatgatggatacgaaaccgtaagctgct tcttaacgacagatcttaaaaaatattgtttaaattggaggtatgaatcaacagctttattcggtgatacttgtaatcag atatttgggttaaaggaattatttaattggctgcaccctcgccttgaaaagagtacaatatatgttggagatccttattg cccgccatcagatattgaacatttaccacttgatgaccatcctgattcaggattttatgttcataatcctaaaggaggaa tagaagggttttgccaaaagttatggacactcatatctatcagtgcaatacatttagcagctgtcaaaatcggtgtaaga gttactgcaatggttcaaggggataatcaagccatagctgttaccacaagagtacctaataattatgattataaagttaa gaaagagattgtttataaagatgtggtaagatttttttgattccttgagagaggtgatggatgatctgggtcatgagctca aactaaatgaaactataataagtagtaaaatgtttatatatagcaaaaggatatactatgacggaagaatccttcctcag gcattaaaagcattgtctagatgtgtttttttggtctgaaacaatcatagatgagacaagatcagcatcctcaaatctggc tacatcgtttgcaaaggccattgagaatggctactcacctgtattgggatatgtatgctcaatcttcaaaaatatccaac agttgtatatagcgcttggaatgaatataaacccaactataacccaaaatattaaagatcaatatttcaggaatattcat tggatgcaatatgcctccttaatccctgctagtgtcggaggatttaattatatggccatgtcaaggtgttttgtcagaaa cattggagatcctacagtcgctgcgttagccgatattaaaagatttataaaagcaaatttgttagatcgaggtgtccttt acagaattatgaatcaagaaccaggcgagtcttctttttttagactgggcctcagatccctattcatgtaacttaccacaa tctcaaaatataaccaccatgataaagaatataactgcaagaaatgtactacaggactcaccaaacccattactatctgg attatttacaagtacaatgatagaagaggatgaggaattagctgagttcctaatggacaggagaataatcctcccaagag ttgcacatgacattttagataattctcttactggaattaggaatgctatagctggtatgttggatacaacaaaatcacta attcgagtagggataagcagaggaggattaacctataacttattaagaaagataagcaactatgatcttgtacaatatga gacacttagtaaaactttaagactaatagtcagtgacaagattaagtatgaagatatgtgctcagtagacctagccatat cattaagacaaaaaatgtggatgcatttatcaggaggaagaatgataaatggacttgaaactccagatcctttagagtta ctgtctggagtaataataacaggatctgaacattgtaggatatgttattcaactgaaggtgaaagcccatatacatggat gtatttaccaggcaatcttaatataggatcagctgagacaggaatagcatcattaagggtcccttactttggatcagtta cagatgagagatctgaagcacaattagggtatatcaaaaatctaagcaaaccagctaaggctgctataagaatagcaatg atatatacttgggcatttgggaatgacgaaatatcttggatggaagcatcacagattgcacaaacacgtgcaaactttac -continued attggatagcttaaagattttgacaccagtgacaacatcaacaaatctatcacacaggttaaaagatactgctactcaga tgaaattttctagtacatcacttattagagtaagcaggttcatcacaatatctaatgataatatgtctattaaagaagca aatgaaactaaagatacaaatcttatttatcaacaggtaatgttaacaggattaagtgtatttgaatatctatttaggtt agaggagagtacaggacataaccctatggtcatgcatctacatatagaggatggatgttgtataaaagagagttacaatg atgagcatatcaatccggagtctacattagagttaatcaaataccctgagagtaatgaatttatatatgataaggaccct ttaaaggatatagatctatcaaaattaatggttataagagatcattcttatacaattgacatgaattactgggatgacac agatattgtacatgcaatatcaatatgtactgcagttacaatagcagatacaatgtcgcagctagatcgggataatctta aggagctggttgtgattgcaaatgatgatgatattaacagtctgataactgaatttctgaccctagatatactagtgttt ctcaaaacatttggagggttactcgtgaatcaatttgcatataccctttatggattgaaaatagaaggaagggatcccat ttgggattatataatgagaacattaaaagacacctcacattcagtacttaaagtattatctaatgcactatctcatccaa aagtgtttaagagattttgggattgtggagttttgaatcctatttatggtcctaatactgctagtcaagatcaagttaag cttgctctctcgatttgcgagtactccttggatctatttatgagagaatggttgaatggagcatcacttgagatctatat ctgtgatagtgacatggaaatagcaaatgacagaagacaagcatttctctcaagacatcttgcctttgtgtgttgtttag cagagatagcatcttttggaccaaatttattaaatctaacatatctagagagacttgatgaattaaaacaatacttagat ctgaacatcaaagaagatcctactcttaaatatgtgcaagtatcaggactgttaattaaatcattcccctcaactgttac gtatgtaaggaaaactgcgattaagtatctgaggattcgtggtattaatccgcctgaaacgattgaagattgggatccca tagaagatgagaatatcttagacaatattgttaaaactgtaaatgacaattgcagtgataatcaaaagagaaataaaagt agttatttctggggattagctctaaagaattatcaagtcgtgaaaataagatccataacgagtgattctgaagttaatga agcttcgaatgttactacacatggaatgacacttcctcagggaggaagttatctatcacatcagctgaggttatttggag taaacagtacaagttgtcttaaagctcttgaattatcacaaatcttaatgagggaagttaaaaaagataaagatagactc tttttaggagaaggagcaggagctatgttagcatgttatgatgctacactcggtcctgcaataaattattataattctgg tttaaatattacagatgtaattggtcaacgggaattaaaaatcttcccatcagaagtatcattagtaggtaaaaaactag gaaatgtaacacagattcttaatcgggtgagggtgttatttaatgggaatcccaattcaacatggataggaaatatggaa tgtgagagtttaatatggagtgaattaaatgataagtcaattggtttagtacattgtgacatggagggagcgataggcaa atcagaagaaactgttctacatgaacattatagtattattaggattacatatttaatcggggatgatgatgttgtcctag tatcaaaaattataccaactattactccgaattggtctaaaatactctatctatacaagttgtattggaaggatgtaagt gtagtgtcccttaaaacatccaatcctgcctcaacagagctttatttaatttcaaaagatgcttactgtactgtaatgga acccagtaatcttgttttatcaaaacttaaaaggatatcatcaatagaagaaaataatctattaaagtggataatcttat caaaaaggaagaataacgagtggttacagcatgaaatcaaagaaggagaaagggattatgggataatgaggccatatcat acagcactgcaaattttggattccaaattaacttaaatcacttagctagagaattttatcaactcctgatttaaccaa cattaataatataattcaaagttttacaagaacaattaaagatgttatgttcgaatgggtcaatatcactcatgacaata aaagacataaattaggaggaagatataatctattcccgcttaaaaataaggggaaattaagattattatcacgaagatta gtactaagctggatatcattatccttatcaaccagattactgacgggccgttttccagatgaaaaatttgaaaatagggc acagaccggatatgtatcattggctgatattgatttagaatccttaaagttattatcaagaaatattgtcaaaaattaca aagaacacataggattaatatcatactggttttgaccaaagaggtcaaaatactaatgaagcttataggaggagtcaaa ctactaggaattcctaaacagtacaaagagttagaggatcgatcatctcagggttatgaatatgataatgaatttgatat tgattaatacataaaaacataaaataaaacacctattcctcacccattcacttccaacaaaatgaaaagtaagaaaaaca tgtaatatatatataccaaacagagtttttctcttgtttggt rB/HPIV3-RSV G_B3CT (SEQ ID NO: 94):
accaaacaagagaagagactggtttgggaatattaattcaaataaaaattaacttaggattaaagaactttaccgaaagg taaggggaaagaaatcctaagagcttagccatgttgagtctattcgacacattcagtgcgcgtaggcaggagaacataac -continued gaaatcagctggtggggctgttattcccgggcaaaaaaacactgtgtctatatttgctcttggaccatcaataacagatg acaatgataaaatgacattggctcttctctttttgtctcattctttagacaatgaaaagcagcatgcgcaaagagctgga tttttagtttctctgttatcaatggcttatgccaacccagaattatatttaacatcaaatggtagtaatgcagatgttaa atatgttatctacatgatagagaaagacccaggaagacagaaatatggtgggtttgtcgtcaagactagagagatggttt atgaaaagacaactgattggatgttcgggagtgatcttgagtatgatcaagacaatatgttgcaaaatggtagaagcact tctacaatcgaggatcttgttcatacttttggatatccatcgtgtcttggagcccttataatccaagtttggataatact tgttaaggctataaccagtatatcaggattgaggaaaggattctttactcggttagaagcatttcgacaagatggaacag ttaaatccagtctagtgttgagcggtgatgcagtagaacaaattggatcaattatgaggtcccaacagagcttggtaaca ctcatggttgaaacactgataacaatgaacacaggcaggaatgatctgacaacaatagaaaagaatatacagattgtagg aaactacatcagagatgcaggtcttgcttcatttttcaacacaatcagatatggcattgagactagaatggcagctctaa ctctgtctacccttagaccggatatcaacagactcaaggcactgatcgagttatatctatcaaaggggccacgtgctcct tttatatgcattttgagagatcccgtgcatggtgagtttgcaccaggcaactatcctgccctctggagttatgcgatggg tgtagcagttgtacaaaacaaggccatgcaacagtatgtaacaggaaggtcttatctggatattgaaatgttccaacttg gtcaagcagtggcacgtgatgccgagtcgcagatgagttcaatattagaggatgaactgggggtcacacaagaagccaag caaagcttgaagaaacacatgaagaacatcagcagttcagatacaacctttcataagcctacaggggggatcagccataga aatggcgatagatgaagaagcagggcagcctgaatccagaggagatcaggatcaaggagatgagcctcggtcatccatag ttccttatgcatgggcagacgaaaccgggaatgacaatcaaactgaatcaactacagaaattgacagcatcaaaactgaa caaagaaacatcagagacaggctgaacaaaagactcaacgagaaaaggaaacagagtgacccgagatcaactgacatcac aaacaacacaaatcaaactgaaatagatgatttgttcagtgcattcggaagcaactagtcacaaagagatgaccaggcgc gccaagtaagaaaaacttaggattaatggacctgcaggatggaatattggaaacacacaaacagcataaataacaccaac aatgaaaccgaaacagccagaggcaaacatagtagcaaggttacaaatgtagcacaaatcacattatccattctggcaat gataatctcaacttcacttataattgcagccatcatattcatagcctcggcaaaccacaaagtcacaccaacaactgcaa tcatacaagatgcaacaagccagatcaagaacacaaccccaacatacctcacccagaatcctcagcttggaatcagtccc tctaatccgtctgaaattacatcacaaatcaccaccatactagcttcaacaacaccaggagtcaagtcaaccctgcaatc cacaacagtcaagaccaaaaacacaacaacaactcaaacacaacccagcaagcccaccacaaaacaacgccaaaacaaac caccaagcaaacccaataatgattttcactttgaagtgttcaactttgtaccctgcagcatatgcagcaacaatccaacc tgctgggctatctgcaaaagaataccaaacaaaaaaccaggaaagaaaaccactaccaagcccacaaaaaaaccaaccct caagacaaccaaaaaagatcccaaacctcaaaccactaaatcaaaggaagtacccaccaccaagcccacagaagagccaa ccatcaacaccaccaaaacaaacatcataactacactactcacctccaacaccacaggaaatccagaactcacaagtcaa atggaaaccttccactcaacttcctccgaaggcaatccaagcccttctcaagtctctacaacatccgagtacccatcaca accttcatctccacccaacacaccacgccagtagtgatagctagcggcgcgccagcaacaagtaagaaaaacttaggatt aatggaaattatccaatccagagacggaaggacaaatccagaatccaaccacaactcaatcaaccaaagattcatggaag acaatgttcaaaacaatcaaatcatggattcttgggaagagggatcaggagataaatcatctgacatctcatcggccctc gacatcattgaattcatactcagcaccgactcccaagagaacacggcagacagcaatgaaatcaacacaggaaccacaag acttagcacgacaatctaccaacctgaatccaaaacaacagaaacaagcaaggaaaatagtggaccagctaacaaaaatc gacagtttggggcatcacacgaacgtgccacagagacaaaagatagaaatgttaatcaggagactgtacagggaggatat aggagaggaagcagcccagatagtagaactgagactatggtcactcgaagaatctccagaagcagcccagatcctaacaa tggaacccaaatccaggaagatattgattacaatgaagttggagagatggataaggactctactaagagggaaatgcgac aatttaaagatgttccagtcaaggtatcaggaagtgatgccattcctccaacaaaacaagatggagacggtgatgatgga agaggcctggaatctatcagtacatttgattcaggatataccagtatagtgactgccgcaacactagatgacgaagaaga actccttatgaagaacaacaggccaagaaagtatcaatcaacaccccagaacagtgacaagggaattaaaaaggggttg -continued gaaggccaaaagacacagacaaacaatcatcaatattggactacgaactcaacttcaaaggatcgaagaagagccagaaa
atcctcaaagccagcacgaatacaggagaaccaacaagaccacagaatggatcccaggggaagagaatcacatcctggaa
catcctcaacagcgagagcggcaatcgaacagaatcaacaaaccaaacccatcagacatcaacctcgggacagaaccaca
caatgggaccaagcagaacaacctccgaaccaaggatcaagacacaaaagacggatggaaaggaaagagaggacacagaa
gagagcactcgatttacagaaagggcgattacattattacagaatcttggtgtaatccaatctgcagcaaaattagacct
ataccaagacaagagagttgtgtgtgtggcgaatgtcctaaacaatgcagatactgcatcaaagatagacttcctagcag
gtttgatgataggagtgtcaatggatcatgataccaaattaaatcagattcagaacgagatattaagtttgaaaactgat
cttaaaaagatggatgaatcacatagaagactaattgagaatcaaaaagaacaattatcactgatcacatcattaatctc
aaatcttaaaattatgacagagagaggagggaagaaggaccaaccagaacctagcgggaggacatccatgatcaagacaa
aagcaaaagaagagaaaataaagaaagtcaggtttgaccctcttatggaaacacagggcatcgagaaaaacatccctgac
ctctatagatcaatagagaaaacaccagaaaacgacacacagatcaaatcagaaataaacagattgaatgatgaatccaa
tgccactagattagtacctagaagaataagcagtacaatgagatcattaataataatcattaacaacagcaatttatcat
caaaagcaaagcaatcatacatcaacgaactcaagctctgcaagagtgacgaggaagtgtctgagttgatggacatgttc
aatgaggatgtcagctcccagtaaaccgccaaccaagggtcaacaccaagaaaaccaatagcacaaaacagccaatcaga
gaccaccccaatacaccaaaccaatcaacacataacaaagatcgcggccgcatagatgattaagaaaaacttaggatgaa
aggactaatcaatcctccgaaacaatgagcatcaccaactccacaatctacacattcccagaatcctctttctccgagaa
tggcaacatagagccgttaccactcaaggtcaatgaacagagaaaggccatacctcatattagggttgtcaagataggag
atccgcccaaacatggatccagatatctggatgtctttttactgggcttctttgagatggaaaggtcaaaagacaggtat
gggagcataagtgatctagatgatgatccaagttacaaggtttgtggctctggatcattgccacttgggttggctagata
caccggaaatgatcaggaactcctacaggctgcaaccaagctcgatatagaagtaagaagaactgtaaaggctacggaga
tgatagtttacactgtacaaaacatcaaacctgaactatatccatggtccagtagattaagaaaagggatgttatttgac
gctaataaggttgcacttgctcctcaatgtcttccactagatagagggataaaattcagggtgatatttgtgaactgcac
agcaattggatcaataactctattcaaaatccctaagtccatggcattgttatcattgcctaatacaatatcaataaatc
tacaagtacatatcaaaacaggagttcagacagattccaaaggagtagttcagattctagatgaaaaaggtgaaaaatca
ctaaatttcatggttcatctcgggttgatcaaaaggaagatgggcagaatgtactcagttgaatattgtaagcagaagat
cgagaagatgagattattattctcattgggattagttggagggatcagcttccacgtcaacgcaactggctctatatcaa
agacattagcaagtcaattagcattcaaaagagaaatctgctatcccctaatggatctgaatccacacttaaattcagtt
atatgggcatcatcagttgaaattacaagggtagatgcagttctccagccttcattacctggcgaattcagatactaccc
aaacatcatagcaaaaggggtcgggaaaatcagacagtaaaatcaacaaccctgatatccaccggtgtattaagccgaag
caaataaaggataatcaaaaacttaggacaaaagaggtcaataccaacaactattagcagtcacactcgcaagaataaga
gagaagggaccaaaaaagtcaaataggagaaatcaaaacaaaaggtacagaacaccagaacaacaaaatcaaaacatcca
actcactcaaaacaaaaattccaaaagagaccggcaacacaacaagcactgaacacaatgccaacttcaatactgctaat
tattacaaccatgatcatggcatctttctgccaaatagatatcacaaaactacagcacgtaggtgtattggtcaacagtc
ccaaagggatgaagatatcacaaaactttgaaacaagatatctaattttgagcctcataccaaaaatagaagactctaac
tcttgtggtgaccaacagatcaagcaatacaagaagttattggatagactgatcatccctttatatgatggattaagatt
acagaaagatgtgatagtaaccaatcaagaatccaatgaaaacactgatcccagaacaaaacgattctttggaggggtaa
ttggaaccattgctctgggagtagcaacctcagcacaaattacagcggcagttgctctggttgaagccaagcaggcaaga
tcagacatcgaaaaactcaaagaagcaattagggacacaaacaaagcagtgcagtcagttcagagctccataggaaattt
aatagtagcaattaaatcagtccaggattatgttaacaaagaaatcgtgccatcgattgcgaggctaggttgtgaagcag
caggacttcaattaggaattgcattaacacagcattactcagaattaacaaacatatttggtgataacataggatcgtta -continued caagaaaaaggaataaaattacaaggtatagcatcattataccgcacaaatatcacagaaatattcacaacatcaacagt tgataaatatgatatctatgatctgttatttacagaatcaataaaggtgagagttatagatgttgacttgaatgattact caatcaccctccaagtcagactccctttattaactaggctgctgaacactcagatctacaaagtagattccatatcatat aacatccaaaacagagaatggtatatccctcttcccagccatatcatgacgaaaggggcatttctaggtggagcagacgt caaagaatgtatagaagcattcagcagctatatatgcccttctgatccaggatttgtattaaaccatgaaatagagagct gcttatcaggaaacatatcccaatgtccaagaacaacggtcacatcagacattgttccaagatatgcatttgtcaatgga ggagtggttgcaaactgtataacaaccacctgtacatgcaacggaattggtaatagaatcaatcaaccacctgatcaagg agtaaaaattataacacataaagaatgtagtacaataggtatcaacggaatgctgttcaatacaaataaagaaggaactc ttgcattctatacaccaaatgatataacactaaacaattctgttgcacttgatccaattgacatatcaatcgagctcaac aaggccaaatcagatctagaagaatcaaaagaatggataagaaggtcaaatcaaaaactagattctattggaaattggca tcaatctagcactacaatcataattattttgataatgatcattatattgtttataattaatataacgataattacaattg caattaagtattacagaattcaaaagagaaatcgagtggatcaaaatgacaagccatatgtactaacaaacaaataacat atctacagatcattagatattaaaattataaaaaacttaggagtaaagttacgcaatccaactctactcatataattgag gaaggacccaatagacaaatccaaattcgagatggaatactggaagcataccaatcacggaaaggatgctggtaatgagc tggagacgtctatggctactcatggcaacaagctcactaataagataatatacatattatggacaataatcctggtgtta ttatcaatagtcttcatcatagtgctaattaattccatcaaaagtgaaaaggcccacgaatcattgctgcaagacataaa taatgagtttatggaaattacagaaaagatccaaatggcatcggataataccaatgatctaatacagtcaggagtgaata caaggcttcttacaattcagagtcatgtccagaattacataccaatatcattgacacaacagatgtcagatcttaggaaa ttcattagtgaaattacaattagaaatgataatcaagaagtgctgccacaaagaataacacatgatgtaggtataaaacc tttaaatccagatgatttttggagatgcacgtctggtcttccatctttaatgaaaactccaaaaataaggttaatgccag ggccgggattattagctatgccaacgactgttgatggctgtgttagaactccgtctttagttataaatgatctgatttat gcttatacctcaaatctaattactcgaggttgtcaggatataggaaaatcatatcaagtcttacagatagggataataac tgtaaactcagacttggtacctgacttaaatcctaggatctctcatacctttaacataaatgacaataggaagtcatgtt ctctagcactcctaaatacagatgtatatcaactgtgttcaactcccaaagttgatgaaagatcagattatgcatcatca ggcatagaagatattgtacttgatattgtcaattatgatggttcaatctcaacaacaagatttaagaataataacataag ctttgatcaaccatatgctgcactatacccatctgttggaccagggatatactacaaaggcaaaataatatttctcgggt atggaggtcttgaacatccaataaatgagaatgtaatctgcaacacaactgggtgccccgggaaaacacagagagactgt aatcaagcatctcatagtccatggttttcagataggaggatggtcaactccatcattgttgttgacaaaggcttaaactc aattccaaaattgaaagtatggacgatatctatgcgacaaaattactgggggtcagaaggaaggttacttctactaggta acaagatctatatatatacaagatctacaagttggcatagcaagttacaattaggaataattgatattactgattacagt gatataaggataaaatggacatggcataatgtgctatcaagaccaggaaacaatgaatgtccatggggacattcatgtcc agatggatgtataacaggagtatatactgatgcatatccactcaatcccacagggagcattgtgtcatctgtcatattag actcacaaaaatcgagagtgaacccagtcataacttactcaacagcaaccgaaagagtaaacgagctggccatcctaaac agaacactctcagctggatatacaacaacaagctgcattacacactataacaaaggatattgttttcatatagtagaaat aaatcataaaagcttaaacacatttcaacccatgttgttcaaaacagagattccaaaaagctgcagttaatcataattaa ccataaatatgcatcaatctatctataatacaagtatatgataagtaatcagcaatcagacaatagacgtacggaaataat aaaaaacttaggagaaaagtgtgcaagaaaaatggacaccgagtcccacagcggcacaacatctgacattctgtaccctg aatgtcacctcaattctcctatagttaaaggaaagatagcacaactgcatacaataatgagtttgcctcagccctacgat atggatgatgattcaatactgattattactagacaaaaaattaaactcaataaattagataaaagacaacggtcaattag gaaattaagatcagtcttaatggaaagagtaagtgatctaggtaaatataccttttatcagatatccagagatgtctagtg aaatgttccaattatgtatacccggaattaataataaaataaatgaattgctaagtaaagcaagtaaaacatataatcaa -continued atgactgatggattaagagatctatgggttactatactatcgaagttagcatcgaaaaatgatggaagtaattatgatat
caatgaagatattagcaatatatcaaatgttcacatgacttatcaatcagacaaatggtataatccattcaagacatggt
ttactattaagtatgacatgagaagattacaaaaagccaaaaatgagattacattcaataggcataaagattataatcta
ttagaagaccaaaagaatatattgctgatacatccagaactcgtcttaatattagataaacaaaattacaatgggtatat
aatgactcctgaattggtactaatgtattgtgatgtagttgaagggaggtggaatataagttcatgtgcaaaattggatc
ctaagttacaatcaatgtattataagggtaacaatttatgggaaataatagatggactattctcgaccttaggagaaaga
acatttgacataatatcactattagaaccacttgcattatcgctcattcaaacttatgacccggttaaacagctcagggg
ggcttttttaaatcacgtgttatcagaaatggaattaatatttgcagctgagtgtacaacagaggaaatacctaatgtgg
attatatagataaaattttagatgtgttcaaagaatcaacaatagatgaaatagcagaaattttctctttcttccgaact
tttggacaccctccattagaggcgagtatagcagcagagaaagttagaaagtatatgtatactgagaaatgcttgaaatt
tgatactatcaataaatgtcatgctattttttgtacaataattataaatggatatagagaaagacatggtggtcaatggc
ctccagttacattacctgtccatgcacatgaatttatcataaatgcatacggatcaaattctgccatatcatatgagaat
gctgtagattattataagagcttcataggaataaaatttgacaagtttatagagcctcaattggatgaagacttaactat
ttatatgaaagataaagcattatccccaaagaaatcaaactgggacacagtctatccagcttcaaacctgttataccgca
ctaatgtgtctcatgattcacgaagattggttgaagtatttatagcagatagtaaatttgatccccaccaagtattagat
tacgtagaatcaggatattggctggatgatcctgaatttaatatctcatatagtttaaaagagaaagaaataaaacaaga
aggtagacttttttgcaaaaatgacatacaagatgagggctacacaagtattatcagaaacattattggcgaatatatag
ggaaattcttccaagagaatgggatggttaaaggagaaattgaattactcaagagactaacaacaatatctatgtctgga
gttccgcggtataatgaggtatacaataattcaaaaagtcacacagaagaacttcaagcttataatgcaattagcagttc
caatttatcttctaatcagaagtcaaagaagtttgaatttaaatctacagatatatacaatgatggatacgaaaccgtaa
gctgcttcttaacgacagatcttaaaaaatattgtttaaattggaggtatgaatcaacagctttattcggtgatacttgt
aatcagatatttgggttaaaggaattatttaattggctgcaccctcgccttgaaaagagtacaatatatgttggagatcc
ttattgcccgccatcagatattgaacatttaccacttgatgaccatcctgattcaggattttatgttcataatcctaaag
gaggaatagaagggttttgccaaaagttatggacactcatatctatcagtgcaatacatttagcagctgtcaaaatcggt
gtaagagttactgcaatggttcaaggggataatcaagccatagctgttaccacaagagtacctaataattatgattataa
agttaagaaagagattgtttataaagatgtggtaagatttttttgattccttgagagaggtgatggatgatctgggtcatg
agctcaaactaaatgaaactataataagtagtaaaatgtttatatatagcaaaaggatatactatgacggaagaatcctt
cctcaggcattaaaagcattgtctagatgtgtttttttggtctgaaacaatcatagatgagacaagatcagcatcctcaaa
tctggctacatcgtttgcaaaggccattgagaatggctactcacctgtattgggatatgtatgctcaatcttcaaaaata
tccaacagttgtatatagcgcttggaatgaatataaacccaactataacccaaaatattaaagatcaatatttcaggaat
attcattggatgcaatatgcctccttaatccctgctagtgtcggaggatttaattatatggccatgtcaaggtgttttgt
cagaaacattggagatcctacagtcgctgcgttagccgatattaaaagatttataaaagcaaatttgttagatcgaggtg
tcctttacagaattatgaatcaagaaccaggcgagtcttcttttttagactgggcctcagatccctattcatgtaactta
ccacaatctcaaaatataaccaccatgataaagaatataactgcaagaaatgtactacaggactcaccaaacccattact
atctggattatttacaagtacaatgatagaagaggatgaggaattagctgagttcctaatggacaggagaataatcctcc
caagagttgcacatgacattttagataattctcttactggaattaggaatgctatagctggtatgttggatacaacaaaa
tcactaattcgagtagggataagcagaggaggattaacctataacttattaagaaagataagcaactatgatcttgtaca
atatgagacacttagtaaaactttaagactaatagtcagtgacaagattaagtatgaagatatgtgctcagtagacctag
ccatatcattaagacaaaaaatgtggatgcatttatcaggaggaagaatgataaatggacttgaaactccagatccttta
gagttactgtctggagtaataataacaggatctgaacattgtaggatatgttattcaactgaaggtgaaagcccatatac -continued atggatgtatttaccaggcaatcttaatataggatcagctgagacaggaatagcatcattaagggtcccttactttggat cagttacagatgagagatctgaagcacaattagggtatatcaaaaatctaagcaaaccagctaaggctgctataagaata gcaatgatatatacttgggcatttgggaatgacgaaatatcttggatggaagcatcacagattgcacaaacacgtgcaaa ctttacattggatagcttaaagattttgacaccagtgacaacatcaacaaatctatcacacaggttaaaagatactgcta ctcagatgaaattttctagtacatcacttattagagtaagcaggttcatcacaatatctaatgataatatgtctattaaa gaagcaaatgaaactaaagatacaaatcttatttatcaacaggtaatgttaacaggattaagtgtatttgaatatctatt taggttagaggagagtacaggacataaccctatggtcatgcatctacatatagaggatggatgttgtataaaagagagtt acaatgatgagcatatcaatccggagtctacattagagttaatcaaataccctgagagtaatgaatttatatatgataag gaccctttaaaggatatagatctatcaaaattaatggttataagagatcattcttatacaattgacatgaattactggga tgacacagatattgtacatgcaatatcaatatgtactgcagttacaatagcagatacaatgtcgcagctagatcgggata atcttaaggagctggttgtgattgcaaatgatgatgatattaacagtctgataactgaatttctgaccctagatatacta gtgtttctcaaaacatttggagggttactcgtgaatcaatttgcatatacccttttatggattgaaaatagaaggaaggga tcccatttgggattatataatgagaacattaaaagacacctcacattcagtacttaaagtattatctaatgcactatctc atccaaaagtgtttaagagattttgggattgtggagttttgaatcctatttatggtcctaatactgctagtcaagatcaa gttaagcttgctctctcgatttgcgagtactccttggatctatttatgagagaatggttgaatggagcatcacttgagat ctatatctgtgatagtgacatggaaatagcaaatgacagaagacaagcatttctctcaagacatcttgcctttgtgtgtt gtttagcagagatagcatcttttggaccaaatttattaaatctaacatatctagagagacttgatgaattaaaacaatac ttagatctgaacatcaaagaagatcctactcttaaatatgtgcaagtatcaggactgttaattaaatcattcccctcaac tgttacgtatgtaaggaaaactgcgattaagtatctgaggattcgtggtattaatccgcctgaaacgattgaagattggg atcccatagaagatgagaatatcttagacaatattgttaaaactgtaaatgacaattgcagtgataatcaaaagagaaat aaaagtagttatttctggggattagctctaaagaattatcaagtcgtgaaaataagatccataacgagtgattctgaagt taatgaagcttcgaatgttactacacatggaatgacacttcctcagggaggaagttatctatcacatcagctgaggttat ttggagtaaacagtacaagttgtcttaaagctcttgaattatcacaaatcttaatgagggaagttaaaaaagataaagat agactctttttaggagaaggagcaggagctatgttagcatgttatgatgctacactcggtcctgcaataaattattataa ttctggtttaaatattacagatgtaattggtcaacgggaattaaaaatcttcccatcagaagtatcattagtaggtaaaa aactaggaaatgtaacacagattcttaatcgggtgagggtgttatttaatgggaatcccaattcaacatggataggaaat atggaatgtgagagtttaatatggagtgaattaaatgataagtcaattggtttagtacattgtgacatggagggagcgat aggcaaatcagaagaaactgttctacatgaacattatagtattattaggattacatatttaatcggggatgatgatgttg tcctagtatcaaaaattataccaactattactccgaattggtctaaaatactctatctatacaagttgtattggaaggat gtaagtgtagtgtcccttaaaacatccaatcctgcctcaacagagctttatttaatttcaaaagatgcttactgtactgt aatggaacccagtaatcttgttttatcaaaacttaaaaggatatcatcaatagaagaaaataatctattaaagtggataa tcttatcaaaaaggaagaataacgagtggttacagcatgaaatcaaagaaggagaaagggattatgggataatgaggcca tatcatacagcactgcaaatttttggattccaaattaacttaaatcacttagctagagaatttttatcaactcctgattt aaccaacattaataatataattcaaagttttacaagaacaattaaagatgttatgttcgaatgggtcaatatcactcatg acaataaaagacataaattaggaggaagatataatctattcccgcttaaaaataaggggaaattaagattattatcacga agattagtactaagctggatatcattatccttatcaaccagattactgacgggccgttttccagatgaaaaatttgaaaa tagggcacagaccggatatgtatcattggctgatattgatttagaatccttaaagttattatcaagaaatattgtcaaaa attacaaagaacacataggattaatatcatactggttttttgaccaaagaggtcaaaatactaatgaagcttataggagga gtcaaactactaggaattcctaaacagtacaaagagttagaggatcgatcatctcagggttatgaatatgataatgaatt tgatattgattaatacataaaaacataaaataaaacacctattcctcacccattcacttccaacaaaatgaaaagtaaga aaaacatgtaatatatatataccaaacagagtttttctcttgtttggt It will be apparent that the precise details of the methods or compositions described may be varied or modified without departing from the spirit of the described embodiments. We claim all such modifications and variations that fall within the scope and spirit of the claims below.

It is claimed:

1. A recombinant chimeric bovine/human parainfluenza virus 3 (rB/HPIV3), comprising:
- a genome comprising, in a 3' to 5' order, a 3' leader region, a BPIV3 N gene, a heterologous gene, BPIV3 P and M genes, HPIV3 F and HN genes, a BPIV3 L gene, and a 5' trailer region;
- wherein the heterologous gene encodes one of:
  - (a) a recombinant RSV G protein comprising a RSV G ectodomain, a BPIV3 HN transmembrane domain, and a BPIV3 HN cytoplasmic tail, wherein the recombinant RSV G protein comprises or consists of the amino acid sequence set forth as any one of SEQ ID NO: 31, 62, 64, 66, or 68, or an amino acid sequence at least 90% identical thereto;
  - (b) a recombinant RSV G protein comprising a RSV G ectodomain, a HPIV3 HN transmembrane domain, and a HPIV3 HN cytoplasmic tail, wherein the recombinant RSV G protein comprises or consists of the amino acid sequence set forth as any one of SEQ ID NO: 70, 72, 74, 76, or 78, or an amino acid sequence at least 90% identical thereto; or
  - (c) a recombinant RSV G protein comprising a RSV G ectodomain, a HPIV1 HN transmembrane domain, and a HPIV1 HN cytoplasmic tail, wherein the recombinant RSV G protein comprises or consists of the amino acid sequence set forth as any one of SEQ ID NO: 80, 82, 84, 86, or 88, or an amino acid sequence at least 90% identical thereto;
- wherein the HPIV3 HN gene encodes a HPIV3 HN protein comprising threonine and proline residues at positions 263 and 370 according to a reference HPIV3 HN protein sequence set forth as SEQ ID NO: 7; and wherein the recombinant B/HPIV3 is infectious, attenuated, and self-replicating.

2. The rB/HPIV3 of claim 1, wherein the RSV G ectodomain comprises or consists of the amino acid sequence set forth as any one of SEQ ID NOs: 23, 48, 50, 52, or 54 or an amino acid sequence at least 90% identical thereto.

3. The rB/HPIV3 of claim 1, wherein the BPIV3 HN transmembrane domain and cytoplasmic tail comprises or consists of the amino acid sequence set forth as SEQ ID NO: 29, or an amino acid sequence at least 90% identical thereto.

4. The rB/HPIV3 of claim 1, wherein the HPIV3 HN transmembrane domain and cytoplasmic tail comprises or consists of the amino acid sequence set forth as SEQ ID NO: 57, or an amino acid sequence at least 90% identical thereto.

5. The rB/HPIV3 of claim 1, wherein the HPIV1 HN transmembrane domain and cytoplasmic tail comprises or consists of the amino acid sequence set forth as SEQ ID NO: 60, or an amino acid sequence at least 90% identical thereto.

6. The rB/HPIV3 of claim 1, wherein the recombinant RSV G protein comprising the RSV G ectodomain, the BPIV3 HN transmembrane domain, and the BPIV3 HN cytoplasmic tail comprises or consists of the amino acid sequence set forth as any one of SEQ ID NOs: 31, 62, 64, 66, or 68, or an amino acid sequence at least 90% identical thereto.

7. The rB/HPIV3 of claim 1, wherein the recombinant RSV G protein comprising the RSV G ectodomain, the HPIV3 HN transmembrane domain, and the HPIV3 HN cytoplasmic tail comprises or consists of the amino acid sequence set forth as any one of SEQ ID NOs: 70, 72, 74, 76, or 78, or an amino acid sequence at least 90% identical thereto.

8. The rB/HPIV3 of claim 1, wherein the recombinant RSV G protein comprising the RSV G ectodomain, the HPIV1 HN transmembrane domain, and the HPIV1 HN cytoplasmic tail comprises or consists of the amino acid sequence set forth as any one of SEQ ID NOs: 80, 82, 84, 86, or 88, or an amino acid sequence at least 90% identical thereto.

9. The rB/HPIV3 of claim 1, wherein the RSV G ectodomain is from a human subtype A RSV or human subtype B RSV.

10. The rB/HPIV3 of claim 1, wherein the RSV G protein is a wild-type RSV G protein from a human subtype A RSV or human subtype B RSV.

11. The rB/HPIV3 of claim 1, wherein:

the BPIV3 N gene encodes an N protein comprising or consisting of the amino acid sequence set forth as SEQ ID NO: 1, or an amino acid sequence at least 90% identical thereto;

the BPIV3 P gene encodes P, C, and V proteins comprising or consisting of the amino acid sequences set forth as SEQ ID NOs: 2, 3, and 4, respectively, or amino acid sequences at least 90% identical thereto;

the BPIV3 M gene encodes an M protein comprising or consisting of the amino acid sequence set forth as SEQ ID NO: 5, or an amino acid sequence at least 90% identical thereto;

the HPIV3 F gene encodes an F protein comprising or consisting of the amino acid sequence set forth as SEQ ID NO: 6, or an amino acid sequence at least 90% identical thereto;

the HPIV3 HN gene encodes an HN protein comprising or consisting of the amino acid sequence set forth as SEQ ID NO: 7, or an amino acid sequence at least 90% identical to SEQ ID NO: 7; and/or the BPIV3 L gene encodes an L protein comprising or consisting of the amino acid sequence set forth as SEQ ID NO: 10, or an amino acid sequence at least 90% identical thereto.

12. The rB/HPIV3 of claim 1, wherein the heterologous gene is codon-optimized for expression in human cells.

13. The rB/HPIV3 of claim 1, wherein the genome comprises an antigenomic cDNA sequence set forth as any one of SEQ ID NOs: 93.

14. The rB/HPIV3 of claim 1, wherein the rB/HPIV3 induces an immune response to RSV G protein, HPIV3 F protein, and HPIV3 HN protein.

15. The rB/HPIV3 of claim 1, wherein the rB/HPIV3 induces an immune response that neutralizes RSV and HPIV3.

16. A nucleic acid molecule comprising the nucleotide sequence of the genome of the rB/HPIV3 of claim 1, or an antigenomic cDNA or RNA sequence of the genome.

17. A vector comprising the isolated nucleic acid molecule of claim 16.

18. An isolated host cell comprising the nucleic acid molecule or vector of claim 16.

19. A method of producing a rB/HPIV3, comprising:

transfecting a permissive cell culture with the vector of claim 17;

incubating the cell culture for a sufficient period of time to allow for viral replication; and purifying the replicated virus to produce the rB/HPIV3.

20. A rB/HPIV3 produced by the method of claim 19.

21. An immunogenic composition comprising the rB/HPIV3 of claim 1 and a pharmaceutically acceptable carrier.

22. A method of eliciting an immune response to respiratory syncytial virus and human parainfluenza virus 3 in a subject comprising administering the immunogenic composition of claim 21 to the subject to generate the immune response.

23. The method of claim 22, comprising intranasal administration of the immunogenic composition.

24. The method of claim 22, wherein the subject is a human.

25. The method of claim 22, wherein the subject is less than one year old.

26. The method of claim 22, wherein the immune response is a protective immune response.

* * * * *